United States Patent
Player et al.

(10) Patent No.: US 7,642,270 B2
(45) Date of Patent: Jan. 5, 2010

(54) 5-OXO-5,8-DIHYDRO-PYRIDO-PYRIMIDINE AS INHIBITORS OF C-FMS KINASE

(75) Inventors: Mark R. Player, Phoenixville, PA (US); Hui Huang, Monroe Township, NJ (US); Daniel A. Hutta, Belle Mead, NJ (US); Renee L. DesJarlais, Saint Davids, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 493 days.

(21) Appl. No.: 11/519,611

(22) Filed: Sep. 12, 2006

(65) Prior Publication Data

US 2007/0060577 A1    Mar. 15, 2007

Related U.S. Application Data

(60) Provisional application No. 60/714,527, filed on Sep. 14, 2005.

(51) Int. Cl.
*A61K 31/44* (2006.01)
*C07D 471/06* (2006.01)

(52) U.S. Cl. ...................... 514/303; 544/279
(58) Field of Classification Search ........... 544/279; 514/303
See application file for complete search history.

(56) References Cited

U.S. PATENT DOCUMENTS

| 2005/0049274 A1 | 3/2005 | Wall et al. | |
| 2008/0114007 A1* | 5/2008 | Player et al. | 514/264.11 |

FOREIGN PATENT DOCUMENTS

| EP | 0014390 | 8/1980 |
| EP | 0787726 | 8/1997 |
| JP | 09221424 | 8/1997 |
| WO | WO 96/34867 | 11/1996 |
| WO | WO 99/09030 | 2/1999 |
| WO | WO 01/70741 | 9/2001 |
| WO | WO 2005/009967 | 2/2005 |
| WO | WO 2007/033232 | 3/2007 |

OTHER PUBLICATIONS

Science (1999), vol. 286, 531-537.*
Cancer and Metastasis Reviews (1998), 17(1), 91-106.*
Huff, Joel R., "HIV Protease: A Novel Chemotherapeutic Target for AIDS," Journal of Medicinal Chemistry, vol. 34, No. 8, Aug. 1991, pp. 2305-2314.*
FDA mulls drug to slow late-stage Alzheimer's [online], [retrieved on Sep. 23, 2003]. Retrived from the internet, URL<http://www.cnn.com/2003/HEALTH/conditions/09/24/alzheimers.drug.ap/index.html>.*
Cecil Textbook of Medicine, 20th Edition (1996), vol. 2, pp. 1992-1996.*
Cecil Textbook of Medicine, 20th edition (1996), vol. 2, pp. 2050-2057.*
Byrn et al., Solid-State Chemistry of Drugs, Second Edition, 1999, pp. 233-247.*
Abstract, "Anti-neoplastic agent effective against solid tumours and leukaemia—comprising 7-substituted 1-thiazolyl-1, 8-naphthyridine derivative, showing high safety", Database WPI Week 199747, Derwent Publications Ltd., London, GB, AN 1997-506304, Appln. No. JP19960351948, filed Dec. 10, 1996.

* cited by examiner

*Primary Examiner*—Rebecca L Anderson
(74) *Attorney, Agent, or Firm*—Thomas Dodd

(57) ABSTRACT

The invention addresses the current need for selective and potent protein tyrosine kinase inhibitors by providing potent inhibitors of c-fms kinase. The invention is directed to the novel compounds of Formula I:

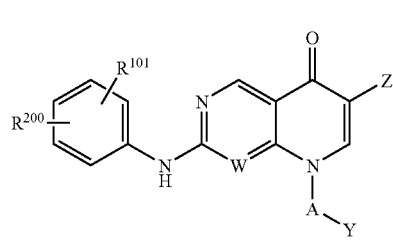

or a solvate, hydrate, tautomer or pharmaceutically acceptable salt thereof, wherein: W, A, Y, Z, $R^{101}$ and $R^{200}$ are described in the specification.

12 Claims, No Drawings

5-OXO-5,8-DIHYDRO-PYRIDO-PYRIMIDINE AS INHIBITORS OF C-FMS KINASE

CROSS REFERENCE TO RELATED APPLICATIONS

This present application claims benefit of U.S. Provisional Patent Application Ser. No. 60/714,527, filed Sep. 14, 2005, which is incorporated herein by reference in its entirety and for all purposes.

BACKGROUND OF THE INVENTION

The invention relates to novel compounds that function as protein tyrosine kinase inhibitors. The family of 5-oxo-5,8-dihydro-pyrido-pyrimidines has exhibited promising pharmaceutical properties in the past; U.S. Pat. No. 4,556,709, JP 09221424 and DE 19532235 are indicative of recent investigations. More particularly, the invention relates to novel compounds that function as inhibitors of c-fms kinase.

c-Fms is a type III receptor tyrosine kinase selectively expressed on macrophages and their progenitors. The extracellular Ig domain of c-fms binds macrophage colony stimulating factor (M-CSF), also known as colony stimulating factor-1 (CSF-1). Binding of CSF-1 induces receptor dimerization and trans-phosphorylation of the intracellular c-fms kinase domain on Y723 and other tyrosine residues. Once phosphorylated, c-fms efficiently phosphorylates several cytoplasmic signaling molecules that lead to de novo gene expression and proliferation. Small molecule inhibitors of the kinase catalytic site of c-fms are expected to prevent CSF-1 induced cellular responses.

Macrophages are a predominant source of tumor necrosis factor (TNF) and interleukin-1 (IL-1) in the destructive pannus of rheumatoid arthritis. TNF and IL-1 activate stromal expression of hematopoietic factors including CSF-1. In turn, CSF-1 recruits monocytes and promotes macrophage survival, functional activation, and in some settings, proliferation. Thus, TNF and CSF-1 interact in a perpetuating cycle that leads to inflammation and joint destruction. The exclusive receptor for CSF-1 is c-fms, and the disclosed invention is a c-fms inhibitor designed to interrupt this cycle.

Macrophages are abundant at sites of chronic inflammation where they are often the most important source of TNF, IL-1, and other cytokines. Moreover, macrophages can be an important source of factors that function in tissue remodeling such as plasminogen activators, matrix metalloproteases, vascular endothelial growth factor, and transforming growth factor-β. The numbers of macrophages present within target tissues have strongly correlated with disease severity in rheumatoid arthritis (Ann Rheum Dis 53 (1994) pp 39-44), immune nephritis (Kidney Int 54 (1998) pp 143-151), and graft rejection (Transpl Int 7 Suppl 1 (1994) pp 577-579). Macrophage numbers are also elevated in atherosclerotic plaque (Arch Pathol Lab Med 109 (1985) pp 445-449), adipose tissue in obesity (J Clin Invest 112 (2003) pp 1796-1898), diabetic nephropathy (Kidney Int 65 (2004) pp 116-128), cardiac hypertrophy (Hypertension 25 (1999) pp 132-138), and in many solid tumors (Trends in Immunology 23 (2002) pp 549-555), particularly breast cancer (J. Experimental Medicine 193 (2001) pp 727-739), where they are thought to contribute to disease progression. Modulation of macrophage function through inhibition of c-fms thus is expected to be useful in treating inflammatory mediated diseases and conditions.

Another example of the invention is the use of any of the compounds described herein in the preparation of a medicament for treating: rheumatoid arthritis, graft rejection, atherosclerosis, obesity, diabetic nephropathy, cardiac hypertrophy and solid tumor diseases, especially breast cancer, in a subject in need of such treatment.

Preclinical data suggest CSF-1/FMS is a particularly viable therapeutic target for rheumatoid arthritis. Recent work has shown that neutralizing antibodies to CSF-1 reduce substantially the severity of collagen-induced arthritis in mice (J Leukoc Biol 68 (2000) pp 144-150). The authors additionally demonstrated that recombinant CSF-1 exacerbated the disease progress in this model. Therefore, a preferred use for the invention is the treatment of rheumatoid arthritis.

SUMMARY OF THE INVENTION

The invention addresses the current need for selective and potent protein tyrosine kinase inhibitors by providing potent inhibitors of c-fms kinase.

The invention is directed to the novel compounds of Formula I:

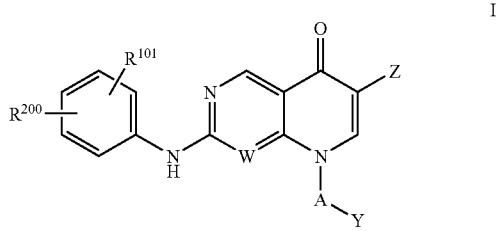

or a solvate, hydrate, tautomer or pharmaceutically acceptable salt thereof, wherein W, A, Y, Z, $R^{101}$ and $R^{200}$ are as defined herein.

The invention is also directed to a method of using a compound of Formula I for inhibiting protein tyrosine kinase activity comprising administering an effective amount of at least one compound of Formula I.

The invention is directed to a method of inhibiting c-fms kinase activity in a subject in need thereof comprising administering to the subject an effective amount of at least one compound of Formula I.

The invention is also directed to a method of treating or ameliorating a c-fms kinase mediated disorder in a subject in need thereof comprising administering to the subject an effective amount of at least one compound of Formula I.

DETAILED DESCRIPTION OF THE INVENTION

This invention is directed to a compound of Formula I:

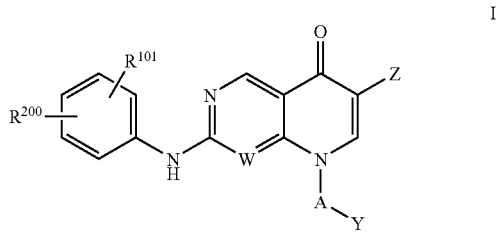

or a form thereof, wherein:
W is N or CH;
A is absent or alkyl;

Y is a ring selected from cycloalkyl, bicycloalkyl, aryl, alkylaryl, cycloalkylaryl, arylcycloalkyl, or heteroaryl provided that Y is not thiazole;

$R^{101}$ is hydrogen, hydroxyl, methyl, halogen, —$CF_3$, or methoxy;

$R^{200}$ is halogen, alkoxy optionally substituted with —CH(OH)—$CH_2$—$NR^{203}R^{204}$, alkyl optionally substituted with $R^{201}$, heterocyclyl optionally substituted with one alkyl and optionally substituted with one $R^{202}$, amino, alkylamino, dialkylamino, —C(O)$(CH_2)_n$$NR^{203}R^{204}$, heteroaryl, or —$R^{300}$—$R^{400}$; wherein n is 0, 1, 2, 3, or 4;

$R^{201}$ is hydroxyl, methyl, halogen, —$CF_3$, amino, alkylamino, dialkylamino or methoxy;

$R^{202}$ is alkyl, —C(O)—$CH_3$, —$CH_2$—C(O)—$CH_3$, —C(O)$(CH_2)_n$$NR^{203}R^{204}$, or —CON-alkyl-$NR^{203}R^{204}$; wherein n is 0, 1, 2, 3, or 4;

$R^{203}$ and $R^{204}$ are independently hydrogen, alkyl, or $R^{203}$ and $R^{204}$ may be taken together to form a ring selected from the following:

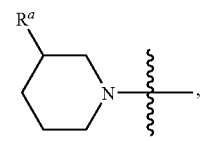 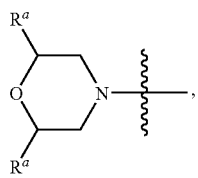

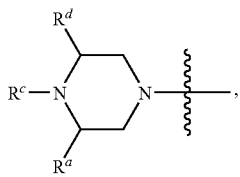 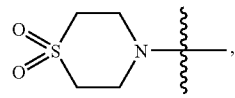

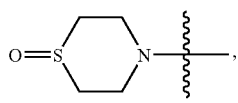 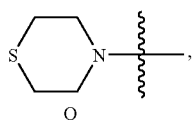

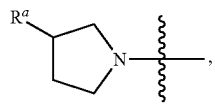 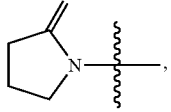

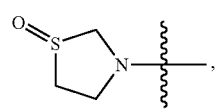 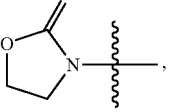

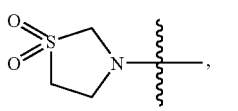 and 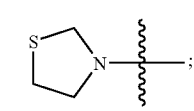;

wherein $R^a$, $R^c$ and $R^d$ are independently hydrogen or alkyl;

$R^{300}$ is alkyl;

$R^{400}$ is —$NR^{403}R^{404}$, —$SO_2NR^{405}R^{406}$, oxazolidinonyl wherein said oxazolidinonyl is optionally substituted with one or two $R^{401}$, piperazinyl wherein said piperazinyl is optionally substituted with $R^{202}$ or pyrrolidinonyl wherein said pyrrolidinonyl is optionally substituted with one or two $R^{401}$;

wherein $R^{401}$ is methyl, —C(O)—$CH_3$, or —$CH_2$—C(O)—$CH_3$;

wherein $R^{403}$ and $R^{404}$ are independently hydrogen, alkyl, or $R^{403}$ and $R^{404}$ may be taken together to form a ring selected from the following:

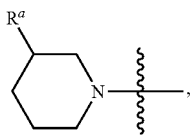 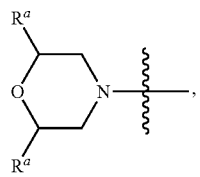

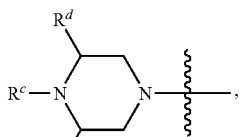 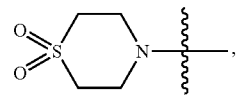

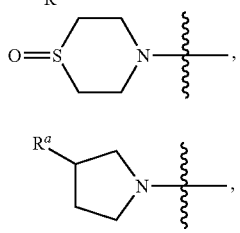 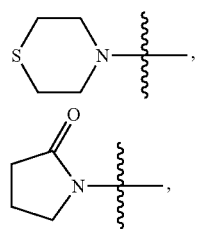

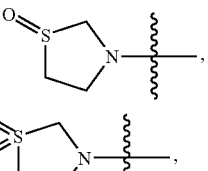 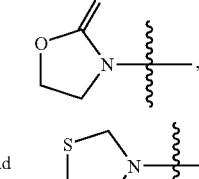

 and 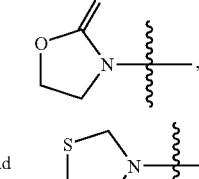;

wherein $R^a$, $R^c$ and $R^d$ are independently hydrogen or alkyl;

$R^{405}$ and $R^{406}$ are independently hydrogen, alkyl, or $R^{405}$ and $R^{406}$ may be taken together to form a ring selected from the following:

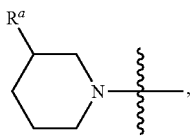 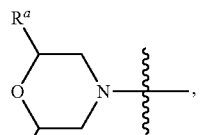

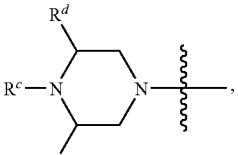 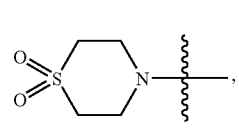

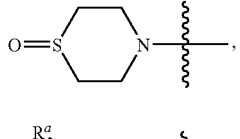 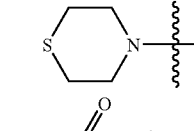

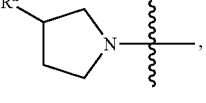 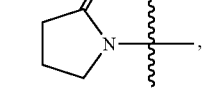

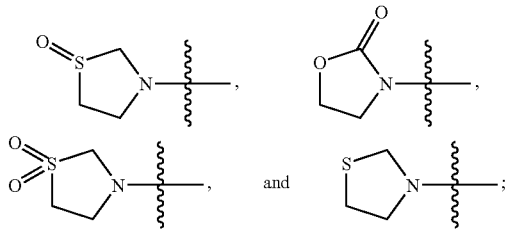

wherein $R^a$, $R^c$ and $R^d$ are independently hydrogen or alkyl; and

Z is $CO_2H$, $CO_2$alkyl, or $CONR^1R^2$; wherein $R^1$ is hydrogen or alkyl; and $R^2$ is hydrogen, alkyl, cycloalkyl, or alkoxy.

An example of the present invention is a compound of Formula I or a form thereof, wherein:

W is N or CH;

A is absent or alkyl;

Y is a ring selected from cycloalkyl, bicycloalkyl, aryl, alkylaryl, cycloalkylaryl, arylcycloalkyl, or heteroaryl provided that Y is not thiazole;

$R^{101}$ is hydrogen, hydroxyl, methyl, halogen, —$CF_3$, or methoxy;

$R^{200}$ is halogen, alkoxy optionally substituted with —CH(OH)—$CH_2$—$NR^{203}R^{204}$, alkyl optionally substituted with $R^{201}$, heterocyclyl optionally substituted with one alkyl and optionally substituted with one $R^{202}$, dialkylamino, —C(O)($CH_2$)$_n$$NR^{203}R^{204}$, heteroaryl, or —$R^{300}$—$R^{400}$; wherein n is 0, 1, 2, 3, or 4;

$R^{201}$ is hydroxyl, methyl, halogen, —$CF_3$, dialkylamino or methoxy;

$R^{202}$ is alkyl, —C(O)—$CH_3$, —$CH_2$—C(O)—$CH_3$, —C(O)($CH_2$)$_n$$NR^{203}R^{204}$, or —CON-alkyl-$NR^{203}R^{204}$; wherein n is 0, 1, 2, 3, or 4;

$R^{203}$ and $R^{204}$ are independently hydrogen, alkyl, or $R^{203}$ and $R^{204}$ may be taken together to form a ring selected from the following:

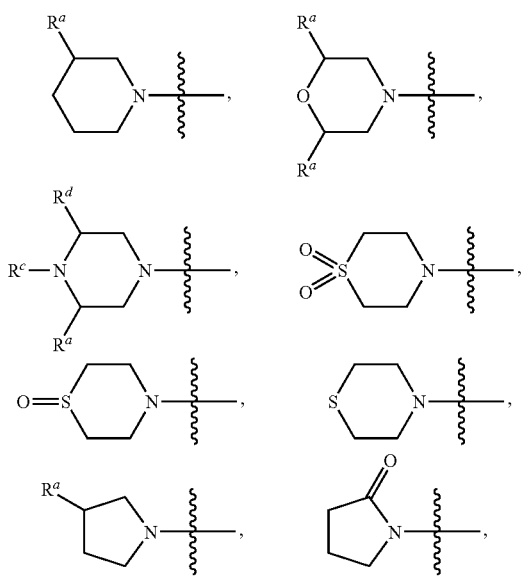

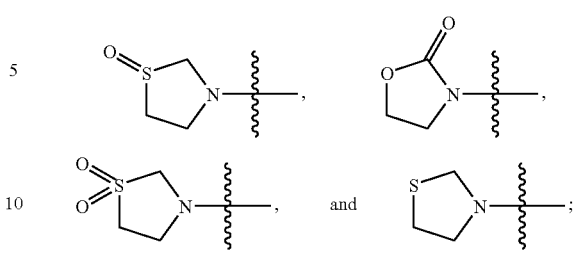

wherein $R^a$, $R^c$ and $R^d$ are independently hydrogen or alkyl;

$R^{300}$ is alkyl;

$R^{400}$ is —$NR^{403}R^{404}$, —$SO_2NR^{405}R^{506}$, oxazolidinonyl wherein said oxazolidinonyl is optionally substituted with one or two $R^{401}$, piperazinyl wherein said piperazinyl is optionally substituted with $R^{202}$ or pyrrolidinonyl wherein said pyrrolidinonyl is optionally substituted with one or two $R^{401}$;

wherein $R^{401}$ is methyl, —C(O)—$CH_3$, or —$CH_2$—C(O)—$CH_3$;

wherein $R^{403}$ and $R^{404}$ are independently hydrogen, alkyl, or $R^{403}$ and $R^{404}$ may be taken together to form a ring selected from the following:

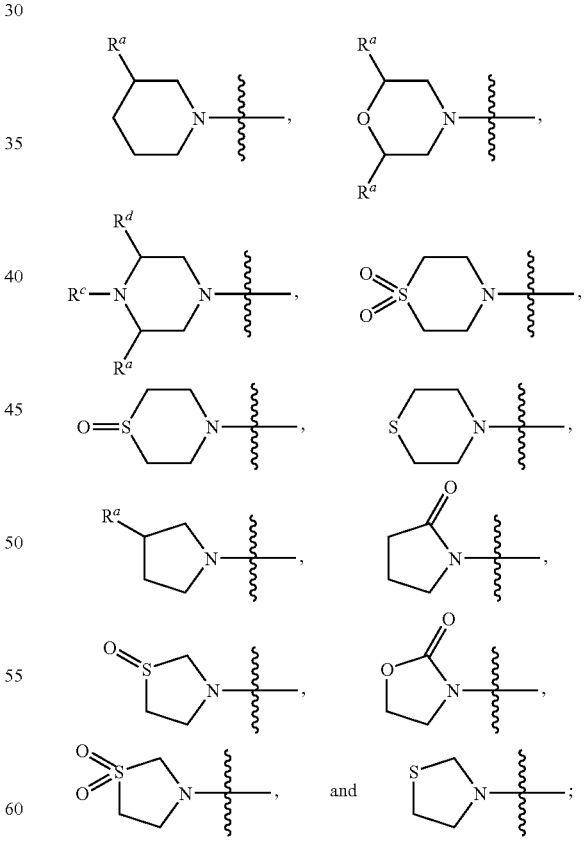

wherein $R^a$, $R^c$ and $R^d$ are independently hydrogen or alkyl;

$R^{405}$ and $R^{406}$ are independently hydrogen, alkyl, or $R^{405}$ and $R^{406}$ may be taken together to form a ring selected from the following:

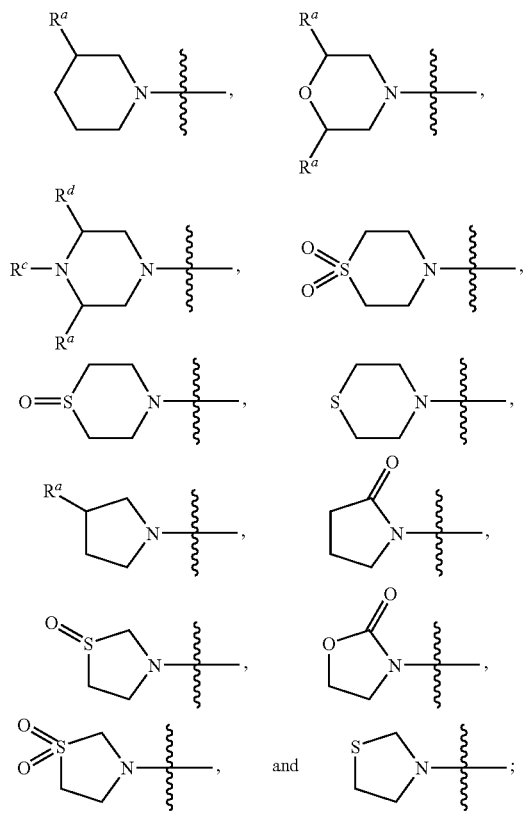

wherein $R^a$, $R^c$ and $R^d$ are independently hydrogen or alkyl; and

Z is $CO_2H$, $CO_2$alkyl, or $CONR^1R^2$; wherein $R^1$ is hydrogen or alkyl; and $R^2$ is hydrogen, alkyl, cycloalkyl, or alkoxy.

Examples of the present invention include those compounds of Formula I or a form thereof wherein one or more of the following limitations are present:

W is N or CH;

A is absent;

Y is a ring selected from cycloalkyl, bicycloalkyl, phenyl, alkylaryl, cycloalkylaryl, arylcycloalkyl, or heteroaryl provided that Y is not thiazole;

$R^{101}$ is hydrogen, hydroxyl, methyl, halogen, —$CF_3$, or methoxy;

$R^{200}$ is halogen, $C_{(1-4)}$alkoxy optionally substituted with —CH(OH)—$CH_2$—$NR^{203}R^{204}$, $C_{(1-4)}$alkyl optionally substituted with $R^{201}$, heterocyclyl optionally substituted with one $C_{(1-4)}$alkyl and optionally substituted with one $R^{202}$, dialkylamino, —C(O)($CH_2$)$_n$$NR^{203}R^{204}$, heteroaryl, or —$R^{300}$—$R^{400}$; wherein n is 0, 1, 2, 3, or 4;

$R^{201}$ is hydroxyl, methyl, halogen, —$CF_3$, dialkylamino or methoxy;

$R^{202}$ is alkyl, —C(O)—$CH_3$, —$CH_2$—C(O)—$CH_3$, —C(O)($CH_2$)$_n$$NR^{203}R^{204}$, —C(O)N($CH_2$)$_n$$NR^{203}R^{204}$; wherein n is 0, 1, 2, 3, or 4;

$R^{203}$ and $R^{204}$ are independently hydrogen, $C_{(1-4)}$alkyl, or $R^{203}$ and $R^{204}$ may be taken together to form a ring selected from the following:

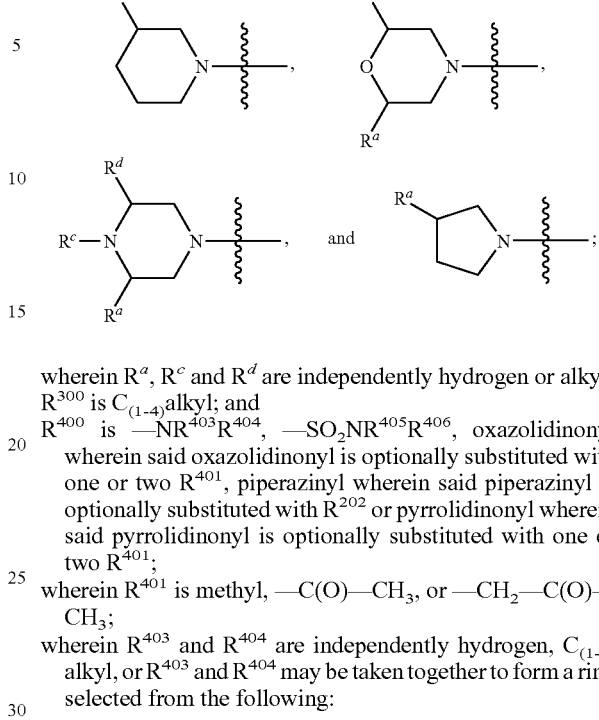

wherein $R^a$, $R^c$ and $R^d$ are independently hydrogen or alkyl;

$R^{300}$ is $C_{(1-4)}$alkyl; and $R^{400}$ is —$NR^{403}R^{404}$, —$SO_2NR^{405}R^{406}$, oxazolidinonyl wherein said oxazolidinonyl is optionally substituted with one or two $R^{401}$, piperazinyl wherein said piperazinyl is optionally substituted with $R^{202}$ or pyrrolidinonyl wherein said pyrrolidinonyl is optionally substituted with one or two $R^{401}$;

wherein $R^{401}$ is methyl, —C(O)—$CH_3$, or —$CH_2$—C(O)—$CH_3$;

wherein $R^{403}$ and $R^{404}$ are independently hydrogen, $C_{(1-4)}$ alkyl, or $R^{403}$ and $R^{404}$ may be taken together to form a ring selected from the following:

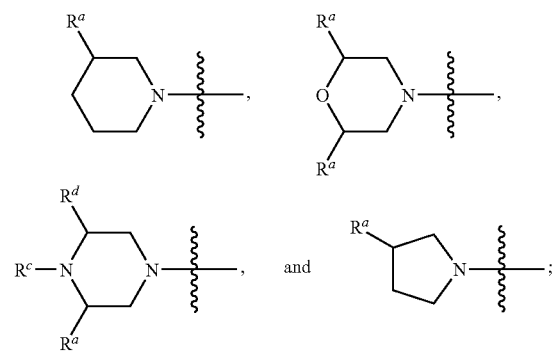

wherein $R^a$, $R^c$ and $R^d$ are independently hydrogen or alkyl; $R^{405}$ and $R^{406}$ are independently hydrogen, $C_{(1-4)}$alkyl, or $R^{405}$ and $R^{406}$ may be taken together to form a ring selected from the following:

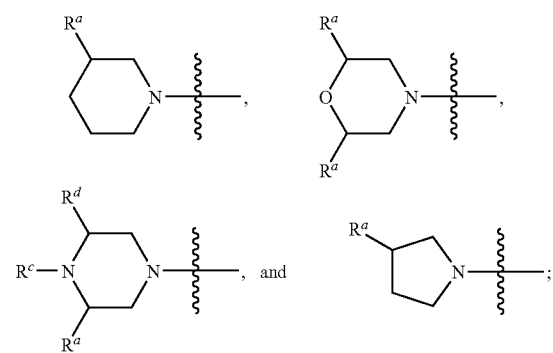

wherein $R^a$, $R^c$ and $R^d$ are independently hydrogen or alkyl; and

Z is $CO_2$alkyl, or $CONR^1R^2$; wherein $R^1$ is hydrogen or $C_{(1-4)}$alkyl; and $R^2$ is hydrogen, $C_{(1-4)}$alkyl, cycloalkyl, or $C_{(1-4)}$alkoxy.

In another embodiment of the invention one or more of the following limitations are present:

W is N;
A is absent;
Y is a ring selected from cycloalkyl or arylcycloalkyl;
$R^{101}$ is hydrogen;
$R^{200}$ is —$R^{300}$—$R^{400}$; and
Z is $CO_2$alkyl, or $CONR^1R^2$; wherein $R^1$ and $R^2$ are independently hydrogen, or $C_{(1-4)}$alkyl.

Examples of the present invention include those compounds of Formula I or a form thereof wherein one or more of the following limitations are present:

W is N;
A is absent;
Y is a ring selected from cycloalkyl or arylcycloalkyl;
$R^{101}$ is hydroxyl, methyl, halogen, —$CF_3$, or methoxy;
$R^{200}$ is piperazine optionally substituted with one or two methyl substituents, piperidine optionally substituted with one or two methyl substituents, morpholine or —$R^{300}$—$R^{400}$ wherein $R^{300}$ is methyl or ethyl and $R^{400}$ is piperazine optionally substituted with one or two methyl substituents; and
Z is $CO_2$alkyl, or $CONR^1R^2$; wherein $R^1$ is hydrogen or $C_{(1-4)}$alkyl; and $R^2$ is hydrogen, $C_{(1-4)}$alkyl, or cycloalkyl.

Examples of the present invention include those compounds of Formula I or a form thereof wherein one or more of the following limitations are present:

W is N;
A is absent;
Y is a ring selected from cyclohexyl, cyclopentyl, bicyclo[2.2.1]heptyl, indanyl, phenyl or 1,2,3,4-tetrahydronaphthalenyl;
$R^{101}$ is hydrogen, hydroxyl, methyl, halogen, —$CF_3$, or methoxy;
$R^{200}$ is heterocyclyl (preferably tetrahydrofuranyl, pyrrolidinyl, piperidinyl, 4-methyl piperazin-1-yl, piperazinyl, morpholinyl, or thiomorpholino), dialkylamino, —$R^{300}$—$R^{400}$, or $C_{(1-4)}$alkyl wherein said $C_{(1-4)}$alkyl is optionally substituted with one or both substituents selected from hydroxyl and dialkylamino;
$R^{300}$ is $C_{(1-4)}$alkyl;
$R^{400}$ is —$NR^{403}R^{404}$, —$SO_2NR^{405}R^{406}$, oxazolidinonyl wherein said oxazolidinonyl is optionally substituted with one or two $R^{401}$, piperazinyl wherein said piperazinyl is optionally substituted with $R^{202}$ or pyrrolidinonyl wherein said pyrrolidinonyl is optionally substituted with one or two $R^{401}$;
wherein $R^{401}$ is methyl, —C(O)—$CH_3$, or —$CH_2$—C(O)—$CH_3$;
wherein $R^{403}$ and $R^{404}$ are independently hydrogen, $C_{(1-4)}$alkyl, or $R^{403}$ and $R^{404}$ may be taken together to form a ring selected from the following:

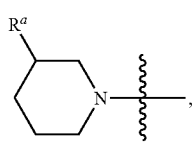, 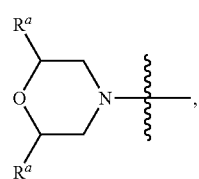,

-continued

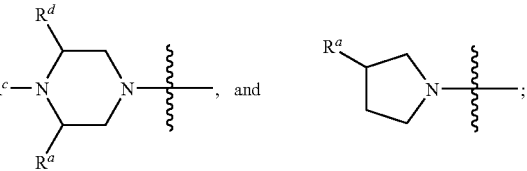

wherein $R^a$, $R^c$ and $R^d$ are independently hydrogen or alkyl;
$R^{405}$ and $R^{406}$ are independently hydrogen, $C_{(1-4)}$alkyl, or $R^{405}$ and $R^{406}$ may be taken together to form a ring selected from the following:

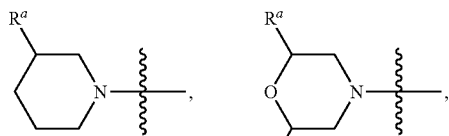

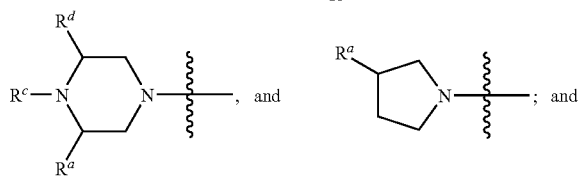

wherein $R^a$, $R^c$ and $R^d$ are independently hydrogen or alkyl;
Z is $CO_2$alkyl, or $CONR^1R^2$; wherein $R^1$ is hydrogen or $C_{(1-4)}$alkyl; and $R^2$ is hydrogen, $C_{(1-4)}$alkyl, cycloalkyl, or $C_{(1-4)}$alkoxy.

Examples of the present invention include those compounds of Formula I or a form thereof wherein one or more of the following limitations are present:

W is N or CH;
A is absent or alkyl;
Y is a ring selected from indan-5-yl, phenyl, cyclohexyl, cyclopentyl, bicyclo[2.2.1]heptyl or adamantan-2-yl;
$R^{101}$ is hydrogen or hydroxyl;
$R^{200}$ is fluorine, alkoxy substituted with —CH(OH)—$CH_2$—N($CH_3$)$_2$, alkyl optionally substituted with $R^{201}$, morpholinyl, piperazinyl optionally substituted with $R^{202}$, 3,5-dimethyl piperazinyl, piperidinyl, piperidinyl substituted with —C(O)-alkyl-N($CH_3$)$_2$, —C(O)-alkyl-piperazinyl (optionally substituted on piperazinyl with alkyl), dimethylamino, —C(O)N($CH_3$)$_2$, heteroaryl, or —$R^{300}$—$R^{400}$;
$R^{201}$ is hydroxyl or dimethylamino;
$R^{202}$ is —$CH_3$;
$R^{300}$ is alkyl; and
$R^{400}$ is —N($CH_3$)$_2$, morpholinyl, —$SO_2NR^{405}R^{406}$, piperazinyl optionally substituted with $R^{202}$ or oxazolidinonyl;
$R^{405}$ and $R^{406}$ are independently hydrogen, alkyl, or $R^{405}$ and $R^{406}$ may be taken together to form the following ring:

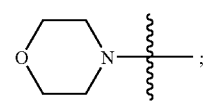

and
Z is $CO_2$alkyl, or $CONR^1R^2$; wherein $R^1$ is hydrogen or alkyl; and $R^2$ is hydrogen, alkyl, cycloalkyl, or alkoxy.

An example of the present invention includes compounds of Formula I or a form thereof wherein:

W is N or CH;

A is absent;

Y is a ring selected from cycloalkyl, bicycloalkyl, phenyl, alkylaryl, cycloalkylaryl, arylcycloalkyl, or heteroaryl provided that Y is not thiazole;

$R^{101}$ is hydrogen, hydroxyl, methyl, halogen, —$CF_3$, or methoxy;

$R^{200}$ is halogen, $C_{(1-4)}$alkoxy optionally substituted with —CH(OH)—$CH_2$—$NR^{203}R^{204}$, $C_{(1-4)}$alkyl optionally substituted with $R^{201}$, heterocyclyl optionally substituted with one $C_{(1-4)}$alkyl and optionally substituted with one $R^{202}$, dialkylamino, —C(O)($CH_2$)$_n$$NR^{203}R^{204}$, heteroaryl, or —$R^{300}$—$R^{400}$; wherein n is 0, 1, 2, 3, or 4;

$R^{201}$ is hydroxyl, methyl, halogen, —$CF_3$, dialkylamino or methoxy;

$R^{202}$ is alkyl, —C(O)—$CH_3$, —$CH_2$—C(O)—$CH_3$, —C(O)($CH_2$)$_n$$NR^{203}R^{204}$, —C(O)N($CH_2$)$_n$$NR^{203}R^{204}$; wherein n is 0, 1, 2, 3, or 4;

$R^{203}$ and $R^{204}$ are independently hydrogen, $C_{(1-4)}$alkyl, or $R^{203}$ and $R^{204}$ may be taken together to form a ring selected from the following:

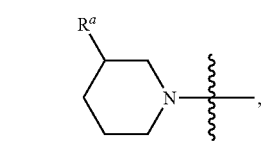 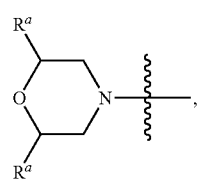

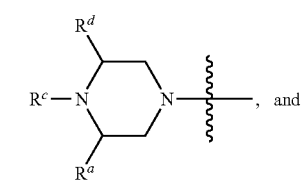, and 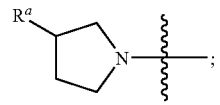;

wherein $R^a$, $R^c$ and $R^d$ are independently hydrogen or alkyl;

$R^{300}$ is $C_{(1-4)}$alkyl; and $R^{400}$ is —$NR^{403}R^{404}$, —$SO_2NR^{405}R^{406}$, oxazolidinonyl wherein said oxazolidinonyl is optionally substituted with one or two $R^{401}$, piperazinyl wherein said piperazinyl is optionally substituted with $R^{202}$ or pyrrolidinonyl wherein said pyrrolidinonyl is optionally substituted with one or two $R^{401}$;

wherein $R^{401}$ is methyl, —C(O)—$CH_3$, or —$CH_2$—C(O)—$CH_3$;

wherein $R^{403}$ and $R^{404}$ are independently hydrogen, $C_{(1-4)}$ alkyl, or $R^{403}$ and $R^{404}$ may be taken together to form a ring selected from the following:

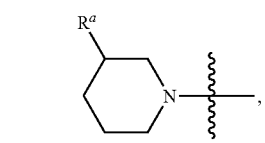 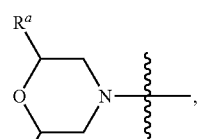

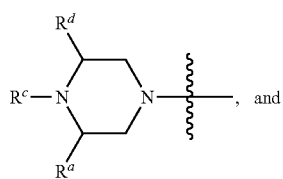, and 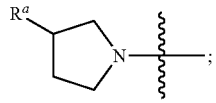;

wherein $R^a$, $R^c$ and $R^d$ are independently hydrogen or alkyl;

$R^{405}$ and $R^{406}$ are independently hydrogen, $C_{(1-4)}$alkyl, or $R^{405}$ and $R^{406}$ may be taken together to form a ring selected from the following:

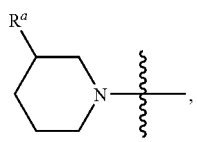 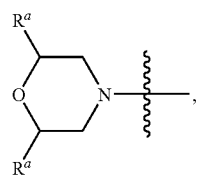

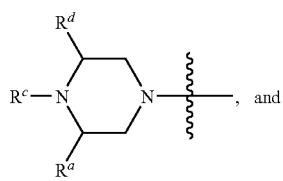, and 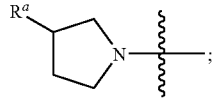;

wherein $R^a$, $R^c$ and $R^d$ are independently hydrogen or alkyl; and

Z is $CO_2H$.

An example of the present invention is a compound of Formula I selected from the group consisting of:

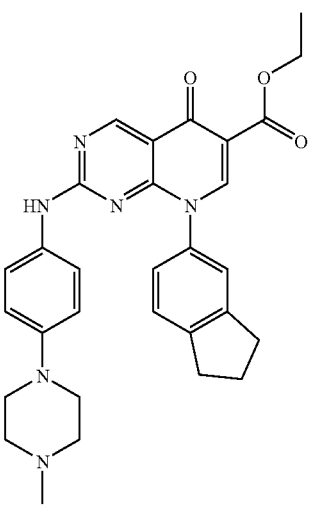

Cpd 1

-continued
Cpd 2
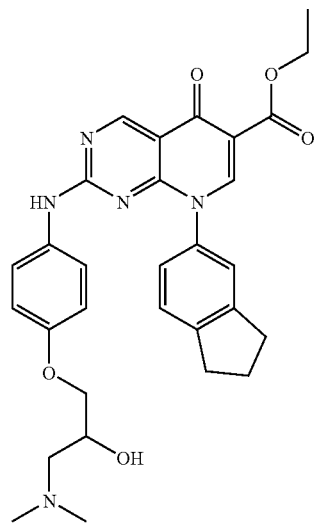
Cpd 5
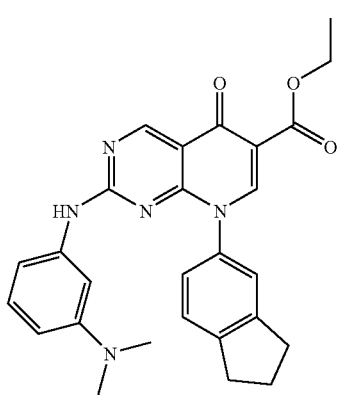
Cpd 3
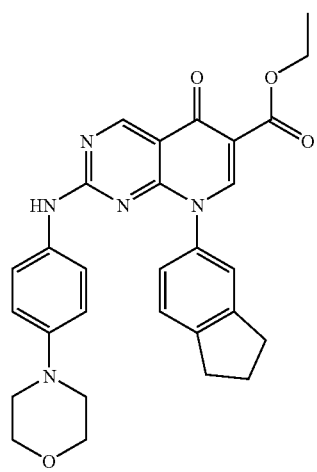
Cpd 6
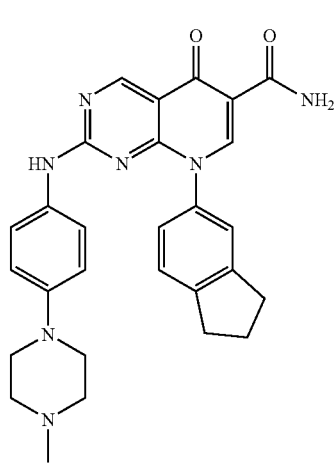
Cpd 4
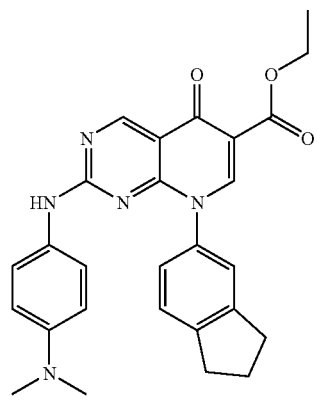
Cpd 7

Cpd 8
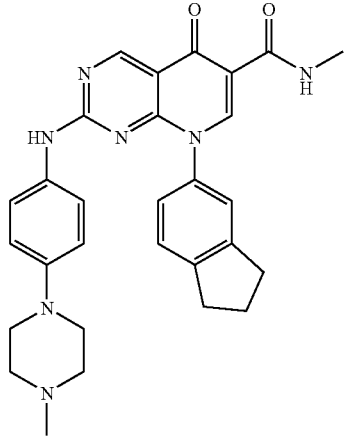
Cpd 11
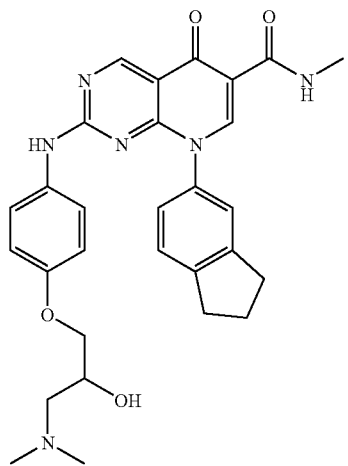
Cpd 9
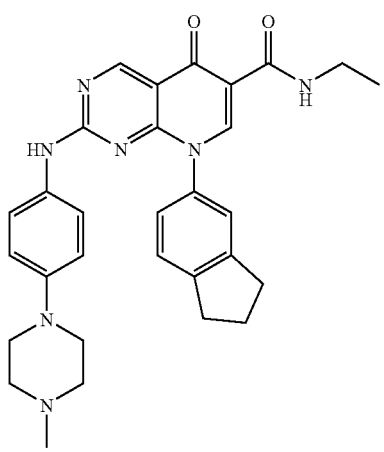
Cpd 12
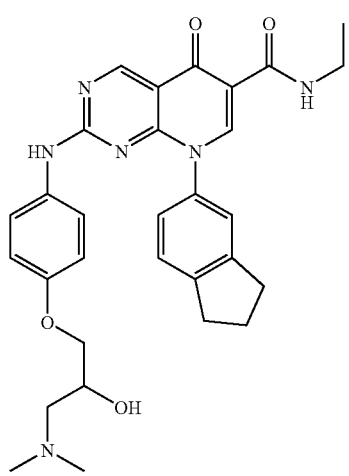
Cpd 10
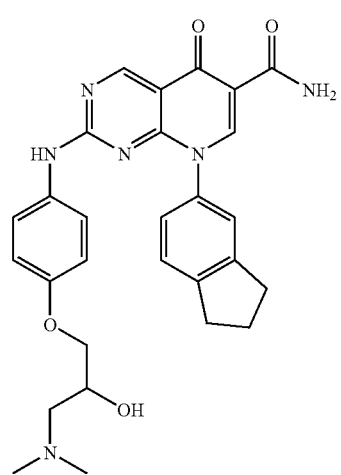
Cpd 13
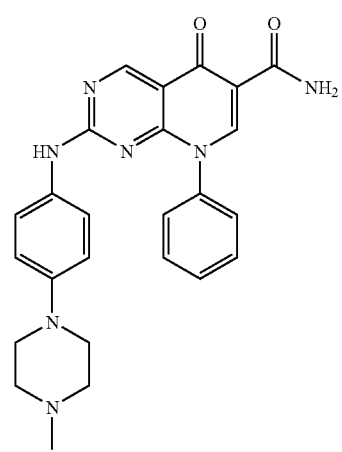

-continued
Cpd 14
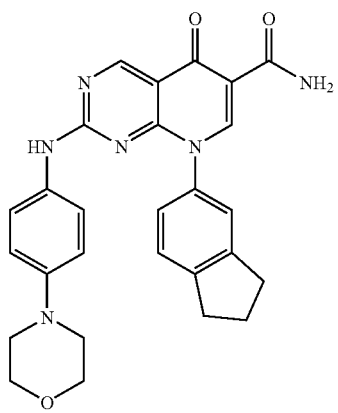
Cpd 15
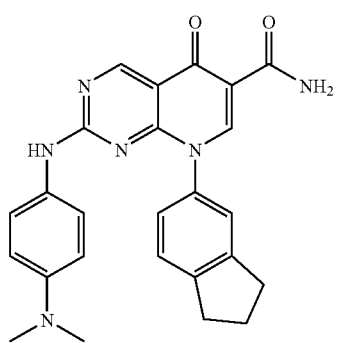
Cpd 16
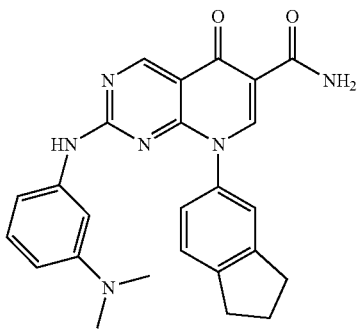
Cpd 17
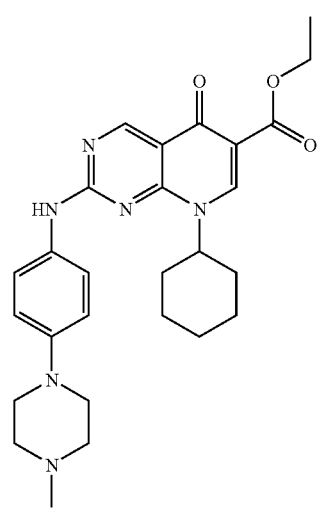
Cpd 18
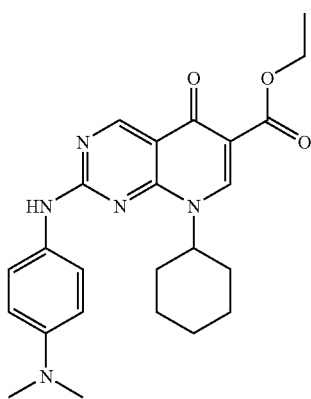
Cpd 19
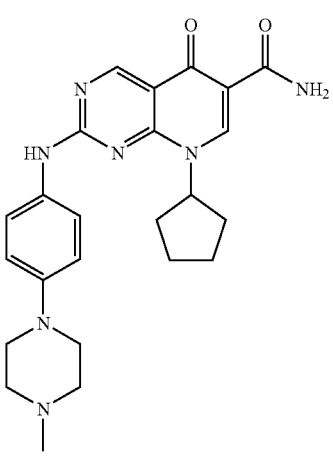
Cpd 20
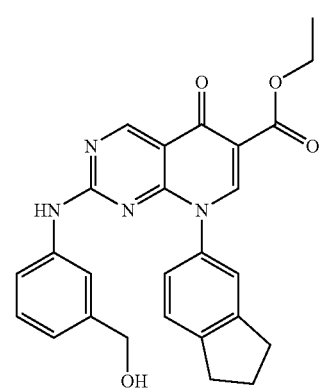
Cpd 21
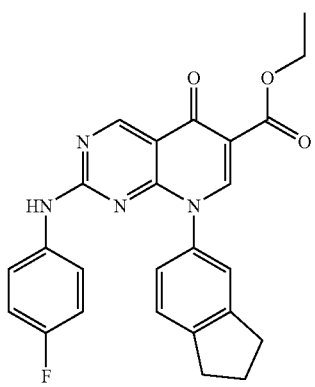

Cpd 22
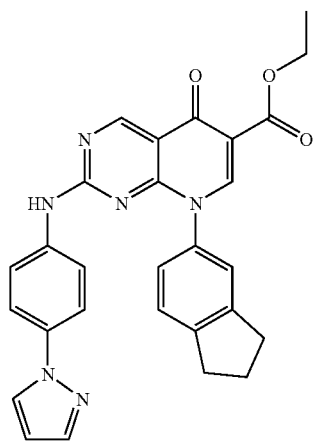
Cpd 25
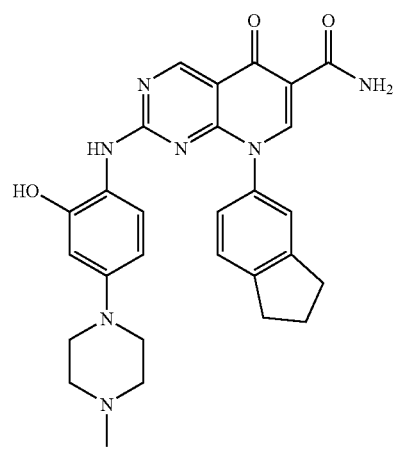
Cpd 23
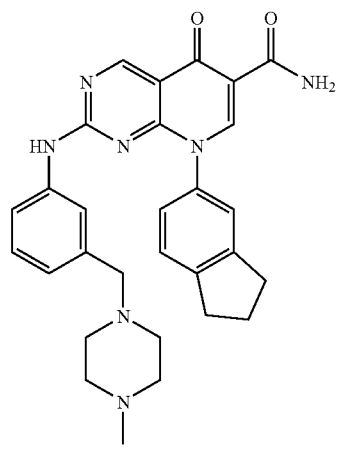
Cpd 26
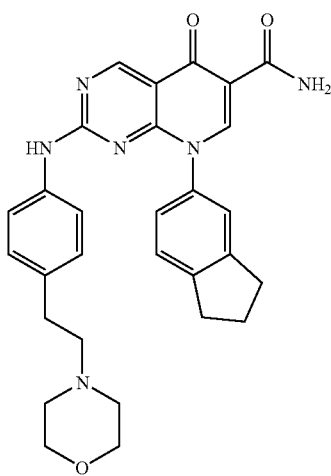
Cpd 24
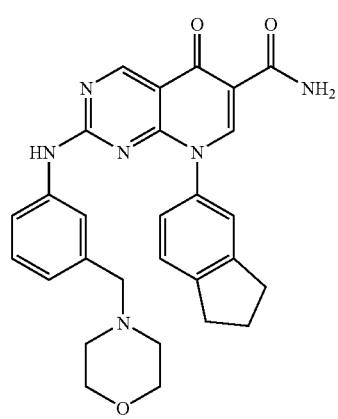
Cpd 27

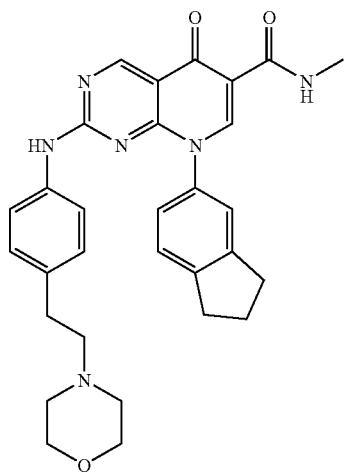
Cpd 28
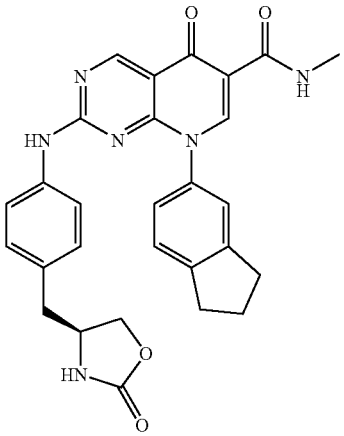
Cpd 31
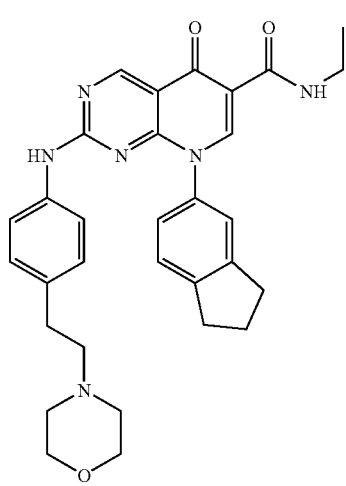
Cpd 29
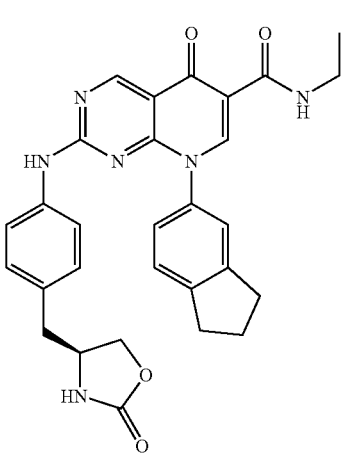
Cpd 32
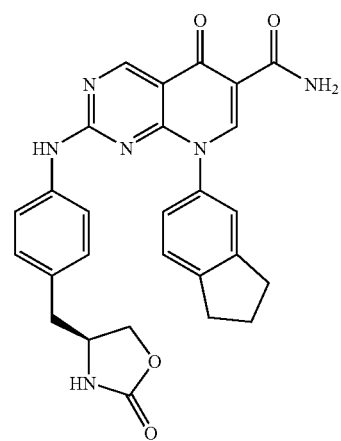
Cpd 30
Cpd 33

Cpd 34
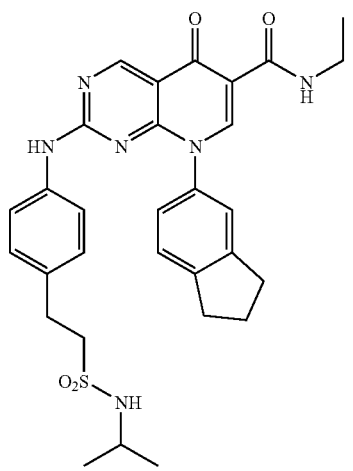
Cpd 35
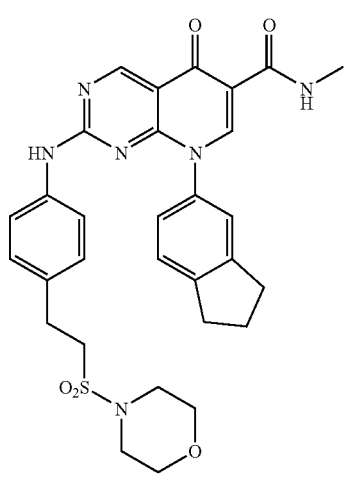
Cpd 36
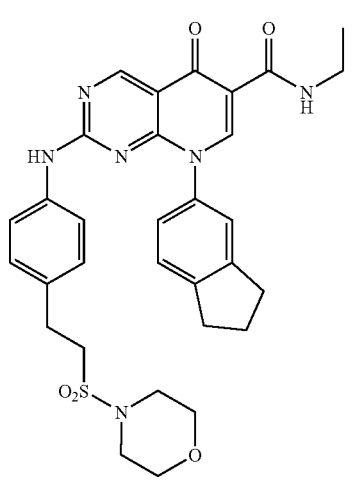
Cpd 37
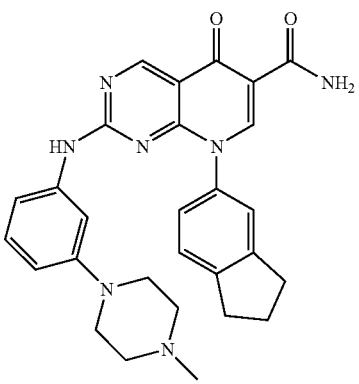
Cpd 38
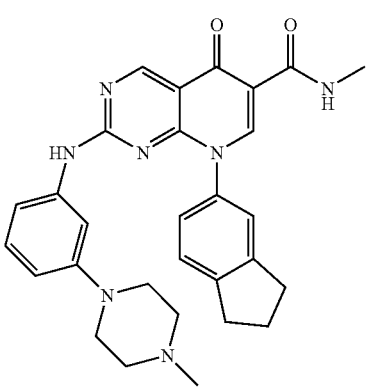
Cpd 39
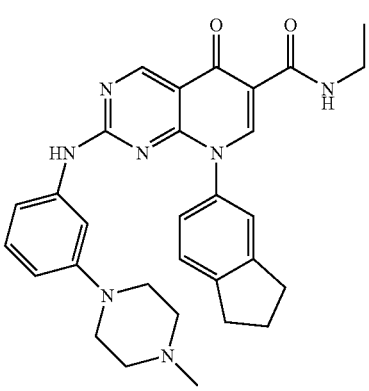
Cpd 40
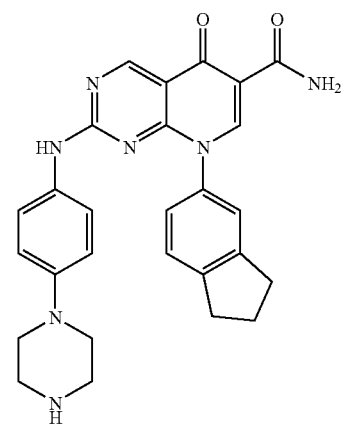

Cpd 41
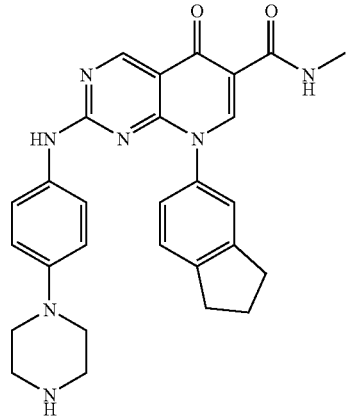
Cpd 42
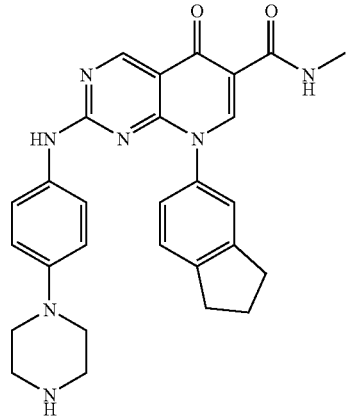
Cpd 43
Cpd 44
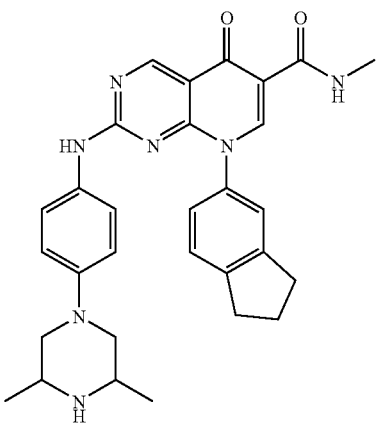
Cpd 45
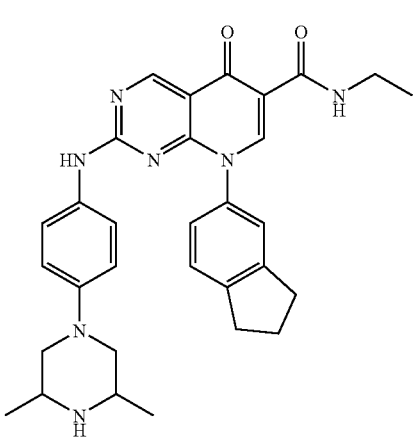
Cpd 46
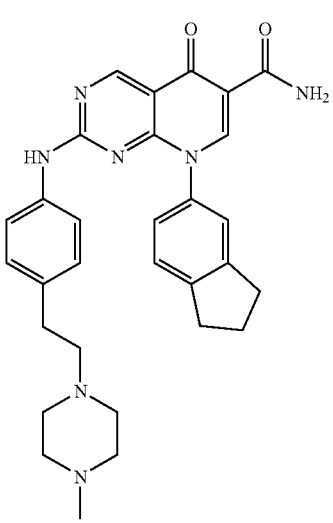

-continued
Cpd 47
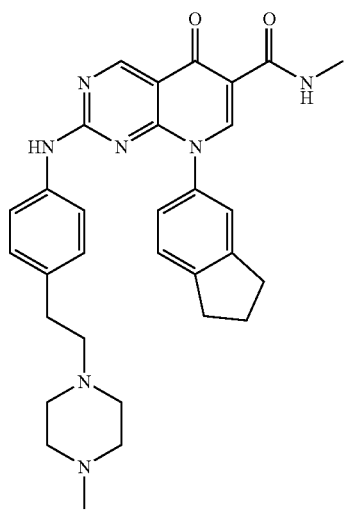
Cpd 48
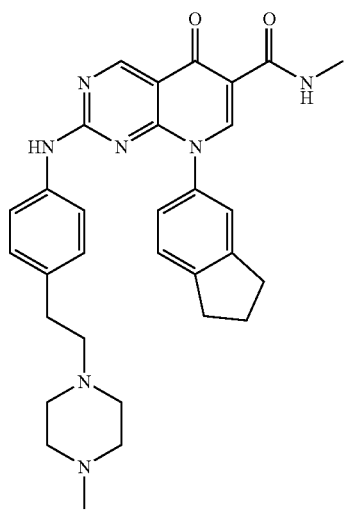
Cpd 49
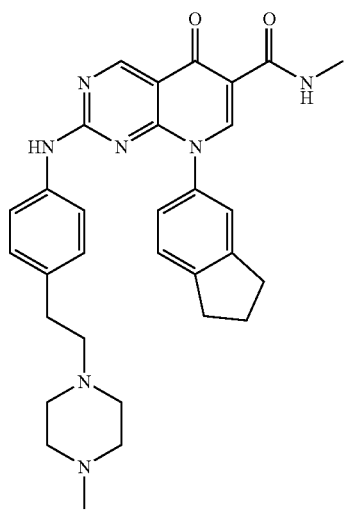
-continued
Cpd 50
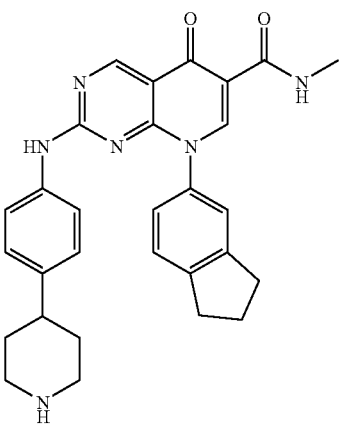
Cpd 51
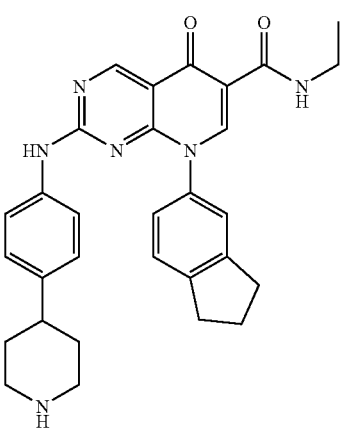
Cpd 52
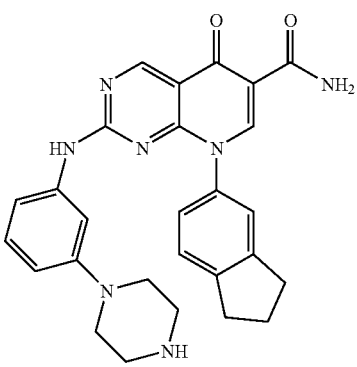
Cpd 534
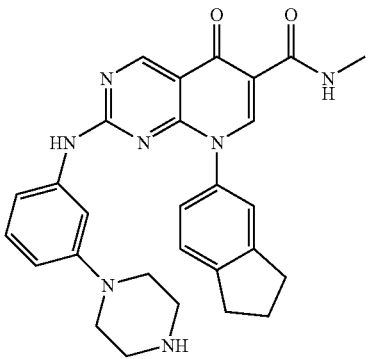

-continued
Cpd 54
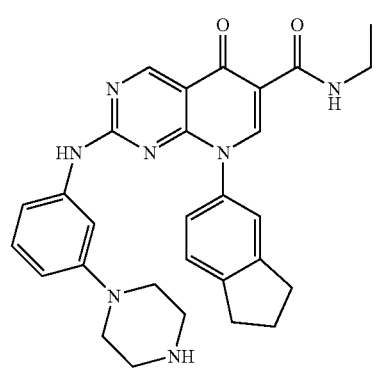
Cpd 55
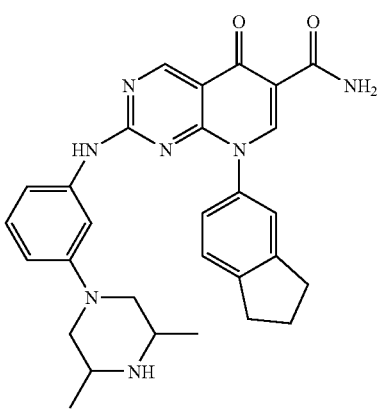
Cpd 56
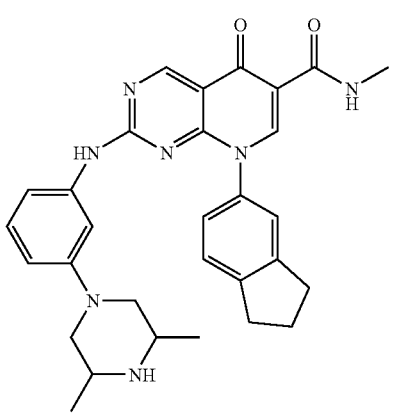
Cpd 57
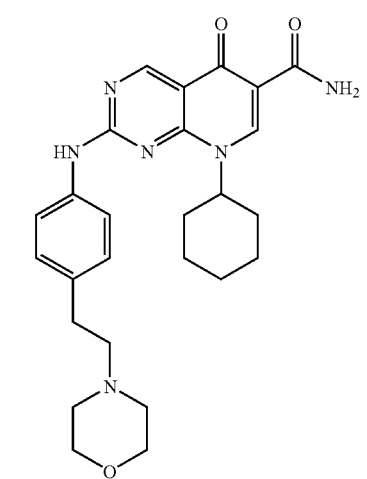
-continued
Cpd 58
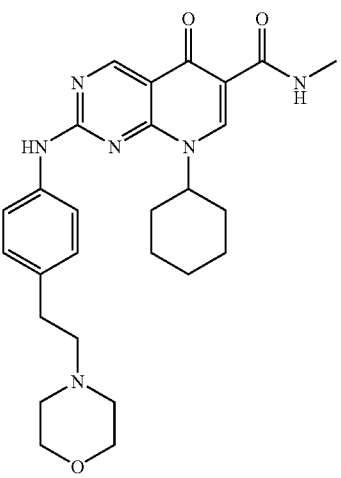
Cpd 59
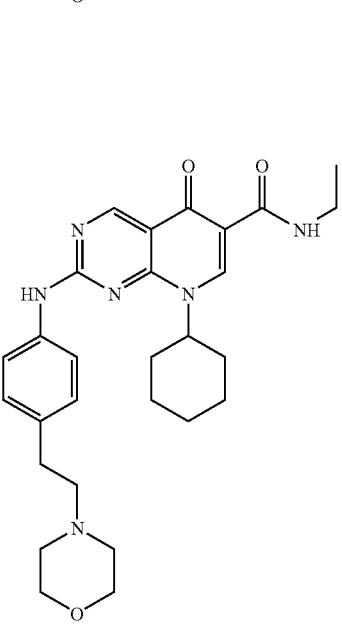
Cpd 60
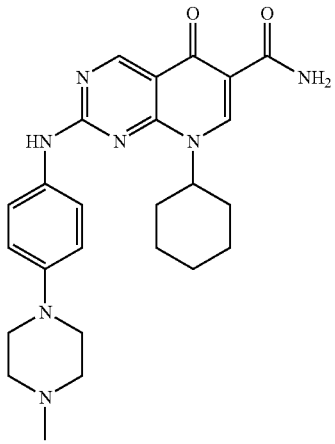

Cpd 61
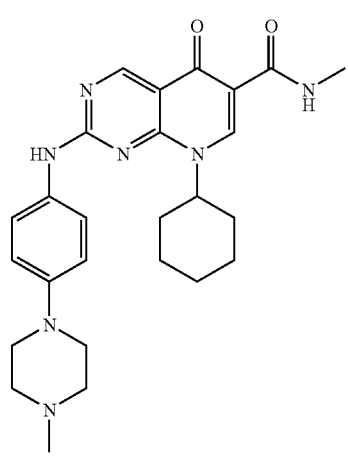
Cpd 62
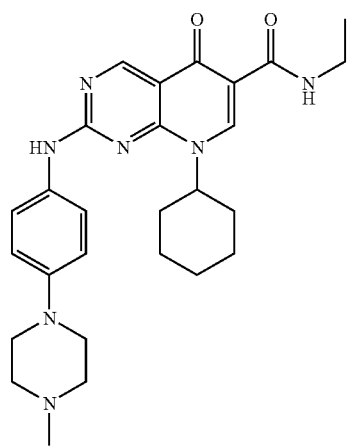
Cpd 63
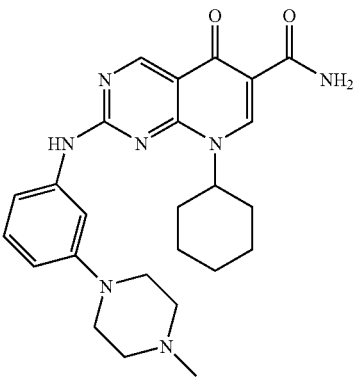
Cpd 64
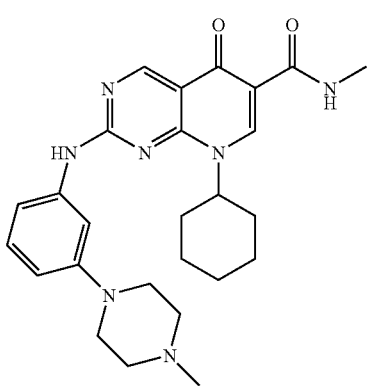
Cpd 65
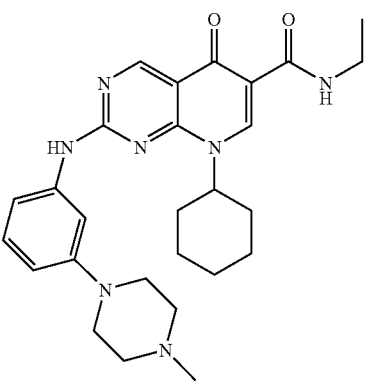
Cpd 66
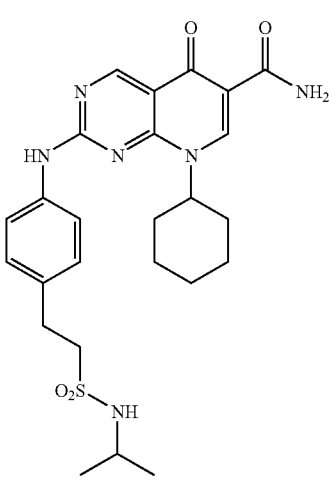
Cpd 67
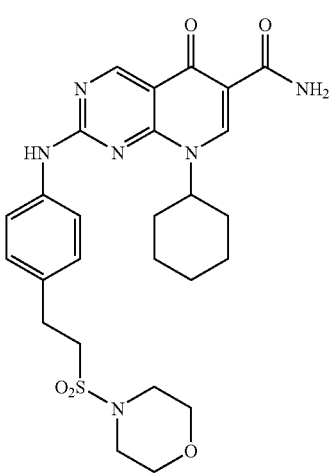

Cpd 68
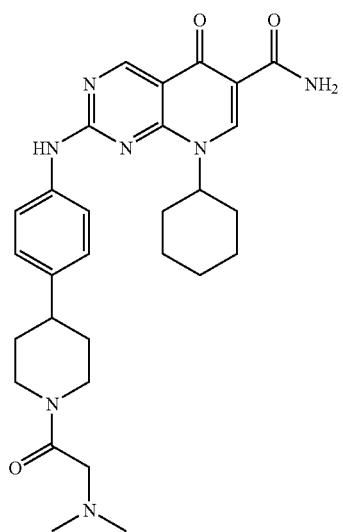
Cpd 69
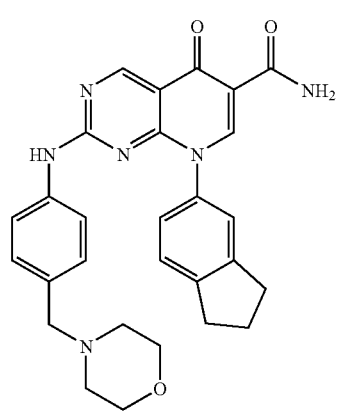
Cpd 70
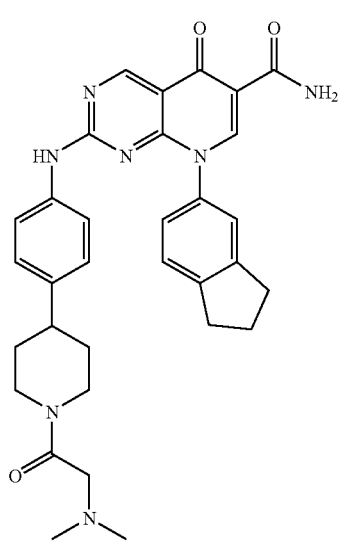
Cpd 71
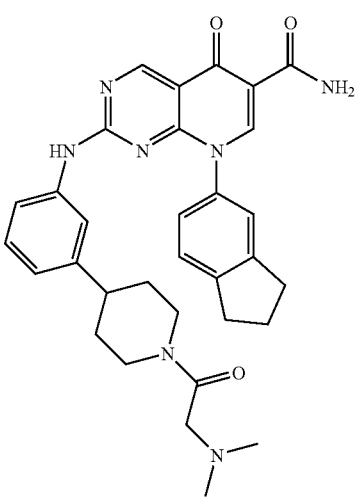
Cpd 72
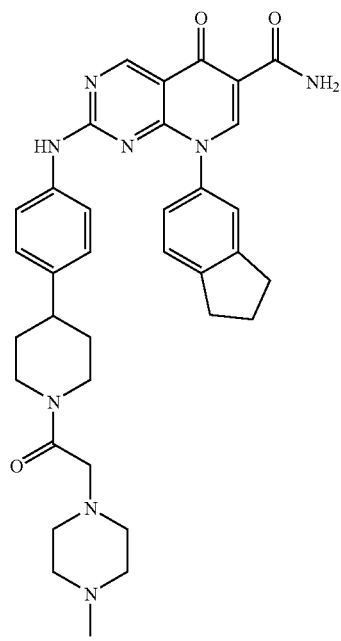

-continued
Cpd 73
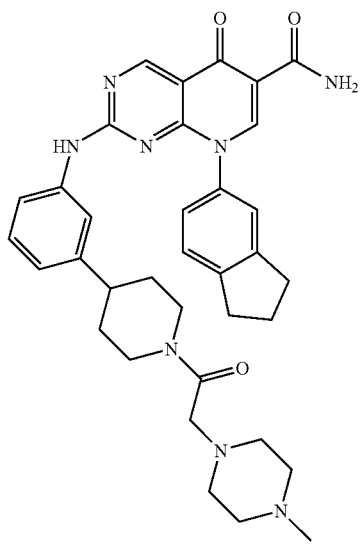
Cpd 74
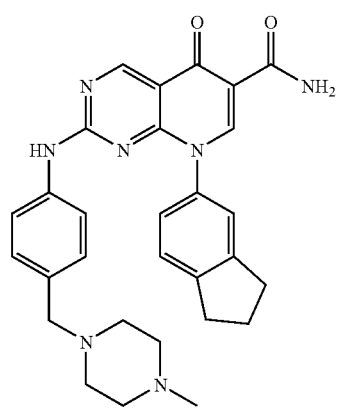
Cpd 75
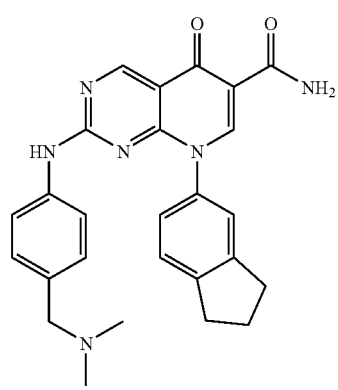
-continued
Cpd 76
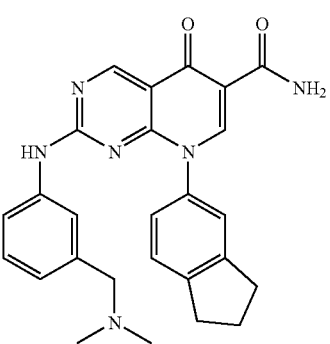
Cpd 77
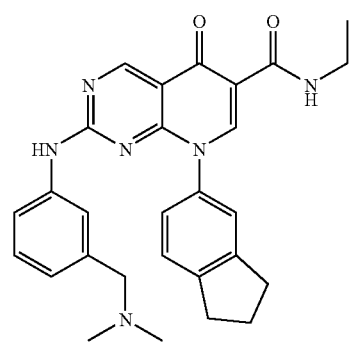
Cpd 78
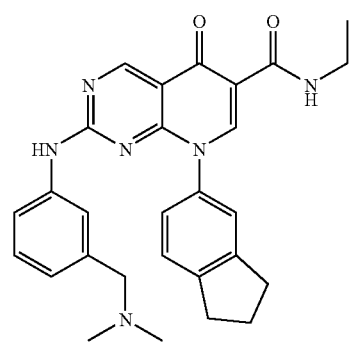
Cpd 79
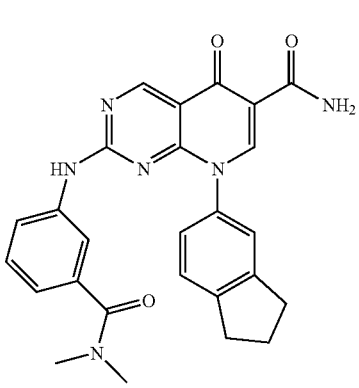

Cpd 80
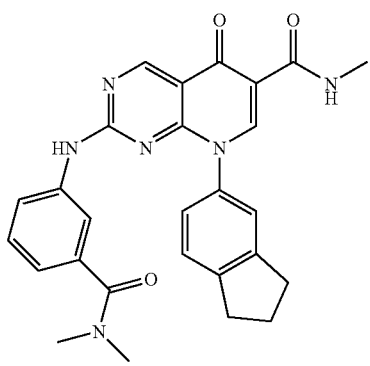

Cpd 81
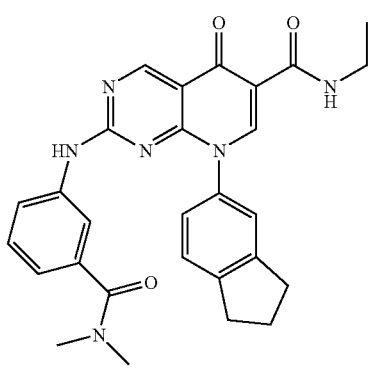

Cpd 82
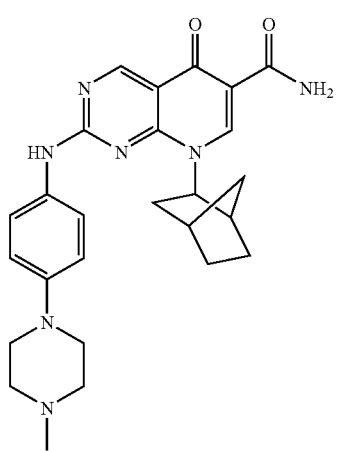

Cpd 83
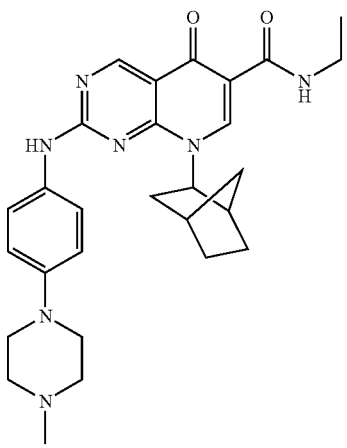

Cpd 84
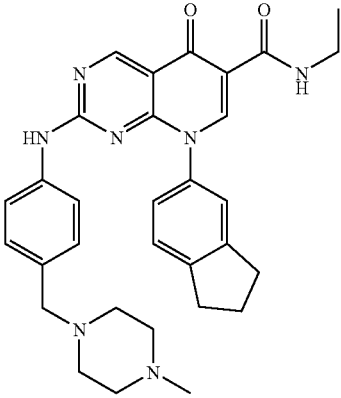

Cpd 85

Examples of the present invention include those compounds of Formula I or a form thereof selected from, but not limited to, the following:

1. 8-indan-5-yl-2-[4-(4-methyl-piperazin-1-yl)-phenylamino]-5-oxo-5,8-dihydro-pyrido[2,3-d]pyrimidine-6-carboxylic acid ethyl ester,
2. 2-[4-(3-dimethyl amino-2-hydroxy-propoxy)-phenylamino]-8-indan-5-yl-5-oxo-5,8-dihydro-pyrido[2,3-d]pyrimidine-6-carboxylic acid ethyl ester,
3. 8-indan-5-yl-2-(4-morpholin-4-yl-phenylamino)-5-oxo-5,8-dihydro-pyrido[2,3-d]pyrimidine-6-carboxylic acid ethyl ester,
4. 2-(4-dimethylamino-phenylamino)-8-indan-5-yl-5-oxo-5,8-dihydro-pyrido[2,3-d]pyrimidine-6-carboxylic acid ethyl ester,
5. 2-(3-dimethylamino-phenylamino)-8-indan-5-yl-5-oxo-5,8-dihydro-pyrido[2,3-d]pyrimidine-6-carboxylic acid ethyl ester,
6. 8-indan-5-yl-2-[4-(4-methyl-piperazin-1-yl)-phenylamino]-5-oxo-5,8-dihydro-pyrido[2,3-d]pyridine-6-carboxylic acid,
7. 8-indan-5-yl-2-[4-(4-methyl-piperazin-1-yl)-phenylamino]-5-oxo-5,8-dihydro-pyrido[2,3-d]pyrimidine-6-carboxylic acid amide,
8. 8-indan-5-yl-2-[4-(4-methyl-piperazin-1-yl)-phenylamino]-5-oxo-5,8-dihydro-pyrido[2,3-d]pyrimidine-6-carboxylic acid methylamide,
9. 8-indan-5-yl-2-[4-(4-methyl-piperazin-1-yl)-phenylamino]-5-oxo-5,8-dihydro-pyrido[2,3-d]pyrimidine-6-carboxylic acid ethylamide, 10  2-[4-(3-dimethylamino-2-hydroxy-propoxy)-phenylamino]-8-indan-5-yl-5-oxo-5,8-dihydro-pyrido[2,3-d]pyrimidine-6-carboxylic acid amide,
11  2-[4-(3-dimethylamino-2-hydroxy-propoxy)-phenylamino]-8-indan-5-yl-5-oxo-5,8-dihydro-pyrido[2,3-d]pyrimidine-6-carboxylic acid methylamide
12  2-[4-(3-dimethylamino-2-hydroxy-propoxy)-phenylamino]-8-indan-5-yl-5-oxo-5,8-dihydro-pyrido[2,3-d]pyrimidine-6-carboxylic acid ethylamide,
13  2-[4-(4-Methyl-piperazin-1-yl)-phenylamino]-5-oxo-8-phenyl-5,8-dihydro-pyrido[2,3-d]pyrimidine-6-carboxylic acid amide,
14  8-indan-5-yl-2-(4-morpholin-4-yl-phenylamino)-5-oxo-5,8-dihydro-pyrido[2,3-d]pyrimidine-6-carboxylic acid amide,
15  2-(4-dimethylamino-phenylamino)-8-indan-5-yl-5-oxo-5,8-dihydro-pyrido[2,3-d]pyrimidine-6-carboxylic acid amide,
16  2-(3-dimethylamino-phenylamino)-8-indan-5-yl-5-oxo-5,8-dihydro-pyrido[2,3-d]pyrimidine-6-carboxylic acid amide,
17  8-cyclohexyl-2-[4-(4-methyl-piperazin-1-yl)-phenylamino]-5-oxo-5,8-dihydro-pyrido[2,3-d]pyrimidine-6-carboxylic acid ethyl ester,
18  8-cyclohexyl-2-(4-dimethylamino-phenylamino)-5-oxo-5,8-dihydro-pyrido[2,3-d]pyrimidine-6-carboxylic acid ethyl ester,
19  8-cyclopentyl-2-[4-(4-methyl-piperazin-1-yl)-phenylamino]-5-oxo-5,8-dihydro-pyrido[2,3-d]pyrimidine-6-carboxylic acid amide,
20  2-(3-hydroxymethyl-phenylamino)-8-indan-5-yl-5-oxo-5,8-dihydro-pyrido[2,3-d]pyrimidine-6-carboxylic acid amide,
21  2-(4-fluoro-phenylamino)-8-indan-5-yl-5-oxo-5,8-dihydro-pyrido[2,3-d]pyrimidine-6-carboxylic acid ethyl ester,
22  8-indan-5-yl-5-oxo-2-(4-pyrazol-1-yl-phenylamino)-5,8-dihydro-pyrido[2,3-d]pyrimidine-6-carboxylic acid amide,
23  8-indan-5-yl-2-[3-(4-methyl-piperazin-1-ylmethyl)-phenylamino]-5-oxo-5,8-dihydro-pyrido[2,3-d]pyrimidine-6-carboxylic acid amide,
24  8-indan-5-yl-2-(3-morpholin-4-ylmethyl-phenylamino)-5-oxo-5,8-dihydro-pyrido[2,3-d]pyrimidine-6-carboxylic acid amide,
25  2-[2-hydroxy-4-(4-methyl-piperazin-1-yl)-phenylamino]-8-indan-5-yl-5-oxo-5,8-dihydro-pyrido[2,3-d]pyrimidine-6-carboxylic acid amide,
26  1-indan-5-yl-7-[4-(4-methyl-piperazin-1-yl)-phenylamino]-4-oxo-1,4-dihydro-[1,6]naphthyridine-3-carboxylic acid amide,
27  8-Indan-5-yl-2-[4-(2-morpholin-4-yl-ethyl)-phenylamino]-5-oxo-5,8-dihydro-pyrido[2,3-d]pyrimidine-6-carboxylic acid amide,
28  8-Indan-5-yl-2-[4-(2-morpholin-4-yl-ethyl)-phenylamino]-5-oxo-5,8-dihydro-pyrido[2,3-d]pyrimidine-6-carboxylic acid methyl amide,
29  8-Indan-5-yl-2-[4-(2-morpholin-4-yl-ethyl)-phenylamino]-5-oxo-5,8-dihydro-pyrido[2,3-d]pyrimidine-6-carboxylic acid ethyl amide,
30  (4S)-8-Indan-5-yl-5-oxo-2-[4-(2-oxo-oxazolidin-4-ylmethyl)-phenylamino]-5,8-dihydro-pyrido[2,3-d]pyrimidine-6-carboxylic acid amide,
31  (4S)-8-Indan-5-yl-5-oxo-2-[4-(2-oxo-oxazolidin-4-ylmethyl)-phenylamino]-5,8-dihydro-pyrido[2,3-d]pyrimidine-6-carboxylic acid methyl amide,
32  (4S)-8-Indan-5-yl-5-oxo-2-[4-(2-oxo-oxazolidin-4-ylmethyl)-phenylamino]-5,8-dihydro-pyrido[2,3-d]pyrimidine-6-carboxylic acid ethyl amide,
33  8-Indan-5-yl-2-[4-(2-isopropylsulfamoyl-ethyl)-phenylamino]-5-oxo-5,8-dihydro-pyrido[2,3-d]pyrimidine-6-carboxylic acid methyl amide,
34  8-Indan-5-yl-2-[4-(2-isopropylsulfamoyl-ethyl)-phenylamino]-5-oxo-5,8-dihydro-pyrido[2,3-d]pyrimidine-6-carboxylic acid ethyl amide,
35  8-Indan-5-yl-2-{4-[2-(morpholine-4-sulfonyl)-ethyl]-phenylamino}-5-oxo-5,8-dihydro-pyrido[2,3-d]pyrimidine-6-carboxylic acid methyl amide,
36  8-Indan-5-yl-2-{4-[2-(morpholine-4-sulfonyl)-ethyl]-phenylamino}-5-oxo-5,8-dihydro-pyrido[2,3-d]pyrimidine-6-carboxylic acid ethyl amide,
37  8-Indan-5-yl-2-[3-(4-methyl-piperazin-1-yl)-phenylamino]-5-oxo-5,8-dihydro-pyrido[2,3-d]pyrimidine-6-carboxylic acid amide,
38  8-Indan-5-yl-2-[3-(4-methyl-piperazin-1-yl)-phenylamino]-5-oxo-5,8-dihydro-pyrido[2,3-d]pyrimidine-6-carboxylic acid methyl amide,
39  8-Indan-5-yl-2-[3-(4-methyl-piperazin-1-yl)-phenylamino]-5-oxo-5,8-dihydro-pyrido[2,3-d]pyrimidine-6-carboxylic acid ethyl amide,
40  8-Indan-5-yl-5-oxo-2-(4-piperazin-1-yl-phenylamino)-5,8-dihydro-pyrido[2,3-d]pyrimidine-6-carboxylic acid amide,
41  8-Indan-5-yl-5-oxo-2-(4-piperazin-1-yl-phenylamino)-5,8-dihydro-pyrido[2,3-d]pyrimidine-6-carboxylic acid methyl amide,
42  8-Indan-5-yl-5-oxo-2-(4-piperazin-1-yl-phenylamino)-5,8-dihydro-pyrido[2,3-d]pyrimidine-6-carboxylic acid ethyl amide,
43  2-[4-(3,5-Dimethyl-piperazin-1-yl)-phenylamino]-8-indan-5-yl-5-oxo-5,8-dihydro-pyrido[2,3-d]pyrimidine-6-carboxylic acid amide,
44  2-[4-(3,5-Dimethyl-piperazin-1-yl)-phenylamino]-8-indan-5-yl-5-oxo-5,8-dihydro-pyrido[2,3-d]pyrimidine-6-carboxylic acid methyl amide,
45  2-[4-(3,5-Dimethyl-piperazin-1-yl)-phenylamino]-8-indan-5-yl-5-oxo-5,8-dihydro-pyrido[2,3-d]pyrimidine-6-carboxylic acid ethyl amide,
46  8-Indan-5-yl-2-{4-[2-(4-methyl-piperazin-1-yl)-ethyl]-phenylamino}-5-oxo-5,8-dihydro-pyrido[2,3-d]pyrimidine-6-carboxylic acid amide,
47  8-Indan-5-yl-2-{4-[2-(4-methyl-piperazin-1-yl)-ethyl]-phenylamino}-5-oxo-5,8-dihydro-pyrido[2,3-d]pyrimidine-6-carboxylic acid methyl amide,
48  8-Indan-5-yl-2-{4-[2-(4-methyl-piperazin-1-yl)-ethyl]-phenylamino}-5-oxo-5,8-dihydro-pyrido[2,3-d]pyrimidine-6-carboxylic acid ethyl amide,
49  8-Indan-5-yl-5-oxo-2-(4-piperidin-4-yl-phenylamino)-5,8-dihydro-pyrido[2,3-d]pyrimidine-6-carboxylic acid amide,
50  8-Indan-5-yl-5-oxo-2-(4-piperidin-4-yl-phenylamino)-5,8-dihydro-pyrido[2,3-d]pyrimidine-6-carboxylic acid methyl amide,
51  8-Indan-5-yl-5-oxo-2-(4-piperidin-4-yl-phenylamino)-5,8-dihydro-pyrido[2,3-d]pyrimidine-6-carboxylic acid ethyl amide,
52  8-Indan-5-yl-5-oxo-2-(3-piperazin-4-yl-phenylamino)-5,8-dihydro-pyrido[2,3-d]pyrimidine-6-carboxylic acid amide,
53  8-Indan-5-yl-5-oxo-2-(3-piperazin-1-yl-phenylamino)-5,8-dihydro-pyrido[2,3-d]pyrimidine-6-carboxylic acid methyl amide, 54 8-Indan-5-yl-5-oxo-2-(3-piperazin-1-yl-phenylamino)-5,8-dihydro-pyrido[2,3-d]pyrimidine-6-carboxylic acid ethyl amide,
55 2-[3-(3,5-Dimethyl-piperazin-1-yl)-phenylamino]-8-indan-5-yl-5-oxo-5,8-dihydro-pyrido[2,3-d]pyrimidine-6-carboxylic acid amide,
56 2-[3-(3,5-Dimethyl-piperazin-1-yl)-phenylamino]-8-indan-5-yl-5-oxo-5,8-dihydro-pyrido[2,3-d]pyrimidine-6-carboxylic acid methyl amide,
57 8-Cyclohexyl-2-[4-(2-morpholin-4-yl-ethyl)-phenylamino]-5-oxo-5,8-dihydro-pyrido[2,3-d]pyrimidine-6-carboxylic acid amide,
58 8-Cyclohexyl-2-[4-(2-morpholin-4-yl-ethyl)-phenylamino]-5-oxo-5,8-dihydro-pyrido[2,3-d]pyrimidine-6-carboxylic acid methyl amide,
59 8-Cyclohexyl-2-[4-(2-morpholin-4-yl-ethyl)-phenylamino]-5-oxo-5,8-dihydro-pyrido[2,3-d]pyrimidine-6-carboxylic acid ethyl amide,
60 8-Cyclohexyl-2-[4-(4-methyl-piperazin-1-yl)-phenylamino]-5-oxo-5,8-dihydro-pyrido[2,3-d]pyrimidine-6-carboxylic acid amide,
61 8-Cyclohexyl-2-[4-(4-methyl-piperazin-1-yl)-phenylamino]-5-oxo-5,8-dihydro-pyrido[2,3-d]pyrimidine-6-carboxylic acid methyl amide,
62 8-Cyclohexyl-2-[4-(4-methyl-piperazin-1-yl)-phenylamino]-5-oxo-5,8-dihydro-pyrido[2,3-d]pyrimidine-6-carboxylic acid ethyl amide,
63 8-Cyclohexyl-2-[3-(4-methyl-piperazin-1-yl)-phenylamino]-5-oxo-5,8-dihydro-pyrido[2,3-d]pyrimidine-6-carboxylic acid amide,
64 8-Cyclohexyl-2-[3-(4-methyl-piperazin-1-yl)-phenylamino]-5-oxo-5,8-dihydro-pyrido[2,3-d]pyrimidine-6-carboxylic acid methyl amide,
65 8-Cyclohexyl-2-[3-(4-methyl-piperazin-1-yl)-phenylamino]-5-oxo-5,8-dihydro-pyrido[2,3-d]pyrimidine-6-carboxylic acid ethyl amide,
66 8-Cyclohexyl-2-[4-(2-isopropylsulfamoyl-ethyl)-phenylamino]-5-oxo-5,8-dihydro-pyrido[2,3-d]pyrimidine-6-carboxylic acid amide,
67 8-Cyclohexyl-2-{4-[2-(morpholine-4-sulfonyl)-ethyl]-phenylamino}-5-oxo-5,8-dihydro-pyrido[2,3-d]pyrimidine-6-carboxylic acid amide,
68 8-Cyclohexyl-2-{4-[1-(2-dimethylamino-acetyl)-piperidin-4-yl]-phenylamino}-5-oxo-5,8-dihydro-pyrido[2,3-d]pyrimidine-6-carboxylic acid amide,
69 8-Indan-5-yl-2-(4-morpholin-4-ylmethyl-phenylamino)-5-oxo-5,8-dihydro-pyrido[2,3-d]pyrimidine-6-carboxylic acid amide,
70 2-{4-[1-(2-Dimethylamino-acetyl)-piperidin-4-yl]-phenylamino}-8-indan-5-yl-5-oxo-5,8-dihydro-pyrido[2,3-d]pyrimidine-6-carboxylic acid amide,
71 2-{3-[1-(2-Dimethylamino-acetyl)-piperidin-4-yl]-phenylamino}-8-indan-5-yl-5-oxo-5,8-dihydro-pyrido[2,3-d]pyrimidine-6-carboxylic acid amide,
72 8-Indan-5-yl-2-(4-{1-[2-(4-methyl-piperazin-1-yl)-acetyl]-piperidin-4-yl}-phenylamino)-5-oxo-5,8-dihydro-pyrido[2,3-d]pyrimidine-6-carboxylic acid amide,
73 8-Indan-5-yl-2-(3-{1-[2-(4-methyl-piperazin-1-yl)-acetyl]-piperidin-4-yl}-phenylamino)-5-oxo-5,8-dihydro-pyrido[2,3-d]pyrimidine-6-carboxylic acid amide,
74 8-Indan-5-yl-2-[4-(4-methyl-piperazin-1-ylmethyl)-phenylamino]-5-oxo-5,8-dihydro-pyrido[2,3-d]pyrimidine-6-carboxylic acid amide,
75 2-(4-Dimethylaminomethyl-phenylamino)-8-indan-5-yl-5-oxo-5,8-dihydro-pyrido[2,3-d]pyrimidine-6-carboxylic acid amide,
76 2-(3-Dimethylaminomethyl-phenylamino)-8-indan-5-yl-5-oxo-5,8-dihydro-pyrido[2,3-d]pyrimidine-6-carboxylic acid amide,
77 2-(3-Dimethylaminomethyl-phenylamino)-8-indan-5-yl-5-oxo-5,8-dihydro-pyrido[2,3-d]pyrimidine-6-carboxylic acid methylamide,
78 2-(3-Dimethylaminomethyl-phenylamino)-8-indan-5-yl-5-oxo-5,8-dihydro-pyrido[2,3-d]pyrimidine-6-carboxylic acid ethylamide,
79 2-(3-Dimethylcarbamoyl-phenylamino)-8-indan-5-yl-5-oxo-5,8-dihydro-pyrido[2,3-d]pyrimidine-6-carboxylic acid amide,
80 2-(3-Dimethylcarbamoyl-phenylamino)-8-indan-5-yl-5-oxo-5,8-dihydro-pyrido[2,3-d]pyrimidine-6-carboxylic acid methylamide,
81 2-(3-Dimethylcarbamoyl-phenylamino)-8-indan-5-yl-5-oxo-5,8-dihydro-pyrido[2,3-d]pyrimidine-6-carboxylic acid ethylamide,
82 8-Bicyclo[2.2.1]hept-2-yl-2-[4-(4-methyl-piperazin-1-yl)-phenylamino]-5-oxo-5,8-dihydro-pyrido[2,3-d]pyrimidine-6-carboxylic acid amide,
83 8-Bicyclo[2.2.1]hept-2-yl-2-[4-(4-methyl-piperazin-1-yl)-phenylamino]-5-oxo-5,8-dihydro-pyrido[2,3-d]pyrimidine-6-carboxylic acid ethylamide,
84 8-Indan-5-yl-2-[4-(4-methyl-piperazin-1-ylmethyl)-phenylamino]-5-oxo-5,8-dihydro-pyrido[2,3-d]pyrimidine-6-carboxylic acid ethylamide, and
85 8-Benzyl-2-[4-(4-methyl-piperazin-1-yl)-phenylamino]-5-oxo-5,8-dihydro-pyrido[2,3-d]pyrimidine-6-carboxylic acid methyl amide.

The most preferred compounds are those having a c-fms $IC_{50}<25$ nm.

The invention also relates to methods of inhibiting protein tyrosine kinase activity in a mammal by administration of a therapeutically effective amount of at least one compound of Formula I. A preferred tyrosine kinase is c-fms.

The compounds of the present invention are further useful as markers for the c-fms receptor. Compounds of formula (I) when used as markers are for example radio-labeled by for example, substituting at least one hydrogen atom with a tritium atom. Other labeling techniques known in the arts can also be used.

An aspect of the use for a compound of Formula (I) includes use of an instant compound as a marker, wherein the compound is labeled with a ligand such as a radioligand (selected from deuterium, tritium and the like).

Compound Forms

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

Certain compounds of Formula (I) may exist in various stereoisomeric or tautomeric forms and mixtures thereof. The invention encompasses all such compounds, including active compounds in the form of essentially pure enantiomers, racemic mixtures and tautomers.

The compounds of the present invention may be present in the form of pharmaceutically acceptable salts. For use in medicines, the "pharmaceutically acceptable salts" of the compounds of this invention refer to nontoxic acidic/anionic or basic/cationic salt forms.

Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, citric acid, tartaric acid, carbonic acid or phosphoric acid.

Furthermore when the compounds of the present invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following: acetate, benzenesulfonate, benzoate, bicarbonate, bisulfate, bitartrate, borate, bromide, calcium, camsylate (or camphosulphonate), carbonate, chloride, clavulanate, citrate, dihydrochloride, edetate, fumarate, gluconate, glutamate, hydrabamine, hydrobromine, hydrochloride, iodide, isothionate, lactate, malate, maleate, mandelate, mesylate, nitrate, oleate, pamoate, palmitate, phosphate/diphosphate, salicylate, stearate, sulfate, succinate, tartrate, tosylate.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (stereoisomers).

The term "optical isomer" means isomers of identical constitution that differ only in the spatial arrangement of their groups. Optical isomers rotate the plane of polarized light in different directions. The term "optical activity" means the degree to which an optical isomer rotates the plane of polarized light.

The term "racemate" or "racemic mixture" means an equimolar mixture of two enanitiomeric species, wherein each of the isolated species rotates the plane of polarized light in the opposite direction such that the mixture is devoid of optical activity.

The term "enantiomer" means an isomer having a nonsuperimposable mirror image. The term "diastereomer" means stereoisomers that are not enantiomers.

The term "chiral" means a molecule which, in a given configuration, cannot be superimposed on its mirror image. This is in contrast to achiral molecules which can be superimposed on their mirror images.

The invention is considered to include the tautomeric forms of all compounds of Formula I. In addition, for chiral embodiments of the invention, the invention is considered to include pure enantiomers, racemic mixtures, as well as mixtures of enantiomers having 0.001% to 99.99% enantiomeric excess. In addition, some of the compounds represented by Formula I may be prodrugs, i.e., derivatives of a drug that possess superior delivery capabilities and therapeutic value as compared to the active drug. Prodrugs are transformed into active drugs by in vivo enzymatic or chemical processes.

The two distinct mirror image versions of the chiral molecule are also known as levo (left-handed), abbreviated L, or dextro (right handed), abbreviated D, depending on which way they rotate polarized light. The symbols "R" and "S" represent the configuration of groups around a stereogenic carbon atom(s).

An example of an enantiomerically enriched form isolated from a racemic mixture includes a dextrorotatory enantiomer, wherein the mixture is substantially free of the levorotatory isomer. In this context, substantially free means the levorotatory isomer may, in a range, comprise less than 25% of the mixture, less than 10%, less than 5%, less than 2% or less than 1% of the mixture according to the formula:

$$\% \text{ levorotatory} = \frac{(\text{mass levorotatory})}{(\text{mass dextrorotatory}) + (\text{mass levorotatory})} \times 100$$

Similarly, an example of an enantiomerically enriched form isolated from a racemic mixture includes a levorotatory enantiomer, wherein the mixture is substantially free of the dextrorotatory isomer. In this context, substantially free means the dextrorotatory isomer may, in a range, comprise less than 25% of the mixture, less than 10%, less than 5%, less than 2% or less than 1% of the mixture according to the formula:

$$\% \text{ dextrorotatory} = \frac{(\text{mass dextrorotatory})}{(\text{mass dextrorotatory}) + (\text{mass levorotatory})} \times 100$$

"Geometric isomer" means isomers that differ in the orientation of substituent atoms in relationship to a carbon-carbon double bond, to a cycloalkyl ring, or to a bridged bicyclic system. Substituent atoms (other than hydrogen) on each side of a carbon-carbon double bond may be in an E or Z configuration. In the "E" configuration, the substituents are on opposite sides in relationship to the carbon-carbon double bond. In the "Z" configuration, the substituents are oriented on the same side in relationship to the carbon-carbon double bond.

Substituent atoms (other than hydrogen) attached to a ring system may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

The isomeric descriptors ("R," "S," "E," and "Z") indicate atom configurations relative to a core molecule and are intended to be used as defined in the literature.

Furthermore, compounds of the present invention may have at least one crystalline, polymorph or amorphous form. The plurality of such forms are included in the scope of the invention. In addition, some of the compounds may form solvates with water (i.e., hydrates) or common organic solvents (e.g., organic esters such as ethanolate and the like). The plurality of such solvates are also intended to be encompassed within the scope of this invention.

Chemical Nomenclature and Definitions

Bond lines drawn into a ring system from a substituent variable indicate that the substituent may be attached to any of the substitutable ring atoms.

As used herein, the following terms are intended to have the following meanings (additional definitions are provided where needed throughout the Specification). The definitions herein may specify that a chemical term has an indicated formula. The particular formula provided is not intended to limit the scope of the invention, but is provided as an illustration of the term. The scope of the per se definition of the term is intended to include the plurality of variations expected to be included by one of ordinary skill in the art.

Definitions

The term "alkyl" refers to both linear and branched chain radicals of up to 8 carbon atoms, unless otherwise indicated, and includes, but is not limited to, methyl, ethyl, propyl, isopropyl, butyl, isobutyl, sec-butyl, tert-butyl, pentyl, isopentyl, hexyl, and isohexyl. The term "$C_{(x-y)}$alkyl" refers to an alkyl chain of length not less than x carbons and not more than y carbons. For example, the term $C_{(1-4)}$alkyl refers to both linear and branched chain radicals of up to 4 carbon atoms. Alkyl radicals or linking groups may be attached to a core molecule via a terminal carbon atom or via a carbon atom within the chain. Similarly, substituent variables may be attached to an alkyl linking group when allowed by available valences.

The term "amino" means an amine group of the formula: —$NH_2$.

The term "alkylamino or dialkylamino" refers to an amino with one or two alkyl substituents, respectively, wherein the amino group is the point of attachment to the rest of the molecule.

The term "aryl" refers to monocyclic or bicyclic aromatic ring systems containing from 6 to 12 carbons in the ring. Alkyl substituents may optionally be present on the ring. Examples include benzene, biphenyl, naphthalene (also referred to as naphthalenyl), azulenyl, anthracenyl and the like. Aryl radicals may be attached to a core molecule and further substituted on any atom when allowed by available valences.

The term "aromatic" refers to a cycloalkylic hydrocarbon ring system having an unsaturated, conjugated π electron system.

The term "aralkyl" refers to a $C_{1-6}$ alkyl group containing an aryl substituent, in which the point of attachment is the alkyl group. Examples include benzyl, phenylethyl or 2-naphthylmethyl. It is possible that both the alkyl and aryl portion may be substituted, and in that case, it is intended that the alkyl group is closer to the core ring structure.

The term "alkylaryl" refers to a $C_{1-6}$ alkyl group containing an aryl substituent, in which the point of attachment is the aryl group. It is possible that both the alkyl and aryl portion may be substituted, and in that case, it is intended that the aryl group is closer to the core ring structure.

The term "alkoxy" refers to a saturated branched or straight chain monovalent hydrocarbon alcohol radical derived by the removal of the hydrogen atom from the hydroxide oxygen substituent on a parent alkane, as in the formula: —O—$C_{1-8}$alkyl. Examples include methoxy, ethoxy, propoxy, isopropoxy and butoxy. The term "$C_{(x-y)}$alkoxy" refers to an alkoxy chain of length not less than x carbons and not more than y carbons. For example, the term $C_{(1-4)}$alkoxy refers to both linear and branched alkoxy chain radicals of up to 4 carbon atoms. An alkoxy radical may be attached to a core molecule and further substituted when allowed by available valences.

The term "arylcycloalkyl" refers to a $C_{8-10}$ fused bicyclic ring system comprising an aryl group and a cycloalkyl group in which the point of attachment is the aryl group, as in a benzofused $C_{3-14}$cycloalkyl ring system defined below. Examples include, but are not limited to 1H-indenyl, indanyl, and 1,2,3,4-tetrahydronaphthalenyl and the like.

The term "cycloalkyl" refers to a saturated or partially unsaturated ring composed of from 3 to 14 carbon atoms. Up to four alkyl substituents may optionally be present on the ring. The term also includes a $C_{3-8}$cycloalkyl, $C_{3-10}$cycloalkyl, $C_{5-6}$cycloalkyl, $C_{5-8}$cycloalkyl, $C_{5-12}$cycloalkyl, $C_{8-10}$cycloalkyl, $C_{9-13}$cycloalkyl, $C_{3-14}$cycloalkyl or benzofused $C_{3-14}$cycloalkyl ring system. Examples include 1,1-dimethyl cyclobutyl, 1,2,3-trimethylcyclopentyl, cyclopropyl, cyclobutyl, cyclopentyl, cyclohexyl, cyclohexyl, cyclohexenyl, cycloheptyl, cyclooctyl, 1H-indenyl, indanyl, 9H-fluorenyl, 1,2,3,4-tetrahydro-naphthalenyl, acenaphthenyl, bicyclo[2.2.1]heptenyl and the like. $C_{3-14}$cycloalkyl radicals may be attached to a core molecule and further substituted on any atom when allowed by available valences.

The term "cycloalkylaryl" refers to a $C_{8-10}$ fused bicyclic ring system comprising an aryl group and a cycloalkyl group in which the point of attachment is the cycloalkyl group, as in a benzofused $C_{3-14}$cycloalkyl ring system defined above, such as 1H-indenyl, indanyl, 1,2,3,4-tetrahydro-naphthalenyl and the like.

The term "bicycloalkyl" refers to a saturated or partially unsaturated fused ring pair composed of from 8 to 10 carbon atoms. Up to four alkyl substituents may optionally be present on the ring. Examples include adamantyl, bicyclo[2.2.1]heptenyl, decahydronaphthalenyl and 1,2,3,4 tetrahydropentalenyl and the like.

The term "hetero" used as a prefix for a ring system refers to the replacement of at least one ring carbon atom with one or more heteroatoms independently selected from N, S, or O. Examples include rings wherein 1, 2, 3 or 4 ring members are a nitrogen atom; or, 0, 1, 2 or 3 ring members are nitrogen atoms and 1 member is an oxygen or sulfur atom. When allowed by available valences, up to two adjacent ring members may be heteroatoms; wherein one heteroatom is nitrogen and the other is one heteroatom selected from N, S or O.

The term "heterocyclyl" refers to a nonaromatic (i.e. saturated or partially unsaturated) ring composed of from 3 to 7 carbon atoms and at least one heteroatom selected from N, O or S. Alkyl substituents and/or carbonyl substituents may optionally be present on the ring. Examples include tetrahydrofuranyl, dihydropyranyl, piperidinyl, 2,5-dimethypiperidinyl, morpholinyl, piperazinyl, thiomorpholinyl, 2H-pyrrole, pyrrolidinyl, pyrrolinyl, pyrazolidinyl, pyrazolinyl, oxazolidinyl, imidazolidinyl, imidazolinyl (also referred to as 4,5-dihydro-1H-imidazolyl), 1,3-dioxolanyl, tetrazolinyl, tetrazolidinyl, 1,4-dioxanyl, 1,4-dithianyl, azetidinyl, azepanyl, hexahydro-1,4-diazepinyl, hexahydro-1,4-oxazepanyl, tetrahydro-thienyl, tetrahydro-pyranyl, tetrahydro-pyridazinyl, 1,3-benzodioxolyl (also referred to as benzo[1,3]dioxolyl), 2,3-dihydro-1,4-benzodioxinyl (also referred to as 2,3-dihydro-benzo[1,4]dioxinyl) and the like. Heterocyclyl radicals may be attached to a core molecule and further substituted on any atom when allowed by available valences.

The term "heteroaryl" refers to 5- to 7-membered mono- or 8- to 10-membered bicyclic aromatic ring systems, any ring of which may consist of from one to four heteroatoms selected from N, O, S, S(O) or $SO_2$ where the nitrogen and sulfur atoms can exist in any allowed oxidation state. Examples include benzoimidazolyl, benzothiazolyl, benzothienyl, benzoxazolyl, furanyl, imidazolyl, isothiazolyl, isoxazolyl, oxazolyl, pyrazinyl, pyrazolyl, pyridinyl, pyrimidinyl, pyrrolyl, quinolinyl, thiazolyl, thienyl, oxadiazolyl, triazolyl, thiadiazolyl, pyridazinyl, indolizinyl, indolyl, azaindolyl, isoindolyl, benzofuranyl, indazolyl, azaindazolyl, benzoisoxazolyl, benzothiadiazolyl, benzotriazolyl, purinyl, 4H-quinolizinyl, quinolinyl, isoquinolinyl, cinnolinyl, phthalzinyl, quinazolinyl, quinoxalinyl, 1,8-naphthyridinyl, pteridinyl and the like. Heteroaryl radicals may be attached to a core molecule and further substituted on any atom when allowed by available valences.

The term "heteroatom" refers to a nitrogen atom, an oxygen atom or a sulfur atom wherein the nitrogen and sulfur atoms can exist in any allowed oxidation states.

The term "sulfonyl" refers to the group —S(O)$_2$R$_z$, where R$_z$ is hydrogen, alkyl, cycloalkyl, haloalkyl, aryl, aralkyl, heteroaryl and heterocyclyl.

The term "halogen" or "halo" means the group fluoro, chloro, bromo or iodo.

The term "substituted," refers to a core molecule on which one or more hydrogen atoms have been replaced with one or more functional radical moieties. The number that is allowed by available valences limits the amount of substituents. Substitution is not limited to the core molecule, but may also occur on a substituent radical, whereby the substituent radical becomes a linking group.

Therapeutic Uses

The compounds of Formula I represent novel potent inhibitors of protein tyrosine kinases, such as c-fms, and may be useful in the prevention and treatment of disorders resulting from actions of these kinases.

The invention also provides methods of inhibiting a protein tyrosine kinase comprising contacting the protein tyrosine kinase with an effective inhibitory amount of at least one of the compounds of Formula I. A preferred tyrosine kinase is c-fms. In one embodiment of inhibiting a protein tyrosine kinase, at least one of the compounds of Formula I is combined with a known tyrosine kinase inhibitor.

In various embodiments of the invention, the protein tyrosine kinases inhibited by the compounds of Formula I are located in cells, in a mammal or in vitro. In the case of mammals, which includes humans, a therapeutically effective amount of a pharmaceutically acceptable form of at least one of the compounds of Formula I is administered.

The invention further provides methods of treating cancer in mammals, including humans, by administration of a therapeutically effective amount of a pharmaceutically acceptable composition of least one compound of Formula I. Exemplary cancers include, but are not limited to, ovarian cancer, uterine cancer, breast cancer, colon cancer, stomach cancer, hairy cell leukemia and non-small lung carcinoma. In one embodiment of the invention, an effective amount of at least one compound of Formula I is administered in combination with an effective amount of a chemotherapeutic agent.

The invention also provides methods of treating cardiovascular and inflammatory diseases in mammals, including humans, by administration of a therapeutically effective amount of a pharmaceutically acceptable form of at least one of the compounds of Formula I. Examples of diseases that may be effectively treated include atherosclerosis, cardiac hypertrophy, glomerulonephritis, rheumatoid arthritis, psoriasis, diabetes, tumor related angiogenesis, restenosis, schizophrenia and Alzheimer's dementia.

When employed as protein tyrosine kinase inhibitors, the compounds of the invention may be administered in an effective amount within the dosage range of about 0.5 mg to about 10 g, preferably between about 0.5 mg to about 5 g, in single or divided daily doses. A preferred dosage is 5 mg/kg, delivered orally. The dosage administered will be affected by factors such as the route of administration, the health, weight and age of the recipient, the frequency of the treatment and the presence of concurrent and unrelated treatments.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamine salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

A representative compound of Formula (I) or a form thereof for use in the therapeutic methods and pharmaceutical compositions, medicines or medicaments described herein includes a compound selected from the group consisting of:

7    8-indan-5-yl-2-[4-(4-methyl-piperazin-1-yl)-phenylamino]-5-oxo-5,8-dihydro-pyrido[2,3-d]pyrimidine-6-carboxylic acid amide, 8    8-indan-5-yl-2-[4-(4-methyl-piperazin-1-yl)-phenylamino]-5-oxo-5,8-dihydro-pyrido[2,3-d]pyrimidine-6-carboxylic acid methyl amide, 9    8-indan-5-yl-2-[4-(4-methyl-piperazin-1-yl)-phenylamino]-5-oxo-5,8-dihydro-pyrido[2,3-d]pyrimidine-6-carboxylic acid ethylamide, 10    2-[4-(3-dimethylamino-2-hydroxy-propoxy)-phenylamino]-8-indan-5-yl-5-oxo-5,8-dihydro-pyrido[2,3-d]pyrimidine-6-carboxylic acid amide, 11    2-[4-(3-dimethylamino-2-hydroxy-propoxy)-phenylamino]-8-indan-5-yl-5-oxo-5,8-dihydro-pyrido[2,3-d]pyrimidine-6-carboxylic acid methylamide 12    2-[4-(3-dimethylamino-2-hydroxy-propoxy)-phenylamino]-8-indan-5-yl-5-oxo-5,8-dihydro-pyrido[2,3-d]pyrimidine-6-carboxylic acid ethylamide, 14  8-indan-5-yl-2-(4-morpholin-4-yl-phenylamino)-5-oxo-5,8-dihydro-pyrido[2,3-d]pyrimidine-6-carboxylic acid amide, 15  2-(4-dimethylamino-phenylamino)-8-indan-5-yl-5-oxo-5,8-dihydro-pyrido[2,3-d]pyrimidine-6-carboxylic acid amide, 16  2-(3-dimethylamino-phenylamino)-8-indan-5-yl-5-oxo-5,8-dihydro-pyrido[2,3-d]pyrimidine-6-carboxylic acid amide, 19    8-cyclopentyl-2-[4-(4-methyl-piperazin-1-yl)-phenylamino]-5-oxo-5,8-dihydro-pyrido[2,3-d]pyrimidine-6-carboxylic acid amide, 23  8-indan-5-yl-2-[3-(4-methyl-piperazin-1-ylmethyl)-phenylamino]-5-oxo-5,8-dihydro-pyrido[2,3-d]pyrimidine-6-carboxylic acid amide, 24 8-indan-5-yl-2-(3-morpholin-4-ylmethyl-phenylamino)-5-oxo-5,8-dihydro-pyrido[2,3-d]pyrimidine-6-carboxylic acid amide, 25 2-[2-hydroxy-4-(4-methyl-piperazin-1-yl)-phenylamino]-8-indan-5-yl-5-oxo-5,8-dihydro-pyrido[2,3-d]pyrimidine-6-carboxylic acid amide, 26 1-indan-5-yl-7-[4-(4-methyl-piperazin-1-yl)-phenylamino]-4-oxo-1,4-dihydro-[1,6]naphthyridine-3-carboxylic acid amide, 27 8-Indan-5-yl-2-[4-(2-morpholin-4-yl-ethyl)-phenylamino]-5-oxo-5,8-dihydro-pyrido[2,3-d]pyrimidine-6-carboxylic acid amide, 28 8-Indan-5-yl-2-[4-(2-morpholin-4-yl-ethyl)-phenylamino]-5-oxo-5,8-dihydro-pyrido[2,3-d]pyrimidine-6-carboxylic acid methyl amide, 29 8-Indan-5-yl-2-[4-(2-morpholin-4-yl-ethyl)-phenylamino]-5-oxo-5,8-dihydro-pyrido[2,3-d]pyrimidine-6-carboxylic acid ethyl amide, 30 (4S)-8-Indan-5-yl-5-oxo-2-[4-(2-oxo-oxazolidin-4-ylmethyl)-phenylamino]-5,8-dihydro-pyrido[2,3-d]pyrimidine-6-carboxylic acid amide, 31 (4S)-8-Indan-5-yl-5-oxo-2-[4-(2-oxo-oxazolidin-4-ylmethyl)-phenylamino]-5,8-dihydro-pyrido[2,3-d]pyrimidine-6-carboxylic acid methyl amide, 32 (4S)-8-Indan-5-yl-5-oxo-2-[4-(2-oxo-oxazolidin-4-ylmethyl)-phenylamino]-5,8-dihydro-pyrido[2,3-d]pyrimidine-6-carboxylic acid ethyl amide, 33 8-Indan-5-yl-2-[4-(2-isopropylsulfamoyl-ethyl)-phenylamino]-5-oxo-5,8-dihydro-pyrido[2,3-d]pyrimidine-6-carboxylic acid methyl amide, 35 8-Indan-5-yl-2-{4-[2-(morpholine-4-sulfonyl)-ethyl]-phenylamino}-5-oxo-5,8-dihydro-pyrido[2,3-d]pyrimidine-6-carboxylic acid methyl amide, 37 8-Indan-5-yl-2-[3-(4-methyl-piperazin-1-yl)-phenylamino]-5-oxo-5,8-dihydro-pyrido[2,3-d]pyrimidine-6-carboxylic acid amide, 38 8-Indan-5-yl-2-[3-(4-methyl-piperazin-1-yl)-phenylamino]-5-oxo-5,8-dihydro-pyrido[2,3-d]pyrimidine-6-carboxylic acid methyl amide, 39 8-Indan-5-yl-2-[3-(4-methyl-piperazin-1-yl)-phenylamino]-5-oxo-5,8-dihydro-pyrido[2,3-d]pyrimidine-6-carboxylic acid ethyl amide, 40 8-Indan-5-yl-5-oxo-2-(4-piperazin-1-yl-phenylamino)-5,8-dihydro-pyrido[2,3-d]pyrimidine-6-carboxylic acid amide, 41 8-Indan-5-yl-5-oxo-2-(4-piperazin-1-yl-phenylamino)-5,8-dihydro-pyrido[2,3-d]pyrimidine-6-carboxylic acid methyl amide, 42 8-Indan-5-yl-5-oxo-2-(4-piperazin-1-yl-phenylamino)-5,8-dihydro-pyrido[2,3-d]pyrimidine-6-carboxylic acid ethyl amide, 43 2-[4-(3,5-Dimethyl-piperazin-1-yl)-phenylamino]-8-indan-5-yl-5-oxo-5,8-dihydro-pyrido[2,3-d]pyrimidine-6-carboxylic acid amide, 44 2-[4-(3,5-Dimethyl-piperazin-1-yl)-phenylamino]-8-indan-5-yl-5-oxo-5,8-dihydro-pyrido[2,3-d]pyrimidine-6-carboxylic acid methyl amide, 45 2-[4-(3,5-Dimethyl-piperazin-1-yl)-phenylamino]-8-indan-5-yl-5-oxo-5,8-dihydro-pyrido[2,3-d]pyrimidine-6-carboxylic acid ethyl amide, 46 8-Indan-5-yl-2-{4-[2-(4-methyl-piperazin-1-yl)-ethyl]-phenylamino}-5-oxo-5,8-dihydro-pyrido[2,3-d]pyrimidine-6-carboxylic acid amide, 47 8-Indan-5-yl-2-{4-[2-(4-methyl-piperazin-1-yl)-ethyl]-phenylamino}-5-oxo-5,8-dihydro-pyrido[2,3-d]pyrimidine-6-carboxylic acid methyl amide, 48 8-Indan-5-yl-2-{4-[2-(4-methyl-piperazin-1-yl)-ethyl]-phenylamino}-5-oxo-5,8-dihydro-pyrido[2,3-d]pyrimidine-6-carboxylic acid ethyl amide, 49 8-Indan-5-yl-5-oxo-2-(4-piperidin-4-yl-phenylamino)-5,8-dihydro-pyrido[2,3-d]pyrimidine-6-carboxylic acid amide, 50 8-Indan-5-yl-5-oxo-2-(4-piperidin-4-yl-phenylamino)-5,8-dihydro-pyrido[2,3-d]pyrimidine-6-carboxylic acid methyl amide, 51 8-Indan-5-yl-5-oxo-2-(4-piperidin-4-yl-phenylamino)-5,8-dihydro-pyrido[2,3-d]pyrimidine-6-carboxylic acid ethyl amide, 52 8-Indan-5-yl-5-oxo-2-(3-piperazin-1-yl-phenylamino)-5,8-dihydro-pyrido[2,3-d]pyrimidine-6-carboxylic acid amide, 53 8-Indan-5-yl-5-oxo-2-(3-piperazin-1-yl-phenylamino)-5,8-dihydro-pyrido[2,3-d]pyrimidine-6-carboxylic acid methyl amide, 54 8-Indan-5-yl-5-oxo-2-(3-piperazin-1-yl-phenylamino)-5,8-dihydro-pyrido[2,3-d]pyrimidine-6-carboxylic acid ethyl amide, 55 2-[3-(3,5-Dimethyl-piperazin-1-yl)-phenylamino]-8-indan-5-yl-5-oxo-5,8-dihydro-pyrido[2,3-d]pyrimidine-6-carboxylic acid amide, 56 2-[3-(3,5-Dimethyl-piperazin-1-yl)-phenylamino]-8-indan-5-yl-5-oxo-5,8-dihydro-pyrido[2,3-d]pyrimidine-6-carboxylic acid methyl amide, 57 8-Cyclohexyl-2-[4-(2-morpholin-4-yl-ethyl)-phenylamino]-5-oxo-5,8-dihydro-pyrido[2,3-d]pyrimidine-6-carboxylic acid amide, 60 8-Cyclohexyl-2-[4-(4-methyl-piperazin-1-yl)-phenylamino]-5-oxo-5,8-dihydro-pyrido[2,3-d]pyrimidine-6-carboxylic acid amide, 63 8-Cyclohexyl-2-[3-(4-methyl-piperazin-1-yl)-phenylamino]-5-oxo-5,8-dihydro-pyrido[2,3-d]pyrimidine-6-carboxylic acid amide, 64 8-Cyclohexyl-2-[3-(4-methyl-piperazin-1-yl)-phenylamino]-5-oxo-5,8-dihydro-pyrido[2,3-d]pyrimidine-6-carboxylic acid methyl amide, 69 8-Indan-5-yl-2-(4-morpholin-4-ylmethyl-phenylamino)-5-oxo-5,8-dihydro-pyrido[2,3-d]pyrimidine-6-carboxylic acid amide, 74 8-Indan-5-yl-2-[4-(4-methyl-piperazin-1-ylmethyl)-phenylamino]-5-oxo-5,8-dihydro-pyrido[2,3-d]pyrimidine-6-carboxylic acid amide, 75 2-(4-Dimethylaminomethyl-phenylamino)-8-indan-5-yl-5-oxo-5,8-dihydro-pyrido[2,3-d]pyrimidine-6-carboxylic acid amide, 76 2-(3-Dimethylaminomethyl-phenylamino)-8-indan-5-yl-5-oxo-5,8-dihydro-pyrido[2,3-d]pyrimidine-6-carboxylic acid amide, 79 2-(3-Dimethylaminomethyl-phenylamino)-8-indan-5-yl-5-oxo-5,8-dihydro-pyrido[2,3-d]pyrimidine-6-carboxylic acid amide, 80 2-(3-Dimethylcarbamoyl-phenylamino)-8-indan-5-yl-5-oxo-5,8-dihydro-pyrido[2,3-d]pyrimidine-6-carboxylic acid methylamide, 82 8-Bicyclo[2.2.1]hept-2-yl-2-[4-(4-methyl-piperazin-1-yl)-phenylamino]-5-oxo-5,8-dihydro-pyrido[2,3-d]pyrimidine-6-carboxylic acid amide, and 84 8-Indan-5-yl-2-[4-(4-methyl-piperazin-1-ylmethyl)-phenylamino]-5-oxo-5,8-dihydro-pyrido[2,3-d]pyrimidine-6-carboxylic acid ethylamide.

General Synthetic Methods

The compounds of Formula I can be prepared by methods known to those who are skilled in the art. The following reaction schemes are only meant to represent examples of the invention and are in no way meant to limit the invention.

The following general reaction schemes display various methods of reaching the compounds of Formula I. It is recognized by those skilled in the art that some compounds of Formula I may be further derivatized to provide additional embodiments of the invention. Representative further derivatizations appear in schemes I, II, and V.

A typical preparation of compounds of the present invention is shown in Scheme I, wherein Ph is phenyl, which may be optionally further substituted with $R^{101}$.

An amine was reacted with ethyl 3-chloropropionate at elevated temperature at the presence of an inorganic base and a catalytic amount of tetrabutylammonium bromide to afford the aminopropionate ester 1-1.

The amine was reacted with ethyl 4-chloro-2-methylthio-5-pyrimidinecarboxylate to produce the corresponding 4-substituted aminopyrimidine 1-2. Cyclization of this diester under Dieckmann conditions afforded the bicyclic compound 1-3.

Subsequent halogenation with bromine followed by dehydrohalogenation gave the unsaturated 1-4 (Eur J Med Chem 9 (2000) pp 585-590). The methylthio group was oxidized to the sulfone 1-5, which was subsequently replaced with an amine by nucleophilic substitution.

The resulting carboxylic ester 1-6 was converted to the carboxylic acid 1-7 via basic hydrolysis. Decarboxylation to give 1-8 occurred when the carboxylic acid was heated in DMSO in the presence of sodium cyanide (Tet Lett 35 (1994) pp 8303-8306).

The carboxylic acid 1-7 was reacted with an amine under normal coupling conditions to form the corresponding amide 1-9. The amide 1-9 could also be prepared directly from the ester 1-6 when the amine $R_1$—$NH_2$ was ammonia, or an alkylamine.

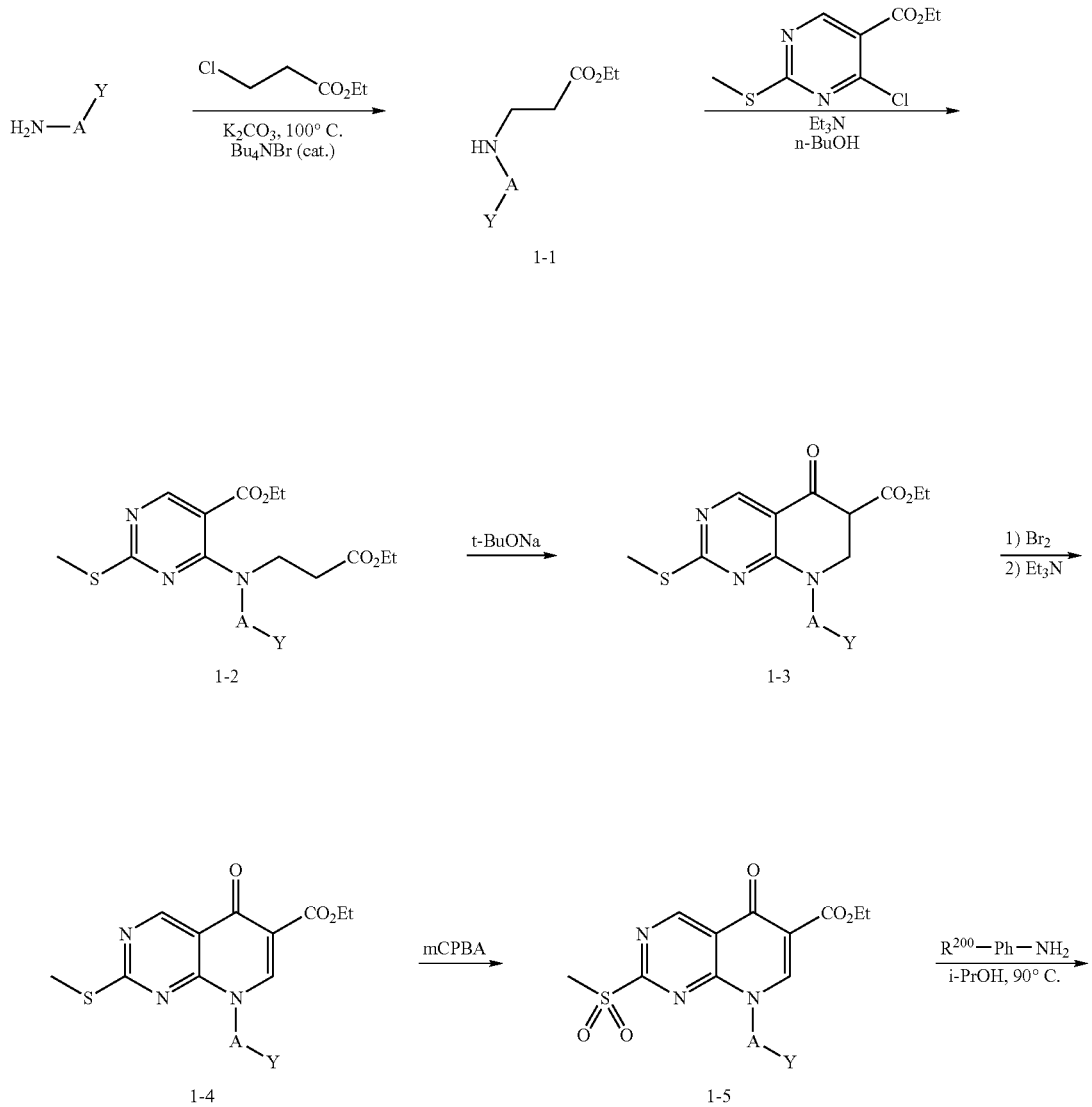

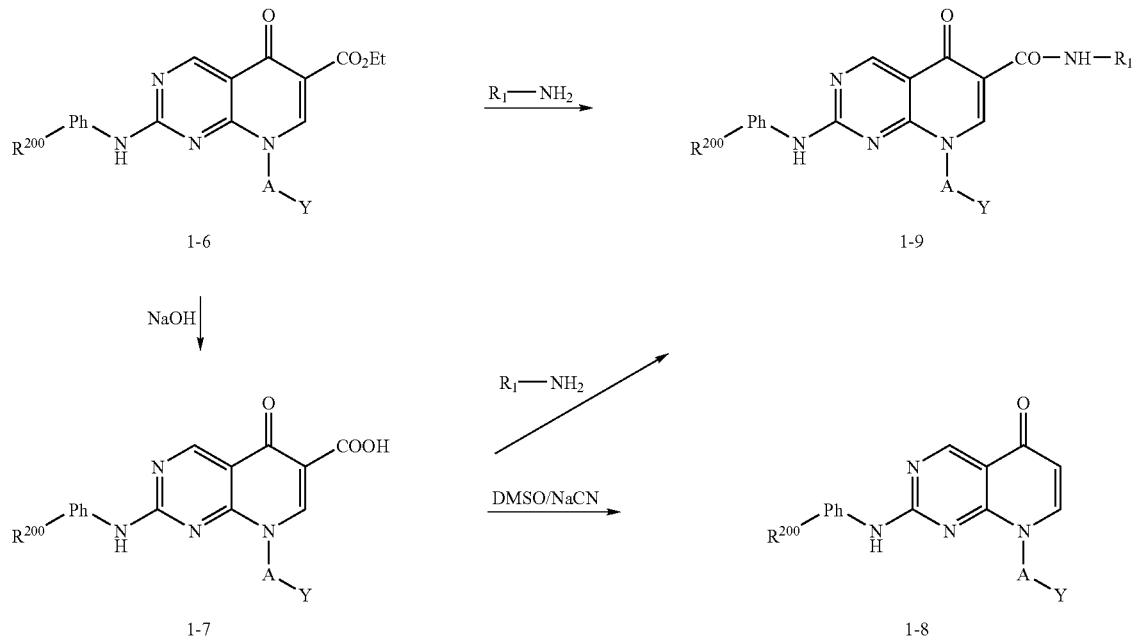

The synthesis was further extended to include the preparation of 5,8-dihydro-pyrido[2,3-d]pyrimidines with a carbonitrile functional group at the $C_6$ position. The method of preparation was identical with that used for preparing the esters (Scheme I) except that suitably 3-substituted aminopropionitriles 2-1 were used in the first step (Scheme II).

Hydrolysis of 2-5 under basic conditions provided the corresponding primary amide 2-6, wherein Ph is phenyl, which may be optionally further substituted with $R^{101}$.

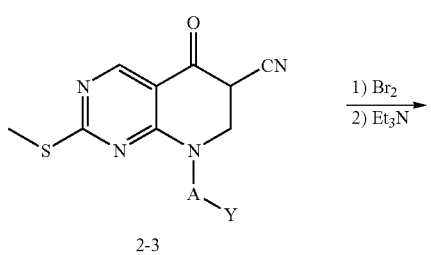

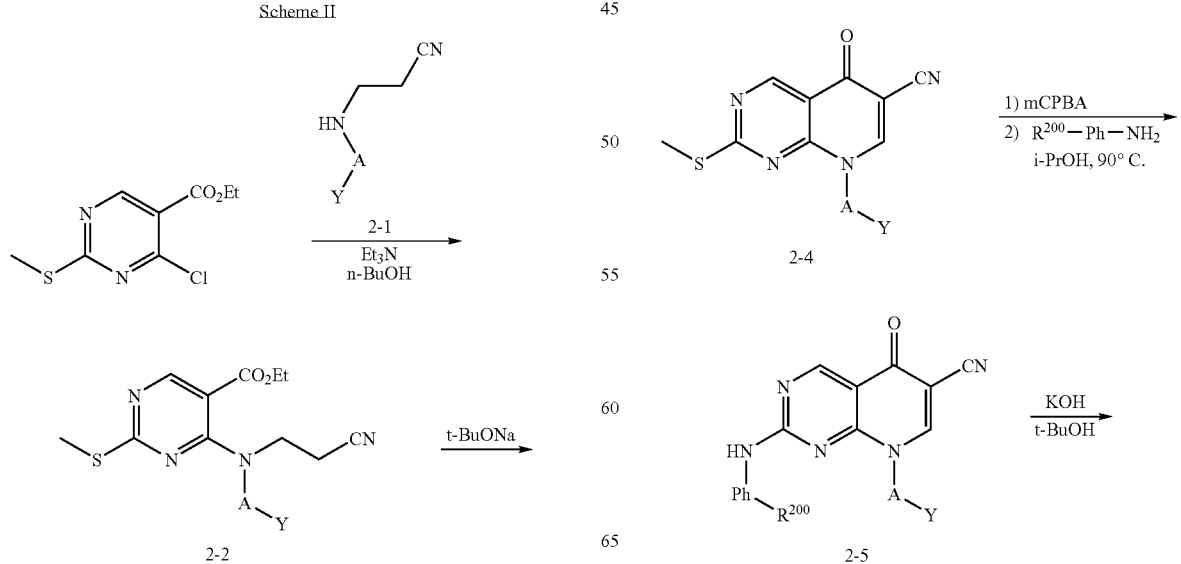

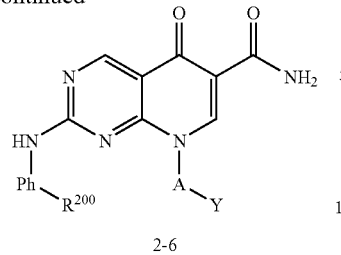

2-6

When 6-amide was the desired product, the intermediate 3-1 was converted to the primary amide 3-2 using liquid ammonia in a pressure bottle (Scheme III). Subsequent oxidation to methyl sulfone and nuclear substitution by an amine provided the desired 6-amide analogs 3-3, wherein Ph is phenyl, which may be optionally further substituted with $R^{101}$.

Scheme III

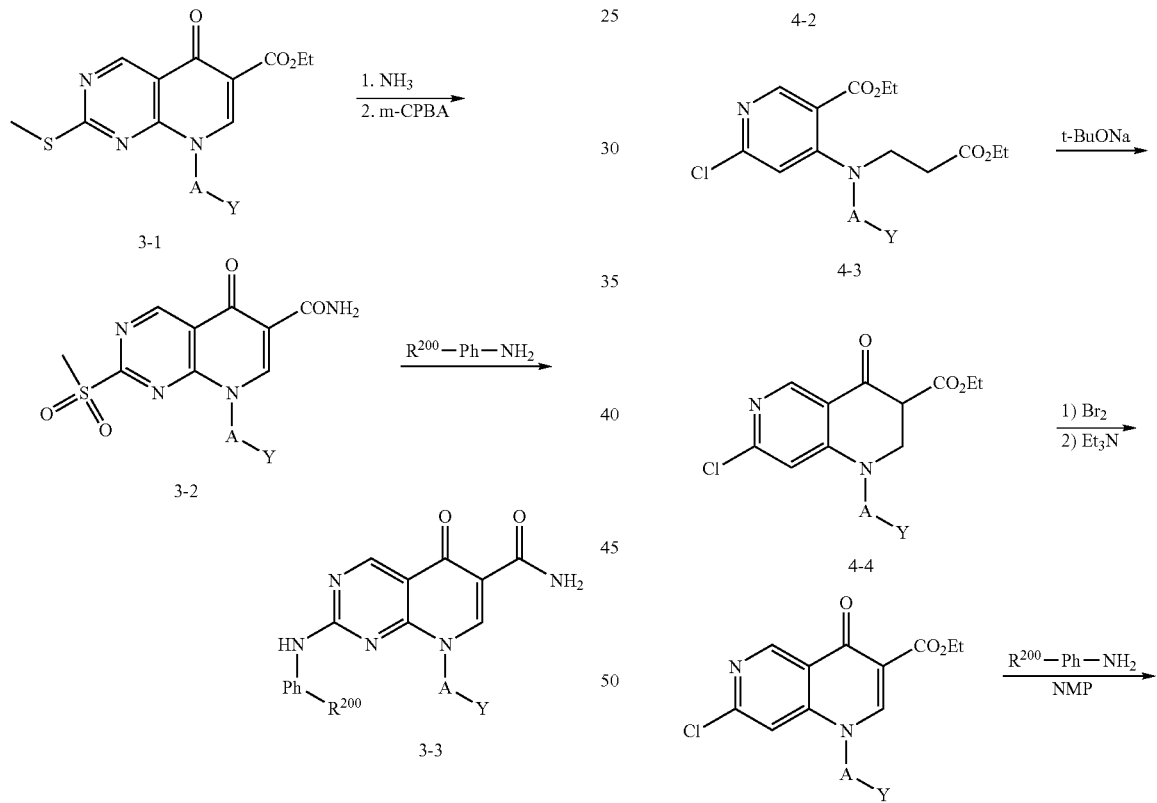

Compounds of formula (I) wherein W is CH were prepared by methods shown in Scheme IV, wherein Ph is phenyl, which may be optionally further substituted with $R^{101}$. 4,6-Dihydroxy-nicotinic acid ethyl ester 4-1 was obtained via two steps from diethyl 1,3-acetonedicarboxylate. Treatment of 4-1 with $POCl_3$ gave 4,6-dichloro-nicotinic acid ethyl ester 4-2. The following nucleophilic substitution and Dieckmann cyclization reactions were similar to the methods outlined in Scheme I. The intermediate 4-5 was treated with an amine in N-methylpyrrolidinone (NMP) under microwave conditions to afford the ester 4-6, which was subsequently converted to the amide 4-7.

Scheme IV

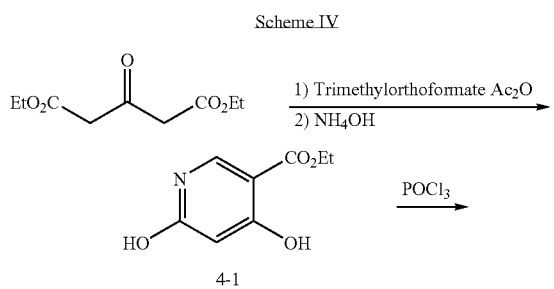

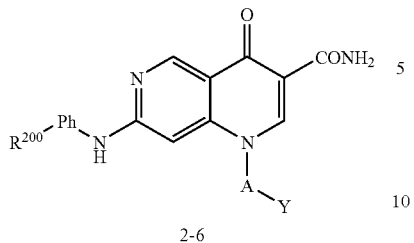

2-6

Where R$^{200}$ is heterocyclyl, alkoxy or dialkylamino, anilines of the form R$^{200}$-phenyl-NH$_2$ were prepared using SNAr reactions as shown in Scheme V (A) followed by hydrogenation converting the nitro group to the amino group. The phenyl portion of the compounds depicted in Scheme V may be optionally substituted with R$^{101}$.

Where R$^{300}$ is alkyl; anilines of the form R$^{400}$-alkyl-phenyl-NH$_2$ were prepared using SN$_2$ reactions as shown in Scheme V (B) followed by hydrogenation converting the nitro group to the amino group.

Where R$^{200}$ is —C(O)(CH$_2$)$_n$NR$^{203}$R$^{204}$, preparation of the aniline R$^{200}$-phenyl-NH$_2$ may be accomplished using SN$_2$ reactions as shown in Scheme V (C) followed by hydrogenation converting the nitro group to the amino group. It is recognized by those skilled in the art that where n=0, the desired product may be obtained from nitrobenzoic acid, nitrobenzoyl chloride and other starting materials.

Alternatively, anilines where R$^{200}$ is piperidinyl substituted with —C(O)-alkyl-NR$^{203}$R$^{204}$, may be obtained according to Scheme V (D and E).

Ketones of formula 5-1 can be converted to a vinyl triflate of formula 5-2 by treatment with a non-nucleophilic base such as LDA and then trapping of the resulting enolate with a triflating reagent such as trifluoromethanesulfonic anhydride or preferably N-phenyltrifluoromethanesulfonimide.

Suzuki coupling of boronic acids or boronate esters of formula 5-3 (prepared by palladium catalyzed borylation, see for example *J. Org. Chem.*, 60: 7508 (1995)) to vinyl triflates of formula 5-2 provided compounds of formula 5-4 (see, for example, *Synthesis*, 993 (1991)). Reduction of the olefin with hydrogen over palladium on carbon gave the aniline 5-5. N-Boc protected anilines of formula 5-6 can be converted to amides of formula 5-7 through normal amide formation reactions (Scheme V, E). Anilines of formula 5-8 were obtained upon acidic deprotection of the Boc group. It is recognized by those skilled in the art that the same procedure described for Scheme V (E) can also be used to generate ureas wherein the R$^{200}$ piperidine is substituted with —C(O)N-alkyl-NR$^{203}$R$^{204}$.

When R$^{300}$ is alkyl, anilines of the form R$^{407}$R$^{408}$NSO$_2$-alkyl-phenyl-NH$_2$ were prepared as described in Scheme V (F). Thioacetate of formula 5-9 was obtained from nucleophilic replacement of bromide with potassium thioacetate. Hydrolysis followed by treatment with thionyl chloride afforded sulfonyl chloride of formula 5-10, which was subsequently converted to sulfonamides of formula 5-11 when treated with various amines. The final nitro reduction provided the anilines of formula 5-12.

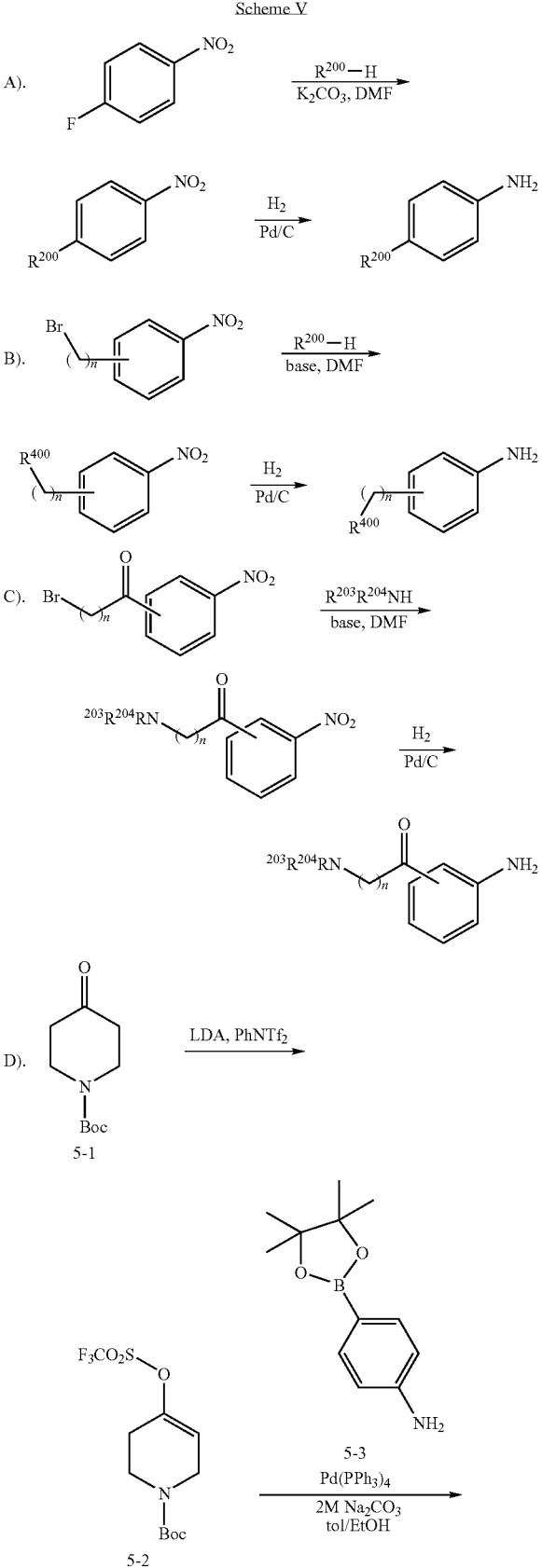

Scheme V

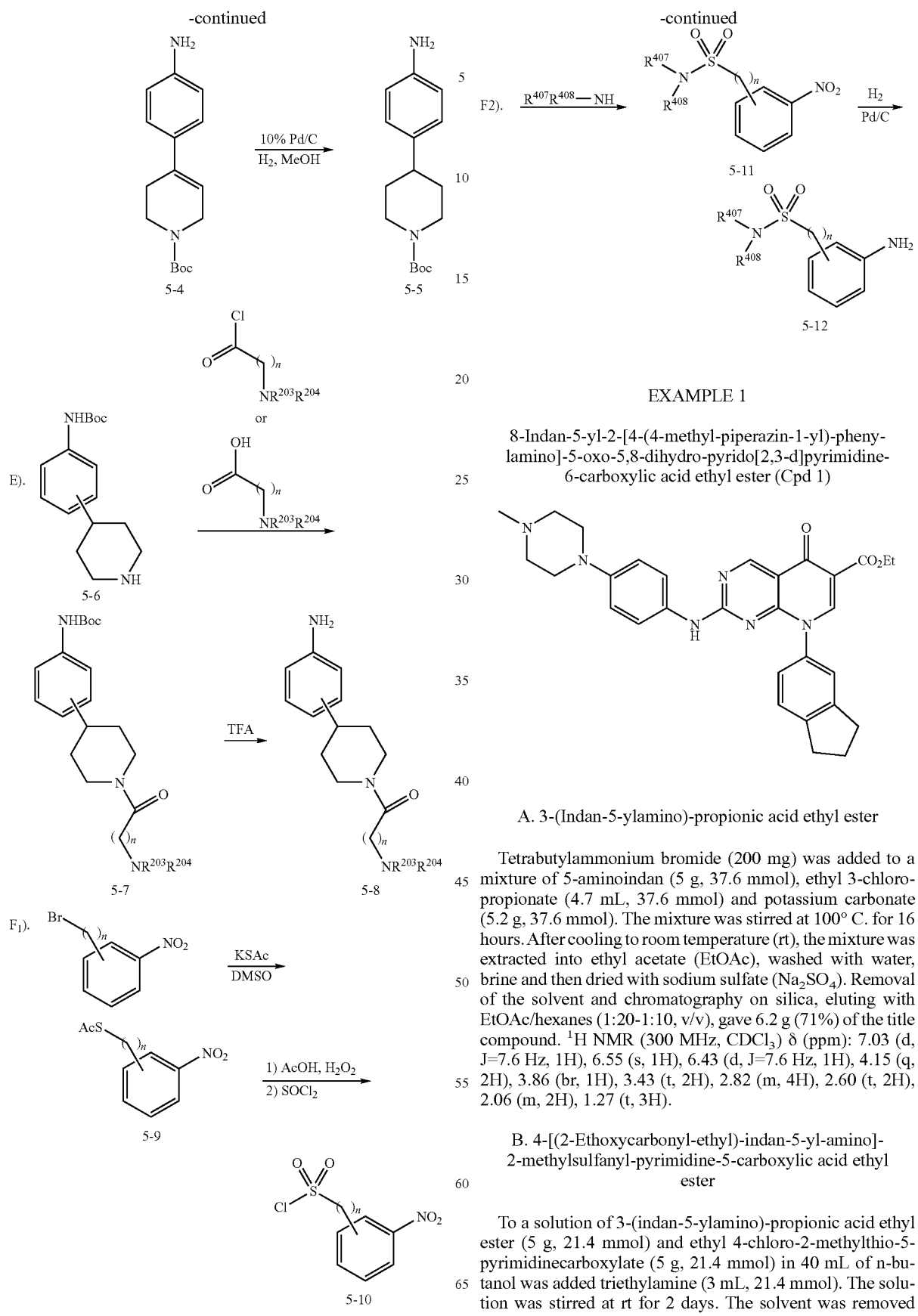

EXAMPLE 1

8-Indan-5-yl-2-[4-(4-methyl-piperazin-1-yl)-phenylamino]-5-oxo-5,8-dihydro-pyrido[2,3-d]pyrimidine-6-carboxylic acid ethyl ester (Cpd 1)

A. 3-(Indan-5-ylamino)-propionic acid ethyl ester

Tetrabutylammonium bromide (200 mg) was added to a mixture of 5-aminoindan (5 g, 37.6 mmol), ethyl 3-chloropropionate (4.7 mL, 37.6 mmol) and potassium carbonate (5.2 g, 37.6 mmol). The mixture was stirred at 100° C. for 16 hours. After cooling to room temperature (rt), the mixture was extracted into ethyl acetate (EtOAc), washed with water, brine and then dried with sodium sulfate ($Na_2SO_4$). Removal of the solvent and chromatography on silica, eluting with EtOAc/hexanes (1:20-1:10, v/v), gave 6.2 g (71%) of the title compound. $^1$H NMR (300 MHz, $CDCl_3$) δ (ppm): 7.03 (d, J=7.6 Hz, 1H), 6.55 (s, 1H), 6.43 (d, J=7.6 Hz, 1H), 4.15 (q, 2H), 3.86 (br, 1H), 3.43 (t, 2H), 2.82 (m, 4H), 2.60 (t, 2H), 2.06 (m, 2H), 1.27 (t, 3H).

B. 4-[(2-Ethoxycarbonyl-ethyl)-indan-5-yl-amino]-2-methylsulfanyl-pyrimidine-5-carboxylic acid ethyl ester To a solution of 3-(indan-5-ylamino)-propionic acid ethyl ester (5 g, 21.4 mmol) and ethyl 4-chloro-2-methylthio-5-pyrimidinecarboxylate (5 g, 21.4 mmol) in 40 mL of n-butanol was added triethylamine (3 mL, 21.4 mmol). The solution was stirred at rt for 2 days. The solvent was removed under vacuum. The residue was extracted into EtOAc, washed with water, brine and then dried with $Na_2SO_4$. Removal of the solvent and chromatography on silica, eluting with EtOAc/hexanes (1:10-1:6, v/v), gave 8.2 g (90%) of the titled compound as a white solid. $^1$H NMR (300 MHz, $CDCl_3$) δ (ppm): 8.22 (s, 1H), 7.16 (d, J=7.6 Hz, 1H), 6.95 (s, 1H), 6.87 (d, J=7.6 Hz, 1H), 4.35 (t, 2H), 4.06 (q, 2H), 3.55 (q, 2H), 2.82 (m, 4H), 2.69 (t, 2H), 2.58 (s, 3H), 2.06(m, 2H), 1.20 (t, 3H), 1.02 (t, 3H).

C. 8-Indan-5-yl-2-methylsulfanyl-5-oxo-5,6,7,8-tetrahydro-pyrido[2,3-d]pyrimidine-6-carboxylic acid ethyl ester To sodium (25 wt % dispersion in paraffin wax, 1.6 g, 16.9 mmol) was added t-butanol (30 mL) under stirring and $N_2$. After 10 minutes, a solution of 4-[(2-ethoxycarbonyl-ethyl)-indan-5-yl-amino]-2-methylsulfanyl-pyrimidine-5-carboxylic acid ethyl ester (6.6 g, 15.4 mmol) in 40 mL of toluene was added to the sodium t-butoxide solution. The mixture was then heated at 90° C. for 30 minutes. The solution was cooled and poured into crushed ice. The solution was adjusted to pH 7 using HCl solution. The precipitates were extracted into EtOAc twice. The solvent was evaporated under vacuum and the product (bright yellow solid, 4 g, 62%) was recrystallized from isopropanol. $^1$H NMR (300 MHz, $CDCl_3$) indicated that the presence of both enol and keto forms in a 4:1 ratio.

D. 8-Indan-5-yl-2-methylsulfanyl-5-oxo-5,8-dihydro-pyrido[2,3-d]pyrimidine-6-carboxylic acid ethyl ester To a solution of 8-indan-5-yl-2-methylsulfanyl-5-oxo-5,6,7,8-tetrahydro-pyrido[2,3-d]pyrimidine-6-carboxylic acid ethyl ester (0.32 g, 0.84 mmol) in 5 mL of methylene chloride ($CH_2Cl_2$) was added bromine (43 μL, 0.84 mmol) slowly under $N_2$. The solution was stirred at room temperature for 2 hours (or to completion). The solvent was removed under vacuum without heating. The residue was redissolved in 2 mL of $CH_2Cl_2$, and was added triethylamine (234 μL, 1.68 mmol) in 1 mL of $CH_2Cl_2$. The solution was stirred at rt for 4 hours. The progress of the reaction was monitored by LC-MS. The solvent was evaporated and the residue was applied onto a silica gel column. The product was eluted with EtOAc/hexanes (1:5-1:2.5, v/v) and obtained as a white solid (0.30 g, 94%). $^1$H NMR (300 MHz, $CDCl_3$) δ (ppm): 9.42 (s, 1H), 8.59 (s, 1H), 7.37 (d, J=7.8 Hz, 1H), 7.24 (s, 1H), 7.16 (d, J=7.8 Hz, 1H), 4.40 (q, 2H), 3.00 (m, 4H), 2.35 (s, 3H), 2.10(m, 2H), 1.40 (t, 3H).

E. 8-indan-5-yl-2-methanesulfonyl-5-oxo-5,8-dihydro-pyrido[2,3-d]pyrimidine-6-carboxylic acid ethyl ester To a solution of 8-indan-5-yl-2-methylsulfanyl-5-oxo-5,8-dihydro-pyrido[2,3-d]pyrimidine-6-carboxylic acid ethyl ester (0.3 g, 0.79 mmol) in 5 mL of $CH_2Cl_2$, was added 3-chloroperoxybenzoic acid (m-CPBA, 69.5%, 431 mg, 1.73 mmol) portionwise. The solution was stirred at room temperature for 3 hours. An aqueous solution of 10% sodium thiosulfate was added to quench the reaction. After 30 minutes saturated sodium bicarbonate solution was added, and the aqueous solution was extracted by $CH_2Cl_2$. The combined $CH_2Cl_2$ solution was washed with brine and dried over $Na_2SO_4$. Removal of the solvent and chromatography on silica, eluting with EtOAc/hexanes (1:3-1:1.6, v/v) gave 0.22 g (67%) of the title compound as an off-white solid. $^1$H NMR (300 MHz, $CDCl_3$) δ (ppm): 9.75 (s, 1H), 8.70 (s, 1H), 7.39 (d, J=7.8 Hz, 1H), 7.24 (s, 1H), 7.16 (d, J=7.8 Hz, 1H), 4.38 (q, 2H), 3.19 (s, 3H), 3.00 (m, 4H), 2.10(m, 2H), 1.40 (t, 3H).

F. 4-(4-Methyl-piperazin-1-yl)-phenylamine

Potassium carbonate (1.9 g, 14.2 mmol) was added to a mixture of 1-fluoro-4-nitrobenzene (1 g, 7.1 mmol) and 1-methyl-piperazine (0.94 mL, 8.5 mmol) in methyl sulfoxide (DMSO, 5 mL). The mixture was stirred at 80° C. for 3 hours. After cooling down, the residue was extracted into EtOAc. The organic layer was washed with water, brine and then dried with $Na_2SO_4$. Removal of the solvent in vacuo yielded an orange solid. The solid was dissolved in 25 mL of methanol and palladium on carbon (10% Pd/C, 50 mg) was added slowly. The system was sealed and blanketed with hydrogen. The mixture was stirred at rt for 16 hours under hydrogen. The catalyst was filtered through a celite pad and the solvent was evaporated to leave a dark purple solid (1.3 g, 80%). $^1$H NMR (300 MHz, $CD_3OD$) δ (ppm): 6.90 (m, 2H), 6.81 (m, 2H), 3.38 (m, 4H), 3.26 (m, 4H), 2.93 (s, 3H).

G. 8-Indan-5-yl-2-[4-(4-methyl-piperazin-1-yl)-phenylamino]-5-oxo-5,8-dihydro-pyrido[2,3-d]pyrimidine-6-carboxylic acid ethyl ester (Cpd 1)

The mixture of 8-Indan-5-yl-2-methanesulfonyl-5-oxo-5,8-dihydro-pyrido[2,3-d]pyrimidine-6-carboxylic acid ethyl ester (11.2 mg, 0.027 mmol) and 4-(4-methyl-piperazin-1-yl)-phenylamine (5.2 mg, 0.027 mmol) in 1 mL of isopropanol was heated to 90° C. for 1 hour. The solvent was evaporated and the residue was re-dissolved in a mixture of methanol and $CH_2Cl_2$ (1:1, v/v) and applied onto a prep-TLC plate (2000 micro). The plate was developed in $NH_4OH$/MeOH/$CH_2Cl_2$ (1:9:90, v/v). 8-indan-5-yl-2-[4-(4-methyl-piperazin-1-yl)-phenylamino]-5-oxo-5,8-dihydro-pyrido[2,3-d]pyrimidine-6-carboxylic acid ethyl ester (Cpd 1) was obtained as a yellow solid (8.6 mg, 61%). $^1$H NMR (300 MHz, $CDCl_3$) δ (ppm): 9.38 (s, 1H), 8.52 (s, 1H), 7.44 (m, 2H), 7.28 (s, 1H), 7.19 (m, 3H), 6.66 (m, 2H), 4.40 (q, 2H), 3.00-3.18 (m, 8H), 2.60 (m, 4H), 2.35 (s, 3H), 2.22 (m, 2H), 1.40 (t, 3H). Mass Spectrum (LCMS, ESI pos.) Calcd. For $C_{30}H_{32}N_6O_3$: 525.25 (M+H), Found: 525.4.

EXAMPLE 2

2-[4-(3-Dimethylamino-2-hydroxy-propoxy)-phenylamino]-8-indan-5-yl-5-oxo-5,8-dihydro-pyrido[2,3-d]pyrimidine-6-carboxylic acid ethyl ester (Cpd 2)

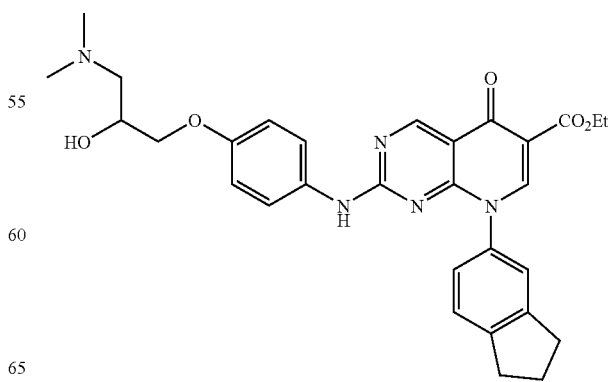

A. 2-(4-Nitro-phenoxymethyl)-oxirane

Potassium carbonate (1.3 g, 9.6 mmol) was added to a mixture of 4-nitrophenol (1.11 g, 8 mmol) and epibromohydrin (1.37 mL, 16 mmol) The mixture was stirred at 100° C. for 18 hours. After cooling down, the residue was extracted into EtOAc. The organic layer was washed with water, brine and then dried with $Na_2SO_4$. Removal of the solvent in vacuo gave an orange residue, which was purified chromatographically on silica eluting with EtOAc/hexanes (1:10, v/v). The product was obtained as a yellow solid (0.8 g, 51%). $^1$H NMR (300 MHz, CDCl$_3$) δ (ppm): 8.21 (m, 2H), 6.98 (m, 2H), 4.37 (dd, J=2.8 Hz, 11.1 Hz, 1H), 4.00 (dd, J=5.9 Hz, 11.1 Hz, 1H), 3.90 (m, 1H), 2.93 (t, J=4.8 Hz, 1H), 2.77 (dd, J=2.8 Hz, 4.8 Hz, 1H).

B. 1-(4-Amino-phenoxy)-3-dimethylamino-propan-2-ol

To a solution of 2-(4-nitro-phenoxymethyl)-oxirane (0.2 g, 1 mmol) in 2 mL of ethanol was added a solution of dimethylamine (2 M in methanol, 2.5 mL). The solution was stirred at 80° C. for 2 hours in a capped vial. The solvent was removed in vacuo. Hydrogenation of the residue using the procedure described in Example 1(f) gave the title compound as a brown solid. $^1$H NMR (300 MHz, CD$_3$OD) δ (ppm): 6.76 (m, 2H), 6.71 (m, 2H), 4.20 (m, 1H), 3.88 (d, 2H), 3.04 (m, 2H), 2.71 (s, 6H).

C. 2-[4-(3-dimethylamino-2-hydroxy-propoxy)-phenylamino]-8-indan-5-yl-5-oxo-5,8-dihydro-pyrido[2,3-d]pyrimidine-6-carboxylic acid ethyl ester Using the procedure outlined in Example 1(g) the title compound was prepared from 1-(4-amino-phenoxy)-3-dimethylamino-propan-2-ol (18 mg, 0.083 mmol) and 8-indan-5-yl-2-methanesulfonyl-5-oxo-5,8-dihydro-pyrido[2,3-d]pyrimidine-6-carboxylic acid ethyl ester (from Example 1(e) above, 34 mg, 0.083 mmol). 3.1 mg of 2-[4-(3-dimethylamino-2-hydroxy-propoxy)-phenylamino]-8-indan-5-yl-5-oxo-5,8-dihydro-pyrido[2,3-d]pyrimidine-6-carboxylic acid ethyl ester was obtained as a yellow solid. $^1$H NMR (300 MHz, CDCl$_3$) δ (ppm): 9.38 (s, 1H), 8.52 (s, 1H), 7.50 (br, 1H), 7.40 (d, 2H), 7.28 (m, 3H), 7.19 (d, 1H), 6.66 (br, 2H), 4.40 (q, 2H), 4.05 (m, 1H), 3.90 (d, 2H), 3.10 (m, 4H), 2.52 (dd, 1H), 2.33 (m, 7H), 2.22 (m, 2H), 1.40 (t, 3H). Mass Spectrum (LCMS, ESI pos.) Calcd. For $C_{30}H_{33}N_5O_5$: 544.25 (M+H), Found: 544.4.

EXAMPLE 3

8-Indan-5-yl-2-(4-morpholin-4-yl-phenylamino)-5-oxo-5,8-dihydro-pyrido[2,3-d]pyrimidine-6-carboxylic acid ethyl ester (Cpd 3)

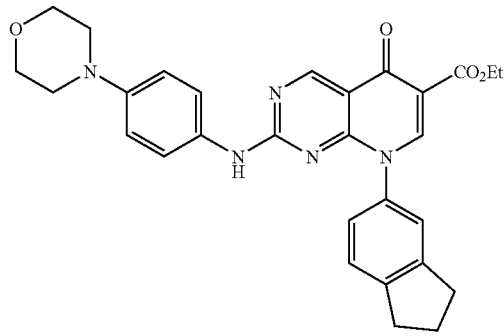

Using the procedure outlined in Example 1 (g) the title compound was prepared from 4-morpholin-4-yl-phenylamine (6.5 mg, 0.036 mmol) and 8-indan-5-yl-2-methanesulfonyl-5-oxo-5,8-dihydro-pyrido[2,3-d]pyrimidine-6-carboxylic acid ethyl ester (from Example 1(e) above, 15 mg, 0.036 mmol). 11.9 mg of 8-indan-5-yl-2-(4-morpholin-4-yl-phenylamino)-5-oxo-5,8-dihydro-pyrido[2,3-d]pyrimidine-6-carboxylic acid ethyl ester was obtained as a yellow solid. $^1$H NMR (400 MHz, CDCl$_3$) δ (ppm): 9.38 (br, 1H), 8.53 (s, 1H), 7.69 (br, 1H), 7.43 (d, 1H), 7.23 (m, 4H), 6.64 (br, 2H), 4.36 (q, 2H), 3.87 (m, 4H), 3.04 (m, 8H), 2.22 (m, 2H), 1.39 (t, 3H). Mass Spectrum (LCMS, ESI pos.) Calcd. For $C_{29}H_{29}N_5O_4$: 512.24 (M+H), Found: 512.4.

EXAMPLE 4

2-(4-Dimethylamino-phenylamino)-8-indan-5-yl-5-oxo-5,8-dihydro-pyrido[2,3-d]pyrimidine-6-carboxylic acid ethyl ester (Cpd 4)

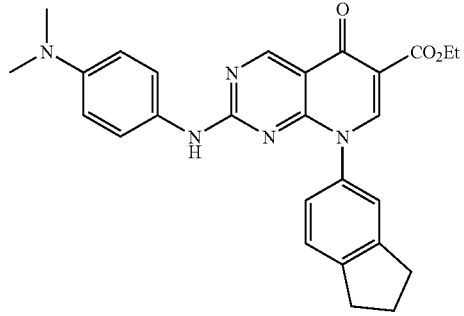

Using the procedure outlined in Example 1(g) the title compound was prepared from 4-dimethylaminoaniline (5 μL, 0.036 mmol) and 8-indan-5-yl-2-methanesulfonyl-5-oxo-5,8-dihydro-pyrido[2,3-d]pyrimidine-6-carboxylic acid ethyl ester (from Example 1(e) above, 15 mg, 0.036 mmol). 7.9 mg of 2-(4-dimethylamino-phenylamino)-8-indan-5-yl-5-oxo-5,8-dihydro-pyrido[2,3-d]pyrimidine-6-carboxylic acid ethyl ester was obtained as a yellow solid. $^1$H NMR (400 MHz, CDCl$_3$) δ (ppm): 9.31 (br, 1H), 8.53 (s, 1H), 7.82 (d, 1H), 7.61 (br, 1H), 7.41 (d, 1H), 7.29 (s, 1H), 7.17 (d, 1H), 6.76 (d, 1H), 6.46 (br, 2H), 4.39 (q, 2H), 3.03 (m, 4H), 2.89 (s, 6H), 2.22 (m, 2H), 1.37 (t, 3H). Mass Spectrum (LCMS, ESI pos.) Calcd. For $C_{27}H_{27}N_5O_3$: 470.21 (M+H), Found: 470.4.

EXAMPLE 5

2-(3-Dimethylamino-phenylamino)-8-indan-5-yl-5-oxo-5,8-dihydro-pyrido[2,3-d]pyrimidine-6-carboxylic acid ethyl ester (Cpd 5)

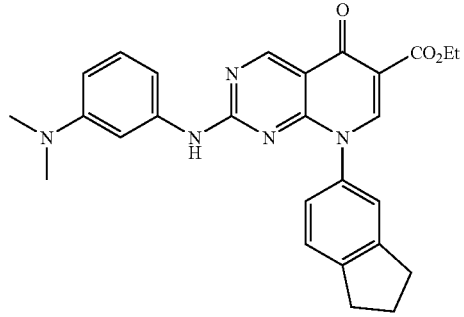

Using the procedure outlined in Example 1(g) the title compound was prepared from 3-dimethylaminoaniline dihydrochloride (7.6 mg, 0.036 mmol) and 8-indan-5-yl-2-methanesulfonyl-5-oxo-5,8-dihydro-pyrido[2,3-d]pyrimidine-6-carboxylic acid ethyl ester (from Example 1(e) above, 15 mg, 0.036 mmol) at the presence of triethylamine (11 μL, 0.072 mmol). 6.6 mg of 2-(3-dimethylamino-phenylamino)-8-indan-5-yl-5-oxo-5,8-dihydro-pyrido[2,3-d]pyrimidine-6-carboxylic acid ethyl ester was obtained as a yellow solid. $^1$H NMR (300 MHz, CDCl$_3$) δ (ppm): 9.41 (br, 1H), 8.53 (s, 1H), 7.47 (br, 1H), 7.40 (d, 1H), 7.29 (s, 1H), 7.18 (d, 1H), 6.90 (m, 2H), 6.50 (m, 2H), 4.39 (q, 2H), 3.00 (m, 4H), 2.80 (s, 6H), 2.21 (m, 2H), 1.37 (t, 3H). Mass Spectrum (LCMS, ESI pos.) Calcd. For C$_{27}$H$_{27}$N$_5$O$_3$: 470.21 (M+H), Found: 470.4.

EXAMPLE 6

8-Indan-5-yl-2-[4-(4-methyl-piperazin-1-yl)-phenylamino]-5-oxo-5,8-dihydro-pyrido[2,3-d]pyrimidine-6-carboxylic acid (Cpd 6)

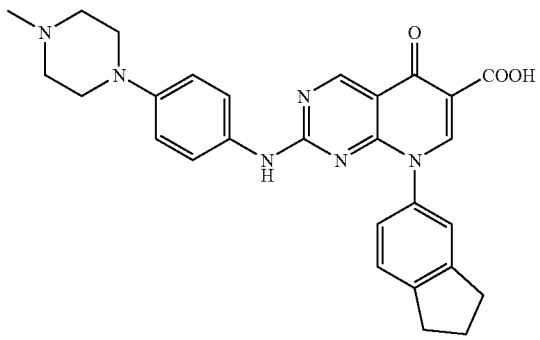

Hydrolysis of 8-indan-5-yl-2-[4-(4-methyl-piperazin-1-yl)-phenylamino]-5-oxo-5,8-dihydro-pyrido[2,3-d]pyrimidine-6-carboxylic acid ethyl ester Cpd 1 (Example 1(g), 50 mg) in a mixture of tetrahydrofuran (THF) and 1 N sodium hydroxide solution at an elevated temperature gave 8-indan-5-yl-2-[4-(4-methyl-piperazin-1-yl)-phenylamino]-5-oxo-5,8-dihydro-pyrido[2,3-d]pyrimidine-6-carboxylic acid Cpd 6, which was purified using preparative HPLC, resulting in a formic acid salt form (28 mg, yellow solid). $^1$H NMR (300 MHz, CDCl$_3$) δ (ppm): 9.38 (s, 1H), 8.80 (s, 1H), 8.35 (br, 1H), 7.83 (br, 1H), 7.42 (m, 2H), 7.20 (m, 4H), 6.65 (br, 2H), 3.20 (m, 4H), 3.03 (m, 4H), 2.88(m, 4H), 2.60(m, 4H), 2.50 (s, 3H), 2.20 (m, 2H). Mass Spectrum (LCMS, ESI pos.) Calcd. For C$_{28}$H$_{28}$N$_6$O$_3$: 497.22 (M+H), Found: 497.5.

EXAMPLE 7

8-Indan-5-yl-2-[4-(4-methyl-piperazin-1-yl)-phenylamino]-5-oxo-5,8-dihydro-pyrido[2,3-d]pyrimidine-6-carboxylic acid amide (Cpd 7)

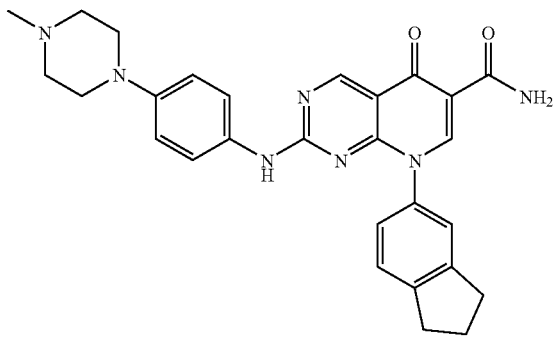

To a solution of 8-indan-5-yl-2-[4-(4-methyl-piperazin-1-yl)-phenylamino]-5-oxo-5,8-dihydro-pyrido[2,3-d]pyrimidine-6-carboxylic acid ethyl ester Cpd 1 (Example 1(g), 10 mg) in 1 mL of methanol was bubbled ammonia at −78° C. for 5 minutes in a pressure bottle (10 mL). The bottle was capped and warmed up to room temperature and stirred for 16 hours. The solvent was evaporated to leave 8-indan-5-yl-2-[4-(4-methyl-piperazin-1-yl)-phenylamino]-5-oxo-5,8-dihydro-pyrido[2,3-d]pyrimidine-6-carboxylic acid amide Cpd 7 as a yellow solid (8.1 mg). $^1$H NMR (400 MHz, DMSO-d$_6$); δ (ppm): 10.24 (s, 1H), 9.17 (s, 1H), 9.03 (s, 1H), 8.52 (s, 1H), 7.62 (d, 1H), 7.44 (m, 2H), 7.33 (d, 1H), 7.27 (m, 2H), 6.57 (m, 2H), 3.00 (m, 4H), 2.93 (m, 4H), 2.42 (m, 4H), 2.20 (s, 3H), 2.13 (m, 2H). Mass Spectrum (LCMS, ESI pos.) Calcd. For C$_{28}$H$_{29}$N$_7$O$_2$: 496.24 (M+H), Found: 496.4.

EXAMPLE 8

8-indan-5-yl-2-[4-(4-methyl-piperazin-1-yl)-phenylamino]-5-oxo-5,8-dihydro-pyrido[2,3-d]pyrimidine-6-carboxylic acid methylamide (Cpd 8)

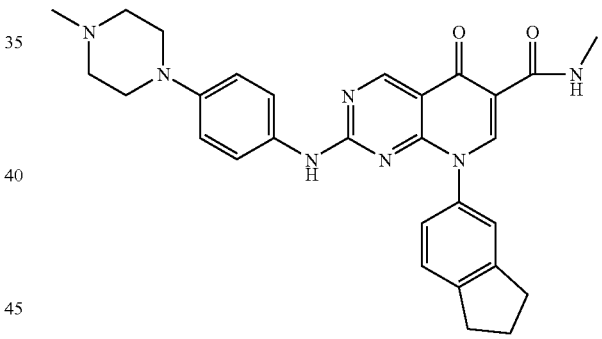

To a solution of 8-indan-5-yl-2-[4-(4-methyl-piperazine-1-yl)-phenylamino]-5-oxo-5,8-dihydro-pyrido[2,3-d]pyrimidine-6-carboxylic acid ethyl ester Cpd 1 (Example 1(g), 5 mg) in 1 mL of methanol was added 1 mL of methylamine (40 wt. % in water). The solution was stirred at 70° C. for 30 minutes. The solvent was evaporated and the product was purified by preparative HPLC. 1.7 mg of 8-indan-5-yl-2-[4-(4-methyl-piperazin-1-yl)-phenylamino]-5-oxo-5,8-dihydro-pyrido[2,3-d]pyrimidine-6-carboxylic acid methylamide Cpd 8 was obtained as yellow solid. $^1$H NMR (400 MHz, CDCl$_3$) δ (ppm): 9.65 (s, 1H), 9.36 (s, 1H), 8.84 (s, 1H), 7.42 (d, 1H), 7.23 (m, 3H), 7.17 (d, 1H), 6.67 (br, 2H), 3.14 (m, 4H), 3.02 (m, 7H), 2.59 (m, 4H), 2.37 (s, 3H), 2.22 (m, 2H). Mass Spectrum (LCMS, ESI pos.) Calcd. For C$_{29}$H$_{31}$N$_7$O$_2$: 510.25 (M+H), Found: 510.2.

EXAMPLE 9

8-indan-5-yl-2-[4-(4-methyl-piperazin-1-yl)-phenylamino]-5-oxo-5,8-dihydro-pyrido[2,3-d]pyrimidine-6-carboxylic acid ethylamide (Cpd 9)

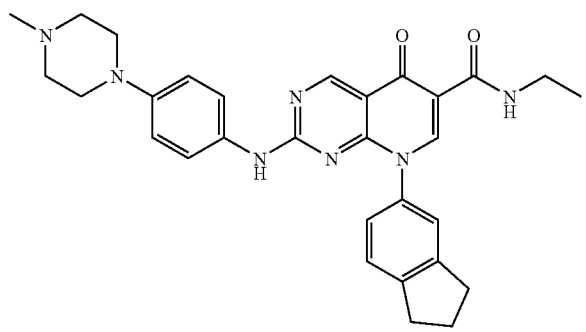

To a solution of 8-indan-5-yl-2-[4-(4-methyl-piperazin-1-yl)-phenylamino]-5-oxo-5,8-dihydro-pyrido[2,3-d]pyrimidine-6-carboxylic acid ethyl ester Cpd 1 (Example 1(g), 5 mg) in 1 mL of methanol was added 1 mL of ethylamine (2 M in methanol). The solution was stirred at 70° C. for 30 minutes. The solvent was evaporated and the product was purified by preparative HPLC as the formic acid salt (1 mg, yellow solid). $^1$H NMR (400 MHz, CDCl$_3$) δ (ppm): 9.71 (m, 1H), 9.35 (s, 1H), 8.83 (s, 1H), 8.24 (br, 1H), 7.69 (br, 1H), 7.42 (d, 1H), 7.27 (m, 3H), 7.17 (d, 1H), 6.67 (br, 2H), 3.50 (m, 2H), 3.25 (m, 4H), 3.03 (m, 4H), 2.92 (m, 4H), 2.55 (s, 3H), 2.22 (m, 2H), 1.27 (t, 3H). Mass Spectrum (LCMS, ESI pos.) Calcd. For C$_{30}$H$_{33}$N$_7$O$_2$: 524.27 (M+H), Found: 524.3.

EXAMPLE 10

2-[4-(3-Dimethyl amino-2-hydroxy-propoxy)-phenylamino]-8-indan-5-yl-5-oxo-5,8-dihydro-pyrido[2,3-d]pyrimidine-6-carboxylic acid amide (Cpd 10)

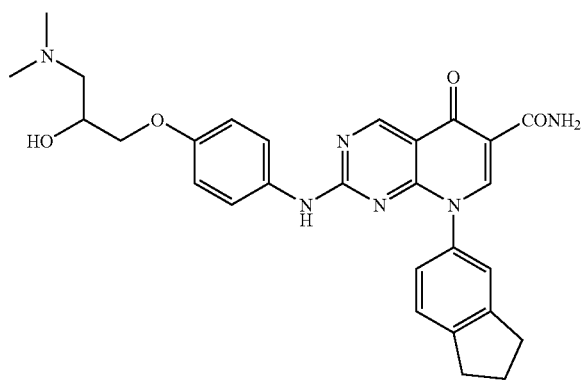

Using the procedure outlined in Example 7 the title compound was prepared from 2-[4-(3-dimethylamino-2-hydroxy-propoxy)-phenylamino]-8-indan-5-yl-5-oxo-5,8-dihydro-pyrido[2,3-d]pyrimidine-6-carboxylic acid ethyl ester (from Example 2(c), 5 mg). 4.3 mg of 2-[4-(3-dimethyl amino-2-hydroxy-propoxy)-phenylamino]-8-indan-5-yl-5-oxo-5,8-dihydro-pyrido[2,3-d]pyrimidine-6-carboxylic acid amide was obtained as a yellow solid. $^1$H NMR (400 MHz, DMSO-d$_6$) δ (ppm): 10.32 (br, 1H), 9.20 (s, 1H), 9.02 (br, 1H), 8.52 (s, 1H), 7.63 (d, 1H), 7.45 (m, 2H), 7.32 (m, 3H), 6.59 (br, 2H), 4.89 (br, 1H), 3.88 (m, 2H), 3.75 (m, 1H), 3.00 (m, 4H), 2.37 (m, 2H), 2.23 (s, 6H), 2.14 (m, 2H). Mass Spectrum (LCMS, ESI pos.) Calcd. For C$_{28}$H$_{30}$N$_6$O$_4$: 515.23 (M+H), Found: 515.3.

EXAMPLE 11

2-[4-(3-Dimethylamino-2-hydroxy-propoxy)-phenylamino]-8-indan-5-yl-5-oxo-5,8-dihydro-pyrido[2,3-d]pyrimidine-6-carboxylic acid methylamide (Cpd 11)

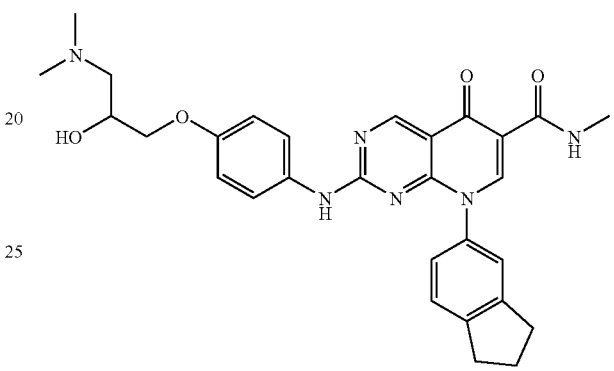

To a solution of 2-[4-(3-dimethylamino-2-hydroxy-propoxy)-phenylamino]-8-indan-5-yl-5-oxo-5,8-dihydro-pyrido[2,3-d]pyrimidine-6-carboxylic acid ethyl ester (from Example 2(c), 8 mg) in 1 mL of methanol was added 1 mL of methylamine (40 wt. % in water). The solution was stirred at 70° C. for 30 minutes. The solvent was evaporated to yield a yellow solid (6.6 mg). $^1$H NMR (400 MHz, CDCl$_3$) δ (ppm): 9.64 (m, 1H), 9.35 (s, 1H), 8.82 (s, 1H), 7.39 (m, 2H), 7.27 (m, 1H), 7.15 (m, 2H), 6.66 (br, 2H), 4.06 (m, 1H), 3.93 (m, 2H), 3.02 (m, 5H), 2.89 (m, 4H), 2.56 (dd, 1H), 2.35 (m, 7H), 2.22 (m, 2H). Mass Spectrum (LCMS, ESI pos.) Calcd. For C$_{29}$H$_{32}$N$_6$O$_4$: 529.25 (M+H), Found: 529.2.

EXAMPLE 12

2-[4-(3-Dimethyl amino-2-hydroxy-propoxy)-phenylamino]-8-indan-5-yl-5-oxo-5,8-dihydro-pyrido[2,3-d]pyrimidine-6-carboxylic acid ethylamide (Cpd 12)

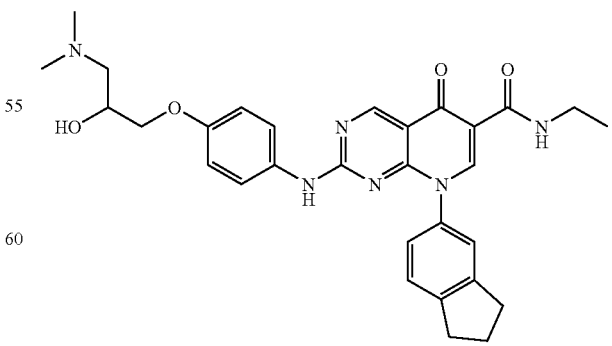

To a solution of 2-[4-(3-dimethylamino-2-hydroxy-propoxy)-phenylamino]-8-indan-5-yl-5-oxo-5,8-dihydro-pyrido[2,3-d]pyrimidine-6-carboxylic acid ethyl ester (from Example 2(c), 8 mg). in 1 mL of methanol was added 1 mL of ethylamine (2M in methanol). The solution was stirred at 70° C. for 30 minutes. The solvent was evaporated and 2-[4-(3-dimethylamino-2-hydroxy-propoxy)-phenylamino]-8-indan-5-yl-5-oxo-5,8-dihydro-pyrido[2,3-d]pyrimidine-6-carboxylic acid ethylamide was purified by preparative HPLC as the trifluoroacetic acid salt (2.7 mg, brown solid). $^1$H NMR (400 MHz, CD$_3$OD) δ (ppm): 10.07 (br, 1H), 9.27 (s, 1H), 8.69 (s, 1H), 7.46 (m, 1H), 7.34 (m, 4H), 7.26 (m, 1H), 6.64 (br, 2H), 4.34 (m, 1H), 3.94 (m, 2H), 3.46 (m, 2H), 3.00 (m, 12H), 2.23 (m, 2H), 1.25 (t, 3H). Mass Spectrum (LCMS, ESI pos.) Calcd. For C$_{30}$H$_{34}$N$_6$O$_4$: 543.26 (M+H), Found: 543.2.

EXAMPLE 13

2-[4-(4-Methyl-piperazin-1-yl)-phenylamino]-5-oxo-8-phenyl-5,8-dihydro-pyrido[2,3-d]pyrimidine-6-carboxylic acid amide (Cpd 13)

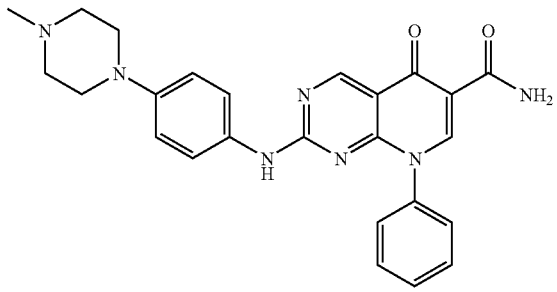

A. 4-[(2-Cyano-ethyl)-phenyl-amino]-2-methylsulfanyl-pyrimidine-5-carboxylic acid ethyl ester The title compound was prepared from ethyl 4-chloro-2-methylthio-5-pyrimidinecarboxylate (3.7 g, 15.8 mmol) and 3-phenylamino-propionitrile (2.3 g, 15.8 mmol) according to the procedure outlined in Example 1 (B). The product was purified chromatographically (silica, EtOAc/hexanes 1:20-1:2, v/v). A white solid was obtained (3.5 g, 65%). $^1$H NMR (300 MHz, CDCl$_3$) δ (ppm): 8.32 (s, 1H), 7.34(m, 2H), 7.20 (m, 1H), 7.13 (m, 2H), 4.32 (t, J=7.1 Hz, 2H), 3.56 (q, J=7.1 Hz, 2H), 2.75 (t, J=7.1 Hz, 2H), 2.55 (s, 3H), 1.00 (t, J=7.2 Hz, 3H).

B. 2-Methylsulfanyl-5-oxo-5-phenyl-5,6,7,8-tetrahydro-pyrido[2,3-d]pyrimidine-6-carbonitrile The title compound was prepared from 4-[(2-cyano-ethyl)-phenyl-amino]-2-methylsulfanyl-pyrimidine-5-carboxylic acid ethyl ester (0.78 g, 2.27 mmol) according to the procedure outlined in Example 1 (C). The product was purified chromatographically (silica, EtOAc/hexanes 1:1-1:0, v/v). A yellow solid was obtained (0.39 g, 58%). $^1$H NMR (300 MHz, CDCl$_3$) indicated that the presence of both enol and keto forms in a 1:1 ratio.

C. 2-Methylsulfanyl-5-oxo-8-phenyl-5,8-dihydro-pyrido[2,3-d]pyrimidine-6-carbonitrile The title compound was prepared from 2-methylsulfanyl-5-oxo-8-phenyl-5,6,7,8-tetrahydro-pyrido[2,3-d]pyrimidine-6-carbonitrile (0.83 g, 2.8 mmol) according to the procedure outlined in Example 1 (D). The product was purified chromatographically (silica, EtOAc/hexanes (1:5-1:2.5, v/v) and obtained as a white solid (0.73 g, 89%). $^1$H NMR (300 MHz, CDCl$_3$) δ (ppm): 9.42 (s, 1H), 8.59 (s, 1H), 7.37 (m, 2H), 7.24 (m, 1H), 7.14 (m, 2H), 2.37 (s, 3H).

D. 2-Methanesulfonyl-5-oxo-8-phenyl-5,8-dihydro-pyrido[2,3-d]pyrimidine-6-carbonitrile The title compound was prepared from 2-methylsulfanyl-5-oxo-8-phenyl-5,8-dihydro-pyrido[2,3-d]pyrimidine-6-carbonitrile (0.73 g, 2.5 mmol) according to the procedure outlined in Example 1 (E). The product was obtained as an off-white solid (0.77 g, 95%). $^1$H NMR (300 MHz, CDCl$_3$) δ (ppm): 9.51 (s, 1H), 8.62 (s, 1H), 7.38 (m, 2H), 7.24 (m, 1H), 7.14 (m, 2H), 3.20 (s, 3H).

E. 2-[4-(4-Methyl-piperazin-1-yl)-phenylamino]-5-oxo-8-phenyl-5,8-dihydro-pyrido[2,3-d]pyrimidine-6-carbonitrile Using the procedure outlined in Example 1(G) the title compound was prepared from 4-(4-methyl-piperazin-1-yl)-phenylamine (32 mg, 0.16 mmol) and 2-methanesulfonyl-5-oxo-8-phenyl-5,8-dihydro-pyrido[2,3-d]pyrimidine-6-carbonitrile (Example 13 (D) above, 50 mg, 0.15 mmol). The product was obtained as a yellow solid (17.1 mg). $^1$H NMR (300 MHz, CDCl$_3$) δ (ppm): 9.34 (s, 1H), 8.55 (br, 1H), 7.61 (m, 3H), 7.41 (d, 2H), 7.24 (m, 2H), 6.55 (d, 2H), 3.00 (m, 4H), 2.55 (m, 4H), 2.35 (s, 3H). Mass Spectrum (LCMS, ESI pos.) Calcd. For C$_{25}$H$_{23}$N$_7$O: 438.20 (M+H), Found: 438.5.

F. 2-[4-(4-Methyl-piperazin-1-yl)-phenylamino]-5-oxo-8-phenyl-5,8-dihydro-pyrido[2,3-d]pyrimidine-6-carboxylic acid amide To a solution of 2-[4-(4-Methyl-piperazin-1-yl)-phenylamino]-5-oxo-8-phenyl-5,8-dihydro-pyrido[2,3-d]pyrimidine-6-carbonitrile (Example 13F, 9 mg) in 1 mL of t-butanol was added potassium hydroxide (ground, 5 mg). The mixture was stirred at 85° C. for 1 hour. After cooling to rt, water was added and the precipitates were extracted into EtOAc. The organic layer was washed with brine and dried over Na$_2$SO$_4$. The solvent was evaporated under vacuum to leave 2-[4-(4-methyl-piperazin-1-yl)-phenylamino]-5-oxo-8-phenyl-5,8-dihydro-pyrido[2,3-d]pyrimidine-6-carboxylic acid amide as a yellow solid (7.2 mg, 79%). $^1$H NMR (300 MHz, CDCl$_3$) δ (ppm): 10.64 (br, 1H), 10.30 (s, 1H), 9.17 (s, 1H), 7.71 (m, 3H), 7.53 (br, 1H), 7.43 (m, 2H), 6.94 (br, 2H), 6.35 (br, 2H), 5.06 (br, 1H), 3.12 (m, 4H), 2.59 (m, 4H), 2.37 (s, 3H). Mass Spectrum (LCMS, ESI pos.) Calcd. For C$_{25}$H$_{25}$N$_7$O$_2$: 456.51 (M+H), Found: 456.6.

EXAMPLE 14

8-indan-5-yl-2-(4-morpholin-4-yl-phenylamino)-5-oxo-5,8-dihydro-pyrido[2,3-d]pyrimidine-6-carboxylic acid amide

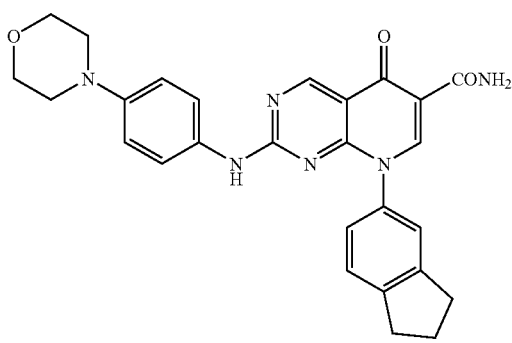

Using the procedure outlined in Example 7, the title compound was prepared from 8-indan-5-yl-2-(4-morpholin-4-yl-phenylamino)-5-oxo-5,8-dihydro-pyrido[2,3-d]pyrimidine-6-carboxylic acid ethyl ester (from Example 3 above, 9 mg, 0.017 mmol). 8-Indan-5-yl-2-(4-morpholin-4-yl-phenylamino)-5-oxo-5,8-dihydro-pyrido[2,3-d]pyrimidine-6-carboxylic acid amide was obtained as a yellow solid (8.6 mg, 100%). $^1$H NMR (400 MHz, CD$_2$Cl$_2$/CD$_3$OD (20:1 v/v)) δ (ppm): 9.22 (br, 1H), 8.68 (br, 1H), 7.35 (br, 1H), 7.10-7.26 (m, 4H), 6.57 (br, 2H), 3.75 (m, 4H), 2.96 (m, 8H), 2.11 (m, 2H). Mass Spectrum (LCMS, ESI pos.) Calcd. For C$_{27}$H$_{26}$N$_6$O$_3$: 483.21 (M+H), Found: 483.2.

EXAMPLE 15

2-(4-Dimethylamino-phenylamino)-8-indan-5-yl-5-oxo-5,8-dihydro-pyrido[2,3-d]pyrimidine-6-carboxylic acid amide (Cpd 15)

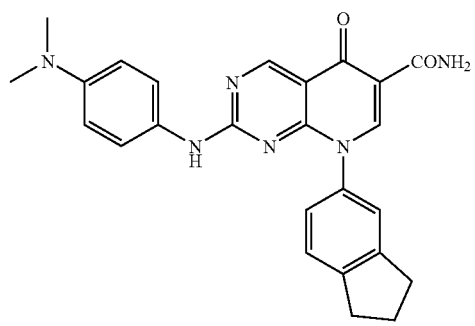

Using the procedure outlined in Example 7, the title compound was prepared from 2-(4-dimethylamino-phenylamino)-8-indan-5-yl-5-oxo-5,8-dihydro-pyrido[2,3-d]pyrimidine-6-carboxylic acid ethyl ester (from Example 4 above, 4.9 mg, 0.010 mmol). 2-(4-Dimethylamino-phenylamino)-8-indan-5-yl-5-oxo-5,8-dihydro-pyrido[2,3-d]pyrimidine-6-carboxylic acid amide was obtained as a yellow solid (3.8 mg, 83%). $^1$H NMR (400 MHz, CD$_2$Cl$_2$/CD$_3$OD (20:1 v/v)) δ (ppm): 9.19 (br, 1H), 8.68 (s, 1H), 7.66 (d, J=9.2 Hz, 1H), 7.35 (d, J=7.9 Hz, 1H), 7.22 (s, 1H), 7.11 (d, J=7.9 Hz, 1H), 6.68 (d, J=9.2 Hz, 1H), 6.38 (br, 1H), 2.94 (m, 4H), 2.79 (s, 6H), 1.96 (m, 2H). Mass Spectrum (LCMS, ESI pos.) Calcd. For C$_{25}$H$_{24}$N$_6$O$_2$: 4441.20 (M+H), Found: 441.2.

EXAMPLE 16

2-(3-Dimethylamino-phenylamino)-8-indan-5-yl-5-oxo-5,8-dihydro-pyrido[2,3-d]pyrimidine-6-carboxylic acid amide (Cpd 16)

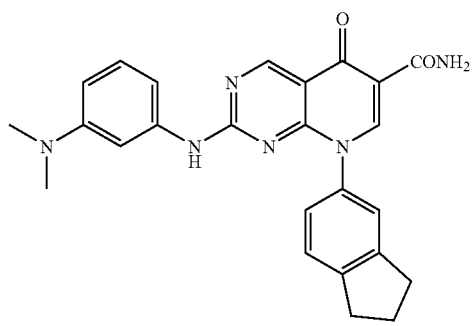

Using the procedure outlined in Example 7 the title compound was prepared from 2-(3-dimethylamino-phenylamino)-8-indan-5-yl-5-oxo-5,8-dihydro-pyrido[2,3-d]pyrimidine-6-carboxylic acid ethyl ester (from Example 5 above, 3.3 mg, 0.007 mmol). 2-(3-Dimethylamino-phenylamino)-8-indan-5-yl-5-oxo-5,8-dihydro-pyrido[2,3-d]pyrimidine-6-carboxylic acid amide was obtained as a yellow solid (2.7 mg, 88%). $^1$H NMR (400 MHz, CD$_2$Cl$_2$/CD$_3$OD (20:1 v/v)) δ (ppm): 9.26 (s, 1H), 8.68 (s, 1H), 7.33 (d, J=7.5 Hz, 1H), 7.22 (s, 1H), 7.18 (d, J=7.5 Hz, 1H), 6.84 (br, 1H), 6.80 (d, J=7.7 Hz, 1H), 6.54 (br, 1H), 6.36 (d, J=7.7 Hz, 1H), 2.96 (m, 4H), 2.71 (s, 6H), 2.10 (m, 2H). Mass Spectrum (LCMS, ESI pos.) Calcd. For C$_{25}$H$_{24}$N$_6$O$_2$: 441.20 (M+H), Found: 441.2.

EXAMPLE 17

8-Cyclohexyl-2-[4-(4-methyl-piperazin-1-yl)-phenylamino]-5-oxo-5,8-dihydro-pyrido[2,3-d]pyrimidine-6-carboxylic acid ethyl ester (Cpd 17)

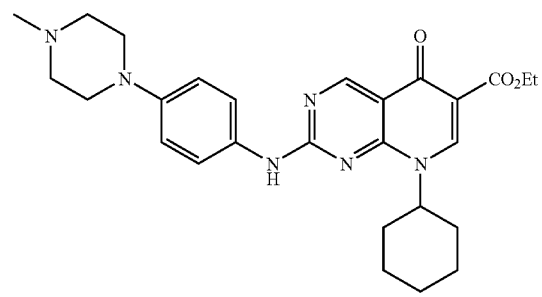

A. 3-Cyclohexylamino-propionic acid ethyl ester

Cyclohexylamine (0.86 g, 8.7 mmol) and 3-chloro-propionic acid ethyl ester (1.18 g, 8.67 mmol) were combined neat and K$_2$CO$_3$ (1.2 g, 8.7 mmol) and a catalytic amount of tetrabutylammonium iodide (ca. 5 mg) was added. The mixture was heated at 80° C. overnight. The resulting mixture was then partitioned between water and DCM. The organic layer was dried (MgSO$_4$) and concentrated to afford 1.25 g (72%) of the title compound. $^1$H-NMR (400 MHz, CDCl$_3$) δ ppm 4.14 (q, 2H, J=7.2 Hz), 2.90 (t, 2H, J=6.6 Hz), 2.50 (t, 2H, J=6.6 Hz), 1.86-1.89 (m, 2H), 1.70-1.75 (m, 2H), 1.58-1.62 (m, 2H), 1.25 (t, 1H, J=7.2 Hz).

B. 4-[Cyclohexyl-(2-ethoxycarbonyl-ethyl)-amino]-2-methylsulfanyl-pyrimidine-5-carboxylic acid ethyl ester 3-Cyclohexylamino-propionic acid ethyl ester (1.0 g, 5.0 mmol) and 4-chloro-2-methylsulfanyl-pyrimidine-5-carboxylic acid ethyl ester (1.17 g, 5.02 mmol) were combined in DCM (15 mL) and diisopropylethylamine (0.81 g, 6.3 mmol) was added. After 16 h, the solution was partitioned between water and DCM and the organic layer was dried (MgSO$_4$) and concentrated. Chromatography (0-20% EtOAc/hexanes gradient) provided 1.63 g (84%) of the title compound. $^1$H-NMR (400 MHz, CDCl$_3$) δ ppm 8.39 (s, 1H) 5.30 (s, 1H), 4.30 (q, 2H, J=7.1 Hz), 4.14 (q, 1H, J=7.1 Hz), 3.76-3.80 (m, 2H), 2.65-2.69 (m, 2H), 2.49 (s, 3H), 1.81-1.84 (m, 2H), 1.34-1.40 (m, 7H), 1.12-1.27 (m, 7H).

C. 8-Cyclohexyl-2-methylsulfanyl-5-oxo-5,6,7,8-tetrahydro-pyrido[2,3-d]pyrimidine-6-carboxylic acid ethyl ester Sodium (25 wt % dispersion in paraffin wax, 0.10 g, 3.8 mmol) was added to t-butanol (1.8 mL) at rt. After 10 minutes, a solution of 4-[cyclohexyl-(2-ethoxycarbonyl-ethyl)-amino]-2-methylsulfanyl-pyrimidine-5-carboxylic acid ethyl ester (1.0 g, 2.5 mmol) in 10 mL of toluene was added to the sodium t-butoxide solution and the resulting mixture was heated at 90° C. for 30 minutes. The reaction mixture was then cooled and the solution was adjusted to pH 7 using a 1N HCl solution. The solution was then extracted with EtOAc (2×20 mL) and the organic layer was dried (MgSO$_4$) and concentrated to provide 0.55 g, (42%) of the title compound. $^1$H NMR indicated the presence of both enol and keto forms in a 1:1.75 ratio. $^1$H-NMR (400 MHz, CDCl$_3$) δ ppm 8.63 (s, 1H), 8.18 (s, 1H), 4.76-4.82 (m), 4.58-4.68 (m), 4.16-4.36 (m), 3.91-3.96 (m), 3.60-3.64 (m), 3.46-3.49 (m), 2.53 (s, 3H), 2.50 (s, 5.25H), 1.86-1.89 (m), 1.71-1.73 (m), 1.32-1.56 (m), 1.26 (t, J=7.2 Hz), 1.10-1.21 (m).

D. 8-Cyclohexyl-2-methylsulfanyl-5-oxo-5,8-dihydro-pyrido[2,3-d]pyrimidine-6-carboxylic acid ethyl ester Bromine (0.15 g, 0.94 mmol) was added to a solution of 8-cyclohexyl-2-methylsulfanyl-5-oxo-5,6,7,8-tetrahydro-pyrido[2,3-d]pyrimidine-6-carboxylic acid ethyl ester (0.28 g, 0.79 mmol) in DCM (10 mL). After 5 min, the solution was concentrated and the crude residue was redissolved in DCM (10 mL) and diisopropylethylamine (0.42 mL, 2.4 mmol) was added. After 15 h, the reaction mixture was partitioned between water and DCM, the organic layer was separated, dried (MgSO$_4$) and concentrated to provide 0.28 g (87%) of the title compound.). Mass Spectrum (LCMS, ESI pos.) Calcd. For C$_{17}$H$_{21}$N$_3$O$_3$S: 347.13, found: (M+H) 348.3.

E. 8-Cyclohexyl-2-methanesulfonyl-5-oxo-5,8-dihydro-pyrido[2,3-d]pyrimidine-6-carboxylic acid ethyl ester m-CPBA (0.33 g, 1.5 mmol of a 70% w/w mixture) was added to a solution of 8-cyclohexyl-2-methylsulfanyl-5-oxo-5,8-dihydro-pyrido[2,3-d]pyrimidine-6-carboxylic acid ethyl ester (0.206 g, 0.59 mmol) in DCM (15 mL). After 2 hours, a 10% solution of Na$_2$SO$_3$ (1 mL) was added and the mixture was partitioned between sat. NaHCO$_3$ and DCM. The organic layer was dried (MgSO$_4$) and concentrated to provide 0.22 g of the title compound. Mass Spectrum (LCMS, ESI pos.) Calcd. For C$_{17}$H$_{21}$N$_3$O$_5$S: 379.12, found: (M+H) 380.1.

F. 8-Cyclohexyl-2-[4-(4-methyl-piperazin-1-yl)-phenylamino]-5-oxo-5,8-dihydro-pyrido[2,3-d]pyrimidine-6-carboxylic acid ethyl ester 8-Cyclohexyl-2-methanesulfonyl-5-oxo-5,8-dihydro-pyrido[2,3-d]pyrimidine-6-carboxylic acid ethyl ester (20 mg, 0.051 mmol) and 4-(4-methyl-piperazin-1-yl)-phenylamine (10 mg, 0.051 mmol) were combined in i-PrOH (2 mL) and heated to 80° C. After 14 h, the solution was concentrated and purified by preparative HPLC (30 mL/min 0-100% H$_2$O/MeCN gradient over 10 min) to provide 7.2 mg (29%) of 8-cyclohexyl-2-[4-(4-methyl-piperazin-1-yl)-phenylamino]-5-oxo-5,8-dihydro-pyrido[2,3-d]pyrimidine-6-carboxylic acid ethyl ester. $^1$H-NMR (400 MHz, CDCl$_3$:) δ ppm 9.32 (s, 1H), 8.31 (s, 1H), 7.57 (d, 2H, J=9.0 Hz), 6.96 (d, 1H, J=8.9 Hz), 4.40 (q, 2H, J=7.1 Hz), 3.25-3.46 (m, 8H), 2.82-2.84 (m, 3H), 1.49-2.0 (m, 8H), 1.41 (t, 3H, J=7.1 Hz). Mass Spectrum (LCMS, ESI pos.) Calcd. For C$_{27}$H$_{34}$N$_6$O$_3$: 490.27, found: (M+H) 491.3.

EXAMPLE 18

8-Cyclohexyl-2-(4-dimethylamino-phenylamino)-5-oxo-5,8-dihydro-pyrido[2,3-d]pyrimidine-6-carboxylic acid ethyl ester (Cpd 18)

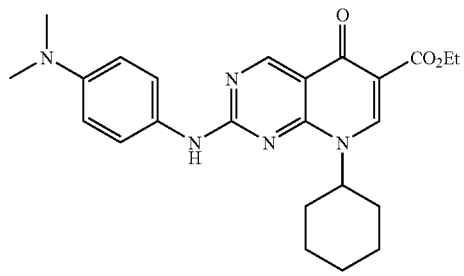

8-Cyclohexyl-2-methanesulfonyl-5-oxo-5,8-dihydro-pyrido[2,3-d]pyrimidine-6-carboxylic acid ethyl ester (Example 17E) (20 mg, 0.051 mmol) and 4-N,N-dimethylaminoaniline (7.8 mg, 0.057 mmol) were combined in i-PrOH (1 mL) and heated to 80° C. After 14 h, the solution was concentrated and purified by preparative HPLC (30 mL/min 0-100% H$_2$O/MeCN gradient over 10 min) to provide 3.4 mg of 8-cyclohexyl-2-(4-dimethylamino-phenylamino)-5-oxo-5,8-dihydro-pyrido[2,3-d]pyrimidine-6-carboxylic acid ethyl ester. $^1$H-NMR (400 MHz, CDCl$_3$:) δ ppm 9.34 (s, 1 H), 8.53 (s, 1 H), 7.73 (m, 1 H), 6.79-6.84 (m, 1 H), 6.62-6.64 (m, 1 H), 5.10-5.17 (m, 1 H), 4.40 (q, 2H, J=7.0 Hz), 3.01 (s, 6H), 2.46-2.07 (m, 10 H), 1.41 (t, 1H, J=7.0 Hz). Mass Spectrum (LCMS, ESI pos.) Calcd. For $C_{24}H_{29}N_5O_3$: 435.23, found: (M+H) 436.3.

EXAMPLE 19

8-Cyclopentyl-2-[4-(4-methyl-piperazin-1-yl)-phenylamino]-5-oxo-5,8-dihydro-pyrido[2,3-d]pyrimidine-6-carboxylic acid amide (Cpd 19)

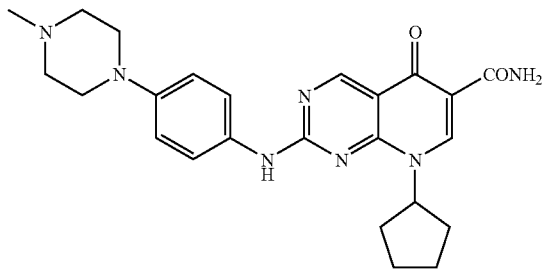

A. 3-Cyclopentylamino-propionic acid ethyl ester

Cyclopentylamine (1.72 g, 17.5 mmol) and 3-chloro-propionic acid ethyl ester (2.4 g, 18 mmol) were combined neat and $K_2CO_3$ (2.4 g, 18 mmol) and a catalytic amount of tetrabutylammonium iodide (ca. 5 mg) was added. The mixture was heated at 80° C. overnight. The resulting mixture was then partitioned between water and DCM. The organic layer was dried (MgSO$_4$) and concentrated to provide 2.68 g (83%) of the title compound. $^1$H-NMR (400 MHz, CDCl$_3$:) δ ppm 4.13 (p, 2H, J=7.0 Hz), 3.07 (p, 1H, J=6.7 Hz), 2.81-2.94 (m, 4H), 2.51 (t, 1H, J=6.5 Hz), 2.44 (t, 1H, J=7.4 Hz), 1.29-1.88 (m, 6H), 1.25 (t, 3H, J=7.1 Hz)

B. 8-Cyclopentyl-2-methylsulfanyl-5-oxo-5,6,7,8-tetrahydro-pyrido[2,3-d]pyrimidine-6-carboxylic acid ethyl ester 3-Cyclopentylamino-propionic acid ethyl ester (1.0 g, 5.4 mmol) and 4-chloro-2-methylsulfanyl-pyrimidine-5-carboxylic acid ethyl ester (1.25 g, 5.4 mmol) were combined in DCM (10 mL) and diisopropylethylamine (0.83 g, 6.5 mmol) was added. After 16 h, the solution was partitioned between water and DCM and the organic layer was dried (MgSO$_4$) and concentrated. Chromatography (0-20% EtOAc/hexanes gradient) provided the title compound that was directly carried on to the next step. Sodium (25 wt % dispersion in paraffin wax, 0.25 g, 6.0 mmol) was added to t-butanol (5.0 mL) at rt. After 10 minutes, a solution of 4-[cyclopentyl-(2-ethoxycarbonyl-ethyl)-amino]-2-methylsulfanyl-pyrimidine-5-carboxylic acid ethyl ester (2.0 g, 5.4 mmol) in 10 mL of toluene was added to the sodium t-butoxide solution and the resulting mixture was heated at 90° C. for 30 minutes. The reaction mixture was then cooled and the solution was adjusted to pH 7 using a 1N HCl solution. The solution was then extracted with EtOAc (2×20 mL) and the organic layer was dried (MgSO$_4$) and concentrated to provide 0.26 g (14%). $^1$H-NMR (400 MHz, CDCl$_3$:) δ ppm 12.0 (br s, 1H), 8.20 (s, 1H), 5.10-5.18 (m, 1H), 4.26-4.31 (m, 3H), 3.72 (q, 2H, J=7.0 Hz), 2.50 (s, 3H), 1.63-1.86 (m, 5H), 1.20-1.35 (m, 5H).

C. 8-Cyclopentyl-2-methylsulfanyl-5-oxo-5,8-dihydro-pyrido[2,3-d]pyrimidine-6-carboxylic acid ethyl ester Bromine (0.13 g, 0.82 mmol) was added to a solution of 8-Cyclopentyl-2-methylsulfanyl-5-oxo-5,6,7,8-tetrahydro-pyrido[2,3-d]pyrimidine-6-carboxylic acid ethyl ester (0.34 g, 0.82 mmol) in DCM (5 mL). After 15 min, the solution was concentrated and the crude residue was redissolved in DCM (5 mL) and triethylamine (0.16 mL, 0.24 mmol) was added. After 15 h, the reaction mixture was partitioned between water and DCM, the organic layer was separated, dried (MgSO$_4$) and concentrated to provide the title compound. Mass Spectrum (LCMS, ESI pos.) Calcd. For $C_{16}H_{19}N_3O_3S$: 333.11, found: (M+H) 334.1.

D. 8-Cyclopentyl-2-methanesulfonyl-5-oxo-5,8-dihydro-pyrido[2,3-d]pyrimidine-6-carboxylic acid ethyl ester m-CPBA (0.45 g, 2.05 mmol of a 77% powder) was added to a solution of 8-cyclopentyl-2-methylsulfanyl-5-oxo-5,8-dihydro-pyrido[2,3-d]pyrimidine-6-carboxylic acid ethyl ester (0.27 g, 0.82 mmol) in DCM (5 mL). After 2 hours, a 10% solution of Na$_2$SO$_3$ (2 mL) was added and the mixture was partitioned between sat. NaHCO$_3$ and DCM. The organic layer was dried (MgSO$_4$) and concentrated to provide the title compound. Mass Spectrum (LCMS, ESI pos.) Calcd. For $C_{16}H_{19}N_3O_5S$: 365.10, found: (M+H) 366.1.

E. 8-Cyclopentyl-2-[4-(4-methyl-piperazin-1-yl)-phenylamino]-5-oxo-5,8-dihydro-pyrido[2,3-d]pyrimidine-6-carboxylic acid amide 8-Cyclopentyl-2-methanesulfonyl-5-oxo-5,8-dihydro-pyrido[2,3-d]pyrimidine-6-carboxylic acid ethyl ester (45 mg, 0.12 mmol) and 4-(4-methyl-piperazin-1-yl)-phenylamine (23 mg, 0.12 mmol) were combined in i-PrOH (1 mL) and heated to 80° C. After 14 h, the solution was concentrated and purified by preparative HPLC (30 mL/min 0-100% H$_2$O/MeCN gradient over 10 min) to provide 19.8 mg of 8-cyclopentyl-2-[4-(4-methyl-piperazin-1-yl)-phenylamino]-5-oxo-5,8-dihydro-pyrido[2,3-d]pyrimidine-6-carboxylic acid ethyl ester. The ester was dissolved in MeOH (2 mL) and cooled to −78° C. in a high pressure vessel. Ammonia was bubbled into the solution for 1 min and the vessel was sealed and allowed to warm to rt. After 14 h, the solution was cooled to −78° C., the vessel was opened and the solution was allowed to warm to rt. The solution was concentrated to provide 5.4 mg of 8-cyclopentyl-2-[4-(4-methyl-piperazin-1-yl)-phenylamino]-5-oxo-5,8-dihydro-pyrido[2,3-d]pyrimidine-6-carboxylic acid amide. $^1$H-NMR (400 MHz, CDCl$_3$:) δ ppm 9.30 (s, 1H), 8.51 (s, 1H), 8.34 (s, 1H), 7.53 (d, 2H, J=8.9 Hz), 6.94 (d, 2H, J=9.0 Hz), 5.23-5.52 (m, 4H), 4.38 (q, 2H, J=7.1 Hz), 3.34-3.36 (m, 4H), 3.00-3.01 (m, 4H), 2.60 (s, 3H), 2.21-2.28 (m, 2H), 1.80-1.93 (m, 6H), 1.40 (t, 3H, J=7.1 Hz). Mass Spectrum (LCMS, ESI pos.) Calcd. For $C_{26}H_{32}N_6O_3$: 476.25, found: (M+H) 477.3.

EXAMPLE 20

2-(3-Hydroxymethyl-phenylamino)-8-indan-5-yl-5-oxo-5,8-dihydro-pyrido[2,3-d]pyrimidine-6-carboxylic acid amide (Cpd 20)

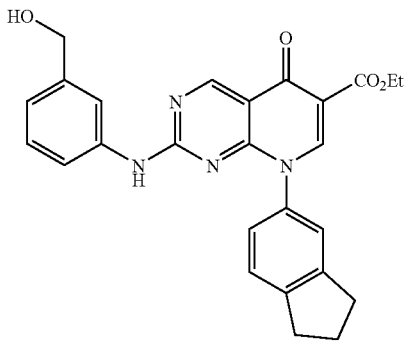

Using the procedure outlined in Example 1(g) the title compound was prepared from (3-amino-phenyl)-methanol (3.2 mg, 0.026 mmol) and 8-indan-5-yl-2-methanesulfonyl-5-oxo-5,8-dihydro-pyrido[2,3-d]pyrimidine-6-carboxylic acid ethyl ester (from Example 1(e) above, 10 mg, 0.026 mmol). 2-(3-Hydroxymethyl-phenylamino)-8-indan-5-yl-5-oxo-5,8-dihydro-pyrido[2,3-d]pyrimidine-6-carboxylic acid amide was obtained as a white solid. $^1$H NMR (400 MHz, CDCl$_3$) δ (ppm): 9.37 (br s, 1H), 8.50 (s, 1H), 7.35-7.45 (m, 3H), 7.02-7.21 (m, 3H), 5.30 (s, 2H), 4.43 (br s, 1H), 4.39 (dd, 2H, J=7.1 Hz, J=14.3 Hz), 3.05 (td, 4H, J=7.5 Hz, J=28.2 Hz), 2.20-2.27 (m, 2H), 1.39 (t, 3H, J=7.1 Hz). Mass Spectrum (LCMS, ESI pos.) Calcd. For C$_{24}$H$_{21}$N$_5$O$_3$: 427.16, found: (M+H) 428.1.

EXAMPLE 21

2-(4-Fluoro-phenylamino)-8-indan-5-yl-5-oxo-5,8-dihydro-pyrido[2,3-d]pyrimidine-6-carboxylic acid ethyl ester (Cpd 21)

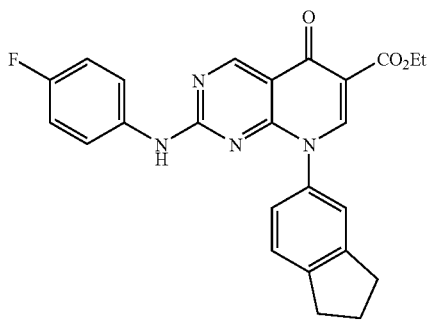

Using the procedure outlined in Example 1(g) 2-(4-fluoro-phenylamino)-8-indan-5-yl-5-oxo-5,8-dihydro-pyrido[2,3-d]pyrimidine-6-carboxylic acid ethyl ester was prepared from 4-fluoroaniline (6 mg, 0.05 mmol) and 8-indan-5-yl-2-methanesulfonyl-5-oxo-5,8-dihydro-pyrido[2,3-d]pyrimidine-6-carboxylic acid ethyl ester (from Example 1(e) above, 21 mg, 0.050 mmol). Purification by preparative HPLC (30 mL/min 0-100% H$_2$O/MeCN gradient over 10 min) provided 2-(4-fluoro-phenylamino)-8-indan-5-yl-5-oxo-5,8-dihydro-pyrido[2,3-d]pyrimidine-6-carboxylic acid ethyl ester (3.6 mg). $^1$H NMR (400 MHz, CDCl$_3$) δ (ppm): 9.21 (s, 1H), 8.44 (s, 1H), 7.84-7.94 (m, 1H), 7.10-7.48 (m, 6H), 4.23 (dd, 1H, J=7.2 Hz, J=14.5 Hz), 2.96 (td, 1H, J=7.3 Hz, J=25.1 Hz), 2.10-2.18 (m, 2H), 1.18-1.40 (m, 7H).). Mass Spectrum (LCMS, ESI pos.) Calcd. For C$_{25}$H$_{21}$FN$_4$O$_3$: 444.16.14, found: (M+H) 445.1.

EXAMPLE 22

8-Indan-5-yl-5-oxo-2-(4-pyrazol-1-yl-phenylamino)-5,8-dihydro-pyrido[2,3-d]pyrimidine-6-carboxylic acid amide (Cpd 22)

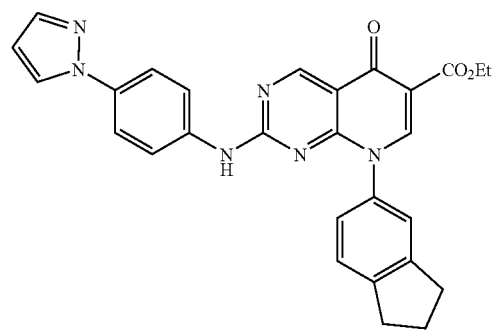

Using the procedure outlined in Example 1(g) 8-indan-5-yl-5-oxo-2-(4-pyrazol-1-yl-phenylamino)-5,8-dihydro-pyrido[2,3-d]pyrimidine-6-carboxylic acid amide was prepared from 4-pyrazol-1-yl-phenylamine (8.0 mg, 0.053 mmol) and 8-indan-5-yl-2-methanesulfonyl-5-oxo-5,8-dihydro-pyrido[2,3-d]pyrimidine-6-carboxylic acid ethyl ester (from Example 1(e) above, 20 mg, 0.053 mmol). 8-Indan-5-yl-5-oxo-2-(4-pyrazol-1-yl-phenylamino)-5,8-dihydro-pyrido[2,3-d]pyrimidine-6-carboxylic acid amide was obtained as a white solid. $^1$H NMR (400 MHz, CDCl$_3$) δ (ppm): 9.30(br s, 1H), 8.48 (s, 1H), 7.75 (s, 1H), 7.64 (s, 1H), 7.13-7.23 (m, 5H), 6.39 (s, 1H), 4.31 (q, 1H, J=7.1 Hz), 3.02 (t, 1H, J=7.3 Hz), 2.94 (t, 1H, J=7.3 Hz), 2.17 (p, 1H, J=7.5 Hz), 1.32 (t, 1H, J=7.1 Hz). Mass Spectrum (LCMS, ESI pos.) Calcd. For C$_{26}$H$_{21}$N$_7$O$_2$: 463.18, found: (M+H) 464.1.

EXAMPLE 23

8-Indan-5-yl-2-[3-(4-methyl-piperazin-1-ylmethyl)-phenylamino]-5-oxo-5,8-dihydro-pyrido[2,3-d]pyrimidine-6-carboxylic acid amide (Cpd 23)

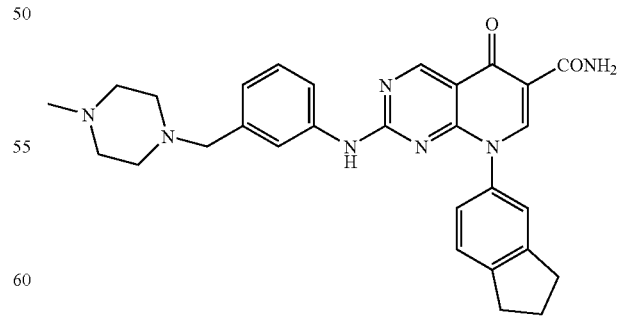

A. 3-(4-Methyl-piperazin-1-ylmethyl)-phenylamine m-Nitrobenzyl bromide (500 mg, 2.31 mmol) was added to a mixture of 1-methylpiperazine (277 mg, 2.77 mmol) and potassium carbonate (414 g, 3.0 mmol) in 5 mL of DMF. The mixture was stirred at 90° C. for 16 hours. After cooling to room temperature, the mixture was extracted into ethyl acetate (EtOAc), washed with water, brine and then dried with sodium sulfate (Na$_2$SO$_4$). Removal of the solvent and chromatography on silica, eluting with EtOAc/CH$_3$OH/ NH$_4$OH (10:1:0.1, v/v), gave 510 mg of 1-methyl-4-(3-nitrobenzyl)-piperazine, which was converted to the title compound under normal hydrogenation conditions. The titled compound was obtained as a yellow solid (450 mg, 95%). $^1$H NMR (400 MHz, CDCl$_3$) δ (ppm): 7.02 (t, J=7.6 Hz, 1H), 6.62 (s, 1H), 6.60 (d, J=7.6 Hz, 1H), 6.54 (d, J=7.6 Hz, 1H), 3.43 (s, 2H), 2.76 (br, 4H), 2.65 (br, 4H), 2.82 (m, 4H), 2.46 (s, 3H).

B. 8-Indan-5-yl-2-methanesulfonyl-5-oxo-5,8-dihydro-pyrido[2,3-d]pyrimidine-6-carboxylic acid amide 8-Indan-5-yl-2-methylsulfanyl-5-oxo-5,8-dihydro-pyrido [2,3-d]pyrimidine-6-carboxylic acid ethyl ester (from Example 1(d), 200 mg, 0.52 mmol) was dissolved in 2 mL of CH$_3$OH. To the solution was bubbled ammonia at −78° C. for 5 minutes in a pressure bottle (15 mL). The bottle was capped and warmed up to room temperature and stirred for 16 hours. The solvent was evaporated to leave an off-white solid. The solid was suspended in 50 mL of CH$_2$Cl$_2$. To the mixture was added m-CPBA (69.5%, 325 mg, 1.3 mmol). The mixture was stirred at r.t. for 4 hrs. An aqueous solution of 10% sodium thiosulfate was added to quench the reaction. After 30 minutes saturated sodium bicarbonate solution was added, and the aqueous solution was extracted by CH$_2$Cl$_2$. The combined CH$_2$Cl$_2$ solution was washed with brine and dried over Na$_2$SO$_4$. Removal of the solvent and chromatography on silica, eluting with EtOAc/hexanes (1:1-2:1, v/v) gave 0.18 g (90%) of the title compound as an off-white solid. $^1$H NMR (400 MHz, DMSO-d$_6$) δ (ppm): 9.75 (s, 1H), 8.75 (s, 1H), 8.69 (d, J=3.3 Hz, 1H), 7.87 (d, J=3.3 Hz, 1H), 7.49 (s, 1H), 7.46 (d, J=8.0 Hz, 1H), 7.38 (d, J=8.0 Hz, 1H), 3.19 (s, 3H), 2.93 (m, 4H), 2.10 (m, 2H).

C. 8-Indan-5-yl-2-[3-(4-methyl-piperazin-1-ylmethyl)-phenylamino]-5-oxo-5,8-dihydro-pyrido[2,3-d]pyrimidine-6-carboxylic acid amide To a suspension of 8-indan-5-yl-2-methanesulfonyl-5-oxo-5,8-dihydro-pyrido[2,3-d]pyrimidine-6-carboxylic acid amide (from Example 23 (b), 7 mg) in 1 mL of i-PrOH was added 3-(4-methyl-piperazin-1-ylmethyl)-phenylamine (5 mg). The mixture was stirred at 90° C. for 1 hr. After cooling down, the solvent was evaporated and the product was purified chromatographically (CH$_2$Cl$_2$/CH$_3$OH/NH$_4$OH (10:1: 0.1, v/v)). The title compound was obtained as white solid (2.7 mg, 29%). $^1$H NMR (400 MHz, CDCl$_3$) δ (ppm): 9.39 (br, 1H), 9.34 (s, 1H), 8.76 (s, 1H), 7.48 (br, 1H), 7.35 (d, J=8.0 Hz, 1H), 7.29 (br, 1H), 7.17 (s, 1H), 7.12 (d, J=8.0 Hz, 1H), 6.94 (br, 2H), 5.67 (br, 1H), 3.29 (br, 2H), 3.00 (t, J=7.3 Hz, 2H), 2.92 (t, J=7.3 Hz, 2H), 2.49 (br, 7H), 2.33 (br, 4H), 2.15 (m, 2H). Mass Spectrum (LCMS, ESI pos.) Calcd. For C$_{29}$H$_{31}$N$_7$O$_2$: 510.25 (M+H), Found: 510.1.

EXAMPLE 24

8-Indan-5-yl-2-(3-morpholin-4-ylmethyl-phenylamino)-5-oxo-5,8-dihydro-pyrido[2,3-d]pyrimidine-6-carboxylic acid amide (Cpd 24)

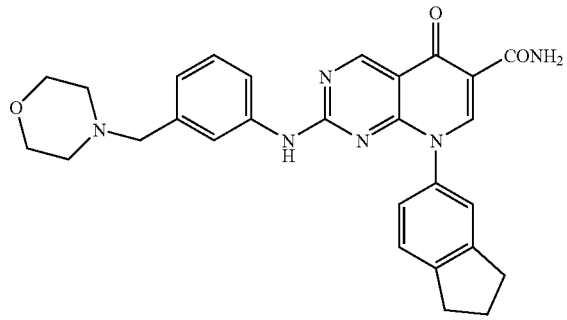

Using the procedure outlined in Example 23 (a and c), the title compound was prepared from 3-morpholin-4-ylmethyl-phenylamine (5 mg) and 8-indan-5-yl-2-methanesulfonyl-5-oxo-5,8-dihydro-pyrido[2,3-d]pyrimidine-6-carboxylic acid amide (from Example 23 (b), 7 mg). Purification by preparative HPLC (32 mL/min, 5-100% H$_2$O/MeCN (0.01% TFA, v/v) gradient over 10 min) gave the title compound as a white solid (3.9 mg, 35%). $^1$H NMR (400 MHz, CDCl$_3$) δ (ppm): 9.55 (br, 1H), 9.42 (s, 1H), 8.83 (s, 1H), 7.60 (br, 1H), 7.50 (br, 1H), 7.43 (d, J=8.0 Hz, 1H), 7.24 (s, 1H), 7.21 (d, J=8.0 Hz, 1H), 7.13 (br, 2H), 6.23 (br, 1H), 4.00 (br, 4H), 3.32 (br, 2H), 3.08 (t, J=7.3 Hz, 2H), 3.00 (t, J=7.3 Hz, 2H), 2.72 (br, 2H), 2.23 (m, 2H). Mass Spectrum (LCMS, ESI pos.) Calcd. For C$_{28}$H$_{28}$N$_6$O$_3$: 497.22 (M+H), Found: 497.1.

EXAMPLE 25

2-[2-Hydroxy-4-(4-methyl-piperazin-1-yl)-phenylamino]-8-indan-5-yl-5-oxo-5,8-dihydro-pyrido[2,3-d]pyrimidine-6-carboxylic acid amide (Cpd 25)

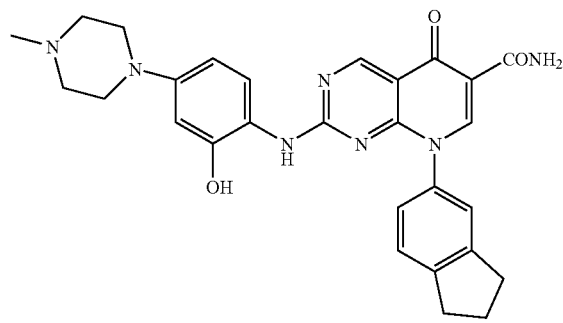

Using the procedure outlined in Example 23 (c), the title compound was prepared from 2-amino-5-(4-methyl-piperazin-1-yl)-phenol (5 mg, prepared using the procedure outlined in Example 1 (F) from 1-fluoro-2-hydroxy-4-nitrobenzene and 1-methyl-piperazine) and 8-indan-5-yl-2-methanesulfonyl-5-oxo-5,8-dihydro-pyrido[2,3-d] pyrimidine-6-carboxylic acid amide (from Example 23 (b), 7 mg). Purification by preparative HPLC (32 mL/min, 5-100% H$_2$O/MeCN (0.01% TFA, v/v) gradient over 10 min) followed by a basic aqueous work-up gave the title compound as a yellow solid (3.7 mg, 40%). $^1$H NMR (400 MHz, CD$_3$OD) δ (ppm): 9.25 (br, 1H), 8.73 (s, 1H), 7.44 (d, J=8.4 Hz, 2H), 7.36 (s, 1H), 7.25 (d, J=7.1 Hz, 1H), 6.45 (s, 1H), 6.02 (br, 1H), 3.20 (br, 2H), 3.03 (m, 6H), 2.65 (s, 3H), 2.22 (m, 2H). Mass Spectrum (LCMS, ESI pos.) Calcd. For C$_{28}$H$_{29}$N$_7$O$_3$: 512.23 (M+H), Found: 512.1.

EXAMPLE 26

1-Indan-5-yl-7-[4-(4-methyl-piperazin-1-yl)-phenylamino]-4-oxo-1,4-dihydro-[1,6]naphthyridine-3-carboxylic acid amide (Cpd 26)

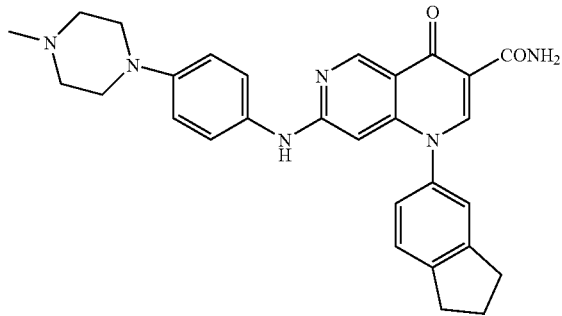

A. 4,6-Dichloro-nicotinic acid ethyl ester

Diethyl 1,3-acetonedicarboxylate (10 mL, 49.5 mmol) was taken in 10 mL of acetic anhydride. To the solution was added trimethylorthoformate (8.2 mL, 49.5 mmol). The mixture was heated to 120° C. for 3 hours. The reaction was then cooled and 10 mL of NH$_4$OH (30%) was added. After stirring for additional 1 hour, the solution was triturated for 3 times in CH$_2$Cl$_2$ to afford 7.3 g of an off-white solid. The solid was suspended in 10 mL of POCl$_3$ and the mixture was heated at 100° C. for 6 hours. The reaction was cooled, quenched with water, and extracted 3 times with EtOAc. The organic layer was dried over Na$_2$SO$_4$ and concentrated in vacuo. Flash chromatography (EtOAc/Hexanes, 1:10 v/v) afforded the title compound as a white solid (6 g, 68%). $^1$H NMR (400 MHz, CDCl$_3$) δ (ppm): 8.79 (s, 1H), 7.42 (s, 1H), 4.38 (q, J=7.1 Hz, 2H), 1.37 (t, J=7.1 Hz, 3H).

B. 6-Chloro-4-[(2-ethoxycarbonyl-ethyl)-indan-5-yl-amino]-nicotinic acid ethyl ester To a solution of 4,6-dichloro-nicotinic acid ethyl ester (2 g, 9 mmol) and 3-(indan-5-ylamino)-propionic acid ethyl ester (from Example 1 (A), 2.3 g, 10 mmol) in 5 mL of DMF was added triethylamine (2 g, 20 mmol). The mixture was stirred at 100° C. for 48 hours. The reaction was cooled, quenched with water, and extracted 3 times with EtOAc. The organic layer was dried over Na$_2$SO$_4$ and concentrated in vacuo. Flash chromatography (EtOAc/Hexanes, 2:10 v/v) afforded the title compound as a white solid (1.6 g, 44%). $^1$H NMR (400 MHz, CDCl$_3$) δ (ppm): 8.22 (s, 1H), 7.15 (d, J=8.0 Hz, 1H), 6.92 (s, 1H), 6.85 (m, 2H), 4.03-4.15 (m, 4H), 3.74 (q, J=7.1 Hz, 2H), 2.85 (t, J=7.4 Hz, 4H), 2.64 (m, 2H), 2.07 (m, 2H), 1.23 (t, J=7.1 Hz, 3H), 1.08 (t, J=7.1 Hz, 3H).

C. 7-Chloro-1-indan-5-yl-4-oxo-1,4-dihydro-[1,6]naphthyridine-3-carboxylic acid ethyl ester Using the procedures outlined in Example 1 (C and D), the title compound was prepared from 6-chloro-4-[(2-ethoxycarbonyl-ethyl)-indan-5-yl-amino]-nicotinic acid ethyl ester (1.6 g, 4 mmol). A white solid was obtained (500 mg, 34%). $^1$H NMR (300 MHz, CDCl$_3$) δ (ppm): 9.38 (s, 1H), 8.46 (s, 1H), 7.47 (d, J=7.8 Hz, 1H), 7.23 (s, 1H), 7.14 (dd, J=2.2 Hz, J=7.8 Hz, 1H), 6.88 (s, 1H), 4.36 (q, J=7.1 Hz, 2H), 3.04 (m, 4H), 2.22 (m, 2H), 1.38 (t, J=7.1 Hz, 3H).

D. 1-Indan-5-yl-7-[4-(4-methyl-piperazin-1-yl)-phenylamino]-4-oxo-1,4-dihydro-[1,6]naphthyridine-3-carboxylic acid amide To a solution of 7-chloro-1-indan-5-yl-4-oxo-1,4-dihydro-[1,6]naphthyridine-3-carboxylic acid ethyl ester (40 mg, 0.11 mmol) and 4-(4-Methyl-piperazin-1-yl)-phenylamine (45 mg, 0.23 mmol) in 1 mL of NMP was added triethylamine (24 mg, 0.24 mmol). The reaction was heated in a microwave reactor at 200° C. for 2 hours. The solvent was evaporated under vacuo and the product was purified by preparative HPLC (32 mL/min, 5-100% H$_2$O/MeCN (0.01% TFA, v/v) gradient over 15 min). The title compound was obtained as a yellow solid (6.9 mg, 10%). $^1$H NMR (400 MHz, CD$_3$OD) δ (ppm): 9.11 (s, 1H), 8.57 (s, 1H), 7.45 (d, J=7.9 Hz, 1H), 7.35 (m, 3H), 7.25 (dd, J=1.9 Hz, J=7.9 Hz, 1H), 6.96 (d, J=8.8 Hz, 2H), 6.13 (s, 1H), 3.40-3.80 (br, 8H), 3.01 (m, 4H), 2.96 (s, 3H), 2.17 (m, 2H). Mass Spectrum (LCMS, ESI pos.) Calcd. For C$_{29}$H$_{30}$N$_6$O$_2$: 495.24 (M+H), Found: 495.1.

EXAMPLE 27

8-Indan-5-yl-2-[4-(2-morpholin-4-yl-ethyl)-phenylamino]-5-oxo-5,8-dihydro-pyrido[2,3-d]pyrimidine-6-carboxylic acid amide (Cpd 27)

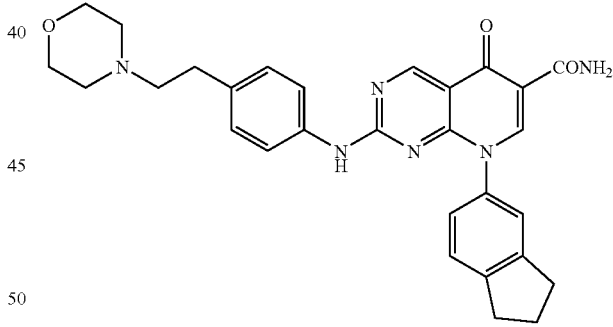

A. 4-(2-Morpholin-4-yl-ethyl)-phenylamine 1-(2-Bromo-ethyl)-4-nitro-benzene (1 g, 4.3 mmol) was added to a mixture of morpholine (435 μL, 5 mmol) and potassium carbonate (690 mg, 5.0 mmol) in 5 mL of DMSO. The mixture was stirred at 100° C. for 1 hour. After cooling to room temperature, the mixture was extracted into ethyl acetate (EtOAc), washed with water, brine and then dried with sodium sulfate (Na$_2$SO$_4$). Removal of the solvent and chromatography on silica, eluting with EtOAc/CH$_3$OH/NH$_4$OH (10:1:0.1, v/v), gave 950 mg of 4-[2-(4-nitro-phenyl)-ethyl]-morpholine, which was converted to the title compound under normal hydrogenation conditions. The title compound was obtained as a yellow solid (880 mg, 99%). $^1$H NMR (400 MHz, CDCl$_3$) δ (ppm): 6.98 (d, J=8.2 Hz, 2H), 6.61 (d, J=8.2 Hz, 2H), 3.73 (t, J=4.5 Hz, 4H), 3.57 (br, 2H), 2.64-2.71 (m, 2H), 2.45-2.56 (m, 6H).

B. 8-Indan-5-yl-2-[4-(2-morpholin-4-yl-ethyl)-phenylamino]-5-oxo-5,8-dihydro-pyrido[2,3-d]pyrimidine-6-carboxylic acid ethyl ester Using the procedure outlined in Example 1(g) the title compound was prepared from 4-(2-morpholin-4-yl-ethyl)-phenylamine (49 mg, 0.24 mmol) and 8-indan-5-yl-2-methanesulfonyl-5-oxo-5,8-dihydro-pyrido[2,3-d]pyrimidine-6-carboxylic acid ethyl ester (from Example 1(e) above, 100 mg, 0.24 mmol). The title compound was obtained as a yellow solid (60 mg, 46%). $^1$H NMR (400 MHz, CDCl$_3$) δ (ppm): 9.29 (s, 1H), 8.45 (s, 1H), 7.50 (br, 1H), 7.37 (d, J=7.9 Hz, 1H), 7.21 (m, 3H), 7.13 (d, J=7.8 Hz, 1H), 6.87 (br, 2H), 4.31 (q, J=7.0 Hz, 2H), 3.69 (br, 4H), 2.96 (t, J=7.4 Hz, 2H), 2.91 (t, J=7.4 Hz, 2H), 2.67 (br, 2H), 2.46 (br, 6H), 2.17 (m, 2H), 1.30 (t, J=7.1 Hz, 3H).

C. 8-Indan-5-yl-2-[4-(2-morpholin-4-yl-ethyl)-phenylamino]-5-oxo-5,8-dihydro-pyrido[2,3-d]pyrimidine-6-carboxylic acid amide Using the procedure outlined in Example 7 the title compound was prepared from 8-indan-5-yl-2-[4-(2-morpholin-4-yl-ethyl)-phenylamino]-5-oxo-5,8-dihydro-pyrido[2,3-d]pyrimidine-6-carboxylic acid ethyl ester (20 mg, 0.037 mmol). A yellow solid was obtained (15.8 mg, 84%). $^1$H NMR (400 MHz, DMSO-d$_6$) δ (ppm): 10.37 (br, 1H), 9.22 (s, 1H), 9.01 (s, 1H), 8.54 (s, 1H), 7.64 (m, 1H), 7.47 (m, 2H), 7.32 (m, 2H), 6.87 (br, 2H), 3.55 (m, 4H), 3.01 (t, J=7.3 Hz, 2H), 2.93 (t, J=7.4 Hz, 2H), 2.61 (m, 2H), 2.37 (m, 6H), 2.14 (m, 2H). Mass Spectrum (LCMS, ESI pos.) Calcd. For C$_{29}$H$_{30}$N$_6$O$_3$: 511.24 (M+H), Found 511.0.

EXAMPLE 28

8-Indan-5-yl-2-[4-(2-morpholin-4-yl-ethyl)-phenylamino]-5-oxo-5,8-dihydro-pyrido[2,3-d]pyrimidine-6-carboxylic acid methyl amide (Cpd 28)

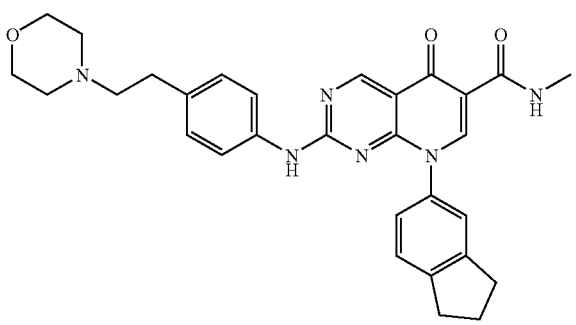

To a solution of 8-indan-5-yl-2-[4-(2-morpholin-4-yl-ethyl)-phenylamino]-5-oxo-5,8-dihydro-pyrido[2,3-d]pyrimidine-6-carboxylic acid ethyl ester (Example 27 (b), 20 mg, 0.037 mmol) in 1 mL methanol was added a solution of methylamine in THF (2N, 2 mL). The mixture was stirred at 80° C. for 4 hours. The solvent was removed by vacuum to leave a yellow solid (17 mg, 87%). $^1$H NMR (400 MHz, CDCl$_3$) δ (ppm): 10.60 (br, 1H), 9.29 (s, 1H), 8.78 (s, 1H), 7.75 (s, 1H), 7.60 (br, 1H), 7.34 (d, J=7.6 Hz, 1H), 7.20 (m, 2H), 7.12 (d, J=7.6 Hz, 1H), 6.87 (br, 2H), 3.69 (br, 4H), 3.01 (t, J=7.3 Hz, 2H), 2.94 (m, 5H), 2.65 (br, 2H), 2.49 (br, 6H), 2.17 (m, 2H). Mass Spectrum (LCMS, ESI pos.) Calcd. For C$_{30}$H$_{32}$N$_6$O$_3$: 525.25 (M+H), Found 525.0.

EXAMPLE 29

8-Indan-5-yl-2-[4-(2-morpholin-4-yl-ethyl)-phenylamino]-5-oxo-5,8-dihydro-pyrido[2,3-d]pyrimidine-6-carboxylic acid ethyl amide (Cpd 29)

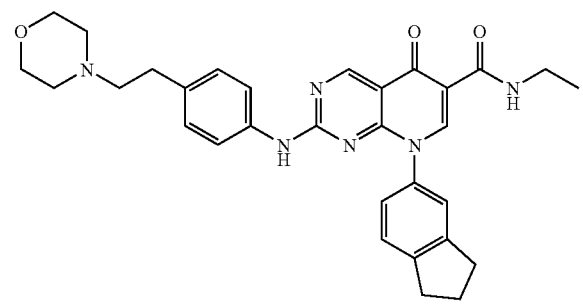

To a solution of 8-indan-5-yl-2-[4-(2-morpholin-4-yl-ethyl)-phenylamino]-5-oxo-5,8-dihydro-pyrido[2,3-d]pyrimidine-6-carboxylic acid ethyl ester (Example 27 (b), 20 mg, 0.037 mmol) in 1 mL methanol was added a solution of ethylamine in THF (2N, 2 mL). The mixture was stirred at 80° C. for 16 hours. The solvent was removed by vacuum to leave a yellow solid (12.7 mg, 64%). $^1$H NMR (400 MHz, CDCl$_3$) δ (ppm): 10.60 (br, 1H), 9.29 (s, 1H), 8.78 (s, 1H), 7.75 (s, 1H), 7.60 (br, 1H), 7.34 (d, J=7.6 Hz, 1H), 7.20 (m, 2H), 7.12 (d, J=7.6 Hz, 1H), 6.87 (br, 2H), 3.69 (br, 4H), 3.42 (q, J=7.1 Hz, 2H), 3.01 (t, J=7.3 Hz, 2H), 2.93 (t, J=7.4 Hz, 2H), 2.65 (br, 2H), 2.49 (br, 6H), 2.17 (m, 2H). 1.08 (t, 7.1 Hz, 3H). Mass Spectrum (LCMS, ESI pos.) Calcd. For C$_{31}$H$_{34}$N$_6$O$_3$: 539.27 (M+H), Found 539.0.

EXAMPLE 30

(4S)-8-Indan-5-yl-5-oxo-2-[4-(2-oxo-oxazolidin-4-ylmethyl)-phenylamino]-5,8-dihydro-pyrido[2,3-d]pyrimidine-6-carboxylic acid amide (Cpd 30)

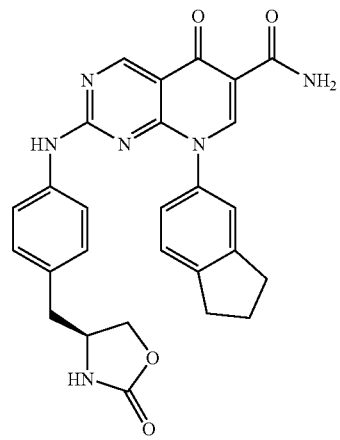

A. (4S)-8-Indan-5-yl-5-oxo-2-[4-(2-oxo-oxazolidin-4-ylmethyl)-phenylamino]-5,8-dihydro-pyrido[2,3-d]pyrimidine-6-carboxylic acid ethyl ester Using the procedure outlined in Example 1(g) the title compound was prepared from (4S)-4-(4-amino-benzyl)-1,3-oxazolidin-2-one (46 mg, 0.24 mmol) and 8-indan-5-yl-2-methanesulfonyl-5-oxo-5,8-dihydro-pyrido[2,3-d]pyrimidine-6-carboxylic acid ethyl ester (from Example 1(e) above, 100 mg, 0.24 mmol). The title compound was obtained as a white solid (56 mg, 44%). $^1$H NMR (400 MHz, CDCl$_3$) δ (ppm): 9.00 (br, 1H), 8.42 (s, 1H), 7.50 (br, 1H), 7.33 (d, J=7.9 Hz, 1H), 7.28 (br, 2H), 7.18 (s, 1H), 7.08 (d, J=7.8 Hz, 1H), 6.81 (br, 2H), 5.88 (s, 1H), 4.41 (t, J=8.2 Hz, 1H), 4.31 (q, J=7.0 Hz, 2H), 4.05 (m, 1H), 3.98 (m, 1H), 2.99 (t, J=7.4 Hz, 2H), 2.92 (t, J=7.4 Hz, 2H), 2.79-2.66 (m, 2H), 2.15 (m, 2H), 1.31 (t, J=7.1 Hz, 3H).

B. (4S)-8-Indan-5-yl-5-oxo-2-[4-(2-oxo-oxazolidin-4-ylmethyl)-phenylamino]-5,8-dihydro-pyrido[2,3-d]pyrimidine-6-carboxylic acid amide Using the procedure outlined in Example 7 the title compound was prepared from (4S)-8-indan-5-yl-5-oxo-2-[4-(2-oxo-oxazolidin-4-ylmethyl)-phenylamino]-5,8-dihydro-pyrido[2,3-d]pyrimidine-6-carboxylic acid ethyl ester (15 mg, 0.028 mmol). A white solid was obtained (9.9 mg, 71%) after a preparative HPLC (32 mL/min 5-100% MeCN/H$_2$O gradient over 10 min) purification. $^1$H NMR (400 MHz, DMSO-d$_6$) δ (ppm): 10.41 (br, 1H), 9.24 (s, 1H), 9.01 (d, J=3.6 Hz, 1H), 8.54 (s, 1H), 7.70 (s, 1H), 7.64 (d, J=3.9 Hz, 1H), 7.45 (m, 2H), 7.36 (m, 3H), 6.89 (br, 2H), 5.72 (s, 1H), 4.21 (t, J=7.8 Hz, 1H), 3.92 (m, 2H), 3.02 (t, J=7.4 Hz, 2H), 2.93 (t, J=7.4 Hz, 2H), 2.73-2.60 (m, 2H), 2.14 (m, 2H). Mass Spectrum (LCMS, ESI pos.) Calcd. For C$_{27}$H$_{24}$N$_6$O$_4$: 497.10 (M+H), Found 497.0.

EXAMPLE 31

(4S)-8-Indan-5-yl-5-oxo-2-[4-(2-oxo-oxazolidin-4-ylmethyl)-phenylamino]-5,8-dihydro-pyrido[2,3-d]pyrimidine-6-carboxylic acid methyl amide (Cpd 31)

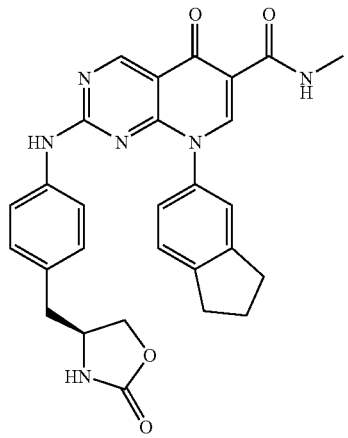

Using the procedure outlined in Example 28 the title compound was prepared from (4S)-8-indan-5-yl-5-oxo-2-[4-(2-oxo-oxazolidin-4-ylmethyl)-phenylamino]-5,8-dihydro-pyrido[2,3-d]pyrimidine-6-carboxylic acid ethyl ester (20 mg, 0.038 mmol). A white solid was obtained (17.3 mg, 89%) after a preparative HPLC (32 mL/min 5-100% MeCN/H$_2$O gradient over 10 min) purification. $^1$H NMR (400 MHz, CDCl$_3$) δ (ppm): 9.58 (t, J=5.6 Hz, 1H), 9.20 (br, 1H), 8.76 (s, 1H), 7.95 (br, 1H), 7.75 (s, 1H), 7.34 (d, J=7.9 Hz, 1H), 7.29 (br, 2H), 7.18 (s, 1H), 7.09 (d, J=7.8 Hz, 1H), 6.85 (br, 2H), 5.22 (s, 1H), 4.42 (t, J=8.2 Hz, 1H), 4.06 (m, 1H), 3.96 (m, 1H), 3.22 (s, 3H), 3.00 (t, J=7.4 Hz, 2H), 2.93 (t, J=7.4 Hz, 2H), 2.80-2.66 (m, 2H), 2.16 (m, 2H). Mass Spectrum (LCMS, ESI pos.) Calcd. For C$_2$H$_{26}$N$_6$O$_4$: 511.20 (M+H), Found 511.0.

EXAMPLE 32

(4S)-8-Indan-5-yl-5-oxo-2-[4-(2-oxo-oxazolidin-4-ylmethyl)-phenylamino]-5,8-dihydro-pyrido[2,3-d]pyrimidine-6-carboxylic acid ethyl amide (Cpd 32)

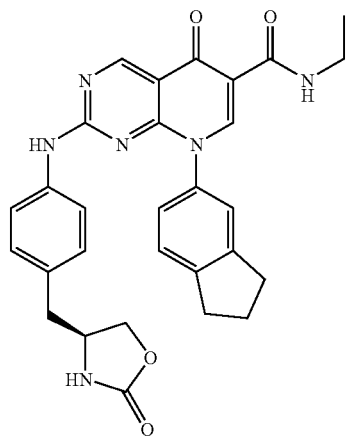

Using the procedure outlined in Example 29 the title compound was prepared from (4S)-8-indan-5-yl-5-oxo-2-[4-(2-oxo-oxazolidin-4-ylmethyl)-phenylamino]-5,8-dihydro-pyrido[2,3-d]pyrimidine-6-carboxylic acid ethyl ester (20 mg, 0.038 mmol). A white solid was obtained (13.5 mg, 68%) after a preparative HPLC (32 mL/min 5-100% MeCN/H$_2$O gradient over 10 min) purification. $^1$H NMR (400 MHz, CDCl$_3$) δ (ppm): 9.58 (t, J=5.6 Hz, 1H), 9.20 (br, 1H), 8.76 (s, 1H), 7.95 (br, 1H), 7.75 (s, 1H), 7.34 (d, J=7.9 Hz, 1H), 7.29 (br, 2H), 7.18 (s, 1H), 7.09 (d, J=7.8 Hz, 1H), 6.85 (br, 2H), 5.22 (s, 1H), 4.42 (t, J=8.2 Hz, 1H), 4.06 (m, 1H), 3.96 (m, 1H), 3.44 (m, 2H), 3.00 (t, J=7.4 Hz, 2H), 2.93 (t, J=7.4 Hz, 2H), 2.80-2.66 (m, 2H), 2.16 (m, 2H), 1.21 (t, J=7.3 Hz, 3H). Mass Spectrum (LCMS, ESI pos.) Calcd. For C$_{29}$H$_{28}$N$_6$O$_4$: 525.22 (M+H), Found 525.0.

EXAMPLE 33

8-Indan-5-yl-2-[4-(2-isopropylsulfamoyl-ethyl)-phenylamino]-5-oxo-5,8-dihydro-pyrido[2,3-d]pyrimidine-6-carboxylic acid methyl amide (Cpd 33)

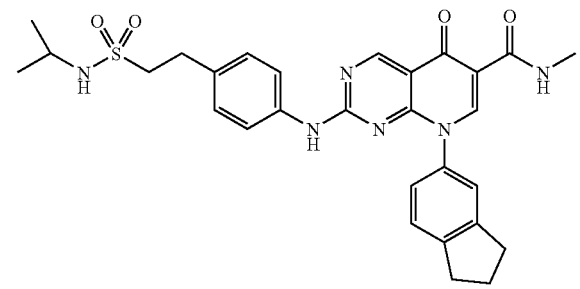

A. 2-(4-Nitro-phenyl)-ethanesulfonyl chloride 1-(2-Bromo-ethyl)-4-nitro-benzene (3 g, 13 mmol) and potassium thioacetate (3 g, 26 mmol) in DMSO (10 mL) were stirred at r.t. for 3 hours. EtOAc was used to dilute the reaction. The organic layer was washed with water twice (2×100 mL), brine and dried over $Na_2SO_4$. The solvent was evaporated under vacuum to give a brown solid (~3 g), which was taken in 50 mL of acetic acid. To the stirring solution was added 20 mL of hydrogen peroxide (30% in water). The resulting yellow solution was stirred at r.t. overnight. Water (50 mL) was added and the solvent was evaporated in vacuum with minimal heating. The yellow residue was dried on high vacuum for two days. Then it was suspended in thionyl chloride (18 mL) and the mixture was heated to reflux (80° C.) for 6 hours. The volatiles were evaporated to leave a yellow solid, which was used for next step without purification.

B. 2-(4-Amino-phenyl)-ethanesulfonic acid isopropylamide 2-(4-Nitro-phenyl)-ethanesulfonyl chloride (300 mg) was suspended in 5 mL of THF. To the stirring solution was added isopropylamine (600 µL) dropwise at r.t. After 5 hours the solvent was evaporated. The nitro product was purified by flash chromatography ($CH_2Cl_2/CH_3OH$ 10:1 v/v) and was converted to the title compound under normal hydrogenation conditions. The title compound was obtained as a yellow solid (182 mg, 54%). $^1$H NMR (300 MHz, $CD_3OD$) δ (ppm): 6.96 (d, J=8.3 Hz, 2H), 6.69 (d, J=8.3 Hz, 2H), 3.53 (m, 1H), 3.19 (m, 2H), 2.91 (m, 2H), 1.20 (s, 3H), 1.18 (s, 3H).

C. 8-Indan-5-yl-2-[4-(2-isopropylsulfamoyl-ethyl)-phenylamino]-5-oxo-5,8-dihydro-pyrido[2,3-d]pyrimidine-6-carboxylic acid ethyl ester Using the procedure outlined in Example 1(g) the title compound was prepared from 2-(4-amino-phenyl)-ethanesulfonic acid isopropylamide (58 mg, 0.24 mmol) and 8-indan-5-yl-2-methanesulfonyl-5-oxo-5,8-dihydro-pyrido[2,3-d]pyrimidine-6-carboxylic acid ethyl ester (from Example 1(e) above, 100 mg, 0.24 mmol). The title compound was obtained as a white solid (50 mg, 36%). $^1$H NMR (400 MHz, $CDCl_3$) δ (ppm): 9.34 (s, 1H), 8.53 (s, 1H), 7.88 (br, 1H), 7.42 (d, J=7.9 Hz, 1H), 7.27 (m, 3H), 7.18 (d, J=7.9 Hz, 1H), 6.94 (br, 2H), 5.88 (s, 1H), 4.37 (q, J=7.1 Hz, 2H), 3.61 (m, 1H), 3.22 (m, 2H), 3.10-2.96 (m, 6H), 2.23 (m, 2H), 1.38 (t, J=7.1 Hz, 3H), 1.25 (s, 3H), 1.22 (s, 3H).

D. 8-indan-5-yl-2-[4-(2-isopropylsulfamoyl-ethyl)-phenylamino]-5-oxo-5,8-dihydro-pyrido[2,3-d]pyrimidine-6-carboxylic acid methyl amide Using the procedure outlined in Example 28 the title compound was prepared from 8-indan-5-yl-2-[4-(2-isopropylsulfamoyl-ethyl)-phenylamino]-5-oxo-5,8-dihydro-pyrido[2,3-d]pyrimidine-6-carboxylic acid ethyl ester (20 mg, 0.034 mmol). A yellow solid was obtained (13.9 mg, 70%). $^1$H NMR (400 MHz, $CDCl_3$) δ (ppm): 9.59 (br, 1H), 9.31 (s, 1H), 8.77 (s, 1H), 7.52 (br, 1H), 7.34 (d, J=7.9 Hz, 1H), 7.24 (m, 3H), 7.09 (d, J=7.9 Hz, 1H), 6.88 (br, 2H), 3.88 (d, J=7.7 Hz, 1H), 3.60 (s, 3H), 3.55 (m, 1H), 3.14 (m, 2H), 3.03-2.90 (m, 6H), 2.16 (m, 2H), 1.15 (s, 3H), 1.13 (s, 3H). Mass Spectrum (LCMS, ESI pos.) Calcd. For $C_{29}H_{32}N_6O_4S$: 561.22 (M+H), Found 561.0.

EXAMPLE 34

8-Indan-5-yl-2-[4-(2-isopropylsulfamoyl-ethyl)-phenylamino]-5-oxo-5,8-dihydro-pyrido[2,3-d]pyrimidine-6-carboxylic acid ethyl amide (Cpd 34)

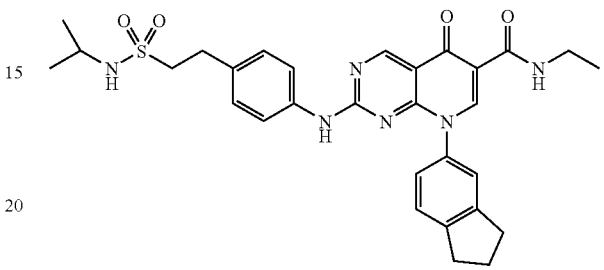

Using the procedure outlined in Example 29 the title compound was prepared from 8-indan-5-yl-2-[4-(2-isopropylsulfamoyl-ethyl)-phenylamino]-5-oxo-5,8-dihydro-pyrido[2,3-d]pyrimidine-6-carboxylic acid ethyl ester (15 mg, 0.026 mmol). A yellow solid was obtained (7.5 mg, 50%). $^1$H NMR (400 MHz, $CDCl_3$) δ (ppm): 9.59 (br, 1H), 9.31 (s, 1H), 8.77 (s, 1H), 7.52 (br, 1H), 7.34 (d, J=7.9 Hz, 1H), 7.24 (m, 3H), 7.09 (d, J=7.9 Hz, 1H), 6.88 (br, 2H), 3.88 (d, J=7.7 Hz, 1H), 3.55 (m, 1H), 3.43 (m, 2H), 3.14 (m, 2H), 3.03-2.90 (m, 6H), 2.16 (m, 2H), 1.20 (t, J=7.3 Hz, 3H), 1.15 (s, 3H), 1.13 (s, 3H). Mass Spectrum (LCMS, ESI pos.) Calcd. For $C_{30}H_{34}N_6O_4S$: 575.24 (M+H), Found 575.0.

EXAMPLE 35

8-Indan-5-yl-2-{4-[2-(morpholine-4-sulfonyl)-ethyl]-phenylamino}-5-oxo-5,8-dihydro-pyrido[2,3-d]pyrimidine-6-carboxylic acid methyl amide (Cpd 35)

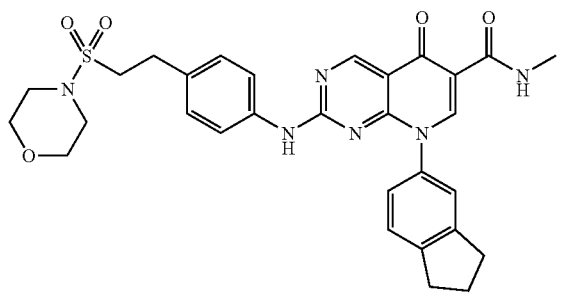

A. 4-[2-(Morpholine-4-sulfonyl)-ethyl]-phenylamine 2-(4-Nitro-phenyl)-ethanesulfonyl chloride (from Example 33 (A), 300 mg) was suspended in 5 mL of THF. To the stirring solution was added morpholine (1 mL) dropwise at r.t. After 5 hours the solvent was evaporated. The nitro product was purified by flash chromatography ($CH_2Cl_2/CH_3OH$ 10:1 v/v) and was converted to the title compound under normal hydrogenation conditions. The title compound was obtained as a yellow solid (167 mg, 52%). $^1$H NMR (400 MHz, CD$_3$OD) δ (ppm): 7.01 (d, J=8.4 Hz, 2H), 6.65 (d, J=8.4 Hz, 2H), 3.72 (t, J=4.7 Hz, 4H), 3.23 (t, J=4.7 Hz, 4H), 3.11 (m, 2H), 2.98 (m, 2H).

B. 8-Indan-5-yl-2-{4-[2-(morpholine-4-sulfonyl)-ethyl]-phenylamino}-5-oxo-5,8-dihydro-pyrido[2,3-d]pyrimidine-6-carboxylic acid ethyl ester Using the procedure outlined in Example 1(g) the title compound was prepared from 4-[2-(morpholine-4-sulfonyl)-ethyl]-phenylamine (65 mg, 0.24 mmol) and 8-indan-5-yl-2-ethanesulfonyl-5-oxo-5,8-dihydro-pyrido[2,3-d]pyrimidine-6-carboxylic acid ethyl ester (from Example 1(e) above, 100 mg, 0.24 mmol). The title compound was obtained as a white solid (42 mg, 29%). $^1$H NMR (400 MHz, CDCl$_3$) δ (ppm): 9.35 (s, 1H), 8.53 (s, 1H), 8.01 (br, 1H), 7.42 (d, J=7.8 Hz, 1H), 7.30 (m, 3H), 7.19 (d, J=7.8 Hz, 1H), 6.94 (br, 2H), 4.37 (q, J=7.1 Hz, 2H), 3.72 (t, J=4.5 Hz, 4H), 3.25 (t, J=4.7 Hz, 4H), 3.08 (m, 6H), 3.01 (t, J=7.4 Hz, 2H), 2.24 (m, 2H), 1.38 (t, J=7.1 Hz, 3H).

C. 8-Indan-5-yl-2-{4-[2-(morpholine-4-sulfonyl)-ethyl]-phenylamino}-5-oxo-5,8-dihydro-pyrido[2,3-d]pyrimidine-6-carboxylic acid methyl amide Using the procedure outlined in Example 28 the title compound was prepared from 8-indan-5-yl-2-{4-[2-(morpholine-4-sulfonyl)-ethyl]-phenylamino}-5-oxo-5,8-dihydro-pyrido[2,3-d]pyrimidine-6-carboxylic acid ethyl ester (12 mg, 0.020 mmol). A yellow solid was obtained (6.4 mg, 54%). $^1$H NMR (400 MHz, CDCl$_3$) δ (ppm): 9.59 (br, 1H), 9.31 (s, 1H), 8.77 (s, 1H), 8.25 (br, 1H), 7.36 (d, J=7.9 Hz, 1H), 7.26 (br, 2H), 7.19 (s, 1H), 7.10 (d, J=7.9 Hz, 1H), 6.89 (br, 2H), 3.67 (t, J=4.7 Hz, 4H), 3.22 (s, 3H), 3.18 (t, J=4.7 Hz, 4H), 3.01 (m, 6H), 2.94 (t, J=7.4 Hz, 2H), 2.17 (m, 2H). Mass Spectrum (LCMS, ESI pos.) Calcd. For C$_{30}$H$_{32}$N$_6$O$_5$S: 589.22 (M+H), Found 589.0.

EXAMPLE 36

8-Indan-5-yl-2-{4-[2-(morpholine-4-sulfonyl)-ethyl]-phenylamino}-5-oxo-5,8-dihydro-pyrido[2,3-d]pyrimidine-6-carboxylic acid ethyl amide (Cpd 36)

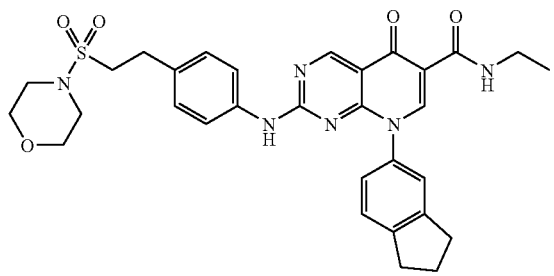

Using the procedure outlined in Example 29 the title compound was prepared from 8-indan-5-yl-2-{4-[2-(morpholine-4-sulfonyl)-ethyl]-phenylamino}-5-oxo-5,8-dihydro-pyrido[2,3-d]pyrimidine-6-carboxylic acid ethyl ester (Example 35 (B), 12 mg, 0.020 mmol). A yellow solid was obtained (7.6 mg, 63%). $^1$H NMR (400 MHz, CDCl$_3$) δ (ppm): 9.59 (br, 1H), 9.31 (s, 1H), 8.77 (s, 1H), 8.25 (br, 1H), 7.36 (d, J=7.9 Hz, 1H), 7.26 (br, 2H), 7.19 (s, 1H), 7.10 (d, J=7.9 Hz, 1H), 6.89 (br, 2H), 3.67 (t, J=4.7 Hz, 4H), 3.43 (m, 2H), 3.18 (t, J=4.7 Hz, 4H), 3.01 (m, 6H), 2.94 (t, J=7.4 Hz, 2H), 2.17 (m, 2H), 1.20 (t, J=7.3 Hz, 3H). Mass Spectrum (LCMS, ESI pos.) Calcd. For C$_{31}$H$_{34}$N$_6$O$_5$S: 603.23 (M+H), Found 602.9

EXAMPLE 37

8-Indan-5-yl-2-[3-(4-methyl-piperazin-1-yl)-phenylamino]-5-oxo-5,8-dihydro-pyrido[2,3-d]pyrimidine-6-carboxylic acid amide (Cpd 37)

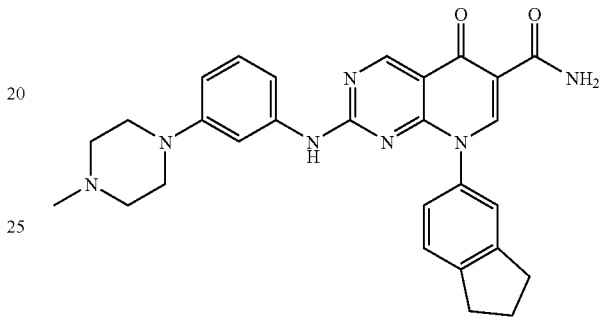

A. 3-(4-Methyl-piperazin-1-yl)-phenylamine

To a suspension of 1-fluoro-3-nitrobenzene (3.77 mL, 35.4 mmol) and potassium carbonate (10 g, 71 mmol) in DMSO (30 mL) was added 1-methyl piperazine (59 mL, 53.2 mmol). The mixture was stirred at 122° C. for 24 hours. After cooing down, the mixture was diluted with water (100 mL) and extracted with EtOAc (3×100 mL). The combined organic layers were washed with brine, dried with sodium sulfate (Na$_2$SO$_4$), and concentrated in vacuo to afford an orange oil. Recrystallization from EtOAc/hexanes gave 4.2 g of 1-(4-methyl-piperazin-1-yl)-3-nitrobenzene, which was reduced via hydrogenation to give the title compound (beige solid, 3 g). $^1$H NMR (400 MHz, CDCl$_3$) δ (ppm): 7.04 (t, J=8.0 Hz, 1H), 6.38 (dd, J=2.3, 8.2 Hz, 1H), 6.26 (t, J=2.2 Hz, 1H), 6.22 (dd, J=2.3, 8.2 Hz, 1H), 3.60 (br, 2H), 3.18 (t, J=4.9 Hz, 4H), 2.55 (t, J=4.9 Hz, 4H), 2.34 (s, 3H).

B. 8-Indan-5-yl-2-[3-(4-methyl-piperazin-1-yl)-phenylamino]-5-oxo-5,8-dihydro-pyrido[2,3-d]pyrimidine-6-carboxylic acid ethyl ester Using the procedure outlined in Example 1(g) the title compound was prepared from 3-(4-methyl-piperazin-1-yl)-phenylamine (50 mg, 0.27 mmol) and 8-indan-5-yl-2-methanesulfonyl-5-oxo-5,8-dihydro-pyrido[2,3-d]pyrimidine-6-carboxylic acid ethyl ester (from Example 1(e) above, 100 mg, 0.24 mmol). The title compound was obtained as a yellow solid (60 mg, 46%). $^1$H NMR (400 MHz, CDCl$_3$) δ (ppm): 9.29 (s, 1H), 8.44 (s, 1H), 7.49 (br, 1H), 7.31 (d, J=7.9 Hz, 1H), 7.20 (m, 2H), 7.09 (d, J=7.8 Hz, 1H), 6.94 (d, J=7.9 Hz, 1H), 6.87 (br, 1H), 6.52 (d, J=7.9 Hz, 1H), 4.32 (q, J=7.1 Hz, 2H), 3.02-2.90 (m, 8H), 2.45 (m, 4H), 2.26 (s, 3H), 2.14 (m, 2H), 1.32 (t, J=7.1 Hz, 3H).

C. 8-Indan-5-yl-2-[3-(4-methyl-piperazine-yl)-phenylamino]-5-oxo-5,8-dihydro-pyrido[2,3-d]pyrimidine-6-carboxylic acid amide Using the procedure outlined in Example 7 the title compound was prepared from 8-indan-5-yl-2-[3-(4-methyl-piperazin-1-yl)-phenylamino]-5-oxo-5,8-dihydro-pyrido[2,3-d]pyrimidine-6-carboxylic acid ethyl ester (from B above, 20 mg, 0.038 mmol). A yellow solid was obtained (8.3 mg, 44%). $^1$H NMR (400 MHz, CD$_2$Cl$_2$) δ (ppm): 9.35 (br, 1H), 9.27 (s, 1H), 8.69 (s, 1H), 7.34 (d, J=8.1 Hz, 1H), 7.21 (s, 1H), 7.12 (d, J=8.1 Hz, 1H), 6.97 (d, J=7.9 Hz, 1H), 6.86 (br, 1H), 6.65 (br, 1H), 6.53 (d, J=7.9 Hz, 1H), 5.91 (br, 1H), 3.00-2.84 (m, 8H), 2.43 (br, 4H), 2.22 (s, 3H), 2.12 (m, 2H). Mass Spectrum (LCMS, ESI pos.) Calcd. For C$_{28}$H$_{29}$N$_7$O$_2$: 496.24 (M+H), Found 496.1.

EXAMPLE 38

8-indan-5-yl-2-[3-(4-methyl-piperazin-1-yl)-phenylamino]-5-oxo-5,8-dihydro-pyrido[2,3-d]pyrimidine-6-carboxylic acid methyl amide (Cpd 38)

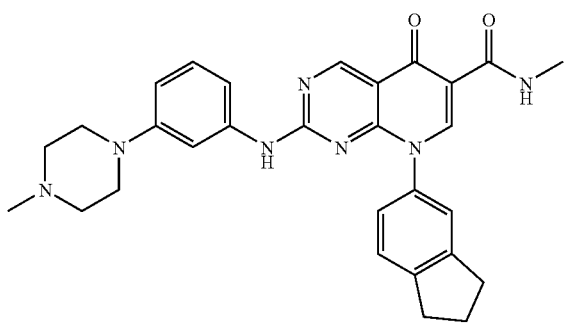

Using the procedure outlined in Example 28 the title compound was prepared from 8-indan-5-yl-2-[3-(4-methyl-piperazin-1-yl)-phenylamino]-5-oxo-5,8-dihydro-pyrido[2,3-d]pyrimidine-6-carboxylic acid ethyl ester (from Example 37(B) above, 15 mg, 0.028 mmol). A yellow solid was obtained (8.8 mg, 62%) after a preparative HPLC (32 mL/min 5-100% MeCN/H$_2$O gradient over 10 min) purification. $^1$H NMR (400 MHz, CDCl$_3$), (ppm): 9.55 (br, 1H), 9.31 (s, 1H), 8.75 (s, 1H), 7.46 (br, 1H), 7.30 (d, J=8.1 Hz, 1H), 7.19 (s, 1H), 7.10 (d, J=8.1 Hz, 1H), 6.98 (d, J=7.9 Hz, 1H), 6.88 (br, 1H), 6.60 (br, 1H), 6.54 (d, J=7.9 Hz, 1H), 3.06-2.89 (m, 11H), 2.45 (m, 4H), 2.27 (s, 3H), 2.12 (m, 2H). Mass Spectrum (LCMS, ESI pos.) Calcd. For C$_{29}$H$_{31}$N$_7$O$_2$: 510.25 (M+H), Found 510.1.

EXAMPLE 39

8-Indan-5-yl-2-[3-(4-methyl-piperazin-1-yl)-phenylamino]-5-oxo-5,8-dihydro-pyrido[2,3-d]pyrimidine-6-carboxylic acid ethyl amide (Cpd 39)

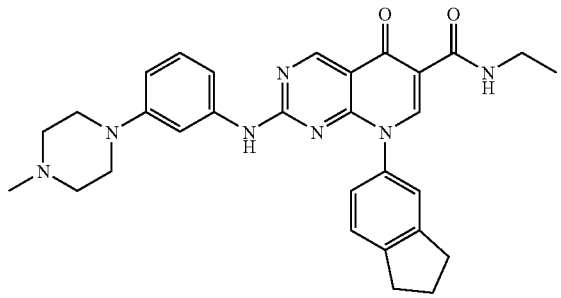

Using the procedure outlined in Example 29 the title compound was prepared from 8-indan-5-yl-2-[3-(4-methyl-piperazin-1-yl)-phenylamino]-5-oxo-5,8-dihydro-pyrido[2,3-d]pyrimidine-6-carboxylic acid ethyl ester (from Example 37(B) above, 15 mg, 0.028 mmol). A yellow solid was obtained (8.6 mg, 59%) after a preparative HPLC (32 mL/min 5-100% MeCN/H$_2$O gradient over 10 min) purification. $^1$H NMR (400 MHz, CDCl$_3$) δ (ppm): 9.62 (br, 1H), 9.31 (s, 1H), 8.75 (s, 1H), 7.46 (br, 1H), 7.30 (d, J=8.1 Hz, 1H), 7.19 (s, 1H), 7.10 (d, J=8.1 Hz, 1H), 6.98 (d, J=7.9 Hz, 1H), 6.88 (br, 1H), 6.64 (br, 1H), 6.56 (d, J=7.9 Hz, 1H), 3.43 (m, 2H), 3.06-2.86 (m, 8H), 2.45 (m, 4H), 2.27 (s, 3H), 2.13 (m, 2H), 1.20 (t, J=7.3 Hz, 1H). Mass Spectrum (LCMS, ESI pos.) Calcd. For C$_{30}$H$_{33}$N$_7$O$_2$: 524.27 (M+H), Found 524.1.

EXAMPLE 40

8-Indan-5-yl-5-oxo-2-(4-piperazin-1-yl-phenylamino)-5,8-dihydro-pyrido[2,3-d]pyrimidine-6-carboxylic acid amide (Cpd 4)

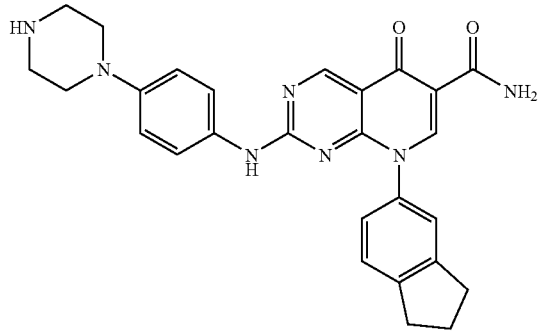

A. 4-(4-Amino-phenyl)-piperazine-1-carboxylic acid tert-butyl ester

To a suspension of 1-fluoro-4-nitrobenzene (1.4 mL, 13 mmol) and potassium carbonate (2.5 g, 18 mmol) in DMSO (10 mL) was added 1-Boc-piperazine (2.75 g, 14.8 mmol). The mixture was stirred at 100° C. for 2 hours. After cooing down, the mixture was diluted with water (50 mL) and extracted with EtOAc (3×50 mL). The combined organic layers were washed with brine, dried with sodium sulfate (Na$_2$SO$_4$), and concentrated in vacuo to afford a yellow solid.

Recrystallization from EtOAC/hexanes gave 4.0 g of 1-(4-Boc-piperazin-1-yl)-4-nitrobenzene, which was reduced via hydrogenation to give the title compound (purple solid, 3 g). $^1$H NMR (400 MHz, CDCl$_3$) δ (ppm): 6.68 (d, J=8.8 Hz, 2H), 6.64 (d, J=8.8 Hz, 2H), 3.56 (t, J=5.0 Hz, 4H), 2.96 (t, J=5.0 Hz, 4H), 1.46 (s, 9H).

B. 8-indan-5-yl-5-oxo-2-(4-piperazin-1-yl-phenylamino)-5,8-dihydro-pyrido[2,3-d]pyrimidine-6-carboxylic acid ethyl ester Using the procedure outlined in Example 1(g) the title compound was prepared from 4-(4-amino-phenyl)-piperazine-1-carboxylic acid tert-butyl ester (52 mg, 0.19 mmol) and 8-indan-5-yl-2-methanesulfonyl-5-oxo-5,8-dihydro-pyrido[2,3-d]pyrimidine-6-carboxylic acid ethyl ester (from Example 1(e) above, 70 mg, 0.17 mmol). A yellow solid was obtained (75 mg, 86%) after a preparative HPLC (32 mL min 5-100% MeCN/H$_2$O gradient over 10 min) purification. The Boc group was removed by treatment with TFA in CH$_2$Cl$_2$ (1:1 v/v) to give the title compound. $^1$H NMR (400 MHz, CDCl$_3$) δ (ppm): 9.25 (s, 1H), 8.45 (s, 1H), 7.61 (br, 1H), 7.35 (d, J=7.9 Hz, 1H), 7.21 (s, 1H), 7.14 (br, 2H), 7.10 (d, J=7.9 Hz, 1H), 6.57 (br, 2H), 4.30 (q, J=7.1 Hz, 2H), 3.02-2.90 (m, 12H), 2.15 (m, 2H), 1.30 (t, J=7.1 Hz, 3H).

C. 8-Indan-5-yl-5-oxo-2-(4-piperazin-1-yl-phenylamino)-5,8-dihydro-pyrido[2,3-d]pyrimidine-6-carboxylic acid amide Using the procedure outlined in Example 7 the title compound was prepared from 8-indan-5-yl-5-oxo-2-(4-piperazin-1-yl-phenylamino)-5,8-dihydro-pyrido[2,3-d]pyrimidine-6-carboxylic acid ethyl ester (from B above, 20 mg, 0.038 mmol). The title compound was obtained as a TFA salt after a preparative HPLC (32 mL/min 5-100% MeCN/H$_2$O gradient over 10 min) purification (12.8 mg, 52%). $^1$H NMR (400 MHz, CD$_2$Cl$_2$/CD$_3$OD 10:1 v/v) δ (ppm): 9.23 (s, 1H), 8.70 (s, 1H), 7.36 (d, J=7.9 Hz, 1H), 7.27 (br, 2H), 7.23 (s, 1H), 7.14 (d, J=7.9 Hz, 1H), 6.63 (br, 2H), 3.25 (m, 2H), 2.96 (m, 4H), 2.13 (m, 2H). Mass Spectrum (LCMS, ESI pos.) Calcd. For C$_{27}$H$_{27}$N$_7$O$_2$: 482.22 (M+H), Found 482.0.

EXAMPLE 41

8-indan-5-yl-5-oxo-2-(4-piperazin-1-yl-phenylamino)-5,8-dihydro-pyrido[2,3-d]pyrimidine-6-carboxylic acid methyl amide (Cpd 41)

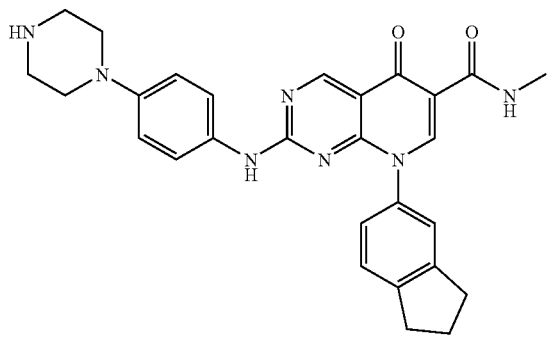

Using the procedure outlined in Example 28 the title compound was prepared from 8-indan-5-yl-5-oxo-2-(4-piperazin-1-yl-phenylamino)-5,8-dihydro-pyrido[2,3-d]pyrimidine-6-carboxylic acid ethyl ester (from Example 40(B) above, 20 mg, 0.039 mmol). A yellow solid was obtained (TFA salt, 12.2 mg, 51%) after a preparative HPLC (32 mL/min 5-100% MeCN/H$_2$O gradient over 10 min) purification. $^1$H NMR (400 MHz, CDCl$_3$/CD$_3$OD 10:1 v/v) δ (ppm): 9.67 (br, 1H), 9.26 (s, 1H), 8.71 (s, 1H), 7.37 (d, J=7.9 Hz, 1H), 7.25 (br, 2H), 7.20 (s, 1H), 7.11 (d, J=7.9 Hz, 1H), 6.58 (br, 2H), 3.24 (m, 8H), 2.97-2.93 (m, 7H), 2.15 (m, 2H). Mass Spectrum (LCMS, ESI pos.) Calcd. For C$_{28}$H$_{29}$N$_7$O$_2$: 496.24 (M+H), Found 496.0.

EXAMPLE 42

8-indan-5-yl-5-oxo-2-(4-piperazin-1-yl-phenylamino)-5,8-dihydro-pyrido[2,3-d]pyrimidine-6-carboxylic acid ethyl amide (Cpd 42)

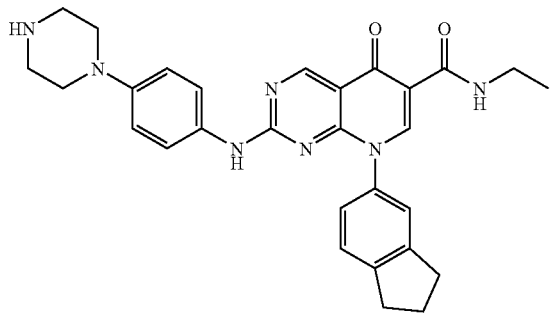

Using the procedure outlined in Example 29 the title compound was prepared from 8-indan-5-yl-5-oxo-2-(4-piperazin-1-yl-phenylamino)-5,8-dihydro-pyrido[2,3-d]pyrimidine-6-carboxylic acid ethyl ester (from Example 40(B) above, 20 mg, 0.039 mmol). A yellow solid was obtained (TFA salt, 4.4 mg, 22%) after a preparative HPLC (32 mL/min 5-100% MeCN/H$_2$O gradient over 10 min) purification. $^1$H NMR (400 MHz, CDCl$_3$/CD$_3$OD 10:1 v/v) δ (ppm): 9.67 (br, 1H), 9.26 (s, 1H), 8.71 (s, 1H), 7.37 (d, J=7.9 Hz, 1H), 7.25 (br, 2H), 7.20 (s, 1H), 7.11 (d, J=7.9 Hz, 1H), 6.58 (br, 2H), 3.42 (m, 2H), 3.25 (m, 8H), 2.91-3.00 (m, 4H), 2.15 (m, 2H), 1.20 (t, J=7.3 Hz, 3H). Mass Spectrum (LCMS, ESI pos.) Calcd. For C$_{29}$H$_{31}$N$_7$O$_2$: 510.25 (M+H), Found 510.0.

EXAMPLE 43

2-[4-(3,5-Dimethyl-piperazin-1-yl)-phenylamino]-8-indan-5-yl-5-oxo-5,8-dihydro-pyrido[2,3-d]pyrimidine-6-carboxylic acid amide (Cpd 43)

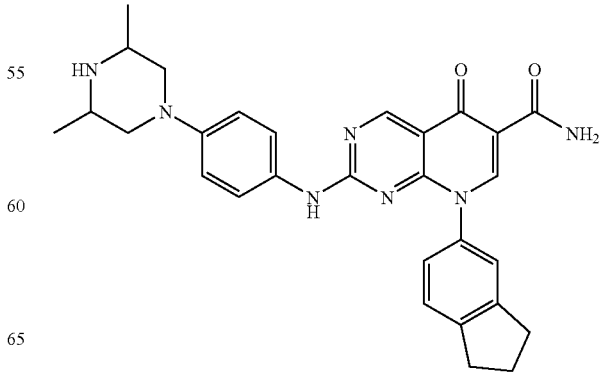

A. 4-(3,5-Dimethyl-piperazin-1-yl)-phenylamine

To a suspension of 1-fluoro-4-nitrobenzene (2.12 mL, 20 mmol) and potassium carbonate (3.5 g, 25 mmol) in DMSO (10 mL) was added 3,5-dimethyl-piperazine (2.5 g, 22 mmol). The mixture was stirred at 100° C. for 2 hours. After cooing down, the mixture was diluted with water (50 mL) and extracted with EtOAc (3×50 mL). The combined organic layers were washed with brine, dried with sodium sulfate ($Na_2SO_4$), and concentrated in vacuo to afford a yellow solid. Recrystallization from EtOAc/hexanes gave 3.9 g of 3,5-dimethyl-1-(4-nitro-phenyl)-piperazine, which was reduced via hydrogenation to give the title compound (purple solid, 3 g). $^1$H NMR (400 MHz, $CDCl_3$) δ (ppm): 6.80 (d, J=8.8 Hz, 2H), 6.64 (d, J=8.8 Hz, 2H), 3.40 (br, 2H), 3.32 (d, J=9.5 Hz, 2H), 3.05 (m, 2H), 2.19 (t, J=10.5 Hz, 2H), 1.12 (s, 3H), 1.10 (s, 3H).

B. 2-[4-(3,5-Dimethyl-piperazin-1-yl)-phenylamino]-8-indan-5-yl-5-oxo-5,8-dihydro-pyrido[2,3-d]pyrimidine-6-carboxylic acid ethyl ester Using the procedure outlined in Example 1(g) the title compound was prepared from 4-(3,5-dimethyl-piperazin-1-yl)-phenylamine (from the previous step, 27 mg, 0.13 mmol) and 8-indan-5-yl-2-methanesulfonyl-5-oxo-5,8-dihydro-pyrido[2,3-d]pyrimidine-6-carboxylic acid ethyl ester (from Example 1(e) above, 50 mg, 0.12 mmol). A yellow solid was obtained (40 mg, 62%) after a preparative HPLC (32 mL/min 5-100% MeCN/$H_2O$ gradient over 10 min) purification. $^1$H NMR (400 MHz, $CDCl_3$) δ (ppm): 9.31 (s, 1H), 8.52 (s, 1H), 7.83 (br, 1H), 7.40 (d, J=7.9 Hz, 1H), 7.27 (s, 1H), 7.20 (br, 2H), 7.17 (d, J=7.9 Hz, 1H), 6.63 (br, 2H), 4.36 (q, J=7.1 Hz, 2H), 3.38 (d, J=10.5 Hz, 2H), 3.03 (m, 6H), 2.24 (m, 4H), 1.38 (t, J=7.1 Hz, 3H), 1.14 (s, 3H), 1.13 (s, 3H).

C. 2-[4-(3,5-Dimethyl-piperazin-1-yl)-phenylamino]-8-indan-5-yl-5-oxo-5,8-dihydro-pyrido[2,3-d]pyrimidine-6-carboxylic acid amide Using the procedure outlined in Example 7 the title compound was prepared from 2-[4-(3,5-dimethyl-piperazin-1-yl)-phenylamino]-8-indan-5-yl-5-oxo-5,8-dihydro-pyrido[2,3-d]pyrimidine-6-carboxylic acid ethyl ester (from B above, 15 mg, 0.028 mmol). The title compound was obtained as a TFA salt after a preparative HPLC (32 mL/min 5-100% MeCN/$H_2O$ gradient over 10 min) purification (10.5 mg, 60%). $^1$H NMR (400 MHz, $CD_2Cl_2/CD_3OD$ 10:1 v/v) δ (ppm): 9.24 (s, 1H), 8.70 (s, 1H), 7.38 (d, J=7.9 Hz, 1H), 7.27 (br, 2H), 7.23 (s, 1H), 7.14 (d, J=7.9 Hz, 1H), 6.62 (br, 2H), 3.49 (d, J=10.5 Hz, 2H), 3.37 (m, 2H), 2.96 (m, 4H), 2.65 (t, J=11.5 Hz, 2H), 2.13 (m, 2H), 1.31 (s, 3H), 1.29 (s, 3H). Mass Spectrum (LCMS, ESI pos.) Calcd. For $C_{29}H_{31}N_7O_2$: 510.25 (M+H), Found 510.0.

EXAMPLE 44

2-[4-(3,5-Dimethyl-piperazin-1-yl)-phenylamino]-8-indan-5-yl-5-oxo-5,8-dihydro-pyrido[2,3-d]pyrimidine-6-carboxylic acid methyl amide (Cpd 44)

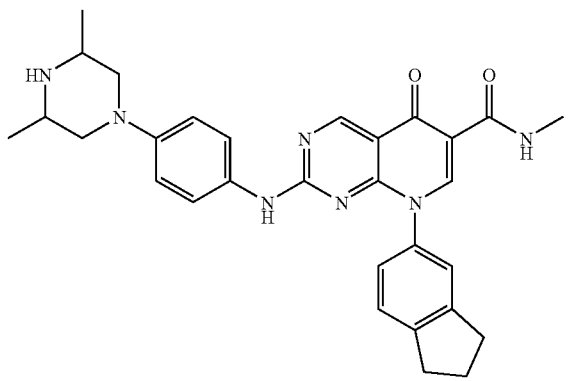

Using the procedure outlined in Example 28 the title compound was prepared from 2-[4-(3,5-dimethyl-piperazin-1-yl)-phenylamino]-8-indan-5-yl-5-oxo-5,8-dihydro-pyrido[2,3-d]pyrimidine-6-carboxylic acid ethyl ester (from Example 43(B) above, 15 mg, 0.028 mmol). A yellow solid was obtained (TFA salt, 9.6 mg, 54%) after a preparative HPLC (32 mL/min 5-100% MeCN/$H_2O$ gradient over 10 min) purification. $^1$H NMR (400 MHz, $CDCl_3$) δ (ppm): 10.14 (br, 1H), 9.62 (m, 1H), 9.26 (s, 1H), 8.98 (br, 1H), 8.75 (s, 1H), 7.35 (d, J=7.9 Hz, 1H), 7.22 (m, 3H), 7.09 (d, J=7.9 Hz, 1H), 6.60 (br, 2H), 3.46-3.38 (m, 4H), 3.00-2.82 (m, 9H), 2.14 (m, 2H), 1.32 (s, 3H), 1.30 (s, 3H). Mass Spectrum (LCMS, ESI pos.) Calcd. For $C_{30}H_{33}N_7O_2$: 524.27 (M+H), Found 524.0.

EXAMPLE 45

2-[4-(3,5-Dimethyl-piperazin-1-yl)-phenylamino]-8-indan-5-yl-5-oxo-5,8-dihydro-pyrido[2,3-d]pyrimidine-6-carboxylic acid ethyl amide (Cpd 45)

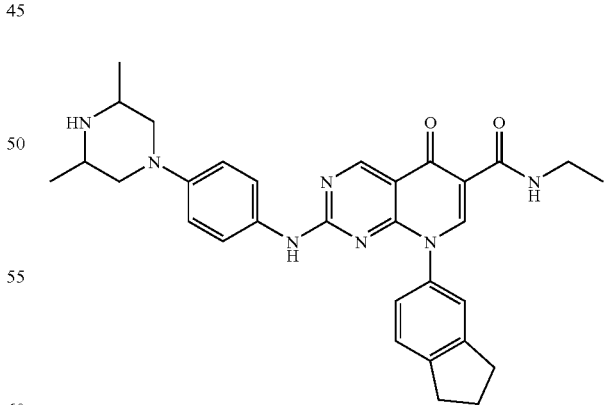

Using the procedure outlined in Example 29, the title compound was prepared from 2-[4-(3,5-dimethyl-piperazin-1-yl)-phenylamino]-8-indan-5-yl-5-oxo-5,8-dihydro-pyrido[2,3-d]pyrimidine-6-carboxylic acid ethyl ester (from Example 43(B) above, 10 mg, 0.018 mmol). A yellow solid was obtained (TFA salt, 5.2 mg, 44%) after a preparative HPLC (32 mL/min 5-100% MeCN/H₂O gradient over 10 min) purification. ¹H NMR (400 MHz, CDCl₃) δ (ppm): 10.14 (br, 1H), 9.62 (m, 1H), 9.26 (s, 1H), 8.98 (br, 1H), 8.75 (s, 1H), 7.35 (d, J=7.9 Hz, 1H), 7.22 (m, 3H), 7.09 (d, J=7.9 Hz, 1H), 6.60 (br, 2H), 3.46-3.38 (m, 4H), 3.00-2.82 (m, 6H), 2.66 (br, 2H), 2.14 (m, 2H), 1.32 (s, 3H), 1.30 (s, 3H), 1.19 (t, J=7.3 Hz, 3H). Mass Spectrum (LCMS, ESI pos.) Calcd. For C₃₁H₃₅N₇O₂: 538.27 (M+H), Found 538.1.

EXAMPLE 46

8-indan-5-yl-2-{4-[2-(4-methyl-piperazin-1-yl)-ethyl]-phenylamino}-5-oxo-5,8-dihydro-pyrido[2,3-d]pyrimidine-6-carboxylic acid amide (Cpd 46)

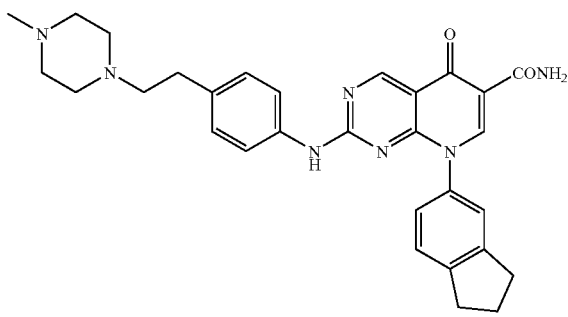

A. 4-[2-(4-Methyl-piperazin-1-yl)-ethyl]-phenylamine 1-(2-Bromo-ethyl)-4-nitro-benzene (0.9 g, 3.9 mmol) was added to a mixture of 1-methyl-piperazine (520 μL, 4.7 mmol) and potassium carbonate (1 g, 4.7 mmol) in 5 mL of DMSO. The mixture was stirred at 100° C. for 2 hour. After cooling to room temperature, the mixture was extracted into ethyl acetate (EtOAc), washed with water, brine and then dried with sodium sulfate (Na₂SO₄). Removal of the solvent and chromatography on silica, eluting with EtOAc/CH₃OH/NH₄OH (10:1:0.1, v/v), gave 850 mg of 1-methyl-4-[2-(4-nitro-phenyl)-ethyl]-piperazine, which was converted to the title compound under normal hydrogenation conditions. The title compound was obtained as a yellow solid (780 mg, 91%). ¹H NMR (400 MHz, CDCl₃) δ (ppm): 6.98 (d, J=8.3 Hz, 2H), 6.61 (d, J=8.3 Hz, 2H), 3.57 (br, 2H), 2.71 (br, 12H), 2.43 (br, 3H).

B. 8-Indan-5-yl-2-{4-[2-(4-methyl-piperazin-1-yl)-ethyl]-phenylamino}-5-oxo-5,8-dihydro-pyrido[2,3-d]pyrimidine-6-carboxylic acid ethyl ester Using the procedure outlined in Example 1(g) the title compound was prepared from 4-[2-(4-methyl-piperazin-1-yl)-ethyl]-phenylamine (53 mg, 0.24 mmol) and 8-indan-5-yl-2-methanesulfonyl-5-oxo-5,8-dihydro-pyrido[2,3-d]pyrimidine-6-carboxylic acid ethyl ester (from Example 1(e) above, 100 mg, 0.24 mmol). The title compound was obtained as a yellow solid (70 mg, 53%). ¹H NMR (400 MHz, CDCl₃) δ (ppm): 9.28 (s, 1H), 8.46 (s, 1H), 7.60 (br, 1H), 7.34 (d, J=7.9 Hz, 1H), 7.21 (s, 1H), 7.16 (br, 2H), 7.12 (d, J=7.9 Hz, 1H), 6.86 (br, 2H), 4.30 (q, J=7.1 Hz, 2H), 2.99 (t, J=7.4 Hz, 2H), 2.93 (t, J=7.4 Hz, 2H), 2.64 (n, 2H), 2.47 (m, 10H), 2.34 (s, 3H), 2.16 (m, 2H), 1.32 (t, J=7.1 Hz, 3H).

C. 8-Indan-5-yl-2-{4-[2-(4-methyl-piperazin-1-yl)-ethyl]-phenylamino}-5-oxo-5,8-dihydro-pyrido[2,3-d]pyrimidine-6-carboxylic acid amide Using the procedure outlined in Example 7 the title compound was prepared from 8-indan-5-yl-2-{4-[2-(4-methyl-piperazin-1-yl)-ethyl]-phenylamino}-5-oxo-5,8-dihydro-pyrido[2,3-d]pyrimidine-6-carboxylic acid ethyl ester (20 mg, 0.036 mmol). A yellow solid was obtained (5.8 mg, 30%). ¹H NMR (400 MHz, DMSO-d₆) δ (ppm): 10.48 (br, 1H), 9.31 (s, 1H), 9.10 (s, 1H), 8.62 (s, 1H), 7.75 (m, 1H), 7.54 (m, 2H), 7.41 (m, 2H), 6.97 (br, 2H), 3.55 (m, 4H), 3.09 (t, J=7.3 Hz, 2H), 3.01 (t, J=7.4 Hz, 2H), 2.71 (m, 2H), 2.57 (m, 13H), 2.22 (m, 2H). Mass Spectrum (LCMS, ESI pos.) Calcd. For C₃₀H₃₃N₇O₂: 524.27 (M+H), Found 524.1.

EXAMPLE 47

8-Indan-5-yl-2-{4-[2-(4-methyl-piperazin-1-yl)-ethyl]-phenylamino}-5-oxo-5,8-dihydro-pyrido[2,3-d]pyrimidine-6-carboxylic acid methyl amide (Cpd 47)

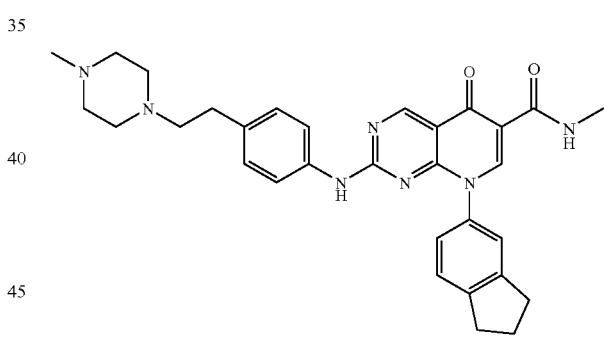

Using the procedure outlined in Example 28 the title compound was prepared from 8-indan-5-yl-2-{4-[2-(4-methyl-piperazin-1-yl)-ethyl]-phenylamino}-5-oxo-5,8-dihydro-pyrido[2,3-d]pyrimidine-6-carboxylic acid ethyl ester (from Example 46(B) above, 20 mg, 0.036 mmol). A yellow solid was obtained (5.1 mg, 26%) after a preparative HPLC (32 mL/min 5-100% MeCN/H₂O gradient over 10 min) purification. ¹H NMR (400 MHz, CDCl₃/CD₃OD 20:1 v/v) δ (ppm): 9.61 (m, 1H), 9.29 (s, 1H), 8.75 (s, 1H), 7.35 (d, J=7.9 Hz, 1H), 7.19 (m, 3H), 7.09 (d, J=7.9 Hz, 1H), 6.84 (br, 2H), 3.00-2.90 (m, 7H), 2.64 (m, 2H), 2.47 (m, 10H), 2.24 (s, 3H), 2.15 (m, 2H). Mass Spectrum (LCMS, ESI pos.) Calcd. For C₃₁H₃₅N₇O₂: 538.29 (M+H), Found 538.1.

EXAMPLE 48

8-Indan-5-yl-2-{4-[2-(4-methyl-piperazin-1-yl)-ethyl]-phenylamino}-5-oxo-5,8-dihydro-pyrido[2,3-d]pyrimidine-6-carboxylic acid ethyl amide (Cpd 48)

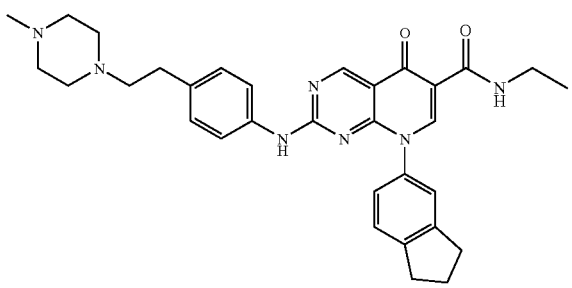

Using the procedure outlined in Example 29 the title compound was prepared from 8-indan-5-yl-2-{4-[2-(4-methyl-piperazin-1-yl)-ethyl]-phenylamino}-5-oxo-5,8-dihydro-pyrido[2,3-d]pyrimidine-6-carboxylic acid ethyl ester (from Example 46(B) above, 20 mg, 0.036 mmol). A yellow solid was obtained (7.1 mg, 36%) after a preparative HPLC (32 mL/min 5-100% MeCN/H$_2$O gradient over 10 min) purification. $^1$H NMR (400 MHz, CDCl$_3$/CD$_3$OD 20:1 v/v) δ (ppm): 9.61 (m, 1H), 9.29 (s, 1H), 8.75 (s, 1H), 7.35 (d, J=7.9 Hz, 1H), 7.19 (m, 3H), 7.09 (d, J=7.9 Hz, 1H), 6.84 (br, 2H), 3.50 (m, 2H), 3.06 (t, J=7.4 Hz, 2H), 2.99 (t, J=7.4 Hz, 2H), 2.73 (m, 2H), 2.53 (m, 10H), 2.31 (s, 3H), 2.22 (m, 2H), 1.26 (t, J=7.3 Hz, 3H). Mass Spectrum (LCMS, ESI pos.) Calcd. For C$_{32}$H$_{37}$N$_7$O$_2$: 552.30 (M+H), Found 552.1.

EXAMPLE 49

8-Indan-5-yl-5-oxo-2-(4-piperidin-4-yl-phenylamino)-5,8-dihydro-pyrido[2,3-d]pyrimidine-6-carboxylic acid amide (Cpd 49)

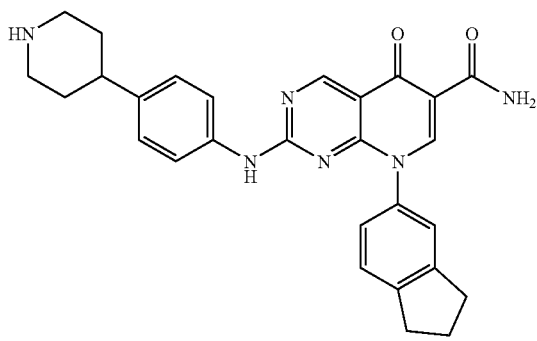

A. 4-(4-Amino-phenyl)-3,6-dihydro-2H-pyridine-1-carboxylic acid tert-butyl ester The title compound was prepared by Suzuki coupling of 4-(4,4,5,5-tetramethyl-[1,3,2]dioxaborolan-2-yl)-phenylamine with 4-trifluoromethanesulfonyloxy-3,6-dihydro-2H-pyridine-1-carboxylic acid tert-butyl ester (Synthesis, 993, (1991)). Mass spectrum (ESI, m/z): Calcd. for C$_{16}$H$_{22}$N$_2$O$_2$, 275.2 (M+H), found 275.1.

B. 4-(4-Amino-phenyl)-piperidine-1-carboxylic acid tert-butyl ester

A solution of 4-(4-amino-phenyl)-3,6-dihydro-2H-pyridine-1-carboxylic acid tert-butyl ester (0.35 g, 1.2 mmol) (as prepared in the previous step) in methanol was hydrogenated over 10% Pd/C at 20 psi for 1 h. The solution was filtered and concentrated to give 0.35 g (100%) of the title compound as a yellow solid. $^1$H NMR (400 MHz, DMSO-d$_6$) δ (ppm): 6.85 (d, J=8.3 Hz, 2H), 6.50 (d, J=8.3 Hz, 2H), 4.81 (s, 2H), 4.012 (m, 2H), 3.85 (br, 2H), 2.44 (m, 1H), 2.66 (m, 2H), 1.42 (m, 11H).

C. 8-Indan-5-yl-5-oxo-2-(4-piperidin-4-yl-phenylamino)-5,8-dihydro-pyrido[2,3-d]pyrimidine-6-carboxylic acid ethyl ester Using the procedure outlined in Example 1(g) the title compound was prepared from 4-(4-amino-phenyl)-piperidine-1-carboxylic acid tert-butyl ester (from the previous step, 66 mg, 0.24 mmol) and 8-indan-5-yl-2-methanesulfonyl-5-oxo-5,8-dihydro-pyrido[2,3-d]pyrimidine-6-carboxylic acid ethyl ester (from Example 1(e), 100 mg, 0.24 mmol). A yellow solid was obtained (75 mg, 51%) after a preparative HPLC (32 mL/min 5-100% MeCN/H$_2$O gradient over 10 min) purification. The Boc group was removed by treatment with TFA in CH$_2$Cl$_2$ (1:1 v/v) to give the title compound. $^1$H NMR (400 MHz, CDCl$_3$) δ (ppm): 9.31 (s, 1H), 8.54 (s, 1H), 7.42 (d, J=7.9 Hz, 1H), 7.29 (br, 2H), 7.27 (s, 1H), 7.18 (d, J=7.9 Hz, 1H), 6.91 (br, 2H), 4.35 (q, J=7.1 Hz, 2H), 3.52 (m, 2H), 3.16 (br, 2H), 2.97 (m, 4H), 2.68 (m, 1H), 2.22 (m, 2H), 1.95 (m, 2H), 1.35 (t, J=7.1 Hz, 3H).

D. 8-indan-5-yl-5-oxo-2-(4-piperidin-4-yl-phenylamino)-5,8-dihydro-pyrido[2,3-d]pyrimidine-6-carboxylic acid amide Using the procedure outlined in Example 7 the title compound was prepared from 8-indan-5-yl-5-oxo-2-(4-piperidin-4-yl-phenylamino)-5,8-dihydro-pyrido[2,3-d]pyrimidine-6-carboxylic acid ethyl ester (27 mg, 0.053 mmol). A yellow solid was obtained as a TFA salt after a preparative HPLC (32 mL/min 5-100% MeCN/H$_2$O gradient over 10 min) purification (24 mg, 76%). $^1$H NMR (400 MHz, DMSO-d$_6$) δ (ppm): 10.48 (br, 1H), 9.31 (s, 1H), 9.10 (s, 1H), 8.62 (s, 1H), 7.75 (m, 1H), 7.54 (m, 2H), 7.41 (m, 2H), 6.97 (br, 2H), 3.55 (m, 4H), 3.09 (t, J=7.3 Hz, 2H), 3.01 (t, J=7.4 Hz, 2H), 2.81 (m, 1H), 2.22 (m, 2H), 1.95 (m, 2H), 1.75 (m, 2H). Mass Spectrum (LCMS, ESI pos.) Calcd. For C$_{28}$H$_{28}$N$_6$O$_2$: 481.23 (M+H), Found 481.1.

EXAMPLE 50

8-Indan-5-yl-5-oxo-2-(4-piperidin-4-yl-phenylamino)-5,8-dihydro-pyrido[2,3-d]pyrimidine-6-carboxylic acid methyl amide (Cpd 50)

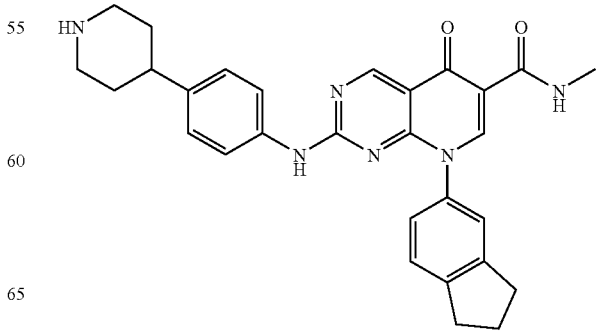

Using the procedure outlined in Example 28 the title compound was prepared from 8-indan-5-yl-5-oxo-2-(4-piperidin-4-yl-phenylamino)-5,8-dihydro-pyrido[2,3-d]pyrimidine-6-carboxylic acid ethyl ester (from Example 48(C) above, 20 mg, 0.039 mmol). A yellow solid was obtained (TFA salt, 8.9 mg, 37%) after a preparative HPLC (32 mL/min 5-100% MeCN/H$_2$O gradient over 10 min) purification. $^1$H NMR (400 MHz, CDCl$_3$/CD$_3$OD 20:1 v/v) δ (ppm): 9.30 (s, 1H), 8.75 (s, 1H), 7.35 (d, J=7.9 Hz, 1H), 7.19 (m, 3H), 7.09 (d, J=7.9 Hz, 1H), 6.84 (br, 2H), 3.48 (m, 2H), 2.97 (m, 11H), 2.62 (m, 1H), 2.16 (m, 2H), 1.88 (m, 2H). Mass Spectrum (LCMS, ESI pos.) Calcd. For C$_{29}$H$_{30}$N$_6$O$_2$: 495.24 (M+H), Found 495.1.

EXAMPLE 51

8-Indan-5-yl-5-oxo-2-(4-piperidin-4-yl-phenylamino)-5,8-dihydro-pyrido[2,3-d]pyrimidine-6-carboxylic acid ethyl amide (Cpd 51)

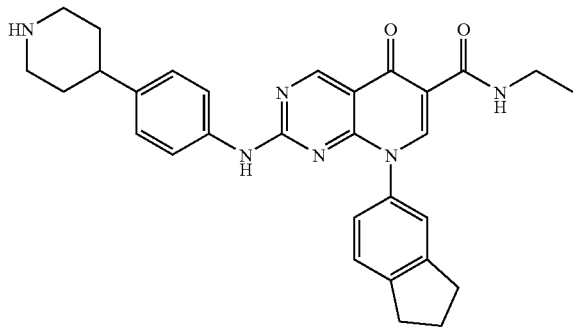

Using the procedure outlined in Example 29 the title compound was prepared from 8-indan-5-yl-5-oxo-2-(4-piperidin-4-yl-phenylamino)-5,8-dihydro-pyrido[2,3-d]pyrimidine-6-carboxylic acid ethyl ester (from Example 48(C) above, 20 mg, 0.039 mmol). A yellow solid was obtained (TFA salt, 7.3 mg, 30%) after a preparative HPLC (32 mL/min 5-100% MeCN/H$_2$O gradient over 10 min) purification. $^1$H NMR (400 MHz, CDCl$_3$/CD$_3$OD 20:1 v/v) δ (ppm): 9.30 (s, 1H), 8.75 (s, 1H), 7.35 (d, J=7.9 Hz, 1H), 7.19 (m, 3H), 7.09 (d, J=7.9 Hz, 1H), 6.84 (br, 2H), 3.48 (m, 4H), 2.97 (m, 8H), 2.64 (m, 1H), 2.20 (m, 2H), 1.90 (m, 2H), 1.26 (t, J=7.3 Hz, 3H). Mass Spectrum (LCMS, ESI pos.) Calcd. For C$_{30}$H$_{32}$N$_6$O$_2$: 509.26 (M+H), Found 509.1.

EXAMPLE 52

8-Indan-5-yl-5-oxo-2-(3-piperazin-1-yl-phenylamino)-5,8-dihydro-pyrido[2,3-d]pyrimidine-6-carboxylic acid amide (Cpd 52)

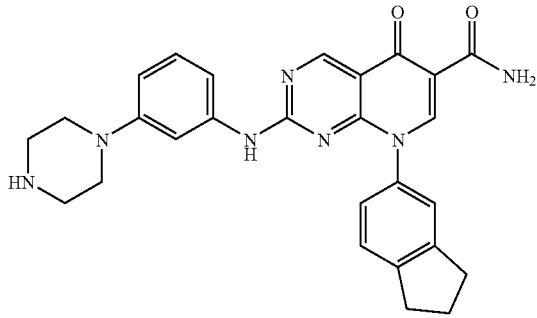

A. 4-(3-Amino-phenyl)-piperazine-1-carboxylic acid tert-butyl ester

Using the procedure outlined in Example 37 (A), the title compound was prepared from 1-fluoro-3-nitrobenzene (1g, 7 mmol) and 1-Boc-piperazine (1.9 g, 10 mmol) $^1$H NMR (400 MHz, CDCl$_3$) δ (ppm): 7.03 (t, J=8.0 Hz, 1H), 6.34 (d, J=8.2 Hz, 1H), 6.23 (m, 2H), 3.62 (br, 2H), 3.53 (m, 4H), 3.07 (m, 2H), 1.47 (s, 9H).

B. 8-Indan-5-yl-5-oxo-2-(3-piperazin-1-yl-phenylamino)-5,8-dihydro-pyrido[2,3-d]pyrimidine-6-carboxylic acid ethyl ester Using the procedure outlined in Example 1(g) the title compound was prepared from 4-(3-amino-phenyl)-piperazine-1-carboxylic acid tert-butyl ester (from the previous step, 54 mg, 0.19 mmol) and 8-indan-5-yl-2-methanesulfonyl-5-oxo-5,8-dihydro-pyrido[2,3-d]pyrimidine-6-carboxylic acid ethyl ester (from Example, 1(e) above, 80 mg, 0.19 mmol). A yellow solid was obtained (60 mg, 62%) after a preparative HPLC (32 mL/min 5-100% MeCN/H$_2$O gradient over 10 min) purification. The Boc group was removed by treatment with TFA in CH$_2$Cl$_2$ (1:1 v/v) to give the title compound. $^1$H NMR (400 MHz, CDCl$_3$/CD$_3$OD 10:1 v/v) δ (ppm): 9.26 (br, 1H), 8.49 (s, 1H), 7.35 (d, J=7.9 Hz, 1H), 7.20 (s, 1H), 7.11 (11, 2H), 6.78 (br, 2H), 6.54 (m, 1H), 4.24 (q, J=7.1 Hz, 2H), 3.98 (m, 4H), 2.29 (m, 4H), 2.96 (m, 4H), 2.14 (m, 2H), 1.27 (t, J=7.1 Hz, 3H).

C. 8-Indan-5-yl-5-oxo-2-(3-piperazin-1-yl-phenylamino)-5,8-dihydro-pyrido[2,3-d]pyrimidine-6-carboxylic acid amide Using the procedure outlined in Example 7 the title compound was prepared from 8-indan-5-yl-5-oxo-2-(3-piperazin-1-yl-phenylamino)-5,8-dihydro-pyrido[2,3-d]pyrimidine-6-carboxylic acid ethyl ester (from the previous step, 20 mg, 0.038 mmol). The title compound was obtained as a TFA salt after a preparative HPLC (32 mL/min 5-100% MeCN/H$_2$O gradient over 10 min) purification (6.9 mg, 30%). $^1$H NMR (400 MHz, DMSO-d$_6$) δ (ppm): 10.21 (br, 1H), 9.20 (s, 1H), 8.96 (s, 1H), 8.63 (s, 1H), 8.48 (s, 1H), 7.61 (d, J=3.4 Hz, 1H), 7.41 (m, 2H), 7.30 (d, J=8.1 Hz, 1H), 7.10 (d, J=7.7 Hz, 1H), 6.81 (br, 1H), 6.57 (d, J=8.5 Hz, 1H), 3.14 (m, 4H), 2.90 (m, 4H), 2.05 (m, 2H). Mass Spectrum (LCMS, ESI pos.) Calcd. For C$_{27}$H$_{27}$N$_7$O$_2$: 482.22 (M+H), Found 482.1.

EXAMPLE 53

8-Indan-5-yl-5-oxo-2-(3-piperazin-1-yl-phenylamino)-5,8-dihydro-pyrido[2,3-d]pyrimidine-6-carboxylic acid methyl amide (Cpd 53)

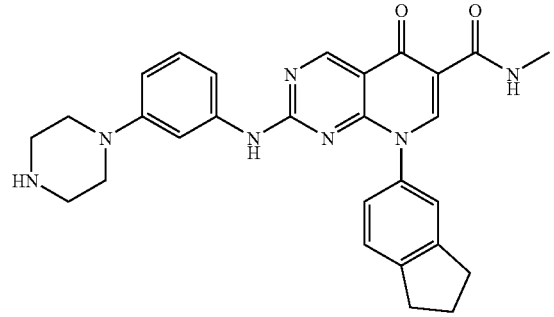

Using the procedure outlined in Example 28 the title compound was prepared from 8-indan-5-yl-5-oxo-2-(3-piperazin-1-yl-phenylamino)-5,8-dihydro-pyrido[2,3-d]pyrimidine-6-carboxylic acid ethyl ester (from Example 52(B) above, 20 mg, 0.039 mmol). A yellow solid was obtained (TFA salt, 13.2 mg, 56%) after a preparative HPLC (32 mL/min 5-100% MeCN/H$_2$O gradient over 10 min) purification. $^1$H NMR (400 MHz, CDCl$_3$/CD$_3$OD 10:1 v/v) δ (ppm): 9.67 (br, 1H), 9.35 (s, 1H), 8.77 (s, 1H), 7.36 (d, J=7.9 Hz, 1H), 7.23 (s, 1H), 7.17 (br, 1H), 7.13 (d, J=7.9 Hz, 1H), 6.87 (br, 1H), 6.67 (br, 1H), 6.57 (m, 1H), 3.27 (m, 4H), 2.97 (m, 7H), 2.44 (br, 4H), 2.16 (m, 2H). Mass Spectrum (LCMS, ESI pos.) Calcd. For C$_{28}$H$_{29}$N$_7$O$_2$: 496.24 (M+H), Found 496.0.

EXAMPLE 54

8-Indan-5-yl-5-oxo-2-(3-piperazin-1-yl-phenylamino)-5,8-dihydro-pyrido[2,3-d]pyrimidine-6-carboxylic acid ethyl amide (Cpd 54)

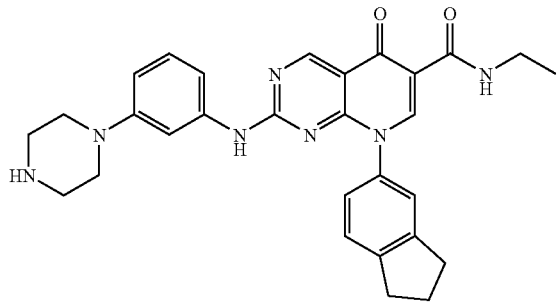

Using the procedure outlined in Example 29 the title compound was prepared from 8-indan-5-yl-5-oxo-2-(3-piperazin-1-yl-phenylamino)-5,8-dihydro-pyrido[2,3-d]pyrimidine-6-carboxylic acid ethyl ester (from Example 52(B) above, 20 mg, 0.039 mmol). A yellow solid was obtained (TFA salt, 8.5 mg, 35%) after a preparative HPLC (32 mL/min 5-100% MeCN/H$_2$O gradient over 10 min) purification. $^1$H NMR (400 MHz, CDCl$_3$/CD$_3$OD 10:1 v/v) δ (ppm): 9.30 (s, 1H), 8.72 (s, 1H), 7.34 (d, J=7.9 Hz, 1H), 7.19 (s, 1H), 7.15 (br, 1H), 7.10 (d, J=7.9 Hz, 1H), 6.84 (br, 1H), 6.61 (br, 1H), 6.54 (m, 1H), 3.41 (m, 2H), 3.22 (m, 4H), 2.96 (m, 4H), 2.77 (br, 4H), 2.14 (m, 2H), 1.18 (t, J=7.3 Hz, 3H). Mass Spectrum (LCMS, ESI pos.) Calcd. For C$_{29}$H$_{31}$N$_7$O$_2$: 510.25 (M+H), Found 510.1.

EXAMPLE 55

2-[3-(3,5-Dimethyl-piperazin-1-yl)-phenylamino]-8-indan-5-yl-5-oxo-5,8-dihydro-pyrido[2,3-d]pyrimidine-6-carboxylic acid amide (Cpd 55)

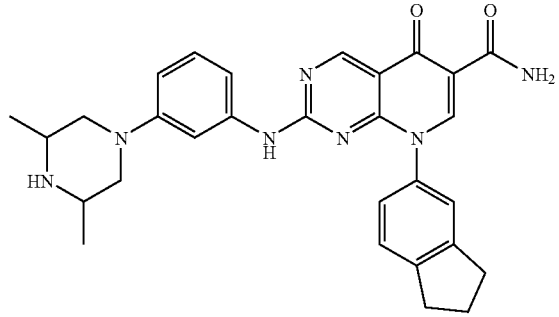

A. 3-(3,5-Dimethyl-piperazin-1-yl)-phenylamine

Using the procedure outlined in Example 37 (A), the title compound was prepared from 1-fluoro-3-nitrobenzene (1 g, 7 mmol) and 3,5-dimethyl-piperazine (1.14 g, 10 mmol). $^1$H NMR (400 MHz, CDCl$_3$) δ (ppm): 7.00 (t, J=8.0 Hz, 1H), 6.33 (d, J=8.2 Hz, 1H), 6.21 (m, 1H), 6.15 (d, J=8.2 Hz, 1H), 3.60 (br, 2H), 3.45 (d, J=9.8 Hz, 2H), 2.98 (m, 1H), 2.22 (t, J=11.3 Hz, 2H), 1.10 (s, 3H), 1.08 (s, 3H).

B. 2-[3-(3,5-Dimethyl-piperazin-1-yl)-phenylamino]-8-indan-5-yl-5-oxo-5,8-dihydro-pyrido[2,3-d]pyrimidine-6-carboxylic acid ethyl ester Using the procedure outlined in Example 1(g) the title compound was prepared from 3-(3,5-dimethyl-piperazin-1-yl)-phenylamine (from the previous step, 52 mg, 0.25 mmol) and 8-indan-5-yl-2-methanesulfonyl-5-oxo-5,8-dihydro-pyrido[2,3-d]pyrimidine-6-carboxylic acid ethyl ester (from Example 1(e) above, 100 mg, 0.24 mmol). A yellow solid was obtained (67 mg, 52%) after a preparative HPLC (32 mL/min 5-100% MeCN/H$_2$O gradient over 10 min) purification. $^1$H NMR (400 MHz, CDCl$_3$) δ (ppm): 9.29 (s, 1H), 8.44 (s, 1H), 7.49 (br, 1H), 7.31 (d, J=7.9 Hz, 1H), 7.20 (m, 2H), 7.09 (d, J=7.8 Hz, 1H), 6.94 (d, J=7.9 Hz, 1H), 6.87 (br, 1H), 6.52 (d, J=7.9 Hz, 1H), 4.32 (q, J=7.1 Hz, 2H), 3.38 (d, J=10.5 Hz, 2H), 3.03 (m, 6H), 2.25 (m, 2H), 2.12 (m, 2H), 1.32 (t, J=7.1 Hz, 3H), 1.10 (s, 3H), 1.08 (s, 3H).

C. 2-[3-(3,5-Dimethyl-piperazin-1-yl)-phenylamino]-8-indan-5-yl-5-oxo-5,8-dihydro-pyrido[2,3-d]pyrimidine-6-carboxylic acid amide Using the procedure outlined in Example 7 the title compound was prepared from 2-[3-(3,5-dimethyl-piperazin-1-yl)-phenylamino]-8-indan-5-yl-5-oxo-5,8-dihydro-pyrido[2,3-d]pyrimidine-6-carboxylic acid ethyl ester (from the previous step, 15 mg, 0.028 mmol). The title compound was obtained as a TFA salt after a preparative HPLC (32 mL/min 5-100% MeCN/H$_2$O gradient over 10 min) purification (10.8 mg, 62%). $^1$H NMR (400 MHz, CDCl$_3$/CD$_3$OD 5:1 v/v) δ (ppm): 9.67 (br, 1H), 9.35 (s, 1H), 8.77 (s, 1H), 7.36 (d, J=7.9 Hz, 1H), 7.23 (s, 1H), 7.17 (br, 1H), 7.13 (d, J=7.9 Hz, 1H), 6.87 (br, 1H), 6.67 (br, 1H), 6.57 (m, 1H), 3.49 (d, J=10.5 Hz, 2H), 3.37 (m, 2H), 2.96 (m, 4H), 2.65 (t, J=11.5 Hz, 2H), 2.13 (m, 2H), 1.31 (s, 3H), 1.29 (s, 3H). Mass Spectrum (LCMS, ESI pos.) Calcd. For C$_{29}$H$_{31}$N$_7$O$_2$: 510.25 (M+H), Found 510.1.

EXAMPLE 56

2-[3-(3,5-Dimethyl-piperazin-1-yl)-phenylamino]-8-indan-5-yl-5-oxo-5,8-dihydro-pyrido[2,3-d]pyrimidine-6-carboxylic acid methyl amide (Cpd 56)

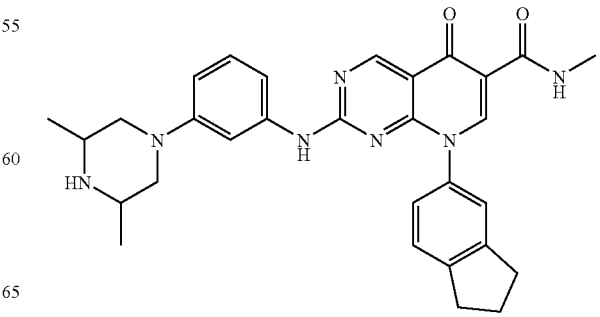

Using the procedure outlined in Example 28 the title compound was prepared from 2-[3-(3,5-dimethyl-piperazin-1-yl)-phenylamino]-8-indan-5-yl-5-oxo-5,8-dihydro-pyrido[2,3-d]pyrimidine-6-carboxylic acid ethyl ester (from Example 55(B), 15 mg, 0.028 mmol). A yellow solid was obtained (TFA salt, 5.3 mg, 30%) after a preparative HPLC (32 mL/min 5-100% MeCN/H$_2$O gradient over 10 min) purification. $^1$H NMR (400 MHz, CDCl$_3$) δ (ppm): 9.67 (br, 1H), 9.34 (s, 1H), 8.77 (s, 1H), 7.36 (d, J=7.9 Hz, 1H), 7.22 (s, 1H), 7.17 (br, 1H), 7.13 (d, J=7.9 Hz, 1H), 6.85 (br, 1H), 6.67 (br, 1H), 6.55 (m, 1H), 3.49 (d, J=10.5 Hz, 2H), 3.37 (m, 2H), 2.97 (m, 7H), 2.74 (m, 4H), 2.13 (m, 2H), 1.33 (s, 3H), 1.31 (s, 3H). Mass Spectrum (LCMS, ESI pos.) Calcd. For C$_{30}$H$_{33}$N$_7$O$_2$: 524.27 (M+H), Found 524.1.

EXAMPLE 57

8-Cyclohexyl-2-[4-(2-morpholin-4-yl-ethyl)-phenylamino]-5-oxo-5,8-dihydro-pyrido[2,3-d]pyrimidine-6-carboxylic acid amide (Cpd 57)

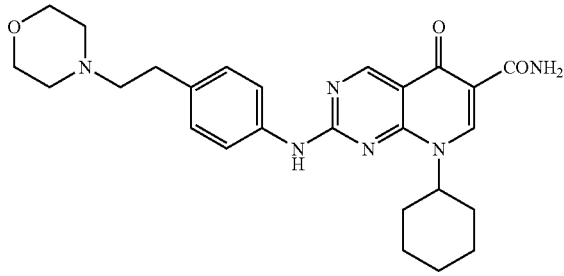

A. 8-Cyclohexyl-2-[4-(2-morpholin-4-yl-ethyl)-phenylamino]-5-oxo-5,8-dihydro-pyrido[2,3-d]pyrimidine-6-carboxylic acid ethyl ester Using the procedure outlined in Example 1(g) the title compound was prepared from 4-(2-morpholin-4-yl-ethyl)-phenylamine (from Example 27(A), 54 mg, 0.26 mmol) and 8-cyclohexyl-2-methanesulfonyl-5-oxo-5,8-dihydro-pyrido[2,3-d]pyrimidine-6-carboxylic acid ethyl ester (from Example 17(e) above, 100 mg, 0.26 mmol). The title compound was obtained as a white solid (77 mg, 59%). $^1$H NMR (400 MHz, CDCl$_3$) δ (ppm): 9.28 (s, 1H), 8.46 (s, 1H), 7.98 (br, 1H), 7.50 (d, J=8.5 Hz, 2H), 7.17 (d, J=8.5 Hz, 2H), 5.04 (m, 1H), 4.32 (q, J=7.1 Hz, 2H), 3.67 (t, J=4.6 Hz, 4H), 2.76 (m, 2H), 2.54 (m, 2H), 2.47 (m, 4H), 1.99 (m, 4H), 1.78 (m, 1H), 1.61 (m, 2H), 1.46 (m, 2H), 1.34 (t, J=7.1 Hz, 3H), 1.23 (m, 1H).

B. 8-Cyclohexyl-2-[4-(2-morpholin-4-yl-ethyl)-phenylamino]-5-oxo-5,8-dihydro-pyrido[2,3-d]pyrimidine-6-carboxylic acid amide Using the procedure outlined in Example 7 the title compound was prepared from 8-cyclohexyl-2-[4-(2-morpholin-4-yl-ethyl)-phenylamino]-5-oxo-5,8-dihydro-pyrido[2,3-d]pyrimidine-6-carboxylic acid ethyl ester (from the previous step, 20 mg, 0.039 mmol). The title compound was obtained as yellow solid after a preparative HPLC (32 mL/min 5-100% MeCN/H$_2$O gradient over 10 min) purification (10.7 mg, 56%). $^1$H NMR (400 MHz, CDCl$_3$) δ (ppm): 9.42 (br, 1H), 9.31 (s, 1H), 8.78 (s, 1H), 7.50 (d, J=8.5 Hz, 2H), 7.17 (d, J=8.5 Hz, 2H), 5.10 (m, 1H), 3.67 (t, J=4.6 Hz, 4H), 2.76 (m, 2H), 2.54 (m, 2H), 2.46 (m, 4H), 1.99 (m, 4H), 1.78-1.19 (m, 10H). Mass Spectrum (LCMS, ESI pos.) Calcd. For C$_{26}$H$_{32}$N$_6$O$_3$: 477.25 (M+H), Found 477.1.

EXAMPLE 58

8-Cyclohexyl-2-[4-(2-morpholin-4-yl-ethyl)-phenylamino]-5-oxo-5,8-dihydro-pyrido[2,3-d]pyrimidine-6-carboxylic acid methyl amide (Cpd 58)

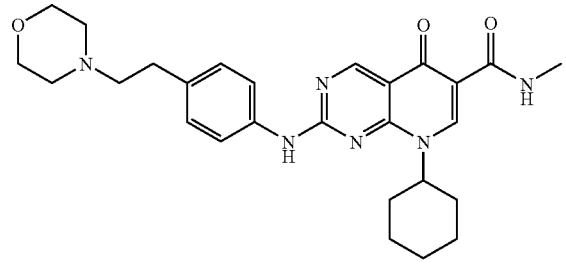

Using the procedure outlined in Example 28 the title compound was prepared from 8-cyclohexyl-2-[4-(2-morpholin-4-yl-ethyl)-phenylamino]-5-oxo-5,8-dihydro-pyrido[2,3-d]pyrimidine-6-carboxylic acid ethyl ester (from Example 57(A), 20 mg, 0.039 mmol). The title compound was obtained as yellow solid after a preparative HPLC (32 mL/min 5-100% MeCN/H$_2$O gradient over 10 min) purification (13.4 mg, 70%). $^1$H NMR (400 MHz, CDCl$_3$) δ (ppm): 9.57 (m, 1H), 9.30 (s, 1H), 8.78 (s, 1H), 7.70 (br, 1H), 7.50 (d, J=8.5 Hz, 2H), 7.16 (d, J=8.5 Hz, 2H), 5.09 (m, 1H), 3.67 (t, J=4.6 Hz, 4H), 2.94 (d, J=4.9 Hz, 3H), 2.76 (m, 2H), 2.54 (m, 2H), 2.46 (m, 4H), 1.97 (m, 4H), 1.71 (m, 3H), 1.44 (m, 2H), 1.23 (m, 1H). Mass Spectrum (LCMS, ESI pos.) Calcd. For C$_{27}$H$_{34}$N$_6$O$_3$: 491.27 (M+H), Found 491.0.

EXAMPLE 59

8-Cyclohexyl-2-[4-(2-morpholin-4-yl-ethyl)-phenylamino]-5-oxo-5,8-dihydro-pyrido[2,3-d]pyrimidine-6-carboxylic acid ethyl amide (Cpd 59)

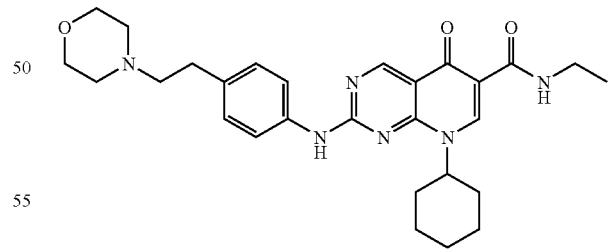

Using the procedure outlined in Example 29, the title compound was prepared from 8-cyclohexyl-2-[4-(2-morpholin-4-yl-ethyl)-phenylamino]-5-oxo-5,8-dihydro-pyrido[2,3-d]pyrimidine-6-carboxylic acid ethyl ester (from Example 57(A), 20 mg, 0.039 mmol). The title compound was obtained as yellow solid after a preparative HPLC (32 mL/min 5-100% MeCN/H$_2$O gradient over 10 min) purification (11.9 mg, 60%). $^1$H NMR (400 MHz, CDCl$_3$) δ (ppm): 9.64 (m, 1H), 9.30 (s, 1H), 8.78 (s, 1H), 7.70 (br, 1H), 7.50 (d, J=8.5 Hz, 2H), 7.16 (d, J=8.5 Hz, 2H), 5.07 (m, 1H), 3.67 (t, J=4.6 Hz, 4H), 3.42 (m, 2H), 2.76 (1H, 2H), 2.54 (m, 2H), 2.46 (1H, 4H), 1.97 (m, 4H), 1.71 (m, 3H), 1.44 (m, 2H), 1.18 (m, 4H). Mass Spectrum (LCMS, ESI pos.) Calcd. For $C_{28}H_{36}N_6O_3$: 505.28 (M+H), Found 505.0.

EXAMPLE 60

8-Cyclohexyl-2-[4-(4-methyl-piperazin-1-yl)-phenylamino]-5-oxo-5,8-dihydro-pyrido[2,3-d]pyrimidine-6-carboxylic acid amide (Cpd 60)

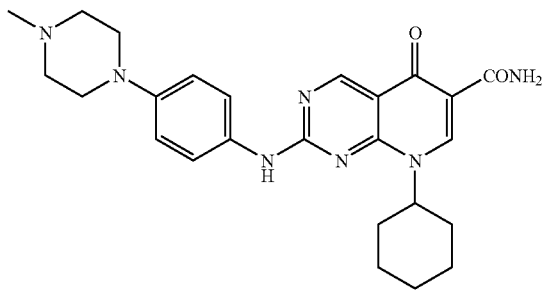

A. 8-Cyclohexyl-2-[4-(4-methyl-piperazin-1-yl)-phenylamino]-5-oxo-5,8-dihydro-pyrido[2,3-d]pyrimidine-6-carboxylic acid ethyl ester Using the procedure outlined in Example 1(g) the title compound was prepared from 4-(4-methyl-piperazin-1-yl)-phenylamine (50 mg, 0.26 mmol) and 8-cyclohexyl-2-methanesulfonyl-5-oxo-5,8-dihydro-pyrido[2,3-d]pyrimidine-6-carboxylic acid ethyl ester (from Example 17(e), 100 mg, 0.26 mmol). The title compound was obtained as a yellow solid (80 mg, 63%). $^1$H NMR (400 MHz, CDCl$_3$) δ (ppm): 9.25 (s, 1H), 8.44 (s, 1H), 7.56 (br, 1H), 7.43 (d, J=8.9 Hz, 2H), 6.87 (d, J=9.0 Hz, 2H), 5.00 (m, 1H), 4.32 (q, J=7.1 Hz, 2H), 3.16 (t, J=4.9 Hz, 4H), 2.55 (t, J=4.9 Hz, 4H), 2.30 (s, 3H), 1.94 (m, 4H), 1.76 (m, 1H), 1.62 (m, 2H), 1.42 (m, 2H), 1.34 (t, J=7.1 Hz, 3H), 1.21 (m, 1H).

B. 8-Cyclohexyl-2-[4-(4-methyl-piperazin-1-yl)-phenylamino]-5-oxo-5,8-dihydro-pyrido[2,3-d]pyrimidine-6-carboxylic acid amide Using the procedure outlined in Example 7 the title compound was prepared from 8-cyclohexyl-2-[4-(4-methyl-piperazin-1-yl)-phenylamino]-5-oxo-5,8-dihydro-pyrido[2,3-d]pyrimidine-6-carboxylic acid ethyl ester (from the previous step, 20 mg, 0.040 mmol). The title compound was obtained as yellow solid after a preparative HPLC (32 mL/min 5-100% MeCN/H$_2$O gradient over 10 min) purification (9.9 mg, 54%). $^1$H NMR (400 MHz, DMSO-d$_6$) δ (ppm): 10.27 (br, 1H), 9.15 (s, 1H), 9.05 (m, 1H), 8.68 (s, 1H), 7.60 (m, 3H), 6.92 (d, J=9.0 Hz, 2H), 4.99 (m, 1H), 3.09 (m, 4H), 2.44 (m, 4H), 2.20 (s, 3H), 1.92 (m, 4H), 1.71 (m, 3H), 1.42 (m, 2H), 1.30 (m, 1H). Mass Spectrum (LCMS, ESI pos.) Calcd. For $C_{25}H_{31}N_7O_2$: 462.25 (M+H), Found 462.0.

EXAMPLE 61

8-Cyclohexyl-2-[4-(4-methyl-piperazin-1-yl)-phenylamino]-5-oxo-5,8-dihydro-pyrido[2,3-d]pyrimidine-6-carboxylic acid methyl amide (Cpd 61)

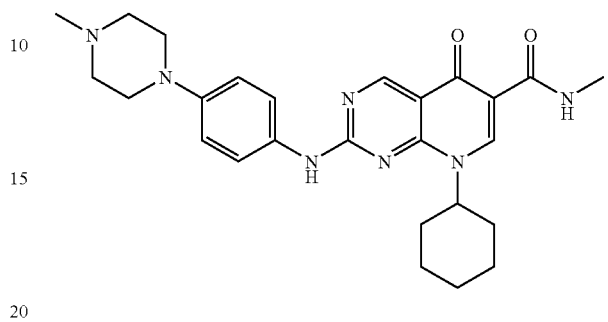

Using the procedure outlined in Example 28 the title compound was prepared from 8-cyclohexyl-2-[4-(4-methyl-piperazin-1-yl)-phenylamino]-5-oxo-5,8-dihydro-pyrido[2,3-d]pyrimidine-6-carboxylic acid ethyl ester (from Example 60(A), 20 mg, 0.040 mmol). The title compound was obtained as yellow solid after a preparative HPLC (32 mL/min 5-100% MeCN/H$_2$O gradient over 10 min) purification (9.0 mg, 47%). $^1$H NMR (400 MHz, CDCl$_3$) δ (ppm): 9.60 (m, 1H), 9.27 (s, 1H), 8.76 (s, 1H), 7.50 (br, 1H), 7.44 (d, J=8.6 Hz, 2H), 6.88 (d, J=9.0 Hz, 2H), 5.05 (m, 1H), 3.14 (m, 4H), 2.92 (d, J=4.9 Hz, 3H), 2.54 (m, 4H), 2.30 (s, 3H), 1.95 (m, 4H), 1.66 (m, 3H), 1.44 (m, 2H), 1.20 (m, 1H). Mass Spectrum (LCMS, ESI pos.) Calcd. For $C_{26}H_{33}N_7O_2$: 476.27 (M+H), Found 476.0.

EXAMPLE 62

8-Cyclohexyl-2-[4-(4-methyl-piperazin-1-yl)-phenylamino]-5-oxo-5,8-dihydro-pyrido[2,3-d]pyrimidine-6-carboxylic acid ethyl amide (Cpd 62)

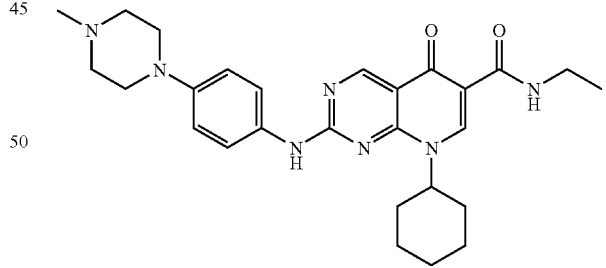

Using the procedure outlined in Example 29 the title compound was prepared from 8-cyclohexyl-2-[4-(4-methyl-piperazin-1-yl)-phenylamino]-5-oxo-5,8-dihydro-pyrido[2,3-d]pyrimidine-6-carboxylic acid ethyl ester (from Example 60(A), 20 mg, 0.040 mmol). The title compound was obtained as yellow solid after a preparative HPLC (32 mL/min 5-100% MeCN/H$_2$O gradient over 10 min) purification (8.3 mg, 42%). $^1$H NMR (400 MHz, CDCl$_3$) δ (ppm): 9.60 (m, 1H), 9.27 (s, 1H), 8.76 (s, 1H), 7.50 (br, 1H), 7.44 (d, J=8.6 Hz, 2H), 6.88 (d, J=9.0 Hz, 2H), 5.05 (m, 1H), 3.42 (m, 2H), 3.14 (m, 4H), 2.54 (m, 4H), 2.30 (s, 3H), 1.95 (m, 4H), 1.66 (m, 3H), 1.44 (m, 2H), 1.23 (m, 1H), 1.18 (t, J=7.3 Hz, 3H). Mass Spectrum (LCMS, ESI pos.) Calcd. For $C_{27}H_{35}N_7O_2$: 490.29 (M+H), Found 490.0.

EXAMPLE 63

8-Cyclohexyl-2-[3-(4-methyl-piperazin-1-yl)-phenylamino]-5-oxo-5,8-dihydro-pyrido[2,3-d]pyrimidine-6-carboxylic acid amide (Cpd 63)

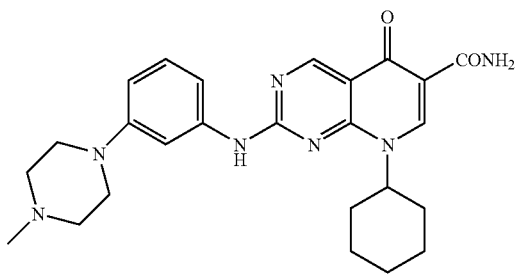

A. 8-Cyclohexyl-2-[3-(4-methyl-piperazin-1-yl)-phenylamino]-5-oxo-5,8-dihydro-pyrido[2,3-d]pyrimidine-6-carboxylic acid ethyl ester Using the procedure outlined in Example 1 (g) the title compound was prepared from 3-(4-methyl-piperazin-1-yl)-phenylamine (from Example 37(A), 55 mg, 0.29 mmol) and 8-cyclohexyl-2-methanesulfonyl-5-oxo-5,8-dihydro-pyrido[2,3-d]pyrimidine-6-carboxylic acid ethyl ester (from Example 17(e), 100 mg, 0.26 mmol). The title compound was obtained as a yellow solid (72 mg, 56%). $^1$H NMR (400 MHz, $CDCl_3$) δ (ppm): 9.27 (s, 1H), 8.46 (s, 1H), 7.75 (br, 1H), 7.29 (m, 1H), 7.22 (d, J=8.5 Hz, 1H), 6.86 (m, 1H), 6.66 (d, J=8.5 Hz, 1H), 5.05 (m, 1H), 4.31 (q, J=7.1 Hz, 2H), 3.17 (t, J=4.9 Hz, 4H), 2.51 (t, J=4.9 Hz, 4H), 2.28 (s, 3H), 1.94 (m, 4H), 1.76-1.19 (m, 6H), 1.34 (t, J=7.1 Hz, 3H).

B. 8-Cyclohexyl-2-[3-(4-methyl-piperazin-1-yl)-phenylamino]-5-oxo-5,8-dihydro-pyrido[2,3-d]pyrimidine-6-carboxylic acid amide Using the procedure outlined in Example 7 the title compound was prepared from 8-cyclohexyl-2-[3-(4-methyl-piperazin-1-yl)-phenylamino]-5-oxo-5,8-dihydro-pyrido[2,3-d]pyrimidine-6-carboxylic acid ethyl ester (from the previous step, 20 mg, 0.040 mmol). The title compound was obtained as yellow solid after a preparative HPLC (32 mL/min 5-100% MeCN/$H_2O$ gradient over 10 min) purification (2.3 mg, 12%). $^1$H NMR (400 MHz, $CDCl_3$) δ (ppm): 9.44 (br, 1H), 9.32 (s, 1H), 8.77 (s, 1H), 7.50 (br, 1H), 7.29 (br, 1H), 7.22 (m, 1H), 6.86 (br, 1H), 6.70 (d, J=8.5 Hz, 1H), 5.67 (br, 1H), 5.11 (I, 1H), 3.18 (m, 4H), 2.52 (m, 4H), 2.29 (s, 3H), 1.95 (m, 4H), 1.69 (m, 3H), 1.44 (m, 2H), 1.20 (m, 1H). Mass Spectrum (LCMS, ESI pos.) Calcd. For $C_{25}H_{31}N_7O_2$: 462.25 (M+H), Found 462.1.

EXAMPLE 64

8-Cyclohexyl-2-[3-(4-methyl-piperazin-1-yl)-phenylamino]-5-oxo-5,8-dihydro-pyrido[2,3-d]pyrimidine-6-carboxylic acid methyl amide (Cpd 64)

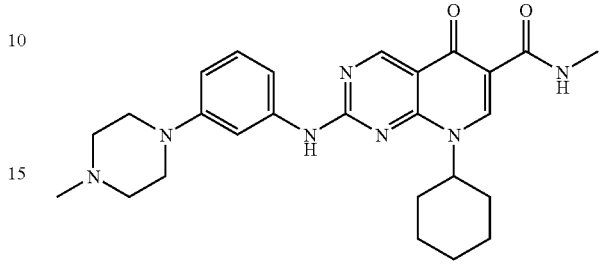

Using the procedure outlined in Example 28 the title compound was prepared from 8-cyclohexyl-2-[3-(4-methyl-piperazin-1-yl)-phenylamino]-5-oxo-5,8-dihydro-pyrido[2,3-d]pyrimidine-6-carboxylic acid ethyl ester (from Example 63(A), 20 mg, 0.040 mmol). The title compound was obtained as yellow solid after a preparative HPLC (32 mL/min 5-100% MeCN/$H_2O$ gradient over 10 min) purification (8.9 mg, 47%). $^1$H NMR (400 MHz, $CDCl_3$) δ (ppm): 9.59 (m, 1H), 9.31 (s, 1H), 8.78 (s, 1H), 7.50 (br, 1H), 7.29 (m, 1H), 7.22 (d, J=8.5 Hz, 1H), 6.87 (m, 1H), 6.68 (d, J=8.5 Hz, 1H), 5.09 (m, 1H), 3.14 (m, 4H), 2.92 (d, J=4.9 Hz, 3H), 2.54 (m, 4H), 2.30 (s, 3H), 1.95 (m, 4H), 1.66 (m, 3H), 1.44 (m, 2H), 1.20 (m, 1H). Mass Spectrum (LCMS, ESI pos.) Calcd. For $C_{26}H_{33}N_7O_2$: 476.27 (M+H), Found 476.1.

EXAMPLE 65

8-Cyclohexyl-2-[3-(4-methyl-piperazin-1-yl)-phenylamino]-5-oxo-5,8-dihydro-pyrido[2,3-d]pyrimidine-6-carboxylic acid ethyl amide (Cpd 65)

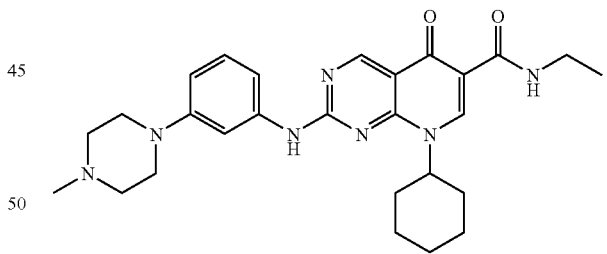

Using the procedure outlined in Example 29 the title compound was prepared from 8-cyclohexyl-2-[3-(4-methyl-piperazin-1-yl)-phenylamino]-5-oxo-5,8-dihydro-pyrido[2,3-d]pyrimidine-6-carboxylic acid ethyl ester (from Example 63(A), 20 mg, 0.040 mmol). The title compound was obtained as yellow solid after a preparative HPLC (32 mL/min 5-100% MeCN/$H_2O$ gradient over 10 min) purification (7.5 mg, 38%). $^1$H NMR (400 MHz, $CDCl_3$) δ (ppm): 9.65 (m, 1H), 9.30 (s, 1H), 8.78 (s, 1H), 7.47 (br, 1H), 7.29 (m, 1H), 7.22 (d, J=8.5 Hz, 1H), 6.87 (m, 1H), 6.68 (d, J=8.5 Hz, 1H), 5.09 (m, 1H), 3.42 (m, 2H), 3.14 (m, 4H), 2.54 (m, 4H), 2.30 (s, 3H), 1.95 (m, 4H), 1.66 (m, 3H), 1.44 (m, 2H), 1.23 (m, 1H), 1.18 (t, J=7.3 Hz, 3H). Mass Spectrum (LCMS, ESI pos.) Calcd. For $C_{27}H_{35}N_7O_2$: 490.29 (M+H), Found 490.1.

EXAMPLE 66

8-Cyclohexyl-2-[4-(2-isopropylsulfamoyl-ethyl)-phenylamino]-5-oxo-5,8-dihydro-pyrido[2,3-d]pyrimidine-6-carboxylic acid amide (Cpd 66)

EXAMPLE 67

8-Cyclohexyl-2-{4-[2-(morpholine-4-sulfonyl)-ethyl]-phenylamino}-5-oxo-5,8-dihydro-pyrido[2,3-d]pyrimidine-6-carboxylic acid amide (Cpd 67)

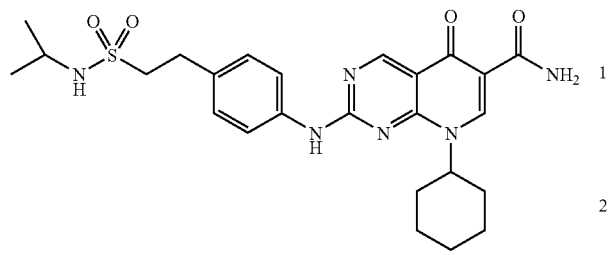

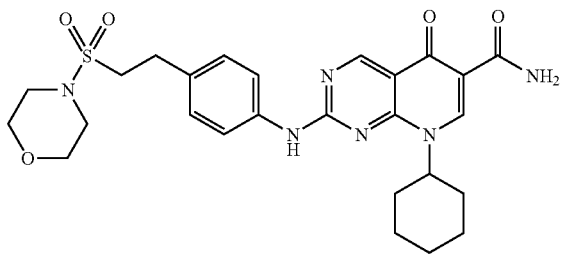

A. 8-Cyclohexyl-2-[4-(2-isopropylsulfamoyl-ethyl)-phenylamino]-5-oxo-5,8-dihydro-pyrido[2,3-d]pyrimidine-6-carboxylic acid ethyl ester Using the procedure outlined in Example 1(g) the title compound was prepared from 2-(4-amino-phenyl)-ethanesulfonic acid isopropylamide (from Example 33(B), 68 mg, 0.28 mmol) and 8-cyclohexyl-2-methanesulfonyl-5-oxo-5,8-dihydro-pyrido[2,3-d]pyrimidine-6-carboxylic acid ethyl ester (from Example 17(e), 100 mg, 0.26 mmol). The title compound was obtained as a yellow solid (50 mg, 35%). $^1$H NMR (400 MHz, CDCl$_3$) δ (ppm): 9.34 (s, 1H), 8.54 (s, 1H), 7.88 (br, 1H), 7.61 (d, J=8.3 Hz, 2H), 7.25 (d, J=8.3 Hz, 2H), 5.10 (m, 1H), 4.40 (q, J=7.1 Hz, 2H), 4.17 (m, 1H), 3.66 (m, 1H), 3.29 (m, 2H), 3.14 (m, 2H), 2.06 (m, 4H), 1.86 (m, 1H), 1.68 (m, 2H), 1.51 (m, 2H), 1.41 (t, J=7.1 Hz, 3H), 1.31(m, 1H), 1.24 (s, 3H), 1.23 (s, 3H).

B. 8-Cyclohexyl-2-[4-(2-isopropylsulfamoyl-ethyl)-phenylamino]-5-oxo-5,8-dihydro-pyrido[2,3-d]pyrimidine-6-carboxylic acid amide Using the procedure outlined in Example 7 the title compound was prepared from 8-cyclohexyl-2-[4-(2-isopropylsulfamoyl-ethyl)-phenylamino]-5-oxo-5,8-dihydro-pyrido[2,3-d]pyrimidine-6-carboxylic acid ethyl ester (from the previous step, 20 mg, 0.037 mmol). The title compound was obtained as yellow solid after a preparative HPLC (32 mL/min 5-100% MeCN/H$_2$O gradient over 10 min) purification (6.6 mg, 35%). $^1$H NMR (400MHz, DMSO-d$_6$) δ (ppm): 10.45 (br, 1H), 9.20 (s, 1H), 9.03 (m, 1H), 8.71 (s, 1H), 7.72 (d, J=7.6 Hz, 2H), 7.58 (m, 1H), 7.26 (d, J=8.3 Hz, 1H), 7.04 (d, J=7.5 Hz, 1H), 5.01 (br, 1H), 3.47 (m, 1H), 3.23 (m, 2H), 2.92 (m, 2H), 1.93 (m, 4H), 1.43 (m, 3H), 1.30 (m, 2H), 1.12 (m, 1H), 1.12 (s, 3H), 1.10 (s, 3H). Mass Spectrum (LCMS, ESI pos.) Calcd. For C$_{25}$H$_{32}$N$_6$O$_4$S: 513.22 (M+H), Found 513.0.

A. 8-Cyclohexyl-2-{4-[2-(morpholine-4-sulfonyl)-ethyl]-phenylamino}-5-oxo-5,8-dihydro-pyrido[2,3-d]pyrimidine-6-carboxylic acid ethyl ester Using the procedure outlined in Example 1 (g) the title compound was prepared from 4-[2-(morpholine-4-sulfonyl)-ethyl]-phenylamine (from Example 35(A), 75 mg, 0.28 mmol) and 8-cyclohexyl-2-methanesulfonyl-5-oxo-5,8-dihydro-pyrido[2,3-d]pyrimidine-6-carboxylic acid ethyl ester (from Example 17(e), 100 mg, 0.26 mmol). The title compound was obtained as a yellow solid (57 mg, 38%). $^1$H NMR (400 MHz, CDCl$_3$) δ (ppm): 9.26 (s, 1H), 8.46 (s, 1H), 7.65 (br, 1H), 7.55 (d, J=8.4 Hz, 2H), 7.19 (d, J=8.4 Hz, 2H), 5.04 (m, 1H), 4.32 (q, J=7.1 Hz, 2H), 3.68 (m, 4H), 3.22 (m, 4H), 3.10 (m, 4H), 2.00 (m, 4H), 1.80 (m, 1H), 1.62 (m, 2H), 1.48 (m, 2H), 1.34 (t, J=7.1 Hz, 3H), 1.31(m, 1H).

B. 8-Cyclohexyl-2-{4-[2-(morpholine-4-sulfonyl)-ethyl]-phenylamino}-5-oxo-5,8-dihydro-pyrido[2,3-d]pyrimidine-6-carboxylic acid amide Using the procedure outlined in Example 7 the title compound was prepared from 8-cyclohexyl-2-{4-[2-(morpholine-4-sulfonyl)-ethyl]-phenylamino}-5-oxo-5,8-dihydro-pyrido[2,3-d]pyrimidine-6-carboxylic acid ethyl ester (from the previous step, 20 mg, 0.035 mmol). The title compound was obtained as yellow solid after a preparative HPLC (32 mL/min 5-100% MeCN/H$_2$O gradient over 10 min) purification (9.2 mg, 49%). $^1$H NMR (400 MHz, CD$_2$Cl$_2$) δ (ppm): 9.26 (br, 1H), 8.76 (s, 1H), 7.62 (d, J=8.0 Hz, 2H), 7.20 (d, J=8.0 Hz, 2H), 5.08 (br, 1H), 3.64 (m, 4H), 3.18 (m, 8H), 1.97 (m, 4H), 1.71 (m, 3H), 1.45 (m, 2H), 1.27 (m, 1H). Mass Spectrum (LCMS, ESI pos.) Calcd. For C$_{26}$H$_{32}$N$_6$O$_5$S: 541.22 (M+H), Found 541.0.

EXAMPLE 68

8-Cyclohexyl-2-{4-[1-(2-dimethylamino-acetyl)-piperidin-4-yl]-phenylamino}-5-oxo-5,8-dihydro-pyrido[2,3-d]pyrimidine-6-carboxylic acid amide (Cpd 68)

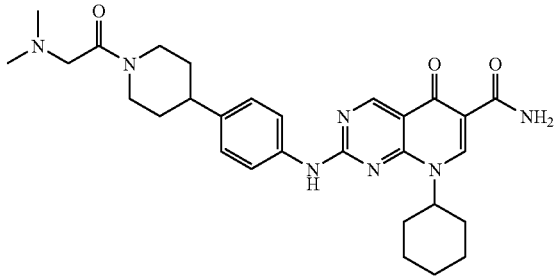

A. 8-Cyclohexyl-2-{4-[1-(2-dimethylamino-acetyl)-piperidin-4-yl]-phenylamino}-5-oxo-5,8-dihydro-pyrido[2,3-d]pyrimidine-6-carboxylic acid ethyl ester Using the procedure outlined in Example 1(g) the title compound was prepared from 4-[1-(2-dimethylamino-acetyl)-piperidin-4-yl]-phenylamine (from Example 70(B)), 73 mg, 0.28 mmol) and 8-cyclohexyl-2-methanesulfonyl-5-oxo-5,8-dihydro-pyrido[2,3-d]pyrimidine-6-carboxylic acid ethyl ester (from Example 17(e), 100 mg, 0.26 mmol). The title compound was obtained as a white solid (40 mg, 25%). $^1$H NMR (400 MHz, CDCl$_3$) δ (ppm): 9.21 (s, 1H), 8.99 (s, 1H), 8.41 (s, 1H), 7.47 (d, J=8.5 Hz, 2H), 7.13 (d, J=8.5 Hz, 2H), 4.96 (m, 3H), 4.31 (q, J=7.1 Hz, 2H), 3.00 (m, 4H), 2.77 (m, 1H), 2.30 (s, 6H), 1.93 (m, 6H), 1.64 (m, 5H), 1.42 (m, 2H), 1.34 (t, J=7.1 Hz, 3H), 1.18(m, 1H).

B. 8-Cyclohexyl-2-{4-[1-(2-dimethylamino-acetyl)-piperidin-4-yl]-phenylamino}-5-oxo-5,8-dihydro-pyrido[2,3-d]pyrimidine-6-carboxylic acid amide Using the procedure outlined in Example 7 the title compound was prepared from 8-cyclohexyl-2-{4-[1-(2-dimethylamino-acetyl)-piperidin-4-yl]-phenylamino}-5-oxo-5,8-dihydro-pyrido[2,3-d]pyrimidine-6-carboxylic acid ethyl ester (from the previous step, 20 mg, 0.036 mmol). The title compound was obtained as yellow solid after a preparative HPLC (32 mL/min 5-100% MeCN/H$_2$O gradient over 10 min) purification (16 mg, 84%). $^1$H NMR (400 MHz, CDCl$_3$) δ (ppm): 9.58 (m, 1H), 9.30 (s, 1H), 9.05 (s, 1H), 8.78 (s, 1H), 7.52 (d, J=8.5 Hz, 2H), 7.20 (d, J=8.5 Hz, 2H), 5.08 (m, 3H), 3.06 (m, 4H), 2.86 (m, 1H), 2.37 (s, 6H), 1.99 (m, 6H), 1.72 (m, 5H), 1.41 (m, 3H), 1.18(m, 1H). Mass Spectrum (LCMS, ESI pos.) Calcd. For C$_{29}$H$_{37}$N$_7$O$_3$: 532.30 (M+H), Found 532.1.

EXAMPLE 69

8-Indan-5-yl-2-(4-morpholin-4-ylmethyl-phenylamino)-5-oxo-5,8-dihydro-pyrido[2,3-d]pyrimidine-6-carboxylic acid amide (Cpd 69)

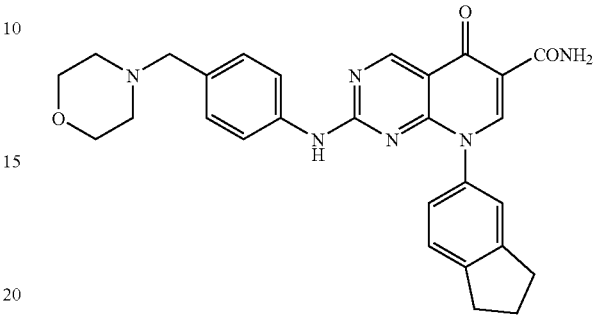

A. 8-Indan-5-yl-2-(4-morpholin-4-ylmethyl-phenylamino)-5-oxo-5,8-dihydro-pyrido[2,3-d]pyrimidine-6-carboxylic acid ethyl ester 8-indan-5-yl-2-methanesulfonyl-5-oxo-5,8-dihydro-pyrido[2,3-d]pyrimidine-6-carboxylic acid ethyl ester (0.28 g, 0.068 mmol) and 4-morpholin-4-ylmethyl-phenylamine (0.013 g, 0.068 mmol) were combined in i-PrOH (1 mL) and heated to 90° C. After 3 h, the reaction mixture was concentrated and purified by preparative HPLC (30 mL/min 5-100% MeCN/H$_2$O gradient over 10 min) and lyophilized to provide 22 mg (62%) of 8-indan-5-yl-2-(4-morpholin-4-ylmethyl-phenylamino)-5-oxo-5,8-dihydro-pyrido[2,3-d]pyrimidine-6-carboxylic acid ethyl ester. $^1$H NMR (300 MHz, CDCl$_3$) δ (ppm): 9.38 (br s, 1H), 8.55 (s, 1H), 7.44 (d, 2H, J=7.6 Hz), 7.05-7.30 (m, 5H), 4.40 (q, 2H, J=7.1 Hz), 3.71 (br s, 4H), 3.43 (s, 2H), 3.09 (t, 2H, J=7.5 Hz), 3.02 (t, 2H, J=7.2 Hz), 2.42 (br s, 4H), 2.21-2.31 (m, 2H), 1.40 (t, 3H, J=7.1 Hz).

B. 8-indan-5-yl-2-(4-morpholin-4-ylmethyl-phenylamino)-5-oxo-5,8-dihydro-pyrido[2,3-d]pyrimidine-6-carboxylic acid amide 8-Indan-5-yl-2-(4-morpholin-4-ylmethyl-phenylamino)-5-oxo-5,8-dihydro-pyrido[2,3-d]pyrimidine-6-carboxylic acid ethyl ester (18 mg, 0.034 mmol) was dissolved in MeOH (2 mL) and cooled to −78° C. in a high pressure vessel. Ammonia was bubbled into the solution for 1 min and the vessel was sealed and allowed to warm to rt. After 14 h, the solution was cooled to −78° C., the vessel was opened and the solution was allowed to warm to rt. The solution was concentrated and water (2 mL) and MeCN (1 mL) was added, the solution frozen and lyophilized to provide 11.6 mg of 8-indan-5-yl-2-(4-morpholin-4-ylmethyl-phenylamino)-5-oxo-5,8-dihydro-pyrido[2,3-d]pyrimidine-6-carboxylic acid amide. $^1$H NMR (400 MHz, CDCl$_3$) δ (ppm): 9.31 (s, 1H), 8.77 (s, 1H), 7.35 (d, 2H, J=7.9 Hz), 7.10 (d, 2H, J=7.3 Hz), 6.91-7.01 (m, 3H), 3.62-3.64 (m, 4H), 3.35 (s, 2H), 3.01 (t, 2H, J=7.2 Hz), 2.92 (t, 2H, J=7.3 Hz), 2.43 (br s, 4H), 2.15-2.19 (m, 2H). Mass Spectrum (LCMS, ESI pos.) Calcd. for C$_{31}$H$_{34}$N$_6$O$_3$: 538.27, Found: 539.2 (M+H).

EXAMPLE 70

2-{4-[1-(2-Dimethylamino-acetyl)-piperidin-4-yl]-phenylamino}-8-indan-5-yl-5-oxo-5,8-dihydro-pyrido[2,3-d]pyrimidine-6-carboxylic acid amide
(Cpd 70)

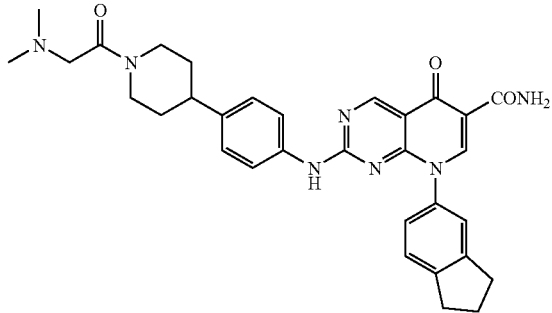

A. {4-[1-(2-Dimethylamino-acetyl)-piperidin-4-yl]-phenyl}-carbamic acid tert-butyl ester Dimethylamino-acetyl chloride (0.14 g, 0.86 mmol) and (4-piperidin-4-yl-phenyl)-carbamic acid tert-butyl ester (0.20 g, 0.72 mmol) were combined in $CH_2Cl_2$ (5 mL) and triethylamine (0.21 g, 2.2 mmol) was added. After 6 h, water (5 mL) was added. The reaction mixture was extracted with $CH_2Cl_2$ (3×5 mL) and the combined organic extracts were dried ($MgSO_4$) and concentrated. The compound was found to be unstable on silica and therefore carried on without further purification. $^1$H NMR (400 MHz, $CDCl_3$) δ (ppm): 9.04 (s, 1H), 7.52 (d, 2H, J=8.5 Hz), 7.16 (d, 2H, J=8.5 Hz), 3.06 (s 2H), 2.76-2.82(m, 2H), 2.59-2.65 (m, 1H), 2.37 (s, 6H), 1.78-1.81 (m, 2H), 1.54-1.64 (m, 2H), 1.48 (s, 9H), 1.30 (br s, 2H).

B. 1-[4-(4-Amino-phenyl)-piperidin-1-yl]-2-dimethylamino-ethanone

{4-[1-(2-Dimethylamino-acetyl)-piperidin-4-yl]-phenyl}-carbamic acid tert-butyl ester (0.72 mmol) was diluted in $CH_2Cl_2$ (3 mL) and TFA (3 mL) was added. After 1 h, the reaction mixture was concentrated. Water (2 mL) was added and the solution was frozen and lyophilized overnight to provide (0.11 g) (59%) of 1-[4-(4-amino-phenyl)-piperidin-1-yl]-2-dimethylamino-ethanone. $^1$H NMR (TFA salt) (400 MHz, $CDCl_3$) δ (ppm): 10.54 (s, 1H), 7.52 (d, 2H, J=8.5 Hz), 7.20 (d, 2H, J=8.5 Hz), 4.10 (s, 2H), 3.34-3.37 (m, 2H), 2.97-3.12 (m, 3H), 2.85 (s, 6H), 1.88-1.91 (m, 2H), 1.69-1.78 (m, 2H).

C. 2-{4-[L-(2-Dimethylamino-acetyl)-piperidin-4-yl]-phenylamino}-8-indan-5-yl-5-oxo-5,8-dihydro-pyrido[2,3-d]pyrimidine-6-carboxylic acid ethyl ester 8-Indan-5-yl-2-methanesulfonyl-5-oxo-5,8-dihydro-pyrido[2,3-d]pyrimidine-6-carboxylic acid ethyl ester (20.5 mg, 0.050 mmol) and 1-[4-(4-amino-phenyl)-piperidin-1-yl]-2-dimethylamino-ethanone di-TFA salt (24 mg g, 0.050 mmol) were combined in i-PrOH (1 mL) and TEA (10.6 mg, 0.11 mmol) was added and the mixture was heated to 90° C. After 3 h, the reaction mixture was concentrated and purified by preparative HPLC (30 mL/min 5-100% MeCN/1120 gradient over 10 min) and lyophilized to provide 24 mg (80%) of 2-{4-[1-(2-Dimethylamino-acetyl)-piperidin-4-yl]-phenylamino}-8-indan-5-yl-5-oxo-5,8-dihydro-pyrido[2,3-d]pyrimidine-6-carboxylic acid ethyl ester. $^1$H NMR (300 MHz, $CDCl_3$) δ (ppm): 9.31 (s, 1H), 9.10 (br s, 1H), 8.48 (s, 1H), 7.51 (d, 2H, J=8.1 Hz), 7.22-7.34 (2H), 7.13-7.16 (m 3H), 4.38 (q, 2H, J=7.0 Hz), 3.09 (br s, 2H), 2.95-3.02 (m, 6H), 2.71-2.80 (m, 2H), 2.39 (s, 6H), 2.11-2.22 (m, 2H), 1.55-1.93 (m, 4H), 1.39 (t, 3H, J=7.2 Hz).

D. 2-{4-[1-(2-Dimethylamino-acetyl)-piperidin-4-yl]-phenylamino}-8-indan-5-yl-5-oxo-5,8-dihydro-pyrido[2,3-d]pyrimidine-6-carboxylic acid amide 2-{4-[1-(2-Dimethylamino-acetyl)-piperidin-4-yl]-phenylamino}-8-indan-5-yl-5-oxo-5,8-dihydro-pyrido[2,3-d]pyrimidine-6-carboxylic acid ethyl ester (20 mg, 0.034 mmol) was dissolved in MeOH (2 mL) and cooled to −78° C. in a high pressure vessel. Ammonia was bubbled into the solution for 1 min and the vessel was sealed and allowed to warm to rt. After 14 h, the solution was cooled to −78° C., the vessel was opened and the solution was allowed to warm to rt. The solution was concentrated and water (2 mL) and MeCN (1 mL) was added, the solution frozen and lyophilized to provide 15 mg of 2-{4-[1-(2-Dimethylamino-acetyl)-piperidin-4-yl]-phenylamino}-8-indan-5-yl-5-oxo-5,8-dihydro-pyrido[2,3-d]pyrimidine-6-carboxylic acid amide. $^1$H NMR (400 MHz, $CDCl_3$) δ (ppm): 9.24 (s, 1H), 8.68 (s, 1H), 7.43 (d, 2H, J=8.4 Hz), 7.16-7.25 (m, 3H), 7.07 (d, 2H, J=8.5 Hz), 3.01 (s, 2H), 2.87-2.93 (m, 4H), 2.30 (s, 6H), 2.04-2.12 (m, 2H), 1.73-1.85 (m, 2H), 1.61 (br s, 4H). Mass Spectrum (LCMS, ESI pos.) Calcd. for $C_{32}H_{35}N_7O_3$ 565.28, Found: 566.3 (M+H).

EXAMPLE 71

2-{3-[1-(2-Dimethylamino-acetyl)-piperidin-4-yl]-phenylamino}-8-indan-5-yl-5-oxo-5,8-dihydro-pyrido[2,3-d]pyrimidine-6-carboxylic acid amide
(Cpd 71)

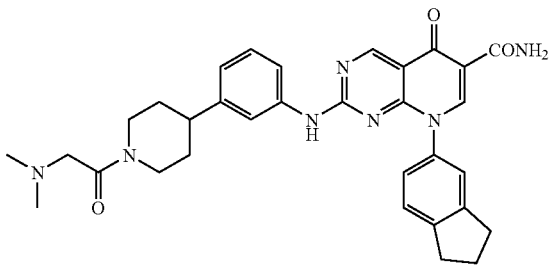

A. 1-[3-(4-Amino-phenyl)-piperidin-1-yl]-2-dimethylamino-ethanone

Dimethylamino-acetyl chloride (0.14 g, 0.86 mmol) and (3-piperidin-4-yl-phenyl)-carbamic acid tert-butyl ester (0.20 g, 0.72 mmol) were combined in $CH_2Cl_2$ (5 mL) and triethylamine (0.21 g, 2.2 mmol) was added. After 6 h, water (5 mL) was added. The reaction mixture was extracted with $CH_2Cl_2$ (3×5 mL) and the combined organic extracts were dried ($MgSO_4$) and concentrated. The compound was found to be unstable on silica and therefore carried on without further purification. (3-Piperidin-4-yl-phenyl)-carbamic acid tert-butyl ester (0.72 mmol) was diluted in CH$_2$Cl$_2$ (3 mL) and TFA (3 mL) was added. After 1 h, the reaction mixture was concentrated. Water (2 mL) was added and the solution was frozen and lyophilized overnight to provide (0.090 g) (48%) of 1-[4-(3-amino-phenyl)-piperidin-1-yl]-2-dimethylamino-ethanone.

B. 2-{3-[1-(2-Dimethylamino-acetyl)-piperidin-4-yl]-phenylamino}-8-indan-5-yl-5-oxo-5,8-dihydro-pyrido[2,3-d]pyrimidine-6-carboxylic acid ethyl ester 8-Indan-5-yl-2-methanesulfonyl-5-oxo-5,8-dihydro-pyrido[2,3-d]pyrimidine-6-carboxylic acid ethyl ester (32.5 mg, 0.079 mmol) and 1-[3-(4-amino-phenyl)-piperidin-1-yl]-2-dimethylamino-ethanone di-TFA salt (38.5 mg g, 0.079 mmol) were combined in i-PrOH (1 mL) and TEA (17 mg, 0.16 mmol) was added and the mixture was heated to 90° C. After 3 h, the reaction mixture was concentrated and purified by preparative HPLC (30 mL/min 5-100% MeCN/H$_2$O gradient over 10 min) and lyophilized to provide 16.5 mg of 2-{3-[1-(2-dimethylamino-acetyl)-piperidin-4-yl]-phenylamino}-8-indan-5-yl-5-oxo-5,8-dihydro-pyrido[2,3-d]pyrimidine-6-carboxylic acid ethyl ester. $^1$H NMR (400 MHz, CDCl$_3$) δ (ppm): 9.23 (s, 1H), 9.08 (br s, 1H), 8.40 (s, 1H), 7.44 (s, 1H), 7.17-7.29 (m, 4H), 7.08 (dd, 1H, J=1.9 Hz, J=7.9 Hz), 6.85 (d, 1H, J=7.6 Hz), 4.29 (q, 2H, J=7.1 Hz), 3.02 (br s, 2H), 2.88-2.93 (m, 5H), 2.66-2.73 (m, 2H), 2.32 (s, 6H), 2.05-2.12 (m, 2H), 1.75-1.84 (m, 2H), 1.55 (br s, 2H), 1.31 (t, 3H, J=7.1 Hz).

C. 2-{3-[1-(2-Dimethylamino-acetyl)-piperidin-4-yl]-phenylamino}-8-indan-5-yl-5-oxo-5,8-dihydro-pyrido[2,3-d]pyrimidine-6-carboxylic acid amide 2-{4-[1-(2-Dimethylamino-acetyl)-piperidin-4-yl]-phenylamino}-8-indan-5-yl-5-oxo-5,8-dihydro-pyrido[2,3-d]pyrimidine-6-carboxylic acid ethyl ester (16 mg, 0.027 mmol) was dissolved in MeOH (2 mL) and cooled to −78° C. in a high pressure vessel. Ammonia was bubbled into the solution for 1 min and the vessel was sealed and allowed to warm to rt. After 14 h, the solution was cooled to −78° C., the vessel was opened and the solution was allowed to warm to rt. The solution was concentrated and water (2 mL) and MeCN (1 mL) was added, the solution frozen and lyophilized to provide 13.6 mg of 2-{3-[1-(2-Dimethylamino-acetyl)-piperidin-4-yl]-phenylamino}-8-indan-5-yl-5-oxo-5,8-dihydro-pyrido[2,3-d]pyrimidine-6-carboxylic acid amide. $^1$H NMR (400 MHz, CDCl$_3$) δ (ppm): 9.49 (br s, 1H), 9.25 (s, 1H), 9.04 (br s, 1H), 8.69 (s, 1H), 7.47 (s, 1H), 7.15-7.27 (m, 2H), 7.07 (d, 2H, J=7.8 Hz), 6.85 (d, 1H, J=7.5 MHz), 5.80 (br s, 1H), 3.00 (s, 2H), 2.87-2.92 (m, 4H), 2.30 (s, 6H), 2.04-2.12 (m, 2H), 1.76-1.87 (m, 2H), 1.57 (br s, 2H). Mass Spectrum (LCMS, ESI pos.) Calcd. for C$_{32}$H$_{35}$N$_7$O$_3$ 565.28, Found: 566.3 (M+H).

EXAMPLE 72

8-Indan-5-yl-2-(4-{1-[2-(4-methyl-piperazin-1-yl)-acetyl]-piperidin-4-yl}-phenylamino)-5-oxo-5,8-dihydro-pyrido[2,3-d]pyrimidine-6-carboxylic acid amide (Cpd 72)

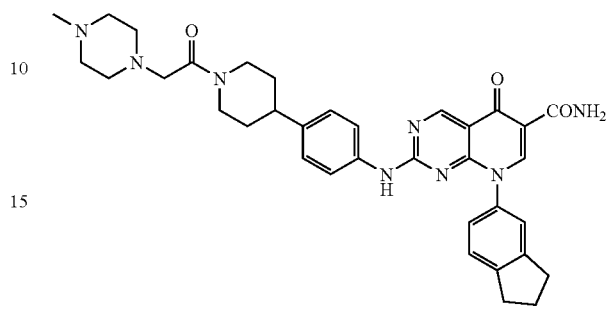

A. 8-Indan-5-yl-2-(4-{1-[2-(4-methyl-piperazin-1-yl)-acetyl]-piperidin-4-yl}-phenylamino)-5-oxo-5,8-dihydro-pyrido[2,3-d]pyrimidine-6-carboxylic acid ethyl ester (4-Piperidin-4-yl-phenyl)-carbamic acid tert-butyl ester (0.20 g, 0.72 mmol), (4-methyl-piperazin-1-yl)-acetic acid (0.11 g, 0.72 mmol), HOBt (0.10 g, 0.72 mmol), DCI (0.14 g, 0.72 mmol), and DIEA (0.10 g, 0.72 mmol) were all combined in DMF (5 mL). After 16 h, water (10 mL) and CH$_2$Cl$_2$ (10 mL) were added. The organic layer was washed with water (3×10 mL), dried (MgSO$_4$) and concentrated. Chromatography (0-15% EtOAc/hexanes gradient) provided 0.24 g (83%) of (4-{1-[2-(4-methyl-piperazin-1-yl)-acetyl]-piperidin-4-yl}-phenyl)-carbamic acid tert-butyl ester. (4-{1-[2-(4-Methyl-piperazin-1-yl)-acetyl]-piperidin-4-yl}-phenyl)-carbamic acid tert-butyl ester (0.72 mmol) was diluted in CH$_2$Cl$_2$ (3 mL) and TFA (3 mL) was added. After 1 h, the reaction mixture was concentrated. Water (2 mL) was added and the solution was frozen and lyophilized overnight to provide (0.16 g) (72%) of 1-[4-(4-Amino-phenyl)-piperidin-1-yl]-2-(4-methyl-piperazin-1-yl)-ethanone. 8-Indan-5-yl-2-methanesulfonyl-5-oxo-5,8-dihydro-pyrido[2,3-d]pyrimidine-6-carboxylic acid ethyl ester (32.5 mg, 0.079 mmol) and 1-[4-(4-Amino-phenyl)-piperidin-1-yl]-2-(4-methyl-piperazin-1-yl)-ethanone tri-TFA salt (52 mg g, 0.079 mmol) were combined in i-PrOH (1 mL) and TEA (25 mg, 0.25 mmol) was added and the mixture was heated to 90° C. After 3 h, the reaction mixture was concentrated and purified by preparative HPLC (30 mL/min 5-100% MeCN/H$_2$O gradient over 10 min) and lyophilized to provide 8.6 mg of 8-indan-5-yl-2-(4-{1-[2-(4-methyl-piperazin-1-yl)-acetyl]-piperidin-4-yl}-phenylamino)-5-oxo-5,8-dihydro-pyrido[2,3-d]pyrimidine-6-carboxylic acid ethyl ester. $^1$H NMR (400 MHz, CDCl$_3$) δ (ppm): 9.23 (s, 1H), 8.39 (s, 1H), 7.40-7.42 (m, 2H), 7.17-7.26 (m, 3H), 7.06-7.09 (m, 2H), 4.30 (q, 2H, J=7.1 Hz), 3.07 (br s, 1H), 2.87-2.93 (m, 6H), 2.48-2.67 (m, 7H), 2.28 (br s, 3H), 2.05-2.12 (m, 2H), 1.72-1.82 (m, 2H), 1.49 (br s, 2H), 1.31 (t, 3H, J=7.1 Hz).

B. 8-Indan-5-yl-2-(4-{1-[2-(4-methyl-piperazin-1-yl)-acetyl]-piperidin-4-yl}-phenylamino)-5-oxo-5,8-dihydro-pyrido[2,3-d]pyrimidine-6-carboxylic acid amide 8-Indan-5-yl-2-(4-{1-[2-(4-methyl-piperazin-1-yl)-acetyl]-piperidin-4-yl}-phenylamino)-5-oxo-5,8-dihydropyrido[2,3-d]pyrimidine-6-carboxylic acid ethyl ester (15 mg, 0.024 mmol) was dissolved in MeOH (2 mL) and cooled to −78° C. in a high pressure vessel. Ammonia was bubbled into the solution for 1 min and the vessel was sealed and allowed to warm to rt. After 14 h, the solution was cooled to −78° C., the vessel was opened and the solution was allowed to warm to rt. The solution was concentrated and water (2 mL) and MeCN (1 mL) was added, the solution frozen and lyophilized to provide 11.6 mg of 8-Indan-5-yl-2-(4-{1-[2-(4-methyl-piperazin-1-yl)-acetyl]-piperidin-4-yl}-phenylamino)-5-oxo-5,8-dihydro-pyrido[2,3-d]pyrimidine-6-carboxylic acid amide. $^1$H NMR (400 MHz, CDCl$_3$) δ (ppm): 9.46 (br s, 1H), 9.25 (s, 1H), 8.80 (br s, 1H), 8.69 (s, 1H), 7.40 (d, 2H, J=8.3 Hz), 7.15-7.24 (m, 3H), 7.07 (d, 2H, J=8.3 Hz), 5.70 (br s, 1H), 3.10 (s, 2H), 2.86-2.92 (m, 6H), 2.68 (br s, 12H), 2.41 (br s, 2H), 2.04-2.12 (m, 2H), 1.74-1.86 (m, 2H0, 1.50 (br s, 2H). Mass Spectrum (LCMS, ESI pos.) Calcd. for C$_{35}$H$_{40}$N$_8$O$_3$: 620.32, Found: 621.3 (M+H).

EXAMPLE 73

8-Indan-5-yl-2-(3-{1-[2-(4-methyl-piperazin-1-yl)-acetyl]-piperidin-4-yl}-phenylamino)-5-oxo-5,8-dihydro-pyrido[2,3-d]pyrimidine-6-carboxylic acid amide (Cpd 73)

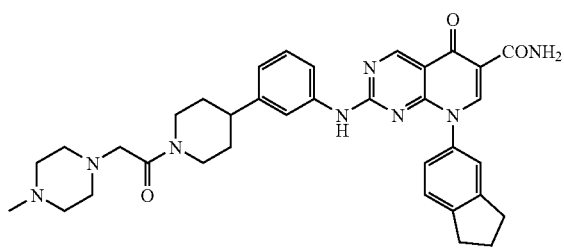

A. 2-{3-[1-(2-Dimethylamino-acetyl)-piperidin-4-yl]-phenylamino}-8-indan-5-yl-5-oxo-5,8-dihydro-pyrido[2,3-d]pyrimidine-6-carboxylic acid ethyl ester (3-Piperidin-4-yl-phenyl)-carbamic acid tert-butyl ester (0.20 g, 0.72 mmol), (4-methyl-piperazin-1-yl)-acetic acid (0.11 g, 0.72 mmol), HOBt (0.10 g, 0.72 mmol), DCI (0.14 g, 0.72 mmol), and DIEA (0.10 g, 0.72 mmol) were all combined in DMF (5 mL). After 16 h, water (10 mL) and CH$_2$Cl$_2$ (10 mL) were added. The organic layer was washed with water (3×10 mL), dried (MgSO$_4$) and concentrated. Chromatography (0-15% EtOAc/hexanes gradient) provided 0.22 g (73%) of 1-[4-(3-Amino-phenyl)-piperidin-1-yl]-2-(4-methyl-piperazin-1-yl)-ethanone. (3-(1-[2-(4-Methyl-piperazin-1-yl)-acetyl]-piperidin-4-yl-1-phenyl)-carbamic acid tert-butyl ester (0.72 mmol) was diluted in CH$_2$Cl$_2$ (3 mL) and TFA (3 mL) was added. After 1 h, the reaction mixture was concentrated. Water (2 mL) was added and the solution was frozen and lyophilized overnight to provide (0.18 g) (81%) of 1-[4-(3-Amino-phenyl)-piperidin-1-yl]-2-(4-methyl-piperazin-1-yl)-ethanone. 8-indan-5-yl-2-methanesulfonyl-5-oxo-5,8-dihydro-pyrido[2,3-d]pyrimidine-6-carboxylic acid ethyl ester (32.5 mg, 0.079 mmol) and 1-[3-(4-amino-phenyl)-piperidin-1-yl]-2-dimethylamino-ethanone di-TFA salt (38.5 mg g, 0.079 mmol) were combined in i-PrOH (1 mL) and TEA (17 mg, 0.16 mmol) was added and the mixture was heated to 90° C. After 3 h, the reaction mixture was concentrated and purified by preparative HPLC (30 mL/min 5-100% MeCN/H$_2$O gradient over 10 min) and lyophilized to provide 16.5 mg of 2-{3-[1-(2-Dimethylamino-acetyl)-piperidin-4-yl]-phenylamino}-8-indan-5-yl-5-oxo-5,8-dihydro-pyrido[2,3-d]pyrimidine-6-carboxylic acid ethyl ester. $^1$H NMR (400 MHz, CDCl$_3$) δ (ppm): 9.23 (s, 1H), 9.08 (br s, 1H), 8.40 (s, 1H), 7.44 (s, 1H), 7.17-7.29 (m, 4H), 7.08 (dd, 1H, J=1.9 Hz, J=7.9 Hz), 6.85 (d, 1H, J=7.6 Hz), 4.29 (q, 2H, J=7.1 Hz), 3.02 (br s, 2H), 2.88-2.93 (m, 5H), 2.66-2.73 (m, 2H), 2.32 (s, 6H), 2.05-2.12 (m, 2H), 1.75-1.84 (m, 2H), 1.55 (br s, 2H), 1.31 (t, 3H, J=7.1 Hz).

B. 2-{3-[1-(2-Dimethylamino-acetyl)-piperidin-4-yl]-phenylamino}-8-indan-5-yl-5-oxo-5,8-dihydro-pyrido[2,3-d]pyrimidine-6-carboxylic acid amide 2-{4-[1-(2-Dimethylamino-acetyl)-piperidin-4-yl]-phenylamino}-8-indan-5-yl-5-oxo-5,8-dihydro-pyrido[2,3-d]pyrimidine-6-carboxylic acid ethyl ester (16 mg, 0.027 mmol) was dissolved in MeOH (2 mL) and cooled to −78° C. in a high pressure vessel. Ammonia was bubbled into the solution for 1 min and the vessel was sealed and allowed to warm to rt. After 14 h, the solution was cooled to −78° C., the vessel was opened and the solution was allowed to warm to rt. The solution was concentrated and water (2 mL) and MeCN (1 mL) was added, the solution frozen and lyophilized to provide 13.6 mg of 8-indan-5-yl-2-(3-{1-[2-(4-methyl-piperazin-1-yl)-acetyl]-piperidin-4-yl}-phenylamino)-5-oxo-5,8-dihydro-pyrido[2,3-d]pyrimidine-6-carboxylic acid amide. $^1$H NMR (400 MHz, CDCl$_3$) δ (ppm): 9.49 (br s, 1H), 9.25 (s, 1H), 9.04 (br s, 1H), 8.69 (s, 1H), 7.47 (s, 1H), 7.15-7.27 (m, 2H), 7.07 (d, 2H, J=7.8 Hz), 6.85 (d, 1H, J=7.5 Hz), 5.80 (br s, 1H), 3.00 (s, 2H), 2.87-2.92 (m, 4H), 2.30 (s, 6H), 2.04-2.12 (m, 2H), 1.76-1.87 (m, 2H), 1.57 (br s, 2H). Mass Spectrum (LCMS, ESI pos.) Calcd. for C$_{35}$H$_{40}$N$_8$O$_3$: 620.32, Found: 621.3 (M+H).

EXAMPLE 74

8-Indan-5-yl-2-[4-(4-methyl-piperazin-1-ylmethyl)-phenylamino]-5-oxo-5,8-dihydro-pyrido[2,3-d]pyrimidine-6-carboxylic acid amide (Cpd 74)

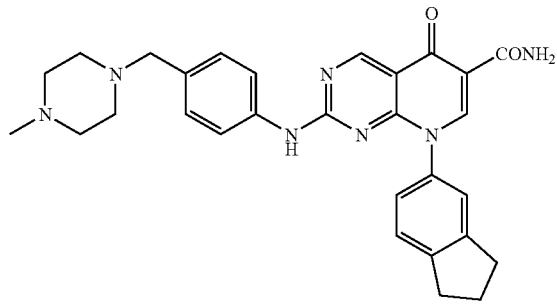

A. 8-Indan-5-yl-2-[4-(4-methyl-piperazin-1-ylmethyl)-phenylamino]-5-oxo-5,8-dihydro-pyrido[2,3-d]pyrimidine-6-carboxylic acid ethyl ester 8-Indan-5-yl-2-methanesulfonyl-5-oxo-5,8-dihydro-pyrido[2,3-d]pyrimidine-6-carboxylic acid ethyl ester (0.098 g, 0.24 mmol) and 4-(4-methyl-piperazin-1-ylmethyl)-phenylamine (0.049 g, 0.24 mmol) were combined in i-PrOH (2 mL) and heated to 90° C. After 3 h, the reaction mixture was concentrated and purified by preparative HPLC (30 mL/min 5-100% MeCN/H₂O gradient over 10 min) and lyophilized to provide 20 mg of 8-Indan-5-yl-2-[4-(4-methyl-piperazin-1-ylmethyl)-phenylamino]-5-oxo-5,8-dihydro-pyrido[2,3-d]pyrimidine-6-carboxylic acid ethyl ester. ¹H NMR (400 MHz, CDCl₃) δ (ppm): 9.36 (s, 1H), 8.54 (s, 1H), 7.43 (d, 2H, J=7.9 Hz), 7.29 (m, 2H), 7.18 (dd, 2H, J=2.0 Hz, J=7.9 Hz), 7.03-7.05 (m, 1H), 4.38 (q, 2H, J=7.1 Hz), 3.44 (s, 2H), 3.08 (t, 2H, J=7.4 Hz), 3.01 (t, 2H, J=7.5 Hz), 2.52 (br s, 8H), 2.36 (s, 3H), 2.19-2.29 (m, 2H), 1.39 (t, 3H, J=7.1 Hz).

B. 8-Indan-5-yl-2-[4-(4-methyl-piperazin-1-ylmethyl)-phenylamino]-5-oxo-5,8-dihydro-pyrido[2,3-d]pyrimidine-6-carboxylic acid amide 8-Indan-5-yl-2-[4-(4-methyl-piperazin-1-ylmethyl)-phenylamino]-5-oxo-5,8-dihydro-pyrido[2,3-d]pyrimidine-6-carboxylic acid ethyl ester (10 mg, 0.020 mmol) was dissolved in MeOH (2 mL) and cooled to −78° C. in a high pressure vessel. Ammonia was bubbled into the solution for 1 min and the vessel was sealed and allowed to warm to rt. After 14 h, the solution was cooled to −78° C., the vessel was opened and the solution was allowed to warm to rt. The solution was concentrated and water (2 mL) and MeCN (1 mL) was added, the solution frozen and lyophilized to provide 6.3 mg of 8-indan-5-yl-2-[4-(4-methyl-piperazin-1-ylmethyl)-phenylamino]-5-oxo-5,8-dihydro-pyrido[2,3-d]pyrimidine-6-carboxylic acid amide. ¹H NMR (400 MHz, CDCl₃) δ (ppm): 9.39 (s, 1H), 9.32 (s, 1H), 8.78 (s, 1H), 7.34 (d, 2H, J=7.8 Hz), 7.10 (d, 2H, J=7.9 Hz), 6.97-6.99 (m, 3H), 5.68 (br s, 1H), 3.37 (s, 2H), 3.00 (t, 2H, J=7.4 Hz), 2.92 (t, 2H, J=7.5 Hz), 2.81 (s, 3H), 2.44 (br s, 4H), 2.28 (br s, 4H), 2.13-2.15 (m, 2H). Mass Spectrum (LCMS, ESI pos.) Calcd. for C₂₉H₃₈N₆O₃: 518.30, Found: 519.2 (M+H).

EXAMPLE 75

2-(4-Dimethylaminomethyl-phenylamino)-8-indan-5-yl-5-oxo-5,8-dihydro-pyrido[2,3-d]pyrimidine-6-carboxylic acid amide (Cpd 75)

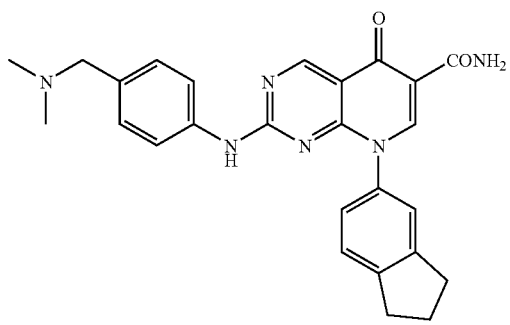

A. 2-(4-Dimethylaminomethyl-phenylamino)-8-indan-5-yl-5-oxo-5,8-dihydro-pyrido[2,3-d]pyrimidine-6-carboxylic acid ethyl ester 8-Indan-5-yl-2-methanesulfonyl-5-oxo-5,8-dihydro-pyrido[2,3-d]pyrimidine-6-carboxylic acid ethyl ester (87 mg, 0.21 mmol) and 4-dimethylaminomethyl-phenylamine (32 mg, 0.21 mmol) were combined in i-PrOH (2 mL) and heated to 90° C. After 3 h, the reaction mixture was concentrated and purified by preparative HPLC (30 mL/min 5-100% MeCN/H₂O gradient over 10 min) and lyophilized to provide 66 mg of 2-(4-Dimethylaminomethyl-phenylamino)-8-indan-5-yl-5-oxo-5,8-dihydro-pyrido[2,3-d]pyrimidine-6-carboxylic acid ethyl ester. ¹H NMR (400 MHz, CDCl₃) δ (ppm): 9.38 (s, 1H), 8.54 (s, 1H), 7.09-7.43 (m, 7H), 4.35-4.42 (m, 2H), 3.57 (s, 2H), 2.90-3.08 (m, 4H), 2.35 (s, 6H), 2.16-2.26 (m, 2H), 1.39 (t, 3H, J=7.1 Hz).

B. 2-(4-Dimethylaminomethyl-phenylamino)-8-indan-5-yl-5-oxo-5,8-dihydro-pyrido[2,3-d]pyrimidine-6-carboxylic acid amide 2-(4-Dimethyl aminomethyl-phenylamino)-8-indan-5-yl-5-oxo-5,8-dihydro-pyrido[2,3-d]pyrimidine-6-carboxylic acid ethyl ester (30 mg, 0.062 mmol) was dissolved in MeOH (2 mL) and cooled to −78° C. in a high pressure vessel. Ammonia was bubbled into the solution for 1 min and the vessel was sealed and allowed to warm to rt. After 14 h, the solution was cooled to −78° C., the vessel was opened and the solution was allowed to warm to rt. The solution was concentrated and water (2 mL) and MeCN (1 mL) was added, the solution frozen and lyophilized to provide 3.5 mg of 2-(4-dimethylaminomethyl-phenylamino)-8-indan-5-yl-5-oxo-5,8-dihydro-pyrido[2,3-d]pyrimidine-6-carboxylic acid amide. ¹H NMR (400 MHz, CDCl₃) δ (ppm): 9.39 (br s, 1H), 9.35 (s, 1H), 8.79 (s, 1H), 7.03-7.45 (m, 7H), 3.01 (t, 2H, J=7.3 Hz), 2.93 (t, 2H, J=7.8 Hz), 2.37 (br s, 2H), 2.10-2.18 (m, 2H), 1.19 (s, 6H). Mass Spectrum (LCMS, ESI pos.) Calcd. for C₂₆H₂₆N₆O₂: 454.21, Found: 455.2 (M+H).

EXAMPLE 76

2-(3-Dimethylaminomethyl-phenylamino)-8-indan-5-yl-5-oxo-5,8-dihydro-pyrido[2,3-d]pyrimidine-6-carboxylic acid amide (Cpd 76)

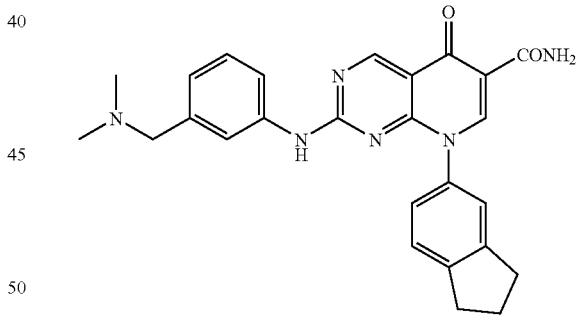

A. 2-(3-Dimethylaminomethyl-phenylamino)-8-indan-5-yl-5-oxo-5,8-dihydro-pyrido[2,3-d]pyrimidine-6-carboxylic acid ethyl ester 8-Indan-5-yl-2-methanesulfonyl-5-oxo-5,8-dihydro-pyrido[2,3-d]pyrimidine-6-carboxylic acid ethyl ester (105 mg, 0.25 mmol) and 3-dimethylaminomethyl-phenylamine (38 mg, 0.25 mmol) were combined in iPrOH (2 mL) and heated to 90° C. After 3 h, the reaction mixture was concentrated and purified by preparative HPLC (30 mL/min 5-100% MeCN/H₂O gradient over 10 min) and lyophilized to provide 56 mg of 2-(3-Dimethylaminomethyl-phenylamino)-8-indan-5-yl-5-oxo-5,8-dihydro-pyrido[2,3-d]pyrimidine-6-carboxylic acid ethyl ester. ¹H NMR (400 MHz, CDCl₃) δ (ppm): 9.31

(br s, 1H), 8.98 (br s, 1H), 8.51 (s, 1H), 8.39 (s, 1H), 7.00-7.53 (m, 7H), 4.28-4.40 (m, 2H), 3.64 (br s, 2H), 2.88-3.09 (m, 4H), 2.40 (s, 6H), 2.05-2.25 (m, 2H), 1.32-1.40 (m, 3H).

B. 2-(3-Dimethylaminomethyl-phenylamino)-8-indan-5-yl-5-oxo-5,8-dihydro-pyrido[2,3-d]pyrimidine-6-carboxylic acid amide 2-(3-Dimethylaminomethyl-phenylamino)-8-indan-5-yl-5-oxo-5,8-dihydro-pyrido[2,3-d]pyrimidine-6-carboxylic acid ethyl ester (20 mg, 0.041 mmol) was dissolved in MeOH (2 mL) and cooled to −78° C. in a high pressure vessel. Ammonia was bubbled into the solution for 1 min and the vessel was sealed and allowed to warm to rt. After 14 h, the solution was cooled to −78° C., the vessel was opened and the solution was allowed to warm to rt. The solution was concentrated and water (2 mL) and MeCN (1 mL) was added, the solution frozen and lyophilized to provide 2.5 mg of 2-(3-dimethylaminomethyl-phenylamino)-8-indan-5-yl-5-oxo-5,8-dihydro-pyrido[2,3-d]pyrimidine-6-carboxylic acid amide. $^1$H NMR (400 MHz, CDCl$_3$) δ (ppm): 9.36 (s, 2H), 8.77 (s, 1H), 6.97-4.45 (m, 7H), 3.00 (t, 2H, J=7.6 Hz), 2.93 (t, 2H, J=7.4 Hz), 2.13-2.21 (m, 2H), 1.47 (br s, 2H), 1.19 (s, 6H). Mass Spectrum (LCMS, ESI pos.) Calcd. for $C_{26}H_{26}N_6O_2$: 454.21, Found: 455.2 (M+H).

EXAMPLE 77

2-(3-Dimethylaminomethyl-phenylamino)-8-indan-5-yl-5-oxo-5,8-dihydro-pyrido[2,3-d]pyrimidine-6-carboxylic acid methylamide (Cpd 77)

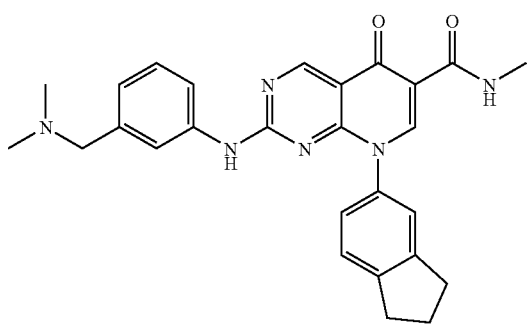

2-(3-Dimethylaminomethyl-phenylamino)-8-indan-5-yl-5-oxo-5,8-dihydro-pyrido[2,3-d]pyrimidine-6-carboxylic acid ethyl ester (15 mg, 0.032 mmol) was dissolved in MeOH (1 mL) and methylamine (1 mL of 1.0 M solution in THF, 1.0 mmol) was added and the reaction mixture was heated at 80° C. After 16 h, the solution was cooled to rt and purified by preparative HPLC (C-18 column, 32 mL/min 5-100% MeCN/H$_2$O gradient over 15 min) and lyophilized to provide 2.3 mg of 2-(3-dimethylaminomethyl-phenylamino)-8-indan-5-yl-5-oxo-5,8-dihydro-pyrido[2,3-d]pyrimidine-6-carboxylic acid methylamide. $^1$H NMR (TFA salt) (400 MHz, CDCl$_3$) δ (ppm): 9.51 (s, 1H), 9.35 (s, 1H), 8.75 (s, 1H), 7.01-7.50 (m, 7H), 3.90 (br s, 2H), 2.90-3.02 (m, 7H), 2.60 (s, 6H), 2.11-2.19 (m, 2H). Mass Spectrum (LCMS, ESI pos.) Calcd. for $C_{27}H_{28}N_6O_2$: 468.23, Found: 469.1 (M+H).

EXAMPLE 78

2-(3-Dimethylaminomethyl-phenylamino)-8-indan-5-yl-5-oxo-5,8-dihydro-pyrido[2,3-d]pyrimidine-6-carboxylic acid ethylamide (Cpd 78)

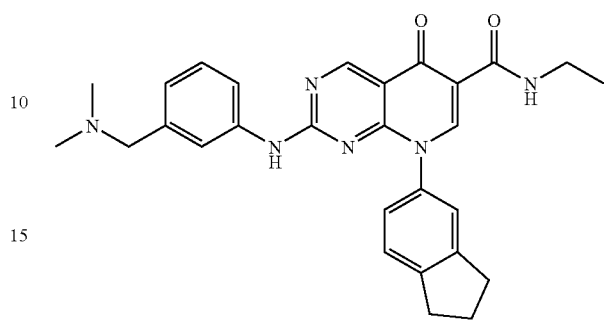

2-(3-Dimethylaminomethyl-phenylamino)-8-indan-5-yl-5-oxo-5,8-dihydro-pyrido[2,3-d]pyrimidine-6-carboxylic acid ethyl ester (15 mg, 0.032 mmol) was dissolved in MeOH (1 mL) and ethylamine (1 mL of 1.0 M solution in THF, 1.0 mmol) was added and the reaction mixture was heated at 80° C. After 16 h, the solution was cooled to it and purified by preparative HPLC (C-18 column, 32 mL/min 5-100% MeCN/H$_2$O gradient over 15 min) and lyophilized to provide 2.1 mg of 2-(3-dimethylaminomethyl-phenylamino)-8-indan-5-yl-5-oxo-5,8-dihydro-pyrido[2,3-d]pyrimidine-6-carboxylic acid methylamide. $^1$H NMR (TFA salt) (400 MHz, CDCl$_3$) δ (ppm): 9.57 (s, 1H), 9.34 (s, 1H), 8.74 (s, 1H), 6.99-7.37 (m, 7H), 3.89 (br s, 2H), 3.39-3.46 (m, 2H), 2.89-3.02 (m, 4H), 2.60 (s, 6H), 2.13-2.17 (m, 2H), 1.19 (t, 1H, J=7.3 Hz). Mass Spectrum (LCMS, ESI pos.) Calcd. for $C_{28}H_{30}N_6O_2$: 482.24, Found: 483.2 (M+H).

EXAMPLE 79

2-(3-Dimethylcarbamoyl-phenylamino)-8-indan-5-yl-5-oxo-5,8-dihydro-pyrido[2,3-d]pyrimidine-6-carboxylic acid amide (Cpd 79)

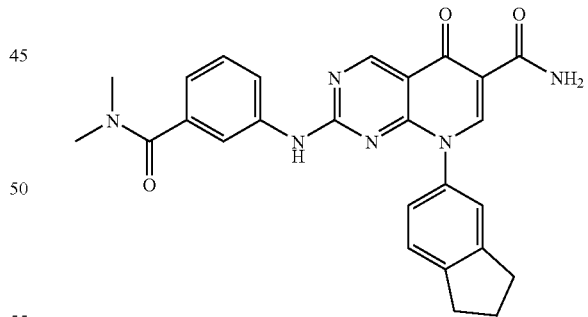

A. 2-(3-Dimethylcarbamoyl-phenylamino)-8-indan-5-yl-5-oxo-5,8-dihydro-pyrido[2,3-d]pyrimidine-6-carboxylic acid ethyl ester 8-Indan-5-yl-2-methanesulfonyl-5-oxo-5,8-dihydro-pyrido[2,3-d]pyrimidine-6-carboxylic acid ethyl ester (20 mg, 0.048 mmol) and 3-amino-N,N-dimethyl-benzamide (8 mg, 0.05 mmol) were combined in i-PrOH (2 mL) and heated to 90° C. After 15 h, the reaction mixture was concentrated and purified by preparative HPLC (C-18 column, 32 mL/min 5-100% MeCN/H₂O gradient over 15 min) and lyophilized to provide 15.6 mg of 2-(3-dimethylcarbamoyl-phenylamino)-8-indan-5-yl-5-oxo-5,8-dihydro-pyrido[2,3-d]pyrimidine-6-carboxylic acid ethyl ester. ¹H NMR (400 MHz, CDCl₃) δ (ppm): 9.31 (s, 1H), 1.13 (s, 1H), 7.46 (br s, 1H), 7.33 (d, 1H, J=7.9 Hz), 7.16-7.21 (m, 2H), 7.10 (d, 1H, J=7.6 Hz), 6.96 (br s, 2H), 4.29 (q, 2H, J=7.1 Hz), 2.97-3.04 (m, 5H), 2.85-2.93 (m, 5H), 2.14 (p, 2H, J=7.4 Hz), 1.29 (t, 3H, J=7.1 Hz)

B. 2-(3-Dimethylcarbamoyl-phenylamino)-8-indan-5-yl-5-oxo-5,8-dihydro-pyrido[2,3-d]pyrimidine-6-carboxylic acid amide 2-(3-Dimethylcarbamoyl-phenylamino)-8-indan-5-yl-5-oxo-5,8-dihydro-pyrido[2,3-d]pyrimidine-6-carboxylic acid ethyl ester (5.2 mg, 0.010 mmol) was dissolved in MeOH (2 mL) and cooled to −78° C. in a high pressure vessel. Ammonia was bubbled into the solution for 1 min and the vessel was sealed and allowed to warm to rt. After 14 h, the solution was cooled to −78° C., the vessel was opened and the solution was allowed to warm to rt. The solution was concentrated and water (2 mL) and MeCN (1 mL) was added, the solution frozen and lyophilized to provide 4.1 mg of 2-(3-dimethylcarbamoyl-phenylamino)-8-indan-5-yl-5-oxo-5,8-dihydro-pyrido[2,3-d]pyrimidine-6-carboxylic acid amide. ¹H NMR (400 MHz, CDCl₃) δ (ppm): 9.42 (s, 1H), 9.29 (s, 1H), 8.88 (s, 1H), 7.49 (m, 4H), 6.88-6.90 (m, 3H), 3.29 (br s, 2H), 2.44-2.93 (m), 1.94-2.15 (m), 1.19-1.76 (m). Mass Spectrum (LCMS, ESI pos.) Calcd. for $C_{26}H_{24}N_6O_3$: 468.19, Found: 469.2 (M+H).

EXAMPLE 80

2-(3-Dimethylcarbamoyl-phenylamino)-8-indan-5-yl-5-oxo-5,8-dihydro-pyrido[2,3-d]pyrimidine-6-carboxylic acid methylamide (Cpd 80)

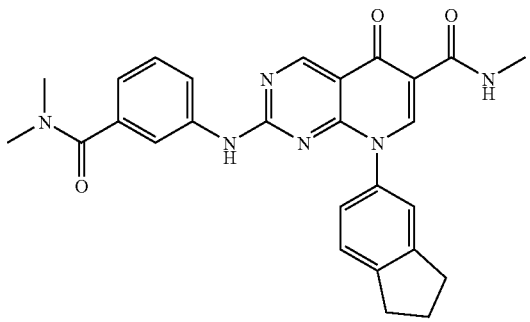

2-(3-Dimethylcarbamoyl-phenylamino)-8-indan-5-yl-5-oxo-5,8-dihydro-pyrido[2,3-d]pyrimidine-6-carboxylic acid ethyl ester (5.2 mg, 0.010 mmol) was dissolved in MeOH (1 mL) and methylamine (1 mL of 1.0 M solution in THF, 1.0 mmol) was added and the reaction mixture was heated at 80° C. After 16 h, the solution was cooled to rt and purified by preparative HPLC (C-18 column, 32 mL/min 5-100% MeCN/H₂O gradient over 15 min) and lyophilized to provide 2.1 mg of 2-(3-dimethylcarbamoyl-phenylamino)-8-indan-5-yl-5-oxo-5,8-dihydro-pyrido[2,3-d]pyrimidine-6-carboxylic acid methylamide. ¹H NMR (TFA salt) (400 MHz, CDCl₃) δ (ppm): 9.56 (br. S, 1H), 9.33 (s, 1H), 8.77 (s, 1H), 7.51 (dd, 1H, J=2.3 Hz, J=9.31 Hz), 7.34 (d, 1H, J=7.9 Hz), 7.11 (dd, 1H, J=1.7 Hz, J=7.8 Hz), 6.99 (br. S, 1H), 2.86-3.05 (m, 13H), 2.12-2.19 (m, 2H). Mass Spectrum (LCMS, ESI pos.) Calcd. for $C_{27}H_{26}N_6O_3$: 482.21, Found: 483.2 (M+H).

EXAMPLE 81

2-(3-Dimethylcarbamoyl-phenylamino)-8-indan-5-yl-5-oxo-5,8-dihydro-pyrido[2,3-d]pyrimidine-6-carboxylic acid ethylamide (Cpd 81)

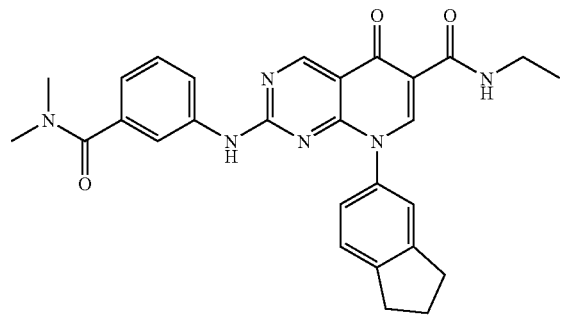

2-(3-Dimethylcarbamoyl-phenylamino)-8-indan-5-yl-5-oxo-5,8-dihydro-pyrido[2,3-d]pyrimidine-6-carboxylic acid ethyl ester (5.2 mg, 0.010 mmol) was dissolved in MeOH (1 mL) and ethylamine (1 mL of 1.0 M solution in THF, 1.0 mmol) was added and the reaction mixture was heated at 80° C. After 16 h, the solution was cooled to rt and purified by preparative HPLC (C-18 column, 32 mL/min 5-100% MeCN/H₂O gradient over 15 min) and lyophilized to provide 2.1 mg of 2-(3-dimethylcarbamoyl-phenylamino)-8-indan-5-yl-5-oxo-5,8-dihydro-pyrido[2,3-d]pyrimidine-6-carboxylic acid ethylamide. ¹H NMR (TFA salt) (400 MHz, CDCl₃) δ (ppm): 9.64 (s, 1H), 9.32 (s, 1H), 8.77 (s, 1H), 7.51 (dd, 1H, J=2.3 Hz, J=9.3 Hz), 7.34 (d, 1H, J=7.8 Hz), 7.17-7.19 (m, 3H), 7.11 (dd, 1H, J=2.0 Hz, J=8.0 Hz), 6.99 (br. S, 1H), 3.44 (dq, 2H, J=5.8 Hz, J=7.3 Hz), 2.86-3.05 (m, 10H), 2.11-2.19 (m, 2H), 1.21 (t, 1H, J=7.3 Hz). Mass Spectrum (LCMS, ESI pos.) Calcd. for $C_{28}H_{28}N_6O_3$: 496.22, Found: 497.2 (M+H).

EXAMPLE 82

8-Bicyclo[2.2.1]hept-2-yl-2-[4-(4-methyl-piperazin-1-yl)-phenylamino]-5-oxo-5,8-dihydro-pyrido[2,3-d]pyrimidine-6-carboxylic acid amide (Cpd 82)

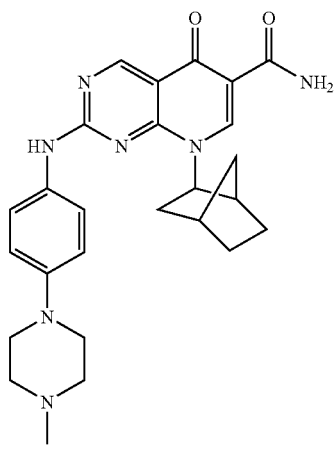

A. 3-(Bicyclo[2.2.1]hept-2-ylamino)-propionic acid ethyl ester

Bicyclo[2.2.1]hept-2-ylamine (2.0 g, 18.0 mmol) and 4-chloro-2-methylsulfanyl-pyrimidine-5-carboxylic acid ethyl ester (2.45 g, 18.0 mmol) were combined neat and $K_2CO_3$ (3.72 g, 27.0 mmol) and a catalytic amount of tetrabutylammonium iodide (ca. 2 mg) was added. The mixture was heated at 80° C. overnight. The resulting mixture was then partitioned between water and DCM. The organic layer was dried ($MgSO_4$) and concentrated to provide 1.5 g of 3-(bicyclo[2.2.1]hept-2-ylamino)-propionic acid ethyl ester. $^1$H NMR (400 MHz, $CDCl_3$) δ (ppm): 5.29 (s, 1H), 4.13 (q, 2H, J=7.1 Hz), 2.77-2.92 (m, 2H), 2.57 (dd, 1H, J=3.1 Hz, J=7.3 Hz), 2.50 (t, 2H, J=6.6 Hz), 2.16-2.20 (m, 2H), 1.57 (ddd, 1H, J=2.2 Hz, J=7.5 Hz, J=12.3 Hz), 1.41-1.49 (m, 3H), 1.25 (t, 3H, J=7.2 Hz), 1.01-1.10 (m, 4H).

B. 8-Bicyclo[2.2.1]hept-2-yl-2-[4-(4-methyl-piperazin-1-yl)-phenylamino]-5-oxo-5,8-dihydro-pyrido[2,3-d]pyrimidine-6-carboxylic acid ethyl ester 3-(Bicyclo[2.2.1]hept-2-ylamino)-propionic acid ethyl ester (1.5 g, 7.1 mmol) and 4-chloro-2-methylsulfanyl-pyrimidine-5-carboxylic acid ethyl ester (1.6 g, 7.1 mmol) were combined in $CH_2Cl_2$ (20 mL) and triethylamine (1.0 g, 10 mmol) was added. After 16 h, water (10 mL) was added the organic layer was separated, dried ($MgSO_4$), and concentrated. Chromatography (10-50% EtOAc/hexanes gradient) provided 1.8 g of 4-[bicyclo[2.2.1]hept-2-yl-(2-ethoxycarbonyl-ethyl)-amino]-2-methylsulfanyl-pyrimidine-5-carboxylic acid ethyl ester. Sodium (30 wt % dispersion in paraffin wax, 0.55 g, 7.2 mmol) was added to t-butanol (5.0 mL) at rt. After 30 minutes, a solution of 4[bicyclo[2.2.1]hept-2-yl-(2-ethoxycarbonyl-ethyl)-amino]-2-methylsulfanyl-pyrimidine-5-carboxylic acid ethyl ester (1.8 g, 4.4 mmol) in 20 mL of toluene was added to the sodium t-butoxide solution and the resulting mixture was heated at 90° C. for 30 minutes. The reaction mixture was then cooled and the solution was adjusted to pH 7 using a 1N HCl solution. The solution was then extracted with EtOAc (2×20 mL) and the organic layer was dried ($MgSO_4$), and concentrated. Recrystallization from i-PrOH provided 0.51 g of 8-bicyclo[2.2.1]hept-2-yl-2-methylsulfanyl-5-oxo-5,6,7,8-tetrahydro-pyrido[2,3-d]pyrimidine-6-carboxylic acid ethyl ester. 8-Bicyclo[2.2.1]hept-2-yl-2-methanesulfonyl-5-oxo-5,8-dihydro-pyrido[2,3-d]pyrimidine-6-carboxylic acid ethyl ester (46 mg, 0.12 mmol) and 4-(4-methyl-piperazin-1-yl)-phenylamine (22 mg, 0.12 mmol) were combined in i-PrOH (2 mL) and heated to 90° C. After 3 h, the reaction mixture was concentrated and purified by preparative HPLC (C-18 column, 32 mL/min 5-100% $MeCN/H_2O$ gradient over 15 min) and lyophilized to provide 11.4 mg of 8-bicyclo[2.2.1]hept-2-yl-2-[4-(4-methyl-piperazin-1-yl)-phenylamino]-5-oxo-5,8-dihydro-pyrido[2,3-d]pyrimidine-6-carboxylic acid ethyl ester. $^1$H NMR (400 MHz, $CDCl_3$) δ (ppm): 9.21 (s, 1H), 8.59 (s, 1H), 7.52 (d, 2H, J=8.9 Hz), 6.87 (d, 2H, J=9.0 Hz), 4.31 (q, 2H, J=7.1 Hz), 3.52-3.62 (m, 4H), 3.28 (br s, 2H), 2.98 (br s, 2H), 2.82 (s, 3H), 2.14-2.53 (m, 5H), 1.58-1.75 (m, 4H), 1.22-1.42 (m, 5H).

C. 8-Bicyclo[2.2.1]hept-2-yl-2-[4-(4-methyl-piperazin-1-yl)-phenylamino]-5-oxo-5,8-dihydro-pyrido[2,3-d]pyrimidine-6-carboxylic acid amide 8-Bicyclo[2.2.1]hept-2-yl-2-[4-(4-methyl-piperazin-1-yl)-phenylamino]-5-oxo-5,8-dihydro-pyrido[2,3-d]pyrimidine-6-carboxylic acid ethyl ester (5.7 mg, 0.11 mmol) was dissolved in MeOH (2 mL) and cooled to −78° C. in a high pressure vessel. Ammonia was bubbled into the solution for 1 min and the vessel was sealed and allowed to warm to rt. After 14 h, the solution was cooled to −78° C., the vessel was opened and the solution was allowed to warm to rt. The solution was concentrated and water (2 mL) and MeCN (1 mL) was added, the Solution frozen and lyophilized to provide 3.2 mg of 8-bicyclo[2.2.1]hept-2-yl-2-[4-(4-methyl-piperazin-1-yl)-phenylamino]-5-oxo-5,8-dihydro-pyrido[2,3-d]pyrimidine-6-carboxylic acid amide. $^1$H NMR (TFA salt) (400 MHz, $CDCl_3$) δ (ppm): 9.36-9.39 (m, 2H), 8.78 (s, 1H), 7.52 (d, 1H, J=7.2 Hz), 7.33 (d, 1H, J=7.9 Hz), 7.12 (d, 1H, J=8.0 Hz), 6.98 (br s, 1H), 5.69 (br s, 1H), 2.86-3.04 (m, 11H), 2.13-2.17 (m, 2H), 1.52 (br s, 6H). Mass Spectrum (LCMS, ESI pos.) Calcd. for $C_{26}H_{31}N_7O_2$: 473.25, Found: 474.3 (M+H).

EXAMPLE 83

8-Bicyclo[2.2.1]hept-2-yl-2-[4-(4-methyl-piperazin-1-yl)-phenylamino]-5-oxo-5,8-dihydro-pyrido[2,3-d]pyrimidine-6-carboxylic acid ethylamide (Cpd 83)

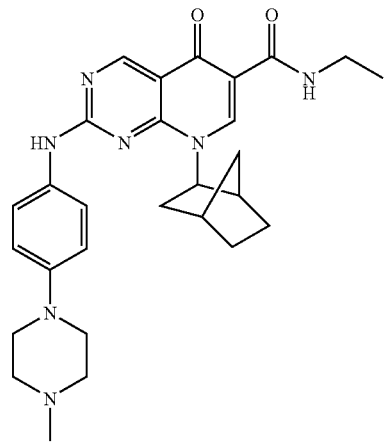

8-Bicyclo[2.2.1]hept-2-yl-2-[4-(4-methyl-piperazin-1-yl)-phenylamino]-5-oxo-5,8-dihydro-pyrido[2,3-d]pyrimidine-6-carboxylic acid ethyl ester (5.7 mg, 0.11 mmol) was dissolved in MeOH (1 mL) and ethylamine (1 mL of 1.0 M solution in THF, 1.0 mmol) was added and the reaction mixture was heated at 80° C. After 16 h, the solution was cooled to rt and purified by preparative HPLC (C-18 column, 32 mL/min 5-100% $MeCN/H_2O$ gradient over 15 min) and lyophilized to provide 3.7 of 8-bicyclo[2.2.1]hept-2-yl-2-[4-(4-methyl-piperazin-1-yl)-phenylamino]-5-oxo-5,8-dihydro-pyrido[2,3-d]pyrimidine-6-carboxylic acid ethylamide. $^1$H NMR (TFA salt) (400 MHz, $CDCl_3$) δ (ppm): 9.62 (s, 1H), 9.26 (s, 1H), 8.90 (s, 1H), 7.54 (d, 2H, J=8.8 Hz), 6.89 (d, 2H, J=8.9 Hz), 4.85-4.88 (m, 1H), 3.26-3.64 (m, 9H), 2.91-2.94 (m, 2H), 2.82 (s, 3H), 2.55 (s, 1H), 2.44 (s, 1H), 2.03 (br s, 8H), 1.59-1.61 (m, 4H), 1.35-1.41 (m, 2H), 1.19 (t, 1H, J=7.3 Hz). Mass Spectrum (LCMS, ESI pos.) Calcd. for $C_{28}H_{35}N_7O_2$: 501.29, Found: 502.3 (M+H).

EXAMPLE 84

8-Indan-5-yl-2-[4-(4-methyl-piperazin-1-ylmethyl)-phenylamino]-5-oxo-5,8-dihydro-pyrido[2,3-d]pyrimidine-6-carboxylic acid ethylamide (Cpd 84)

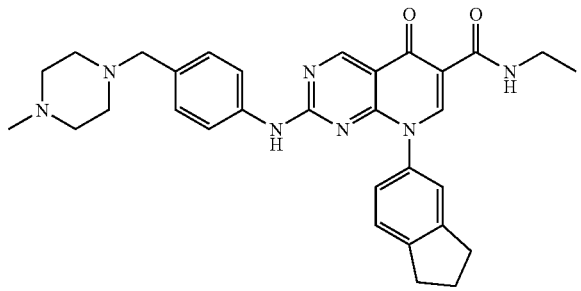

8-Indan-5-yl-2-[4-(4-methyl-piperazin-1-ylmethyl)-phenylamino]-5-oxo-5,8-dihydro-pyrido[2,3-d]pyrimidine-6-carboxylic acid ethyl ester (9.2 mg, 0.017 mmol) was dissolved in MeOH (1 mL) and ethylamine (1 mL of 1.0 M solution in THF, 1.0 mmol) was added and the reaction mixture was heated at 80° C. After 16 h, the solution was cooled to rt and purified by preparative HPLC (C-18 column, 32 mL/min 5-100% MeCN/H$_2$O gradient over 15 min) and lyophilized to provide 5.2 mg of 8-indan-5-yl-2-[4-(4-methyl-piperazin-1-ylmethyl)-phenylamino]-5-oxo-5,8-dihydro-pyrido[2,3-d]pyrimidine-6-carboxylic acid ethylamide. $^1$H NMR TFA salt (400 MHz, CDCl$_3$) δ (ppm): 9.38 (br s, 1H), 9.37 (s, 1H), 8.84 (s, 1H), 7.58-7.60 (m, 1H), 7.40-7.47 (m, 2H), 7.16 (dd, 2H, J=2.0 Hz, J=7.9 Hz), 7.05 (br s, 2H), 3.43-3.55 (m, 4H), 3.07 (t, 2H, J=7.3 Hz), 2.99 (t, 2H, J=7.4 Hz), 2.53 (br s, 8H), 2.36 (s, 3H), 2.18-2.27 (m, 2H), 1.15-1.39 (m, 3H). Mass Spectrum (LCMS, ESI pos.) Calcd. for C$_{31}$H$_{35}$N$_7$O$_2$: 537.29, Found: 538.3 (M+H).

EXAMPLE 85

8-Benzyl-2-[4-(4-methyl-piperazin-1-yl)-phenylamino]-5-oxo-5,8-dihydro-pyrido[2,3-d]pyrimidine-6-carboxylic acid methylamide (Cpd 85)

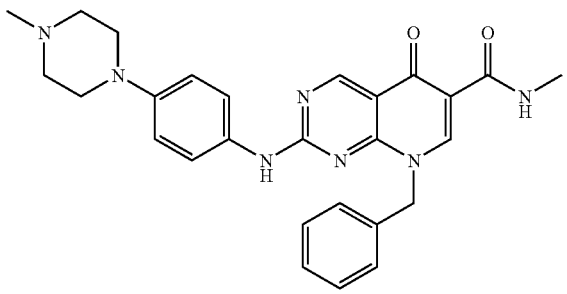

A. 4-[Benzyl-(2-ethoxycarbonyl-ethyl)-amino]-2-methylsulfanyl-pyrimidine-5-carboxylic acid ethyl ester 3-Benzylamino-propionic acid ethyl ester (2.0 g, 9.6 mmol) and 4-chloro-2-methylsulfanyl-pyrimidine-5-carboxylic acid ethyl ester (2.2 g, 9.6 mmol) were combined in DCM (50 mL) and triethylamine (1.5 g, 14.5 mmol) was added. After 14 h, water (25 mL) was added and the organic layer was separated, dried (MgSO$_4$), and concentrated. Chromatography on silica (0-30% EtOAc/hexanes gradient) provided 2.91 g of 4-[benzyl-(2-ethoxycarbonyl-ethyl)-amino]-2-methylsulfanyl-pyridine-5-carboxylic acid ethyl ester. $^1$H NMR (400 MHz, CDCl$_3$) δ (ppm): 8.46 (s, 1H), 7.23-7.33 (m, 5H), 4.75 (s, 2H), 4.21 (q, 2H, J=7.2 Hz), 4.06-4.15 (m, 2H), 3.77 (t, 2H, J=7.2 Hz), 2.66-2.70 (app t, 2H), 2.45 (s, 3H), 1.19-1.29 (m, 6H).

B. 8-Benzyl-2-methylsulfanyl-5-oxo-5,6,7,8-tetrahydro-pyrido[2,3-d]pyrimidine-6-carboxylic acid ethyl ester Sodium (30 wt % dispersion in paraffin wax, 0.55 g, 7.2 mmol) was added to t-butanol (5.0 mL) at rt. After 30 minutes, a solution of 4-[benzyl-(2-ethoxycarbonyl-ethyl)-amino]-2-methylsulfanyl-pyrimidine-5-carboxylic acid ethyl ester (2.9 g, 7.2 mmol) in 20 mL of toluene was added to the sodium t-butoxide solution and the resulting mixture was heated at 90° C. for 30 minutes. The reaction mixture was then cooled and the solution was adjusted to pH 7 using a 1N HCl solution. The solution was then extracted with EtOAc (2×20 mL) and the organic layer was dried (MgSO$_4$), and concentrated. Recrystallization from i-PrOH provided 1.53 g of 8-benzyl-2-methylsulfanyl-5-oxo-5,6,7,8-tetrahydro-pyrido[2,3-d]pyrimidine-6-carboxylic acid ethyl ester. $^1$H NMR mixture of tautomers in a 2.3:1 ratio, (400 MHz, CDCl$_3$) δ (ppm): 8.65 (s, 1H), 8.25 (s, 1H), 7.24-7.36 (m, 5H), 5.07 (d, 1H, J=14.9 Hz), 4.83 (d, 1H, J=14.9 Hz), 4.79 (s, 2H), 4.17-4.22 (m, 2H), 2.51 (s, 1.3H), 2.46 (s, 3H), 0.85-0.89 (m, 3H).

C. 8-Benzyl-2-methylsulfanyl-5-oxo-5,8-dihydro-pyrido[2,3-d]pyrimidine-6-carboxylic acid ethyl ester Bromine (0.68 g, 4.3 mmol) was added to a solution of 8-benzyl-2-methylsulfanyl-5-oxo-5,6,7,8-tetrahydro-pyrido[2,3-d]pyrimidine-6-carboxylic acid ethyl ester (1.53 g, 4.28 mmol) in DCM (20 mL). After 30 minutes, the reaction mixture was concentrated. The residue was redissolved in DCM (20 mL) and triethylamine (1.08 g, 10.7 mmol) was added. After 15 h, water (10 mL) was added, the organic layer separated, dried (MgSO$_4$), and concentrated. Chromatography on silica (0-50% EtOAc/hexanes gradient) provided 0.39 g 8-benzyl-2-methylsulfanyl-5-oxo-5,8-dihydro-pyrido[2,3-d]pyrimidine-6-carboxylic acid ethyl ester. $^1$H NMR (400 MHz, CDCl$_3$) δ (ppm): 9.26 (s, 1H), 8.51 (s, 1H), 7.21-7.29 (m, 5H), 5.45 (s, 2H), 4.27 (q, 2H, J=7.1 Hz), 2.48 (s, 3H), 1.30 (t, 3H, J=7.1 Hz).

D. 8-Benzyl-2-ethanesulfonyl-5-oxo-5,8-dihydro-pyrido[2,3-d]pyrimidine-6-carboxylic acid ethyl ester D. 8-Benzyl-2-methylsulfanyl-5-oxo-5,6,7,8-tetrahydro-pyrido[2,3-d]pyrimidine-6-carboxylic acid ethyl ester (0.39 g, 1.1 mmol) and m-CPBA (0.61 g (77% w/w), 2.7 mmol) were combined in DCM (20 mL). After 2 hours, a 10% solution of Na$_2$SO$_3$ (5 mL) was added and the mixture was partitioned between sat. NaHCO$_3$ and DCM. The organic layer was dried (MgSO$_4$) and concentrated. Chromatography on silica (25-100% EtOAc/hexanes gradient) provided 0.21 g of 8-benzyl-2-methanesulfonyl-5-oxo-5,8-dihydro-pyrido[2,3-d]pyrimidine-6-carboxylic acid ethyl ester. $^1$H NMR (400 MHz, CDCl$_3$) δ (ppm): 9.70 (s, 1H), 8.72 (s, 1H), 7.38-7.41 (m, 5H), 5.57 (s, 2H), 4.40 (q, 2H, J=7.1 Hz), 3.38 (s, 3H), 1.40 (t, 3H, J=7.1 Hz).

E. 8-Benzyl-2-[4-(4-methyl-piperazin-1-yl)-phenylamino]-5-oxo-5,8-dihydro-pyrido[2,3-d]pyrimidine-6-carboxylic acid methylamide 8-Benzyl-2-[4-(4-methyl-piperazin-1-yl)-phenylamino]-5-oxo-5,8-dihydro-pyrido[2,3-d]pyrimidine-6-carboxylic acid ethyl ester (7.6 mg, 0.015 mmol) was dissolved in MeOH (1 mL) and methylamine (1 mL of 1.0 M solution in THF, 1.0 mmol) was added and the reaction mixture was heated at 80° C. After 16 h, the solution was cooled to rt and purified by preparative HPLC (C-18 column; 32 mL/min 5-100% MeCN/$H_2O$ gradient over 15 mm) and lyophilized to provide 1.3 mg of 8-benzyl-2-[4-(4-methyl-piperazin-1-yl)-phenylamino]-5-oxo-5,8-dihydro-pyrido[2,3-d]pyrimidine-6-carboxylic acid methylamide. $^1$H NMR (TFA salt) (400 MHz, $CDCl_3$) δ (ppm): 9.54 (br s, 1H), 9.25 (s, 1H), 8.70 (s, 1H), 7.23-7.30 (m, 5H), 7.13-7.15 (m, 2H), 6.83 (d, 2H, J=8.9 Hz), 5.35 (s, 2H), 3.13 (br s, 4H), 2.91 (s, 3H), 2.53 (br s, 4H), 2.30 (br s, 3H). Mass Spectrum (LCMS, ESI pos.) Calcd. for $C_{27}H_{29}N_7O_2$: 483.24, Found: 484.3 (M+H).

BIOLOGICAL EXAMPLES

Example 1

Autophosphorylation, Fluorescence Polarization Competition Immunoassay

An autophosphorylation, fluorescence polarization competition immunoassay was used to determine the potency for c-fms inhibition exhibited by selected compounds of Formula I. The assay was performed in black 96-well microplates (LJL BioSystems). The assay buffer used was 100 mM 4-(2-hydroxyethyl)piperazine 1-ethanesulfonic acid (HEPES), pH 7.5, 1 mM 1,4-dithio-DL-threitol (DTT), 0.01% (v/v) Tween-20. Compounds were diluted in assay buffer containing 4% dimethylsulfoxide (DMSO) just prior to the assay. To each well, 5 µL of compound were added followed by the addition of 3 µL of a mix containing 33 nM c-fms and 16.7 mM $MgCl_2$ (Sigma) in assay buffer. The kinase reaction was initiated by adding 2 µL of 5 mM ATP (Sigma) in assay buffer. The final concentrations in the assay were 10 nM c-fms, 1 mM ATP, 5 mM $MgCl_2$, 2% DMSO. Control reactions were ran in each plate: in positive and negative control wells, assay buffer (made 4% in DMSO) was substituted for the compound; in addition, positive control wells received 1.2 µL of 50 mM ethylenediaminetetraaceticacid (EDTA).

The plates were incubated at room temperature for 45 min. At the end of the incubation, the reaction was quenched with 1.2 µL of 50 mM EDTA (EDTA was not added to the positive control wells at this point; see above). Following a 5-min incubation, each well received 10 µL of a 1:1:3 mixture of anti-phosphotyrosine antibody, 10×, PTK green tracer, 10× (vortexed), FP dilution buffer, respectively (all from PanVera, cat. # P2837). The plate was covered, incubated for 30 min at room temperature and the fluorescence polarization was read on the Analyst. The instrument settings were: 485 nm excitation filter; 530 nm emission filter; Z height: middle of well; G factor: 0.93. Under these conditions, the fluorescence polarization values for positive and negative controls were approximately 300 and 150, respectively, and were used to define the 100% and 0% inhibition of the c-fms reaction.

The $IC_{50}$ values shown in Table 1 are averages of three independent measurements.

TABLE 1 c-fms Autophosphorylation $IC_{50}$ Values

| Cpd | $IC_{50}$ (µM) |
|---|---|
| 1 | 0.28 |
| 2 | 0.44 |
| 3 | 2.9 |
| 4 | >10 |
| 5 | 0.59 |
| 6 | 1.1 |
| 7 | 0.013 |
| 8 | 0.031 |
| 9 | 0.068 |
| 10 | 0.013 |
| 11 | 0.046 |
| 12 | 0.077 |
| 13 | 0.73 |
| 14 | 0.019 |
| 15 | 0.07 |
| 16 | 0.012 |
| 17 | 1.7 |
| 18 | 10 |
| 19 | 0.056 |
| 20 | 1.4 |
| 21 | 10 |
| 22 | >10 |
| 23 | 0.014 |
| 24 | 0.018 |
| 25 | 0.093 |
| 26 | 0.056 |
| 27 | 0.01 |
| 28 | 0.03 |
| 29 | 0.033 |
| 30 | 0.012 |
| 31 | 0.02 |
| 32 | 0.033 |
| 33 | 0.1 |
| 34 | >1 |
| 35 | 0.08 |
| 36 | 1.0 |
| 37 | 0.008 |
| 38 | 0.009 |
| 39 | 0.013 |
| 40 | 0.005 |
| 41 | 0.011 |
| 42 | 0.016 |
| 43 | 0.007 |
| 44 | 0.008 |
| 45 | 0.012 |
| 46 | 0.008 |
| 47 | 0.015 |
| 48 | 0.032 |
| 49 | 0.008 |
| 50 | 0.015 |
| 51 | 0.025 |
| 52 | 0.005 |
| 53 | 0.008 |
| 54 | 0.011 |
| 55 | 0.006 |
| 56 | 0.01 |
| 57 | 0.026 |
| 58 | 0.12 |
| 59 | 0.19 |
| 60 | 0.035 |
| 61 | 0.16 |
| 62 | 0.19 |
| 63 | 0.021 |
| 64 | 0.05 |
| 65 | 0.11 |
| 66 | 0.12 |
| 67 | 0.12 |
| 68 | 0.13 |
| 69 | 0.018 |
| 70 | 1.1 |
| 71 | 7.4 |
| 72 | 4.1 |
| 73 | >1 |
| 74 | 0.032 |
| 75 | 0.021 |

TABLE 1-continued c-fms Autophosphorylation IC$_{50}$ Values

| Cpd | IC$_{50}$ (μM) |
|---|---|
| 76 | 0.018 |
| 77 | 0.15 |
| 78 | 0.14 |
| 79 | 0.062 |
| 80 | 0.074 |
| 81 | 0.11 |
| 82 | 0.081 |
| 83 | 0.3 |
| 84 | 0.032 |
| 85 | 0.42 |

Example 2

Peptide (Non-Phosphorylated) Assay

A fluorescence polarization competition immunoassay was used to measure compound inhibition of CSF-1R phosphorylation of tyrosine on a synthetic CSF-1R$_{555-568}$ peptide (SYEGNSYTFIDPTQ). The assay was performed in black 96-well microplates (Cat # 42-000-0117, Molecular Devices, Sunnyvale, Calif.). To each well, 5 μL of compound (in 4% DMSO) were mixed with 2 μL of 3.5 nM CSF-1R, 25 mM MgCl$_2$ in assay buffer (100 mM HEPES, pH 7.5, 1 mM DTT, 0.01% Tween-20), and 2 μL of 1540 μM peptide in assay buffer. The kinase reaction was initiated by adding 1 μL of 10 mM ATP in assay buffer. The final concentrations in the 10 μL reaction mixture were 100 mM HEPES, pH 7.5, 1 mM DTT, 0.01% Tween-20, 2% DMSO, 308 μM SYEGNSYTFIDPTQ, 1 mM ATP, 5 mM MgCl$_2$, and 0.7 nM CSF-1R. Positive and negative control wells were included on each plate, where 4% DMSO in assay buffer was substituted for the compound; in addition, positive control wells received 1.2 μL of 50 mM EDTA before the start of the reaction.

The plates were covered and incubated at room temperature for 80 min. Reactions were stopped by addition of 1.2 μL of 50 mM EDTA. Each well then received 10 μL of a 1:1:3 mixture of 10× anti-phosphotyrosine antibody, 10×PTK green tracer, and FP dilution buffer, respectively (Cat. # P2837, Invitrogen, Carlsbad, Calif.). The plates were covered, incubated for 30 min at room temperature, and the fluorescence polarization was read on an Analyst plate reader (Molecular Devices). Instrument settings were: 485 nm excitation, 530 nm emission, with a 505 nm cut-off filter; Z height: middle of well; G factor: 0.93. Under these conditions, the fluorescence polarization values for positive and negative controls were approximately 290 and 160, respectively, and were used to define 100% and 0% inhibition of the CSF-1R reaction.

The IC$_{50}$ values reported in Table 2 are the mean of at least three determinations.

TABLE 2 c-fms Peptide IC$_{50}$ Values

| Cpd | IC$_{50}$ (μM) |
|---|---|
| 7 | 0.0039 |
| 10 | 0.0027 |
| 11 | 0.0056 |
| 16 | 0.0043 |
| 23 | 0.0015 |
| 28 | 0.0016 |

TABLE 2-continued c-fms Peptide IC$_{50}$ Values

| Cpd | IC$_{50}$ (μM) |
|---|---|
| 40 | 0.00024 |
| 43 | 0.00058 |
| 44 | 0.00053 |
| 46 | 0.00074 |
| 47 | 0.0013 |
| 49 | 0.00049 |
| 50 | 0.00097 |
| 52 | 0.00042 |
| 53 | 0.00046 |
| 54 | 0.0011 |
| 55 | 0.00051 |
| 56 | 0.0011 |

While the foregoing specification teaches the principles of the present invention, with examples provided for the purpose of illustration, it will be understood that the practice of the invention encompasses all of the usual variations, adaptations and/or modifications come within the scope of the following claims and their equivalents.

All publications disclosed in the above specification are hereby incorporated by reference in full.

We claim:
1. A compound of Formula I:

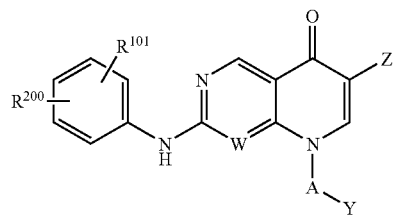

or a salt, stereoisomer, tautomer or ester thereof, wherein:

W is N or CH;

A is absent or alkyl;

Y is a ring selected from cycloalkyl, bicycloalkyl, aryl, alkylaryl, cycloalkylaryl, arylcycloalkyl, or heteroaryl provided that Y is not thiazole;

$R^{101}$ is hydrogen, hydroxyl, methyl, halogen, —CF$_3$, or methoxy;

$R^{200}$ is halogen, alkoxy optionally substituted with —CH(OH)—CH$_2$—NR$^{203}$R$^{204}$, alkyl optionally substituted with $R^{201}$, heterocyclyl optionally substituted with one alkyl and optionally substituted with one $R^{202}$, amino, alkylamino, dialkylamino, —C(O)(CH$_2$)$_n$NR$^{203}$R$^{204}$, heteroaryl, or —R$^{300}$—R$^{400}$; wherein n is 0, 1, 2, 3, or 4;

$R^{201}$ is hydroxyl, methyl, halogen, —CF$_3$, amino, alkyl amino, dialkylamino or methoxy;

$R^{202}$ is alkyl, —C(O)—CH$_3$, —CH$_2$—C(O)—CH$_3$, —C(O)(CH$_2$)$_n$NR$^{203}$R$^{204}$, or —CON-alkyl-NR$^{203}$R$^{204}$; wherein n is 0, 1, 2, 3, or 4;

$R^{203}$ and $R^{204}$ are independently hydrogen, alkyl, or $R^{203}$ and $R^{204}$ may be taken together to form a ring selected from the following:

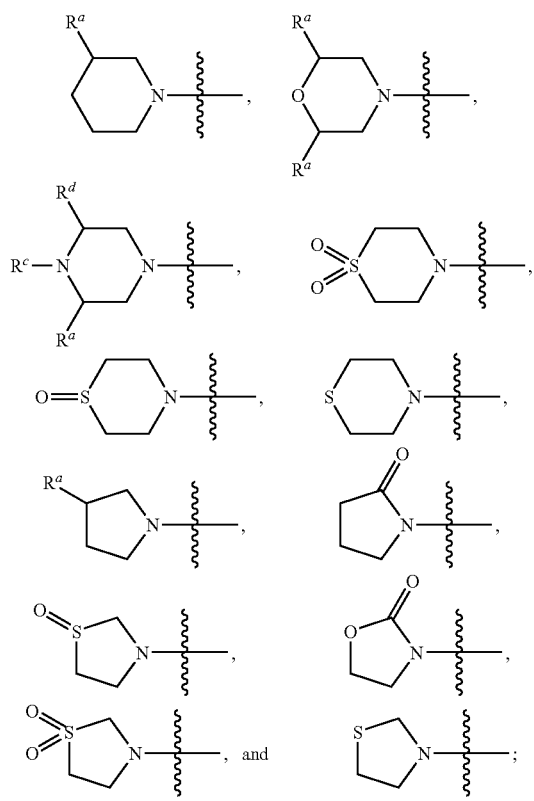

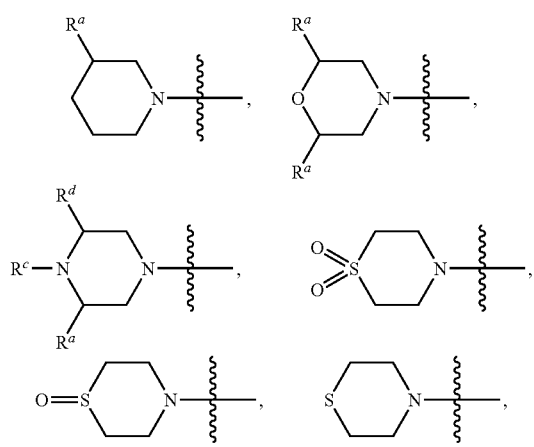

wherein $R^a$, $R^c$ and $R^d$ are independently hydrogen or alkyl;

$R^{300}$ is alkyl;

$R^{400}$ is —$NR^{403}R^{404}$, —$SO_2NR^{405}R^{406}$, oxazolidinonyl wherein said oxazolidinonyl is optionally substituted with one or two $R^{401}$, piperazinyl wherein said piperazinyl is optionally substituted with $R^{202}$ or pyrrolidinonyl wherein said pyrrolidinonyl is optionally substituted with one or two $R^{401}$;

wherein $R^{401}$ is methyl, —C(O)—$CH_3$, or —$CH_2$—C(O)—$CH_3$;

wherein $R^{403}$ and $R^{404}$ are independently hydrogen, alkyl, or $R^{403}$ and $R^{404}$ may be taken together to form a ring selected from the following:

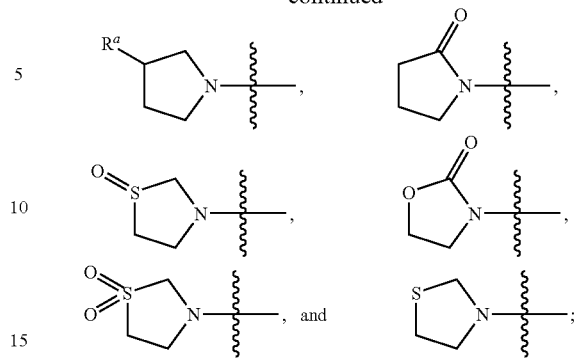

wherein $R^a$, $R^c$ and $R^d$ are independently hydrogen or alkyl;

$R^{405}$ and $R^{406}$ are independently hydrogen, alkyl, or $R^{405}$ and $R^{406}$ may be taken together to form a ring selected from the following:

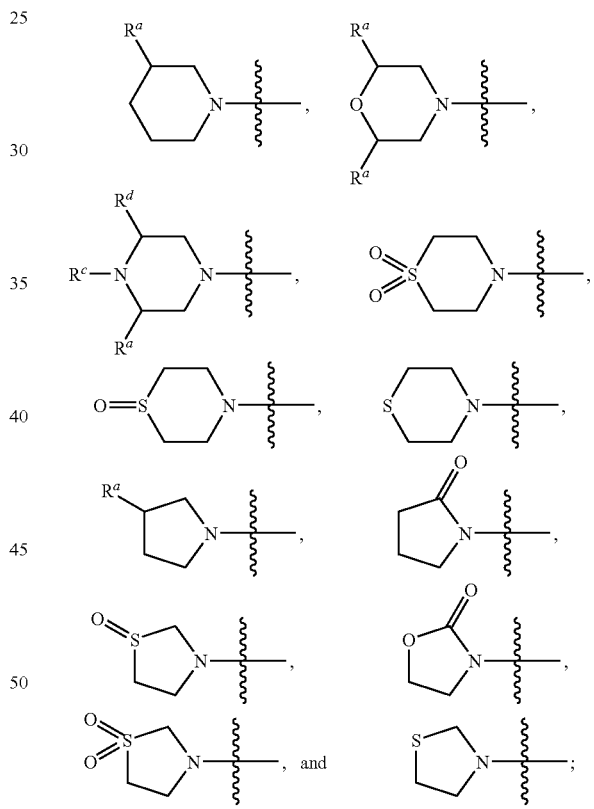

wherein $R^a$, $R^c$ and $R^d$ are independently hydrogen or alkyl; and

Z is $CO_2H$, $CO_2$alkyl, or $CONR^1R^2$; wherein $R^1$ is hydrogen or alkyl; and $R^2$ is hydrogen, alkyl, cycloalkyl, or alkoxy.

2. The compound of claim 1 wherein:

A is absent;

Y is a ring selected from cycloalkyl, bicycloalkyl, phenyl, alkylaryl, cycloalkylaryl, arylcycloalkyl, or heteroaryl provided that Y is not thiazole;

$R^{200}$ is halogen, $C_{(1-4)}$alkoxy optionally substituted with —CH(OH)—CH$_2$—NR$^{203}$R$^{204}$, $C_{(1-4)}$alkyl optionally substituted with R$^{201}$, heterocyclyl optionally substituted with one $C_{(1-4)}$alkyl and optionally substituted with one R$^{202}$, dialkylamino, —C(O)(CH$_2$)$_n$NR$^{203}$R$^{204}$, heteroaryl, or —R$^{300}$—R$^{400}$; wherein n is 0, 1, 2, 3, or 4;

$R^{201}$ is hydroxyl, methyl, halogen, —CF$_3$, dialkylamino or methoxy;

$R^{202}$ is alkyl, —C(O)—CH$_3$, —CH$_2$—C(O)—CH$_3$, —C(O)(CH$_2$)$_n$NR$^{203}$R$^{204}$, —C(O)N(CH$_2$)$_n$NR$^{203}$R$^{204}$; wherein n is 0, 1, 2, 3, or 4;

$R^{203}$ and $R^{204}$ are independently hydrogen, $C_{(1-4)}$alkyl, or $R^{203}$ and $R^{204}$ may be taken together to form a ring selected from the following:

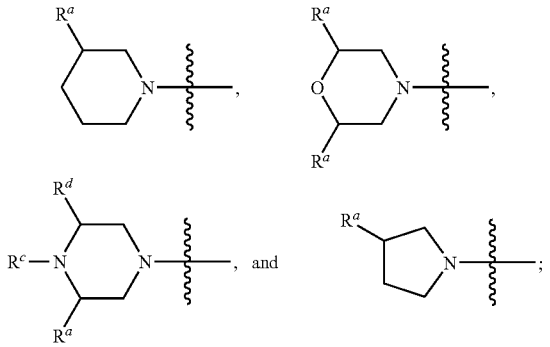

wherein $R^a$, $R^c$ and $R^d$ are independently hydrogen or alkyl;

$R^{300}$ is $C_{(1-4)}$alkyl; and $R^{400}$ is —NR$^{403}$R$^{404}$, —SO$_2$NR$^{405}$R$^{406}$, oxazolidinonyl wherein said oxazolidinonyl is optionally substituted with one or two R$^{401}$, piperazinyl wherein said piperazinyl is optionally substituted with R$^{202}$ or pyrrolidinonyl wherein said pyrrolidinonyl is optionally substituted with one or two R$^{401}$;

wherein $R^{401}$ is methyl, —C(O)—CH$_3$, or —CH$_2$—C(O)—CH$_3$;

wherein $R^{403}$ and $R^{404}$ are independently hydrogen, $C_{(1-4)}$ alkyl, or $R^{403}$ and $R^{404}$ may be taken together to form a ring selected from the following:

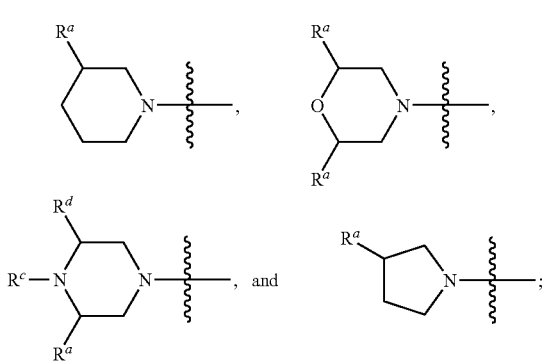

wherein $R^a$, $R^c$ and $R^d$ are independently hydrogen or alkyl;

$R^{405}$ and $R^{406}$ are independently hydrogen, $C_{(1-4)}$alkyl, or $R^{405}$ and $R^{406}$ may be taken together to form a ring selected from the following:

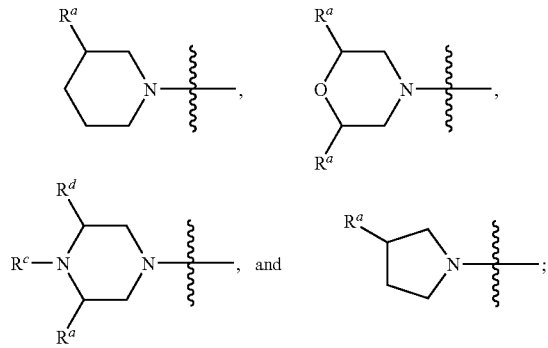

wherein $R^a$, $R^c$ and $R^d$ are independently hydrogen or alkyl; and

Z is CO$_2$alkyl, or CONR$^1$R$^2$; wherein R$^1$ is hydrogen or $C_{(1-4)}$alkyl; and R$^2$ is hydrogen, $C_{(1-4)}$alkyl, cycloalkyl, or $C_{(1-4)}$alkoxy.

3. The compound of claim 1 wherein:

Y is a ring selected from indan-5-yl, phenyl, cyclohexyl, cyclopentyl, cbicyclo[2.2.1]heptyl or adamantan-2-yl;

$R^{101}$ is hydrogen or hydroxyl;

$R^{200}$ is fluorine, alkoxy substituted with —CH(OH)—CH$_2$—N(CH$_3$)$_2$, alkyl optionally substituted with R$^{201}$, morpholinyl, piperazinyl optionally substituted with R$^{202}$, 3,5-dimethyl piperazinyl, piperidinyl, piperidinyl substituted with —CO-alkyl-N(CH$_3$)$_2$, —C(O)-alkyl-piperazinyl (optionally substituted on piperazinyl with alkyl), dimethylamino, —C(O)N(CH$_3$)$_2$, heteroaryl, or —R$^{300}$—R$^{400}$;

$R^{201}$ is hydroxyl or dimethylamino;

$R^{202}$ is —CH$_3$;

$R^{300}$ is alkyl; and $R^{400}$ is —N(CH$_3$)$_2$, morpholinyl, —SO$_2$NR$^{405}$R$^{406}$, piperazinyl optionally substituted with R$^{202}$ or oxazolidinonyl;

$R^{405}$ and $R^{406}$ are independently hydrogen, alkyl, or $R^{405}$ and $R^{406}$ may be taken together to form the following ring:

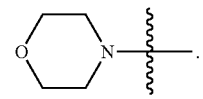

4. The compounds of claim 1 wherein:

W is N;

A is absent;

Y is a ring selected from cycloalkyl or arylcycloalkyl;

$R^{200}$ is piperazine optionally substituted with one or two methyl substituents, piperidine optionally substituted with one or two methyl substituents, morpholine or —R$^{300}$—R$^{400}$ wherein R$^{300}$ is methyl or ethyl and R$^{400}$ is piperazine optionally substituted with one or two methyl substituents.

Z is CO$_2$alkyl, or CONR$^1$R$^2$; wherein R$^1$ is hydrogen or $C_{(1-4)}$alkyl; and R$^2$ is hydrogen, $C_{(1-4)}$alkyl, or cycloalkyl.

5. A compound of Formula I wherein:

W is N or CH;

A is absent;

Y is a ring selected from cycloalkyl, bicycloalkyl, phenyl, alkylaryl, cycloalkylaryl, arylcycloalkyl, or heteroaryl provided that Y is not thiazole;

$R^{101}$ is hydrogen, hydroxyl, methyl, halogen, —CF$_3$, or methoxy;

$R^{200}$ is halogen, C$_{(1-4)}$alkoxy optionally substituted with —CH(OH)—CH$_2$—NR$^{203}$R$^{204}$, C$_{(1-4)}$alkyl optionally substituted with R$^{201}$, heterocyclyl optionally substituted with one C$_{(1-4)}$alkyl and optionally substituted with one R$^{202}$, dialkylamino, —C(O)(CH$_2$)$_n$NR$^{203}$R$^{204}$, heteroaryl, or —R$^{300}$—R$^{400}$; wherein n is 0, 1, 2, 3, or 4;

$R^{201}$ is hydroxyl, methyl, halogen, —CF$_3$, dialkylamino or methoxy;

$R^{202}$ is alkyl, —C(O)—CH$_3$, —CH$_2$—C(O)—CH$_3$, —C(O)(CH$_2$)$_n$NR$^{203}$—R$^{204}$, —C(O)N(CH$_2$)$_n$ NR$^{203}$R$^{204}$; wherein n is 0, 1, 2, 3, or 4;

$R^{203}$ and $R^{204}$ are independently hydrogen, C$_{(1-4)}$alkyl, or $R^{203}$ and $R^{204}$ may be taken together to form a ring selected from the following:

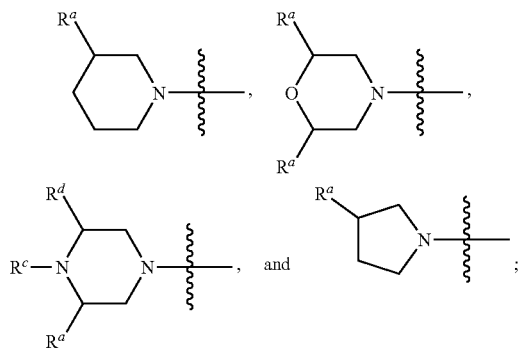

wherein $R^a$, $R^c$ and $R^d$ are independently hydrogen or alkyl;

$R^{300}$ is C$_{(1-4)}$alkyl; and $R^{400}$ is —NR$^{403}$R$^{404}$, —SO$_2$NR$^{405}$R$^{406}$, oxazolidinonyl wherein said oxazolidinonyl is optionally substituted with one or two R$^{401}$, piperazinyl wherein said piperazinyl is optionally substituted with R$^{202}$ or pyrrolidinonyl wherein said pyrrolidinonyl is optionally substituted with one or two R$^{401}$;

wherein $R^{401}$ is methyl, —C(O)—CH$_3$, or —CH$_2$—C(O)—CH$_3$;

wherein $R^{403}$ and $R^{404}$ are independently hydrogen, C$_{(1-4)}$ alkyl, or $R^{403}$ and $R^{404}$ may be taken together to form a ring selected from the following:

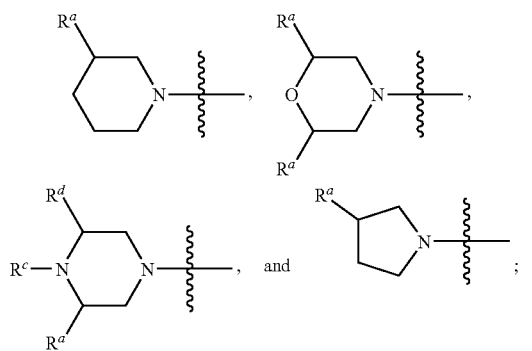

wherein $R^a$, $R^c$ and $R^d$ are independently hydrogen or alkyl;

$R^{405}$ and $R^{406}$ are independently hydrogen, C$_{(1-4)}$alkyl, or $R^{405}$ and $R^{406}$ may be taken together to form a ring selected from the following:

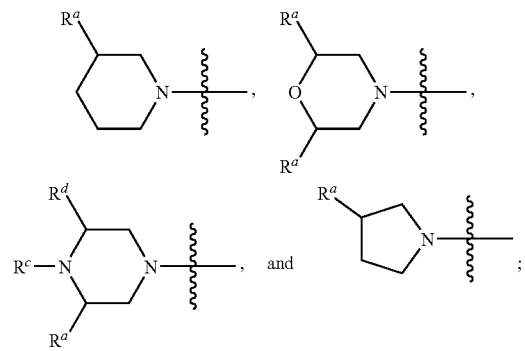

wherein $R^a$, $R^c$ and $R^d$ dare independently hydrogen or alkyl; and

Z is CO$_2$H.

6. A compound selected from the group consisting of:

8-indan-5-yl-2-[4-(4-methyl-piperazin-1-yl)-phenylamino]-5-oxo-5,8-dihydro-pyrido[2,3-d]pyrimidine-6-carboxylic acid ethyl ester, 2-[4-(3-dimethylamino-2-hydroxy-propoxy)-phenylamino]-8-indan-5-yl-5-oxo-5,8-dihydro-pyrido[2,3-d] pyrimidine-6-carboxylic acid ethyl ester, 8-indan-5-yl-2-(4-morpholin-4-yl-phenylamino)-5-oxo-5,8-dihydro-pyrido[2,3-d]pyrimidine-6-carboxylic acid ethyl ester, 2-(4-dimethylamino-phenylamino)-8-indan-5-yl-5-oxo-5, 8-dihydro-pyrido[2,3-d]pyrimidine-6-carboxylic acid ethyl ester, 2-(3-dimethyl amino-phenylamino)-8-indan-5-yl-5-oxo-5,8-dihydro-pyrido[2,3-d]pyrimidine-6-carboxylic acid ethyl ester, 8-indan-5-yl-2-[4-(4-methyl-piperazin-1-yl)-phenylamino]-5-oxo-5,8-dihydro-pyrido[2,3-d]pyrimidine-6-carboxylic acid, 8-indan-5-yl-2-[4-(4-methyl-piperazin-1-yl)-phenylamino]-5-oxo-5,8-dihydro-pyrido[2,3-d]pyrimidine-6-carboxylic acid amide, 8-indan-5-yl-2-[4-(4-methyl-piperazin-1-yl)-phenylamino]-5-oxo-5,8-dihydro-pyrido[2,3-d]pyrimidine-6-carboxylic acid methylamide, 8-indan-5-yl-2-[4-(4-methyl-piperazin-1-yl)-phenylamino]-5-oxo-5,8-dihydro-pyrido[2,3-d]pyrimidine-6-carboxylic acid ethylamide, 2-[4-(3-dimethylamino-2-hydroxy-propoxy)-phenylamino]-8-indan-5-yl-5-oxo-5,8-dihydro-pyrido[2,3-d] pyrimidine-6-carboxylic acid amide, 2-[4-(3-dimethylamino-2-hydroxy-propoxy)-phenylamino]-8-indan-5-yl-5-oxo-5,8-dihydro-pyrido[2,3-d] pyrimidine-6-carboxylic acid methylamide 2-[4-(3-dimethylamino-2-hydroxy-propoxy)-phenylamino]-8-indan-5-yl-5-oxo-5,8-dihydro-pyrido[2,3-d] pyrimidine-6-carboxylic acid ethylamide, 2-[4-(4-Methyl-piperazin-1-yl)-phenylamino]-5-oxo-8-phenyl-5,8-dihydro-pyrido[2,3-d]pyrimidine-6-carboxylic acid amide, 8-indan-5-yl-2-(4-morpholin-4-yl-phenylamino)-5-oxo-5,8-dihydro-pyrido[2,3-d]pyrimidine-6-carboxylic acid amide, 2-(4-dimethylamino-phenylamino)-8-indan-5-yl-5-oxo-5,8-dihydro-pyrido[2,3-d]pyrimidine-6-carboxylic acid amide, 2-(3-dimethylamino-phenylamino)-8-indan-5-yl-5-oxo-5,8-dihydro-pyrido[2,3-d]pyrimidine-6-carboxylic acid amide, 8-cyclohexyl-2-[4-(4-methyl-piperazin-1-yl)-phenylamino]-5-oxo-5,8-dihydro-pyrido[2,3-d]pyrimidine-6-carboxylic acid ethyl ester, 8-cyclohexyl-2-(4-dimethylamino-phenylamino)-5-oxo-5,8-dihydro-pyrido[2,3-d]pyrimidine-6-carboxylic acid ethyl ester, 8-cyclopentyl-2-[4-(4-methyl-piperazin-1-yl)-phenylamino]-5-oxo-5,8-dihydro-pyrido[2,3-d]pyrimidine-6-carboxylic acid amide, 2-(3-hydroxymethyl-phenylamino)-8-indan-5-yl-5-oxo-5,8-dihydro-pyrido[2,3-d]pyrimidine-6-carboxylic acid amide, 2-(4-fluoro-phenylamino)-8-indan-5-yl-5-oxo-5,8-dihydro-pyrido[2,3-d]pyrimidine-6-carboxylic acid ethyl ester, 8-indan-5-yl-5-oxo-2-(4-pyrazol-1-yl-phenylamino)-5,8-dihydro-pyrido[2,3-d]pyrimidine-6-carboxylic acid amide, 8-indan-5-yl-2-[3-(4-methyl-piperazin-1-ylmethyl)-phenylamino]-5-oxo-5,8-dihydro-pyrido[2,3-d]pyrimidine-6-carboxylic acid amide, 8-indan-5-yl-2-(3-morpholin-4-ylmethyl-phenylamino)-5-oxo-5,8-dihydro-pyrido[2,3-d]pyrimidine-6-carboxylic acid amide, 2-[2-hydroxy-4-(4-methyl-piperazin-1-yl)-phenylamino]-8-indan-5-yl-5-oxo-5,8-dihydro-pyrido[2,3-d]pyrimidine-6-carboxylic acid amide, 1-indan-5-yl-7-[4-(4-methyl-piperazin-1-yl)-phenylamino]-4-oxo-1,4-dihydro-[1,6]naphthyridine-3-carboxylic acid amide, 8-Indan-5-yl-2-[4-(2-morpholin-4-yl-ethyl)-phenylamino]-5-oxo-5,8-dihydro-pyrido[2,3-d]pyrimidine-6-carboxylic acid amide, 8-Indan-5-yl-2-[4-(2-morpholin-4-yl-ethyl)-phenylamino]-5-oxo-5,8-dihydro-pyrido[2,3-d]pyrimidine-6-carboxylic acid methyl amide, 8-Indan-5-yl-2-[4-(2-morpholin-4-yl-ethyl)-phenylamino]-5-oxo-5,8-dihydro-pyrido[2,3-d]pyrimidine-6-carboxylic acid ethyl amide, (4S)-8-Indan-5-yl-5-oxo-2-[4-(2-oxo-oxazolidin-4-ylmethyl)-phenylamino]-5,8-dihydro-pyrido[2,3-d]pyrimidine-6-carboxylic acid amide, (4S)-8-indan-5-yl-5-oxo-2-[4-(2-oxo-oxazolidin-4-ylmethyl)-phenylamino]-5,8-dihydro-pyrido[2,3-d]pyrimidine-6-carboxylic acid methyl amide, (4S)-8-Indan-5-yl-5-oxo-2-[4-(2-oxo-oxazolidin-4-ylmethyl)-phenylamino]-5,8-dihydro-pyrido[2,3-d]pyrimidine-6-carboxylic acid ethyl amide, 8-Indan-5-yl-2-[4-(2-isopropylsulfamoyl-ethyl)-phenylamino]-5-oxo-5,8-dihydro-pyrido[2,3-d]pyrimidine-6-carboxylic acid methyl amide, 8-Indan-5-yl-2-[4-(2-isopropylsulfamoyl-ethyl)-phenylamino]-5-oxo-5,8-dihydro-pyrido[2,3-d]pyrimidine-6-carboxylic acid ethyl amide, 8-Indan-5-yl-2-{4-[2-(morpholine-4-sulfonyl)-ethyl]-phenylamino}-5-oxo-5,8-dihydro-pyrido[2,3-d]pyrimidine-6-carboxylic acid methyl amide, 8-Indan-5-yl-2-{4-[2-(morpholine-4-sulfonyl)-ethyl]-phenylamino}-5-oxo-5,8-dihydro-pyrido[2,3-d]pyrimidine-6-carboxylic acid ethyl amide, 8-Indan-5-yl-2-[3-(4-methyl-piperazin-1-yl)-phenylamino]-5-oxo-5,8-dihydro-pyrido[2,3-d]pyrimidine-6-carboxylic acid amide, 8-Indan-5-yl-2-[3-(4-methyl-piperazin-1-yl)-phenylamino]-5-oxo-5,8-dihydro-pyrido[2,3-d]pyrimidine-6-carboxylic acid methyl amide, 8-Indan-5-yl-2-[3-(4-methyl-piperazin-1-yl)-phenylamino]-5-oxo-5,8-dihydro-pyrido[2,3-d]pyrimidine-6-carboxylic acid ethyl amide, 8-Indan-5-yl-5-oxo-2-(4-piperazin-1-yl-phenylamino)-5,8-dihydro-pyrido[2,3-d]pyrimidine-6-carboxylic acid amide, 8-Indan-5-yl-5-oxo-2-(4-piperazin-1-yl-phenylamino)-5,8-dihydro-pyrido[2,3-d]pyrimidine-6-carboxylic acid methyl amide, 8-Indan-5-yl-5-oxo-2-(4-piperazin-1-yl-phenylamino)-5,8-dihydro-pyrido[2,3-d]pyrimidine-6-carboxylic acid ethyl amide, 2-[4-(3,5-Dimethyl-piperazin-1-yl)-phenylamino]-8-indan-5-yl-5-oxo-5,8-dihydro-pyrido[2,3-d]pyrimidine-6-carboxylic acid amide, 2-[4-(3,5-Dimethyl-piperazin-1-yl)-phenylamino]-8-indan-5-yl-5-oxo-5,8-dihydro-pyrido[2,3-d]pyrimidine-6-carboxylic acid methyl amide, 2-[4-(3,5-Dimethyl-piperazin-1-yl)-phenylamino]-8-indan-5-yl-5-oxo-5,8-dihydro-pyrido[2,3-d]pyrimidine-6-carboxylic acid ethyl amide, 8-Indan-5-yl-2-{4-[2-(4-methyl-piperazin-1-yl)-ethyl]-phenylamino}-5-oxo-5,8-dihydro-pyrido[2,3-d]pyrimidine-6-carboxylic acid amide, 8-Indan-5-yl-2-{4-[2-(4-methyl-piperazin-1-yl)-ethyl]-phenylamino}-5-oxo-5,8-dihydro-pyrido[2,3-d]pyrimidine-6-carboxylic acid methyl amide, 8-Indan-5-yl-2-{4-[2-(4-methyl-piperazin-1-yl)-ethyl]-phenylamino}-5-oxo-5,8-dihydro-pyrido[2,3-d]pyrimidine-6-carboxylic acid ethyl amide, 8-Indan-5-yl-5-oxo-2-(4-piperidin-4-yl-phenylamino)-5,8-dihydro-pyrido[2,3-d]pyrimidine-6-carboxylic acid amide, 8-Indan-5-yl-5-oxo-2-(4-piperidin-4-yl-phenylamino)-5,8-dihydro-pyrido[2,3-d]pyrimidine-6-carboxylic acid methyl amide, 8-Indan-5-yl-5-oxo-2-(4-piperidin-4-yl-phenylamino)-5,8-dihydro-pyrido[2,3-d]pyrimidine-6-carboxylic acid ethyl amide, 8-Indan-5-yl-5-oxo-2-(3-piperazin-1-yl-phenylamino)-5,8-dihydro-pyrido[2,3-d]pyrimidine-6-carboxylic acid amide, 8-Indan-5-yl-5-oxo-2-(3-piperazin-1-yl-phenylamino)-5,8-dihydro-pyrido[2,3-d]pyrimidine-6-carboxylic acid methyl amide, 8-Indan-5-yl-5-oxo-2-(3-piperazin-1-yl-phenylamino)-5,8-dihydro-pyrido[2,3-d]pyrimidine-6-carboxylic acid ethyl amide, 2-[3-(3,5-Dimethyl-piperazin-1-yl)-phenylamino]-8-indan-5-yl-5-oxo-5,8-dihydro-pyrido[2,3-d]pyrimidine-6-carboxylic acid amide, 2-[3-(3,5-Dimethyl-piperazin-1-yl)-phenylamino]-8-indan-5-yl-5-oxo-5,8-dihydro-pyrido[2,3-d]pyrimidine-6-carboxylic acid methyl amide, 8-Cyclohexyl-2-[4-(2-morpholin-4-yl-ethyl)-phenylamino]-5-oxo-5,8-dihydro-pyrido[2,3-d]pyrimidine-6-carboxylic acid amide, 8-Cyclohexyl-2-[4-(2-morpholin-4-yl-ethyl)-phenylamino]-5-oxo-5,8-dihydro-pyrido[2,3-d]pyrimidine-6-carboxylic acid methyl amide,
8-Cyclohexyl-2-[4-(2-morpholin-4-yl-ethyl)-phenylamino]-5-oxo-5,8-dihydro-pyrido[2,3-d]pyrimidine-6-carboxylic acid ethyl amide,
8-Cyclohexyl-2-[4-(4-methyl-piperazin-1-yl)-phenylamino]-5-oxo-5,8-dihydro-pyrido[2,3-d]pyrimidine-6-carboxylic acid amide,
8-Cyclohexyl-2-[4-(4-methyl-piperazin-1-yl)-phenylamino]-5-oxo-5,8-dihydro-pyrido[2,3-d]pyrimidine-6-carboxylic acid methyl amide,
8-Cyclohexyl-2-[4-(4-methyl-piperazin-1-yl)-phenylamino]-5-oxo-5,8-dihydro-pyrido[2,3-d]pyrimidine-6-carboxylic acid ethyl amide,
8-Cyclohexyl-2-[3-(4-methyl-piperazin-1-yl)-phenylamino]-5-oxo-5,8-dihydro-pyrido[2,3-d]pyrimidine-6-carboxylic acid amide,
8-Cyclohexyl-2-[3-(4-methyl-piperazin-1-yl)-phenylamino]-5-oxo-5,8-dihydro-pyrido[2,3-d]pyrimidine-6-carboxylic acid methyl amide,
8-Cyclohexyl-2-[3-(4-methyl-piperazin-yl)-phenylamino]-5-oxo-5,8-dihydro-pyrido[2,3-d]pyrimidine-6-carboxylic acid ethyl amide,
8-Cyclohexyl-2-[4-(2-isopropylsulfamoyl-ethyl)-phenylamino]-5-oxo-5,8-dihydro-pyrido[2,3-d]pyrimidine-6-carboxylic acid amide,
8-Cyclohexyl-2-{4-[2-(morpholine-4-sulfonyl)-ethyl]-phenylamino}-5-oxo-5,8-dihydro-pyrido[2,3-d]pyrimidine-6-carboxylic acid amide,
8-Cyclohexyl-2-{4-[1-(2-dimethylamino-acetyl)-piperidin-4-yl]-phenylamino}-5-oxo-5,8-dihydro-pyrido[2,3-d]pyrimidine-6-carboxylic acid amide,
8-Indan-5-yl-2-(4-morpholin-4-ylmethyl-phenylamino)-5-oxo-5,8-dihydro-pyrido[2,3-d]pyrimidine-6-carboxylic acid amide,
2-{4-[1-(2-Dimethylamino-acetyl)-piperidin-4-yl]-phenylamino}-8-indan-5-yl-5-oxo-5,8-dihydro-pyrido[2,3-d]pyrimidine-6-carboxylic acid amide,
2-{3-[1-(2-Dimethylamino-acetyl)-piperidin-4-yl]-phenylamino}-8-indan-5-yl-5-oxo-5,8-dihydro-pyrido[2,3-d]pyrimidine-6-carboxylic acid amide,
8-Indan-5-yl-2-(4-{1-[2-(4-methyl-piperazin-1-yl)-acetyl]-piperidin-4-yl}-phenylamino)-5-oxo-5,8-dihydro-pyrido[2,3-d]pyrimidine-6-carboxylic acid amide,
8-Indan-5-yl-2-(3-{1-[2-(4-methyl-piperazin-1-yl)-acetyl]-piperidin-4-yl}-phenylamino)-5-oxo-5,8-dihydro-pyrido[2,3-d]pyrimidine-6-carboxylic acid amide,
8-Indan-5-yl-2-[4-(4-methyl-piperazin-1-ylmethyl)-phenylamino]-5-oxo-5,8-dihydro-pyrido[2,3-d]pyrimidine-6-carboxylic acid amide,
2-(4-Dimethylaminomethyl-phenylamino)-8-indan-5-yl-5-oxo-5,8-dihydro-pyrido[2,3-d]pyrimidine-6-carboxylic acid amide,
2-(3-Dimethylaminomethyl-phenylamino)-8-indan-5-yl-5-oxo-5,8-dihydro-pyrido[2,3-d]pyrimidine-6-carboxylic acid amide,
2-(3-Dimethylaminomethyl-phenylamino)-8-indan-5-yl-5-oxo-5,8-dihydro-pyrido[2,3-d]pyrimidine-6-carboxylic acid methylamide,
2-(3-Dimethylaminomethyl-phenylamino)-8-indan-5-yl-5-oxo-5,8-dihydro-pyrido[2,3-d]pyrimidine-6-carboxylic acid ethylamide,
2-(3-Dimethylcarbamoyl-phenylamino)-8-indan-5-yl-5-oxo-5,8-dihydro-pyrido[2,3-d]pyrimidine-6-carboxylic acid amide,
2-(3-Dimethylcarbamoyl-phenylamino)-8-indan-5-yl-5-oxo-5,8-dihydro-pyrido[2,3-d]pyrimidine-6-carboxylic acid methylamide,
2-(3-Dimethylcarbamoyl-phenylamino)-8-indan-5-yl-5-oxo-5,8-dihydro-pyrido[2,3-d]pyrimidine-6-carboxylic acid ethylamide,
8-Bicyclo[2.2.1]hept-2-yl-2-[4-(4-methyl-piperazin-1-yl)-phenylamino]-5-oxo-5,8-dihydro-pyrido[2,3-d]pyrimidine-6-carboxylic acid amide,
8-Bicyclo[2.2.1]hept-2-yl-2-[4-(4-methyl-piperazin-1-yl)-phenylamino]-5-oxo-5,8-dihydro-pyrido[2,3-d]pyrimidine-6-carboxylic acid ethylamide,
8-Indan-5-yl-2-[4-(4-methyl-piperazin-1-ylmethyl)-phenylamino]-5-oxo-5,8-dihydro-pyrido[2,3-d]pyrimidine-6-carboxylic acid ethylamide, and
8-Benzyl-2-[4-(4-methyl-piperazin-1-yl)-phenylamino]-5-oxo-5,8-dihydro-pyrido[2,3-d]pyrimidine-6-carboxylic acid methylamide.

7. A compound selected from the group consisting of:
8-indan-5-yl-2-[4-(4-methyl-piperazin-1-yl)-phenylamino]-5-oxo-5,8-dihydro-pyrido[2,3-d]pyrimidine-6-carboxylic acid amide,
8-indan-5-yl-2-[4-(4-methyl-piperazin-1-yl)-phenylamino]-5-oxo-5,8-dihydro-pyrido[2,3-d]pyrimidine-6-carboxylic acid methylamide,
8-indan-5-yl-2-[4-(4-methyl-piperazin-1-yl)-phenylamino]-5-oxo-5,8-dihydro-pyrido[2,3-d]pyrimidine-6-carboxylic acid ethylamide,
2-[4-(3-dimethylamino-2-hydroxy-propoxy)-phenylamino]-8-indan-5-yl-5-oxo-5,8-dihydro-pyrido[2,3-d]pyrimidine-6-carboxylic acid amide,
2-[4-(3-dimethylamino-2-hydroxy-propoxy)-phenylamino]-8-indan-5-yl-5-oxo-5,8-dihydro-pyrido[2,3-d]pyrimidine-6-carboxylic acid methyl amide
2-[4-(3-dimethylamino-2-hydroxy-propoxy)-phenylamino]-8-indan-5-yl-5-oxo-5,8-dihydro-pyrido[2,3-d]pyrimidine-6-carboxylic acid ethylamide,
8-indan-5-yl-2-(4-morpholin-4-yl-phenylamino)-5-oxo-5,8-dihydro-pyrido[2,3-d]pyrimidine-6-carboxylic acid amide,
2-(4-dimethylamino-phenylamino)-8-indan-5-yl-5-oxo-5,8-dihydro-pyrido[2,3-d]pyrimidine-6-carboxylic acid amide,
2-(3-dimethylamino-phenylamino)-8-indan-5-yl-5-oxo-5,8-dihydro-pyrido[2,3-d]pyrimidine-6-carboxylic acid amide,
8-cyclopentyl-2-[4-(4-methyl-piperazin-1-yl)-phenylamino]-5-oxo-5,8-dihydro-pyrido[2,3-d]pyrimidine-6-carboxylic acid amide,
8-indan-5-yl-2-[3-(4-methyl-piperazin-1-ylmethyl)-phenylamino]-5-oxo-5,8-dihydro-pyrido[2,3-d]pyrimidine-6-carboxylic acid amide,
8-indan-5-yl-2-(3-morpholin-4-ylmethyl-phenylamino)-5-oxo-5,8-dihydro-pyrido[2,3-d]pyrimidine-6-carboxylic acid amide,
2-[2-hydroxy-4-(4-methyl-piperazin-1-yl)-phenylamino]-8-indan-5-yl-5-oxo-5,8-dihydro-pyrido[2,3-d]pyrimidine-6-carboxylic acid amide,
1-Indan-5-yl-7-[4-(4-methyl-piperazin-1-yl)-phenylamino]-4-oxo-1,4-dihydro-[1,6]naphthyridine-3-carboxylic acid amide,
8-Indan-5-yl-2-[4-(2-morpholin-4-yl-ethyl)-phenylamino]-5-oxo-5,8-dihydro-pyrido[2,3-d]pyrimidine-6-carboxylic acid amide,
8-Indan-5-yl-2-[4-(2-morpholin-4-yl-ethyl)-phenylamino]-5-oxo-5,8-dihydro-pyrido[2,3-d]pyrimidine-6-carboxylic acid methyl amide, 8-Indan-5-yl-2-[4-(2-morpholin-4-yl-ethyl)-phenylamino]-5-oxo-5,8-dihydro-pyrido[2,3-d]pyrimidine-6-carboxylic acid ethyl amide, (4S)-8-Indan-5-yl-5-oxo-2-[4-(2-oxo-oxazolidin-4-ylmethyl)-phenylamino]-5,8-dihydro-pyrido[2,3-d]pyrimidine-6-carboxylic acid amide, (4S)-8-Indan-5-yl-5-oxo-2-[4-(2-oxo-oxazolidine-4-ylmethyl)-phenylamino]-5,8-dihydro-pyrido[2,3-d]pyrimidine-6-carboxylic acid methyl amide, (4S)-8-Indan-5-yl-5-oxo-2-[4-(2-oxo-oxazolidin-4-ylmethyl)-phenylamino]-5,8-dihydro-pyrido[2,3-d]pyrimidine-6-carboxylic acid ethyl amide, 8-Indan-5-yl-2-[4-(2-isopropylsulfamoyl-ethyl)-phenylamino]-5-oxo-5,8-dihydro-pyrido[2,3-d]pyrimidine-6-carboxylic acid methyl amide, 8-Indan-5-yl-2-{4-[2-(morpholine-4-sulfonyl)-ethyl]-phenylamino}-5-oxo-5,8-dihydro-pyrido[2,3-d]pyrimidine-6-carboxylic acid methyl amide, 8-Indan-5-yl-2-[3-(4-methyl-piperazin-1-yl)-phenylamino]-5-oxo-5,8-dihydro-pyrido[2,3-d]pyrimidine-6-carboxylic acid amide, 8-Indan-5-yl-2-[3-(4-methyl-piperazin-1-yl)-phenylamino]-5-oxo-5,8-dihydro-pyrido[2,3-d]pyrimidine-6-carboxylic acid methyl amide, 8-Indan-5-yl-2-[3-(4-methyl-piperazin-1-yl)-phenylamino]-5-oxo-5,8-dihydro-pyrido[2,3-d]pyrimidine-6-carboxylic acid ethyl amide, 8-Indan-5-yl-5-oxo-2-(4-piperazin-1-yl-phenylamino)-5,8-dihydro-pyrido[2,3-d]pyrimidine-6-carboxylic acid amide, 8-Indan-5-yl-5-oxo-2-(4-piperazin-1-yl-phenylamino)-5,8-dihydro-pyrido[2,3-d]pyrimidine-6-carboxylic acid methyl amide, 8-Indan-5-yl-5-oxo-2-(4-piperazin-1-yl-phenylamino)-5,8-dihydro-pyrido[2,3-d]pyrimidine-6-carboxylic acid ethyl amide, 2-[4-(3,5-Dimethyl-piperazin-1-yl)-phenylamino]-8-indan-5-yl-5-oxo-5,8-dihydro-pyrido[2,3-d]pyrimidine-6-carboxylic acid amide, 2-[4-(3,5-Dimethyl-piperazin-1-yl)-phenylamino]-8-indan-5-yl-5-oxo-5,8-dihydro-pyrido[2,3-d]pyrimidine-6-carboxylic acid methyl amide, 2-[4-(3,5-Dimethyl-piperazin-1-yl)-phenylamino]-8-indan-5-yl-5-oxo-5,8-dihydro-pyrido[2,3-d]pyrimidine-6-carboxylic acid ethyl amide, 8-Indan-5-yl-2-{4-[2-(4-methyl-piperazin-1-yl)-ethyl]-phenylamino}-5-oxo-5,8-dihydro-pyrido[2,3-d]pyrimidine-6-carboxylic acid amide, 8-Indan-5-yl-2-{4-[2-(4-methyl-piperazin-1-yl)-ethyl]-phenylamino}-5-oxo-5,8-dihydro-pyrido[2,3-d]pyrimidine-6-carboxylic acid methyl amide, 8-Indan-5-yl-2-{4-[2-(4-methyl-piperazin-1-yl)-ethyl]-phenylamino}-5-oxo-5,8-dihydro-pyrido[2,3-d]pyrimidine-6-carboxylic acid ethyl amide, 8-Indan-5-yl-5-oxo-2-(4-piperidin-4-yl-phenylamino)-5,8-dihydro-pyrido[2,3-d]pyrimidine-6-carboxylic acid amide, 8-Indan-5-yl-5-oxo-2-(4-piperidin-4-yl-phenylamino)-5,8-dihydro-pyrido[2,3-d]pyrimidine-6-carboxylic acid methyl amide, 8-Indan-5-yl-5-oxo-2-(4-piperidin-4-yl-phenylamino)-5,8-dihydro-pyrido[2,3-d]pyrimidine-6-carboxylic acid ethyl amide, 8-Indan-5-yl-5-oxo-2-(3-piperazin-1-yl-phenylamino)-5,8-dihydro-pyrido[2,3-d]pyrimidine-6-carboxylic acid amide, 8-Indan-5-yl-5-oxo-2-(3-piperazin-1-yl-phenylamino)-5,8-dihydro-pyrido[2,3-d]pyrimidine-6-carboxylic acid methyl amide, 8-Indan-5-yl-5-oxo-2-(3-piperazin-1-yl-phenylamino)-5,8-dihydro-pyrido[2,3-d]pyrimidine-6-carboxylic acid ethyl amide, 2-[3-(3,5-Dimethyl-piperazin-1-yl)-phenylamino]-8-indan-5-yl-5-oxo-5,8-dihydro-pyrido[2,3-d]pyrimidine-6-carboxylic acid amide, 2-[3-(3,5-Dimethyl-piperazin-1-yl)-phenylamino]-8-indan-5-yl-5-oxo-5,8-dihydro-pyrido[2,3-d]pyrimidine-6-carboxylic acid methyl amide, 8-Cyclohexyl-2-[4-(2-morpholin-4-yl-ethyl)-phenylamino]-5-oxo-5,8-dihydro-pyrido[2,3-d]pyrimidine-6-carboxylic acid amide, 8-Cyclohexyl-2-[4-(4-methyl-piperazin-1-yl)-phenylamino]-5-oxo-5,8-dihydro-pyrido[2,3-d]pyrimidine-6-carboxylic acid amide, 8-Cyclohexyl-2-[3-(4-methyl-piperazin-1-yl)-phenylamino]-5-oxo-5,8-dihydro-pyrido[2,3-d]pyrimidine-6-carboxylic acid amide, 8-Cyclohexyl-2-[3-(4-methyl-piperazin-1-yl)-phenylamino]-5-oxo-5,8-dihydro-pyrido[2,3-d]pyrimidine-6-carboxylic acid methyl amide, 8-Indan-5-yl-2-(4-morpholin-4-ylmethyl-phenylamino)-5-oxo-5,8-dihydro-pyrido[2,3-d]pyrimidine-6-carboxylic acid amide, 8-Indan-5-yl-2-[4-(4-methyl-piperazin-1-ylmethyl)-phenylamino]-5-oxo-5,8-dihydro-pyrido[2,3-d]pyrimidine-6-carboxylic acid amide, 2-(4-Dimethylaminomethyl-phenylamino)-8-indan-5-yl-5-oxo-5,8-dihydro-pyrido[2,3-d]pyrimidine-6-carboxylic acid amide, 2-(3-Dimethylaminomethyl-phenylamino)-8-indan-5-yl-5-oxo-5,8-dihydro-pyrido[2,3-d]pyrimidine-6-carboxylic acid amide, 2-(3-Dimethylcarbamoyl-phenylamino)-8-indan-5-yl-5-oxo-5,8-dihydro-pyrido[2,3-d]pyrimidine-6-carboxylic acid amide, 2-(3-Dimethylcarbamoyl-phenyl amino)-8-indan-5-yl-5-oxo-5,8-dihydro-pyrido[2,3-d]pyrimidine-6-carboxylic acid methylamide, 8-Bicyclo[2.2.1]hept-2-yl-2-[4-(4-methyl-piperazin-1-yl)-phenylamino]-5-oxo-5,8-dihydro-pyrido[2,3-d]pyrimidine-6-carboxylic acid amide, and 8-Indan-5-yl-2-[4-(4-methyl-piperazin-1-ylmethyl)-phenylamino]-5-oxo-5,8-dihydro-pyrido[2,3-d]pyrimidine-6-carboxylic acid ethylamide.

8. A pharmaceutical composition, comprising a compound of claim 1 and a pharmaceutically acceptable carrier.

9. A method for inhibiting protein tyrosine kinase activity, comprising contacting the kinase with an effective inhibitory amount of at least one compound of claim 1.

10. A method according to claim 9, wherein the protein tyrosine kinase is c-fms.

11. A pharmaceutical dosage form comprising a pharmaceutically acceptable carrier and from about 0.5 mg to about 10 g of at least one compound of claim 1.

12. A dosage form according to claim 11 adapted for parenteral or oral administration.

* * * * *